US011472788B2

(12) United States Patent
Wang et al.

(10) Patent No.: US 11,472,788 B2
(45) Date of Patent: Oct. 18, 2022

(54) BENZOIMIDAZOLES AS SELECTIVE INHIBITORS OF INDOLEAMINE 2,3-DIOXYGENASES

(71) Applicant: BEIGENE, LTD., Grand Cayman (KY)

(72) Inventors: Hexiang Wang, Beijing (CN); Yunhang Guo, Beijing (CN); Zhiwei Wang, Beijing (CN); Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 37 days.

(21) Appl. No.: 16/758,203

(22) PCT Filed: Nov. 24, 2018

(86) PCT No.: PCT/CN2018/117347
§ 371 (c)(1),
(2) Date: Apr. 22, 2020

(87) PCT Pub. No.: WO2019/101188
PCT Pub. Date: May 31, 2019

(65) Prior Publication Data
US 2020/0317638 A1    Oct. 8, 2020

(30) Foreign Application Priority Data

Nov. 25, 2017 (WO) ................ PCT/CN2017/112996

(51) Int. Cl.
| | | |
|---|---|---|
| *C07D 401/08* | (2006.01) |
| *A61P 31/18* | (2006.01) |
| *A61P 35/00* | (2006.01) |
| *C07D 401/14* | (2006.01) |
| *C07D 235/08* | (2006.01) |
| *C07D 235/10* | (2006.01) |
| *C07D 401/12* | (2006.01) |
| *C07D 405/14* | (2006.01) |
| *C07D 491/056* | (2006.01) |
| *C07D 413/14* | (2006.01) |
| *C07D 471/04* | (2006.01) |
| *C07D 487/04* | (2006.01) |

(52) U.S. Cl.
CPC ............ *C07D 401/08* (2013.01); *A61P 31/18* (2018.01); *A61P 35/00* (2018.01); *C07D 401/14* (2013.01)

(58) Field of Classification Search
CPC ................ C07D 401/08; C07D 401/14; C07D 235/08; C07D 235/10; C07D 401/12; C07D 405/14; C07D 413/14; C07D 471/04; C07D 487/04; C07D 491/056; A61P 31/18; A61P 35/00
See application file for complete search history.

(56) References Cited

U.S. PATENT DOCUMENTS

| | | |
|---|---|---|
| 6,737,421 B1 | 5/2004 | Lubish et al. |
| 7,220,856 B2 | 5/2007 | Dunning et al. |
| 7,442,701 B2 | 10/2008 | Blurton et al. |
| 7,915,284 B2 | 3/2011 | Almario Garcia et al. |
| 9,260,434 B2 | 2/2016 | Mautino et al. |
| 10,233,190 B2 | 3/2019 | Mautino et al. |
| 10,280,163 B2 | 5/2019 | Wang et al. |
| 10,647,714 B2 | 5/2020 | Wang et al. |
| 10,882,856 B2 | 1/2021 | Wang et al. |
| 2005/0282853 A1 | 12/2005 | Boykin et al. |
| 2016/0002249 A1 | 1/2016 | Mautino et al. |
| 2016/0159776 A1 | 6/2016 | Fan et al. |
| 2018/0072716 A1 | 3/2018 | Wang et al. |
| 2018/0354908 A1 | 12/2018 | Cowley et al. |
| 2019/0284184 A1 | 9/2019 | Wang et al. |
| 2019/0292189 A1 | 9/2019 | Feng et al. |
| 2020/0024273 A1 | 1/2020 | Wang et al. |

FOREIGN PATENT DOCUMENTS

| | | |
|---|---|---|
| CN | 1349510 A | 5/2002 |
| CN | 1678586 A | 10/2005 |
| CN | 1930159 A | 3/2007 |
| CN | 101516881 A | 8/2009 |
| CN | 102532144 A | 7/2012 |
| CN | 103547579 A | 1/2014 |
| CN | 103923088 A | 7/2014 |
| CN | 104140426 A | 11/2014 |
| CN | 104230896 A | 12/2014 |
| CN | 105189466 A | 12/2015 |
| CN | 109476669 A | 3/2019 |
| CN | 109574988 A | 4/2019 |
| JP | H09-071586 | 3/1997 |
| JP | 2014-511876 A | 5/2014 |
| WO | WO-03106430 A1 | 12/2003 |

(Continued)

OTHER PUBLICATIONS

Verweij, M., 2000 Preventive Medicine Between Obligation and Aspiration 2000, Springer Science and Business Media p. 1-190; Ch. 3; 31 p.*

Muller, A. J., "Inhibition of indoleamine 2, 3-dioxygenase, an immunoregulatory target of the cancer suppression gene Bin1, potentiates cancer chemotherapy." Nature medicine 11.3 (2005): 312-319.*

Spranger, S., "Mechanism of tumor rejection with doublets of CTLA-4, PD-1/PD-L1, or IDO blockade involves restored IL-2 production and proliferation of CD8+ T cells directly within the tumor microenvironment." Journal for immunotherapy of cancer 2.1 (2014): 1-14.*

(Continued)

*Primary Examiner* — John M Mauro
(74) *Attorney, Agent, or Firm* — Cooley LLP

(57) ABSTRACT

Disclosed herein are novel benzoimidazoles and pharmaceutical compositions comprising at least one such novel benzoimidazoles, processes for the preparation thereof, and the method for using the same in therapy. In particular, disclosed herein are certain novel benzoimidazoles that are useful for inhibiting indoleamine 2, 3-dioxygenase and for treating diseases or disorders mediated thereby.

7 Claims, No Drawings

(56) References Cited

FOREIGN PATENT DOCUMENTS

| WO | WO 2004/002960 | | 1/2004 |
|---|---|---|---|
| WO | WO 2004/035549 | | 4/2004 |
| WO | WO 2008/034974 | | 3/2008 |
| WO | WO 2008/110523 | | 9/2008 |
| WO | WO 2012/142237 | | 10/2012 |
| WO | WO-2013107164 | A1 | 7/2013 |
| WO | WO 2014/159248 | | 10/2014 |
| WO | WO 2016/071293 | | 5/2016 |
| WO | WO 2016/161960 | | 10/2016 |
| WO | WO 2018/039512 | | 3/2018 |
| WO | WO 2018/054365 | | 3/2018 |
| WO | WO 2019/101188 | | 5/2019 |
| WO | WO-2020233676 | A1 | 11/2020 |

OTHER PUBLICATIONS

Holmgaard, R. B., "Indoleamine 2, 3-dioxygenase is a critical resistance mechanism in antitumor T cell immunotherapy targeting CTLA-4." Journal of Experimental Medicine 210.7 (2013): 1389-1402.*

Uyttenhove, C., "Evidence for a tumoral immune resistance mechanism based on tryptophan degradation by indoleamine 2, 3-dioxygenase." Nature medicine 9.10 (2003): 1269-1274.*

International Search Report and Written Opinion for International Application No. PCT/CN2016/078787, dated Jun. 30, 2016, 12 pages.

Extended European Search Report for European Application No. 16776135.2, dated Feb. 13, 2019, 4 pages.

Extended European Search Report for European Application No. 17852432.8, dated Mar. 18, 2020, 8 pages.

International Search Report and Written Opinion for International Application No. PCT/CN2017/103051, dated Dec. 27, 2017, 12 pages.

International Search Report and Written Opinion for International Application No. PCT/CN2018/117347, dated Feb. 25, 2019, 11 pages.

Blatcher, P. et al., "A direct method for the substitution of imidazo[1,5-a]pyridines at position 5," Tetrahedron Letters, vol. 21, Issue 22, pp. 2195-2196 (Dec. 1980).

Davey, D. et al., "Cardiotonic Agents, 1. Novel 8-Aryl-Substituted Imidazo[1, 2-a]-and-[1, 5-a]pyridines and Imidazo[1, 5-a]pyridinones as potential positive inotropic agents," J. Med. Chem., vol. 30, No. 8, Dec. 1987, pp. 1337-1342.

Jeankumar, V. U. et al., "Engineering another class of anti-tubercular lead: Hit to lead optimization of an intriguing class of gyrase ATPase inhibitors," European Journal of Medicinal Chemistry, vol. 122, Oct. 2016, pp. 216-231.

Kumar, S. et al., "Structure Based Development of Phenylimidazole-Derived Inhibitors of Indoleamine 2,3-Dioxygenase," J. Med. Chem., vol. 51, No. 16, Jul. 2008, pp. 4968-4977.

Tojo, S. et al., "Crystal structures and structure activity relationships of imidazothiazole derivatives as IDO1 inhibitors," ACS Medicinal Chemistry Letters, vol. 5, Issue 10, pp. 1119-1123 (Aug. 2014).

Potula, R. et al., "Inhibition of indoleamine 2,3-dioxygenase (IDO) enhances elimination of virus-infected macrophages in an animal model of HIV-1 encephalitis," Blood, vol. 106, Issue 7, Oct. 2005, pp. 2382-2390.

Boasso, A. et al., "Combined Effect of Antiretroviral Therapy and Blockade of IDO in SIV-Infected Rhesus Macaques," The Journal of Immunology, 2009, vol. 182, pp. 4313-4320.

Pilotte, L. et al., "Reversal of tumoral immune resistance by inhibition of tryptophan 2,3-dioxygenase," PNAS, Feb. 14, 2012, vol. 109, No. 7, pp. 2497-2502.

Fallarino, F. et al., "T cell apoptosis by tryptophan catabolism," Cell Death and Differentiation, 2002, vol. 9, pp. 1069-1077.

Smith, C. et al., "IDO Is a Nodal Pathogenic Driver of Lung Cancer and Metastasis Development," Cancer Discovery, 2012, vol. 2, No. 8, pp. 722-735.

International Search Report and Written Opinion for International Application No. PCT/CN2020/091602, dated Aug. 21, 2020, 17 pages.

Lopez-Rodriguez, M. L. et al., "Benzimidazole derivatives. Part 5: Design and synthesis of new benzimidazole-arylpiperazine derivatives acting as mixed 5-HT1A/5-HT3 ligands," Bioorganic & Medicinal Chemistry, vol. 12, Issue 19, Aug. 2004, pp. 5181-5191.

\* cited by examiner

BENZOIMIDAZOLES AS SELECTIVE INHIBITORS OF INDOLEAMINE 2,3-DIOXYGENASES

CROSS-REFERENCE TO RELATED APPLICATIONS

This application is a U.S. National Stage Application under 35 U.S.C. § 371 of International Application No. PCT/CN2018/117347, filed Nov. 24, 2018, which claims the benefit of International Patent Application No. PCT/CN2017/112996, filed on Nov. 25, 2017, the disclosures of which are hereby incorporated by reference in their entireties for all purposes.

FIELD OF THE INVENTION

Disclosed herein are novel benzoimidazoles and pharmaceutical compositions comprising at least one such novel benzoimidazoles, processes for the preparation thereof, and the method for using the same in therapy. In particular, disclosed herein are certain novel benzoimidazoles that are useful for inhibiting indoleamine 2,3-dioxygenase and for treating diseases or disorders mediated thereby.

BACKGROUND OF THE INVENTION

Indoleamine 2,3-dioxygenase 1 (IDO1, EC 1.13.11.42, also known as indoleamine 2,3-dioxygenase) is the first and rate-limiting enzyme in the tryptophan-kynurenine pathway that degrades the essential amino acid L-tryptophan (L-Trp) to N-formal-kynurenine, which can be subsequently metabolized through a series of steps to form NAD. IDO1 enzyme is expressed in the placenta, the mucosal and lymphoid tissues, and in inflammatory lesions (Yamazaki F, et. al., Biochem J. 1985; 230:635-8; Blaschitz A, et. al., *PLoS ONE*. 2011; 6:e21774). In the latter two, it is expressed primarily by antigen-presenting cells (APC), mainly dendritic cells (DC) and macrophages, and in cells exposed to interferon-gamma (IFNγ) and other pro-inflammatory stimuli. In human cells, the depletion of L-Trp resulting from IDO1 activity as well as the production of a series of immunoregulatory metabolites, collectively known as "kynurenines", can suppress the proliferation and differentiation of effector T cells [Frumento G, et. al., (2002), *Journal of Experimental Medicine* 196: 459-468], and markedly enhance the suppressor activity of regulatory T cells [Sharma M D, et al. (2009), *Blood* 113: 6102-6111]. As a result, IDO1 controls and fine-tunes both innate and adaptive immune responses [Grohmann U, et al. (2002), *Nature Immunology* 3: 1097-1101] under a variety of conditions, including pregnancy [Munn D H, et al. (1998), *Science* 281: 1191-1193], transplantation [Palafox D, et al. (2010), *Transplantation Reviews* 24: 160-165], infection [Boasso A, et al. (2009), *Amino Acids* 37: 89-89], chronic inflammation [Romani L, et al. (2008), *Nature* 451: 211-U212], autoimmunity [Platten M, et al. (2005), Science 310: 850-855], neoplasia, and depression [Maes M, et. al., Life Sci. 2002 6; 71(16): 1837-48; Myint A M, et. al., (2012), Journal of Neural Transmission 119: 245-251].

Several lines of evidence suggest that IDO is involved in induction of immune tolerance. The immunosuppressive effect of IDO1 was demonstrated first in a mouse model of fetal protection against maternal immune rejection. Treatment of pregnant mice with a tryptophan analog that inhibits IDO1, which is constitutively expressed in the placenta, resulted in T cell-mediated rejection of allogeneic embryos [Munn D H, et al. (1998), *Science* 281: 1191-1193]. Subsequent studies developed this concept as a mechanism to defeat immune surveillance in cancer (reviewed in [Prendergast GC (2008), Oncogene 27(28):3889-3900; Munn D H, et. al., (2007), J Clin Invest 117(5):1147-1154]). Indoleamine 2,3-dioxygenase is widely overexpressed in tumor cells where it has been associated predominantly with poor prognosis [Uyttenhove C, et. al., (2003), Nat Med 9(10):1269-1274; Liu X, et. al., (2009), Curr Cancer Drug Targets 9(8):938-95]. Expression of IDO by immunogenic mouse tumor cells prevents their rejection by preimmunized mice [Uyttenhove C. et. al., Nat Med. 2003 October; 9(10): 1269-74. Epub 2003 Sep. 21]. IDO activity is shown to suppress T cells [Fallarino F, et. al., (2002), Cell Death Differ 9:1069-1077; Frumento G, et. al., (2002), J Exp Med 196(4):459-468; Terness P, et. al., (2002), J Exp Med 196(4):447-457] and NK cells [Della Chiesa M, et. al., (2006), Blood 108(13):4118-4125], and also that IDO was critical to support the formation and activity of Tregs [Fallarino F, et. al., (2003), Nat Immunol 4(12):1206-1212] and myeloid-derived suppressor cells (MDSCs) [Smith C, et. al., (2012), Cancer Discovery 2(8):722-735.]. It has been suggested that the efficacy of therapeutic vaccination of cancer patients might be improved by concomitant administration of an IDO inhibitor [Uyttenhove C. et. al., Nat Med. 2003 October; 9(10):1269-74. Epub 2003 Sep. 21]. It has been shown that the IDO inhibitor, 1-MT, can synergize with chemotherapeutic agents to reduce tumor growth in mice, suggesting that IDO inhibition may also enhance the antitumor activity of conventional cytotoxic therapies [Muller A J, et. al., Nat Med. 2005 March; 11(3):312-9]. It has also been shown that IDO inhibitors can synergize with anti-CTLA-4 antibody or anti-PDL-1 antibody in inhibiting tumor growth in mouse models [Holmgaard R B, et. al., J Exp Med. 2013 Jul. 1; 210(7):1389-402; Spranger S, et. al., J Immunother Cancer. 2014, 2:3].

It has been proposed that IDO is induced chronically by HIV infection, and is further increased by opportunistic infections, and that the chronic loss of Trp initiates mechanisms responsible for cachexia, dementia and diarrhea and possibly immunosuppression of AIDS patients [Brown, et al., 1991, Adv. Exp. Med. Biol., 294: 425-35]. To this end, it has recently been shown that IDO inhibition can enhance the levels of virus-specific T cells and, concomitantly, reduce the number of virally infected macrophages in a mouse model of HIV [Portula et al., 2005, Blood, 106:2382-90]. Simian Immunodeficiency Virus (SIV) is very similar to Human Immunodeficiency Virus (HIV) and it is used to study the condition in animal models. In both HIV and SIV, the level of virus in the blood, or 'viral load', is important because when the viral load is high, the disease progress and it depletes the patient's immune system. This eventually leads to the onset of Acquired Immune Deficiency Syndrome (AIDS), where the patient cannot fight infections which would be innocuous in healthy individuals. It has also been reported that monkeys with the simian form of HIV treated with an IDO inhibitor, called D-1mT alongside Anti-Retroviral Therapy (ART), reduced their virus levels in the blood to undetectable levels, therefore when combined with ARTs, IDO inhibitors may help HIV patients not responding to treatment in the future [Adriano Boasso, et. al., J. Immunol., April 2009; 182: 4313-4320].

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis)

and depression, therapeutic agents aimed at suppression of tryptophan degradation by inhibiting IDO activity are of interests. Inhibitors of IDO can be used as effective cancer therapy as they could reverse the immunosuppressive effects of tumor microenvironment and activate anti-tumor activity of T cells. IDO inhibitors could also be useful in activation of immune responses in HIV infection. Inhibition of IDO may also be an important treatment strategy for patients with neurological or neuropsychiatric diseases or disorders such as depression. The compounds, compositions and methods herein help meet the current need for IDO modulators.

Tryptophan 2,3-dioxygenase (TDO, EC 1.13.11.11) catalyzes the same Trp degradation reaction as IDO1. TDO is primarily expressed in the liver in humans, where acts as the main regulator of systemic tryptophan levels. More recently, TDO was also found to be expressed in the brain, where it may regulate the production of neuroactive tryptophan metabolites such as kynurenic acid and quinolinic acid [Kanai M, et. al., Mol Brain 2009; 2:8]. Two recent studies [Opitz C A, et. al., Nature 2011; 478:197-203; Pilotte L, et. al., Proc Natl Acad Sci USA. 2012, 109(7):2497-502] point to the significance of TDO activity in certain cancers where it is expressed constitutively (particularly malignant glioma, hepatocellular carcinoma, melanoma, and bladder cancer). Functional studies in human tumors indicate that constitutive TDO enzymatic activity is sufficient to sustain biologically relevant tryptophan catabolism that is capable of suppressing antitumor immune responses [Opitz C A, et. al., Nature 2011; 478:197-203; Pilotte L, et. al., Proc Natl Acad Sci USA. 2012, 109(7):2497-502]. TDO expression by tumors is reported to prevent rejection by immunized mice. A specific TDO inhibitor is shown to restore the ability of mice to reject TDO-expressing tumors without causing significant toxicity [Pilotte L, et. al., Proc Natl Acad Sci USA. 2012, 109(7):2497-502]. Therefore, inhibitors of TDO can potentially be used as a single agent or in combination with other anti-cancer therapies to treat a variety of human cancers.

Small molecule inhibitors of IDO are being developed to treat or prevent IDO-related diseases such as those described above. Fox example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2006/122150; WO 2009/073620; WO 2009/132238; WO 2011/056652, WO 2012/142237; WO 2013/107164; WO 2014/066834; WO 2014/081689; WO 2014/141110; WO 2014/150646; WO 2014/150677; WO 2015006520; WO 2015/067782; WO 2015/070007; WO 2015/082499; WO 2015/119944; WO 2015/121812; WO 2015/140717; WO 2015/150697; WO 2015/173764; WO2015/188085; WO 2016/026772; WO 2016/024233; WO2016/026772; WO 2016/037026; WO 2016/040458; WO 2016/051181; WO 2016/059412; WO 2016/071283; WO 2016/071293; WO 2016/073738; WO 2016/073770; WO 2016/073774; US 2015328228; US 2015266857; WO 2016/155545; WO 2016/161279; WO 2016/161279; WO 2016/161269; WO 2016/165613; WO 2016/16942; 1 WO 2016/210414; WO 2017/002078; WO 2017/007700; WO 2017/024996; WO 2017/075341; WO 2017/101884; WO 2017/106062; WO 2017/117393; WO 2017/120591; WO 2017/124822; WO 2017/129139; WO 2017/133258; WO 2017/134555; WO 2017/139414; WO 2017/140272; WO 2017/140274; WO 2017/143874; WO 2017/149469; WO 2017/152857; WO 2017/153459; WO 2017/181849; WO 2017/185959; WO 2017/189386; WO 2017/192811; WO 2017/192815; WO 2017/192813; WO 2017/192840; WO 2017/192844; WO 2017/19514. In particular, the compounds of WO 2012/142237 and WO 2014/159248 encompass a series of tricyclic imidazoisoindoles with potent IDO inhibitory activity.

However, no benzoimidazoles has been reported as an IDO inhibitor. Disclosed herein are novel benzoimidazoles exhibiting IDO inhibitory activity. Specifically, disclosed herein are novel benzoimidazoles exhibiting selective inhibitory activity for IDO1 over TDO.

SUMMARY OF THE INVENTION

Disclosed herein is a compound selected from a compound of Formula (I)

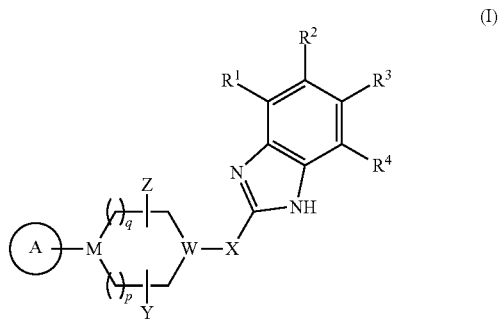

or a stereoisomer thereof, or a pharmaceutically acceptable salt thereof,
wherein:
M is CH or N;
W is CH or N;
p is 1, 2 or 3;
q is 0, 1 or 2;
X is —$CR^5R^6$—, —$CHR^5CHR^6$— or a single bond;
Y and Z are each independently hydrogen, halogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl; or Z and Y, together with the atoms to which they are attached, form a bridged cyclic or heterocyclic ring optionally substituted with a substituent selected from halogen, $C_{1-4}$ haloalkyl, $C_{1-4}$ alkyl and $C_{1-4}$alkoxy;
Ring A is a monocyclic or bicyclic aromatic hydrocarbon ring or a monocyclic or bicyclic aromatic heterocyclic ring, each having 5- to 10-ring members; and Ring A is optionally substituted with at least one substituent $R^7$ as long as valence and stability permit;
$R^1$, $R^2$, $R^3$ and $R^4$ are each independently hydrogen, halogen, cyano, $C_{1-8}$ alkyl, $C_{3-8}$ cycloalkyl, $C_{2-8}$ alkenyl, $C_{2-8}$ alkynyl, heterocyclyl, aryl, heteroaryl, —$C(O)NR^8R^9$, nitro, —$C(O)OR^8$, —$C(O)R^8$, —$OR^8$, —$SR^8$, —$NR^8R^9$, —$SO_2R^8$, —$SO_2NR^8R^9$, —$SOR^8$, —$NR^8SO_2R^9$, —$NR^8SOR^9$, —$NR^8C(O)OR^9$ or —$NR^8C(O)R^9$, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^{10}$; or ($R^1$ and $R^2$) or ($R^2$ and $R^3$) or ($R^3$ and $R^4$), together with the atoms to which they are attached, form a heterocyclyl ring or a heteroaryl ring, said ring comprising 0, 1 or 2 heteroatoms independently selected from —NH—, —O—, —S—, —SO— or —SO$_2$—, and said ring is optionally substituted with halogen, oxo, $C_{1-4}$ haloalkyl and $C_{1-4}$ alkyl;

$R^5$ and $R^6$ are each independently hydrogen, halogen, cyano, $C_{1-4}$alkyl, $C_{1-4}$haloalkyl, $C_{1-4}$ alkoxy, or $C_{3-6}$cycloalkyl; or ($R^5$ and $R^6$), and/or ($R^5$ and Y), together with the atoms to which they are attached, form a fused cyclopropyl ring;

$R^7$ is independently hydrogen, halogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^{10}$;

$R^8$ and $R^9$ are each independently hydrogen, $C_{1-8}$ alkyl, $C_{3-8}$ cycloalkyl, heterocyclyl, aryl, or heteroaryl, wherein said $C_{1-8}$ alkyl, $C_{3-8}$ cycloalkyl, heterocyclyl, aryl, and heteroaryl are each independently optionally substituted with 1 or 2 substituent $R^{10}$; or $R^8$ and $R^9$, together with the atoms to which they are attached, form a 3- to 8-membered saturated or partially or fully unsaturated ring comprising 0, 1 or 2 additional heteroatoms independently selected from —NH—, —O—, —S—, —SO— or —SO$_2$—, and said ring is optionally substituted with at least one substituent $R^{10}$;

$R^{10}$, at each occurrence, is independently hydrogen, halogen, $C_{1-8}$ haloalkyl, $C_{1-8}$ alkyl, $C_{2-8}$ alkenyl, $C_{3-8}$ cycloalkyl, aryl, heteroaryl, heterocyclyl, $C_{2-8}$ alkynyl, oxo, —$C_{1-4}$ alkyl-NR$^a$R$^b$, —CN, —OR$^a$, —NR$^a$R$^b$, —C(O)R$^a$, —C(O)OR$^a$, —CONR$^a$R$^b$, —C(=NR$^a$)NR$^b$R$^c$, nitro, —NR$^a$C(O)R$^b$, —NR$^a$C(O)NR$^a$R$^b$, —NR$^a$C(O)OR$^b$, —SO$_2$R$^a$, —NR$^a$SO$_2$NR$^b$R$^c$, —NR$^a$SOR$^b$ or —NR$^a$SO$_2$R$^b$, wherein said $C_{1-8}$ alkyl, $C_{1-8}$ haloalkyl, $C_{3-8}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein R$^a$, R$^b$, and R$^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl, or (R$^a$ and R$^b$), and/or (R$^b$ and R$^c$) together with the atoms to which they are attached, form a ring selected from a heterocyclyl or heteroaryl ring optionally substituted by halogen, $C_{1-4}$ haloalkyl or $C_{1-4}$ alkyl.

Also disclosed herein is a pharmaceutical composition comprising at least one pharmaceutically acceptable excipient and a compound selected from compounds of Formula (I), or a stereoisomer thereof, or a pharmaceutically acceptable salt thereof disclosed herein.

Also disclosed herein is a method of treating cancer responsive to inhibition of IDO and/or TDO comprising administering to a subject in need of treating for such cancer an amount of a compound selected from compounds of Formula (I), or a stereoisomer thereof, or a pharmaceutically acceptable salt thereof disclosed herein effective to treat the cancer.

Also disclosed herein is a use of a compound selected from compounds of Formula (I), or a stereoisomer thereof, or a pharmaceutically acceptable salt thereof disclosed herein in manufacture of a medicament for treatment of the disorders or diseases above.

Also disclosed herein is a use of a compound selected from compounds of Formula (I), or a stereoisomer thereof, or a pharmaceutically acceptable salt thereof disclosed herein in manufacture of a medicament for inhibition of IDO and/or TDO.

Also disclosed herein is a use of a compound selected from compounds of Formula (I), or a stereoisomer thereof, or a pharmaceutically acceptable salt thereof disclosed herein in the manufacture of a medicament for treating cancer.

DETAILED DESCRIPTION OF THE INVENTION

As used herein, the following words, phrases and symbols are generally intended to have the meanings as set forth below, except to the extent that the context in which they are used indicates otherwise.

The following abbreviations and terms have the indicated meanings throughout:

The phrase "a" or "an" entity as used herein refers to one or more of that entity. For example, a compound refers to one or more compounds or at least one compound. For another example, " . . . substituted with a substituent . . . " means that one or more substituents are substituted as long as valence and stability permit. As such, the terms "a" (or "an"), "one or more", and "at least one" can be used interchangeably herein.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "alkyloxy" herein refers to an alkyl group as defined above bonded to oxygen, represented by —Oalkyl. Examples of an alkyloxy, e.g., $C_{1-6}$ alkyloxy or $C_{1-4}$ alkyloxy includes, but not limited to, methoxy, ethoxyl, isopropoxy, propoxy, n-butoxy, tert-butoxy, pentoxy and hexoxy and the like.

The term "haloalkyl" herein refers to an alkyl group in which one or more hydrogen is/are replaced by one or more halogen atoms such as fluoro, chloro, bromo, and iodo. Examples of the haloalkyl include $C_{1-6}$haloalkyl or $C_{1-4}$haloalkyl, but not limited to F$_3$C—, ClCH$_2$—, CF$_3$CH$_2$—, CF$_3$CCl$_2$—, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems, such as

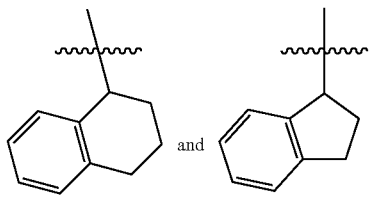

wherein the wavy lines indicate the points of attachment. The ring may be saturated or have at least one double bond (i.e. partially unsaturated), but is not fully conjugated, and is not aromatic, as aromatic is defined herein.

The term "aryl" used alone or in combination with other terms refers to a group selected from:

5- and 6-membered carbocyclic aromatic rings, for example, phenyl;

bicyclic ring systems such as 7 to 12 membered bicyclic ring systems wherein at least one ring is carbocyclic and aromatic, selected, for example, from naphthalene, and indane; and tricyclic ring systems such as 10 to 15 membered tricyclic ring systems wherein at least one ring is carbocyclic and aromatic, for example, fluorene.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, for example, but not limited to, phenyl, naphth-1-yl, naphth-2-yl, anthracenyl, phenanthrenyl rings, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The terms "aromatic heterocyclic ring" and "heteroaryl" are used interchangeable throughout the disclosure herein. In some embodiments, a monocyclic or bicyclic aromatic heterocyclic ring has 5- to 10-ring forming members with 1, 2, 3, or 4 heteroatom ring members independently selected from nitrogen, sulfur and oxygen and the remaining ring members being carbon. In some embodiments, the monocyclic or bicyclic aromatic heterocyclic ring is a monocyclic or bicyclic ring comprising 1 or 2 heteroatom ring members independently selected from nitrogen, sulfur and oxygen. In some embodiments, the monocyclic or bicyclic aromatic heterocyclic ring is a 5- to 6-membered heteroaryl ring, which is monocyclic and which has 1 or 2 heteroatom ring members independently selected from nitrogen, sulfur and oxygen. In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. In some embodiments, a heterocyclyl group is 4- to 7-membered monocyclic ring with one heteroatom selected from N, O and S. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco [3.1.0]hexanyl, 3-azabicyclo[4.1.0]heptanyl and azabicyclo [2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

Some of the compounds disclosed herein may exist with different points of attachment of hydrogen, referred to as tautomers. For example, compounds including carbonyl —CH$_2$C(O)— groups (keto forms) may undergo tautomerism to form hydroxyl —CH═C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or MosheR$^a$s acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of at least one compound of Formula (I), such as salts of enantiomers, and/or salts of diastereomers.

"Treating", "treat" or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat" as defined above, a disease or disorder in a subject.

The term "at least one substituent" disclosed herein includes, for example, from 1 to 4, such as from 1 to 3, further as 1 or 2, substituents, provided that valence and stability permit. For example, "at least one substituent $R^7$" disclosed herein includes from 1 to 4, such as from 1 to 3, further as 1 or 2, substituents selected from the list of $R^7$ as disclosed herein; and "at least one substituent $R^{10}$" disclosed herein includes from 1 to 4, such as from 1 to 3, further as 1 or 2, substituents selected from the list of $R^{10}$ as disclosed herein.

In the first aspect, disclosed herein is a compound of Formula (I):

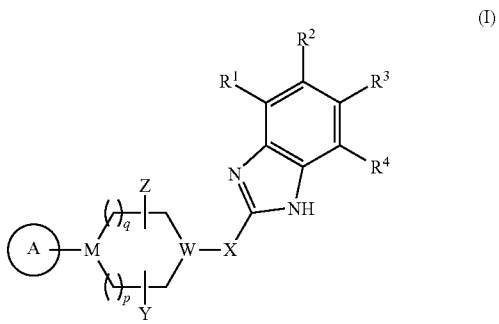

or a stereoisomer thereof, or a pharmaceutically acceptable salt thereof, wherein:

M is CH or N;

W is CH or N;

p is 1, 2 or 3;

q is 0, 1 or 2;

X is —$CR^5R^6$—, —$CHR^5CHR^6$— or a single bond;

Y and Z are each independently hydrogen, halogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl; or Z and Y, together with the atoms to which they are attached, form a bridged cyclic or heterocyclic ring optionally substituted with a substituent selected from halogen, $C_{1-4}$ haloalkyl, $C_{1-4}$ alkyl and $C_{1-4}$ alkoxy;

Ring A is a monocyclic or bicyclic aromatic hydrocarbon ring or a monocyclic or bicyclic aromatic heterocyclic ring, each having 5- to 10-ring members; and Ring A is optionally substituted with at least one substituent $R^7$;

$R^1$, $R^2$, $R^3$ and $R^4$ are each independently hydrogen, halogen, cyano, $C_{1-8}$ alkyl, $C_{3-8}$ cycloalkyl, $C_{2-8}$ alkenyl, $C_{2-8}$ alkynyl, heterocyclyl, aryl, heteroaryl, —$C(O)NR^8R^9$, nitro, —$C(O)OR^8$, —$C(O)R^8$, —$OR^8$, —$SR^8$, —$NR^8R^9$, —$SO_2R^8$, —$SO_2NR^8R^9$, —$SOR^8$, —$NR^8SO_2R^9$, —$NR^8SOR^9$, —$NR^8C(O)OR^9$ or —$NR^8C(O)R^9$, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^{10}$; or ($R^1$ and $R^2$) or ($R^2$ and $R^3$) or ($R^3$ and $R^4$), together with the atoms to which they are attached, form a heterocyclyl ring or a heteroaryl ring, said ring comprising 0, 1 or 2 heteroatoms independently selected from —NH, —O—, —S—, —SO— or —$SO_2$—, and said ring is optionally substituted with halogen, oxo, $C_{1-4}$ haloalkyl and $C_{1-4}$ alkyl;

$R^5$ and $R^6$ are each independently hydrogen, halogen, cyano, $C_{1-4}$ alkyl, $C_{1-4}$ haloalkyl, $C_{1-4}$ alkoxy, or $C_{3-6}$ cycloalkyl; or ($R^5$ and $R^6$), and/or ($R^5$ and Y), together with the atoms to which they are attached, form a fused cyclopropyl ring;

$R^7$ is independently hydrogen, halogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^{10}$;

$R^8$ and $R^9$ are each independently hydrogen, $C_{1-8}$ alkyl, $C_{3-8}$ cycloalkyl, heterocyclyl, aryl, or heteroaryl, wherein said $C_{1-8}$ alkyl, $C_{3-8}$ cycloalkyl, heterocyclyl, aryl, and heteroaryl are each independently optionally substituted with 1 or 2 substituent $R^{10}$; or $R^8$ and $R^9$, together with the atoms to which they are attached, form a 3- to 8-membered saturated or partially or fully unsaturated ring comprising 0, 1 or 2 additional heteroatoms independently selected from —NH, —O—, —S—, —SO— or —SO$_2$—, and said ring is optionally substituted with at least one substituent $R^{10}$;

$R^{10}$, at each occurrence, is independently hydrogen, halogen, $C_{1-8}$ haloalkyl, $C_{1-8}$ alkyl, $C_{2-8}$ alkenyl, $C_{3-8}$ cycloalkyl, aryl, heteroaryl, heterocyclyl, $C_{2-8}$ alkynyl, oxo, —$C_{1-4}$ alkyl-NR$^a$R$^b$, —CN, —OR, —NR$^a$R$^b$, —C(O)R$^a$, —C(O)OR$^a$, —CONR$^a$R$^b$, —C(=NR$^a$)NR$^b$R$^c$, nitro, —NR$^a$C(O)R$^b$, —NR$^a$C(O)NR$^a$R$^b$, —NR$^a$C(O)OR$^b$, —SO$_2$R$^a$, —NR$^a$SO$_2$NR$^b$R$^c$, —NR$^a$SOR$^b$ or —NR$^a$SO$_2$R$^b$, wherein said $C_{1-8}$ alkyl, $C_{1-8}$ haloalkyl, $C_{3-8}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein R$^a$, R$^b$, and R$^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl, or (R$^a$ and R$^b$), and/or (R$^b$ and R$^c$) together with the atoms to which they are attached, form a ring selected from a heterocyclyl or heteroaryl ring optionally substituted by halogen, $C_{1-4}$ haloalkyl or $C_{1-4}$ alkyl.

In one embodiment of the first aspect, p is 1, and q is 1. In another embodiment, p is 1 and q is 0. In one embodiment of the first aspect, W is N and M is CH. In another embodiment, W and M are both N. In further another embodiment, W and M are both CH. In yet further embodiment, W is CH and M is N.

Preferably, the

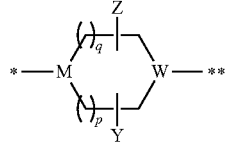

moiety is

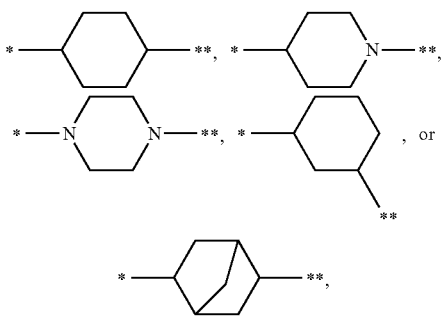

wherein * indicates a link to the ring A, and ** indicates a link to X.

In one embodiment, X is —CR$^5$R$^6$—, wherein R$^5$ is $C_{1-4}$alkyl, $C_{1-4}$haloalkyl, $C_{1-4}$alkoxy, or $C_{3-6}$-cycloalkyl, and R$^6$ is hydrogen. In another embodiment, X is —CR$^5$R$^6$—, wherein R is $C_{1-4}$alkyl, $C_{1-4}$haloalkyl, $C_{1-4}$alkoxy, or $C_{3-6}$cycloalkyl, and R$^6$ is hydrogen, and the

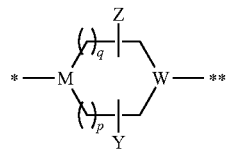

moiety is

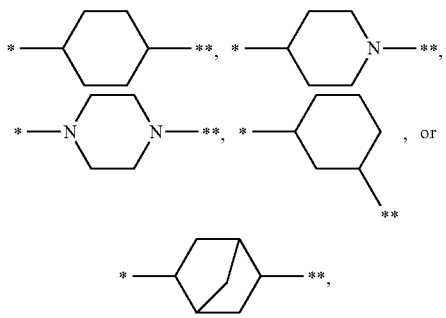

wherein * indicates a link to the ring A, and ** indicates a link to X. In a further preferred embodiment, R$^5$ is methyl, trifluoromethyl, methoxy, or cyclopropyl, and R$^6$ is hydrogen. Specifically, the compound of Formula (I) is a compound selected from benzoimidazoles of Formulas (Ia) and/or (Ib):

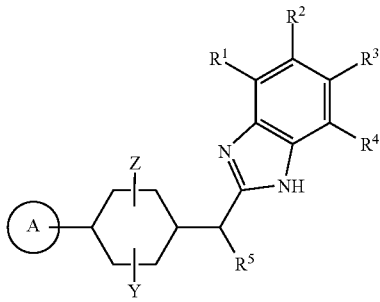

(Ia)

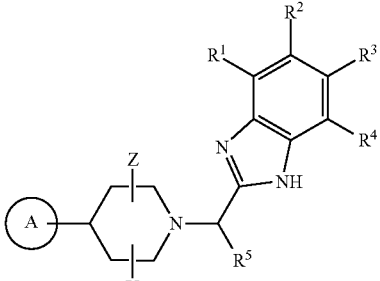

(Ib)

wherein the variables R$^1$, R$^2$, R$^3$, R$^4$, R$^5$, Z, Y and A are defined as for Formula (I).

In one embodiment, Z and Y, together with the atoms to which they are attached, form a bridged bicyclic ring optionally substituted with a substituent selected from halogen, $C_{1-4}$ haloalkyl, $C_{1-4}$ alkyl and $C_{1-4}$alkoxy. Preferably, Z and Y, together with the atoms to which they are attached, form a bridged bicyclic ring selected from bicyclo[2.2.1]heptyl (e.g., bicyclo[2.2.1]heptan-2-yl), born-2-yl, bicyclo[2.2.2]octyl, bicyclo[3.2.1]octyl, bicyclo[3.3.1]nonyl, or bicyclo[3.3.2.]decyl. More preferably, the bridged bicyclic ring is bicyclo[2.2.1]heptyl or bicyclo[2.2.2]octyl.

In one embodiment, R and $R^4$ are each independently hydrogen, halogen, $C_{1-8}$ alkyl, —C(O)$NR^8R^9$, $COOR^8$, or $NR^8R^9$; preferably H, halogen, or $C_{1-8}$ alkyl; more preferably, H, F, or methyl.

In one embodiment, $R^2$ and $R^3$ are each independently hydrogen, halogen, cyano, $C_{1-8}$ alkyl, $C_{3-8}$ cycloalkyl, heterocyclyl, aryl, heteroaryl, —C(O)$OR^8$; —C(O)$NR^8R^9$, —$OR^8$, —$NR^8R^9$, —$NR^8SO_2R^9$, —$SO_2R^8$, —$SO_2NR^8R^9$, or —$COR^8$, wherein said $C_{1-8}$ alkyl, $C_{3-8}$ cycloalkyl, heterocyclyl, aryl, and heteroaryl are each independently optionally substituted with 1 or 2 substituent $R^{10}$, and wherein $R^8$ and $R^9$ are each independently hydrogen, $C_{1-8}$ alkyl, $C_{3-8}$ cycloalkyl, heterocyclyl, aryl, or heteroaryl, wherein said $C_{1-8}$ alkyl, $C_{3-8}$ cycloalkyl, heterocyclyl, aryl, and heteroaryl are each independently optionally substituted with 1 or 2 substituent $R^{10}$, wherein $R^{10}$ is defined as in Formula (I).

Preferably, $R^2$ and $R^3$ are each independently hydrogen, halogen (preferably F, Cl, Br), cyano, $C_{1-8}$ alkyl (preferably methyl, ethyl, propyl, isopropyl, butyl, t-butyl), $C_{3-8}$ cycloalkyl (preferably cyclopropyl), heterocyclyl (e.g., piperidinyl), aryl, heteroaryl (preferably oxazolyl (e.g., oxazol-5-yl), oxadiazolyl (e.g., 1,2,4-oxadiazol-3-yl), pyrazolyl (e.g., 1H-pyrazol-1-yl), pyridinyl (e.g., pyridin-3-yl, pyridin-4-yl), pyrimidinyl (e.g., pyrimidin-2-yl)), —C(O)$OR^8$ (wherein $R^8$ is H, $C_{1-8}$ alkyl, such as methyl, ethyl, propyl, isopropyl, t-butyl; or $C_{3-8}$cycloalkyl, such as cyclopropyl); —C(O)$NR^8R^9$, —$OR^8$ (wherein $R^8$ is $C_{1-8}$alkyl, or $C_{3-8}$cycloalkyl (preferably cyclopropyl)), —$NR^8SO_2R$ (wherein $R^8$ and $R^9$ are each H or $C_{1-8}$ alkyl), —$NR^8R^9$ (wherein $R^8$ and $R^9$ are each hydrogen or $C_{1-8}$ alkyl), —$SO_2R^8$ (wherein $R^8$ is $C_{1-8}$ alkyl), —$SO_2NR^8R^9$ (wherein $R^8$ and $R^9$ are each H or $C_{1-8}$alkyl), or —$COR^8$ (wherein R is H or $C_{1-8}$alkyl), wherein said $C_{1-8}$ alkyl, $C_{3-8}$ cycloalkyl, heterocyclyl, aryl, and heteroaryl in $R^2$ or $R^3$ are each independently optionally substituted with 1 or 2 substituent $R^{10}$ and said $C_{1-8}$alkyl or $C_{3-8}$cycloalkyl in $R^8$ or $R^9$ are each independently optionally substituted with 1 or 2 substituent $R^{10}$.

Preferably, one of $R^2$ and $R^3$ is —C(O)$NR^8R^9$, wherein $R^8$ and $R^9$ are each independently H, $C_{1-8}$ alkyl (more preferably methyl, ethyl), $C_{3-8}$cycloalkyl (more preferably cyclopropyl, cyclobutyl, cyclohexyl), or aryl (e.g., phenyl), said $C_{1-8}$ alkyl, $C_{3-8}$ cycloalkyl, or aryl are each independently optionally substituted with 1 or 2 substituent $R^{10}$, or $R^8$ and $R^9$, together with the nitrogen atom to which they are attached, form a 3-, 4-, 5-, or 6-membered saturated ring comprising 0 additional heteroatom, and said ring is optionally substituted with at least one substituent $R^{10}$; preferably, R and $R^9$, together with the nitrogen atom to which they are attached, form azetidin-1-yl, azetidin-1-yl, pyrrolidin-1-yl, or piperidin-1-yl).

In one embodiment, $R^2$ and $R^3$, together with the atoms to which they are attached, form a heterocyclyl ring comprising two oxygen atoms. Preferably, $R^2$ and $R^3$, together with the atoms to which they are attached, form a 5H-[1,3]dioxolo[4',5':4,5]benzo[1,2-d]imidazole ring.

In one embodiment, $R^2$ and $R^3$, together with the atoms to which they are attached, form a heterocyclyl ring, said ring comprising zero or two nitrogen atoms. Preferably, $R^2$ and $R^3$, together with the atoms to which they are attached, form a imidazo[4,5-g]quinazoline ring (optionally substituted with oxo, e.g., to form a 3,7-dihydro-8H-imidazo[4,5-g]quinazolin-8-one group) or a imidazo[4,5-g]quinoline ring (optionally substituted with oxo, e.g., to form a 7,8-dihydro-3H-imidazo[4,5-g]quinolin-6(5H)-one group), or a 1H-naphtho[2,3-d]imidazole ring.

In one embodiment, $R^1$ and $R^2$, together with the atoms to which they are attached, form a heteroaryl ring, said ring comprising one nitrogen atoms. Preferably, $R^1$ and $R^2$, together with the atoms to which they are attached, form a 3H-imidazo[4,5-f]quinoline.

In one embodiment, $R^3$ and $R^4$, together with the atoms to which they are attached, form a heteroaryl ring, said ring comprising zero or one nitrogen atoms. Preferably, $R^3$ and $R^4$, together with the atoms to which they are attached, form a 1H-naphtho[2,1-d]imidazole ring.

In some embodiment, ring A is phenyl or naphthalenyl ring. In some embodiment, ring A is a monocyclic or bicyclic aromatic heterocyclic ring having 5- to 10-ring members comprising 1, 2, 3, or 4 heteroatoms selected from O, S, and N.

In some embodiment, ring A is a monocyclic aromatic heterocyclic ring having 5- to 6-ring members comprising 1 or 2 heteroatoms selected from O, S, and N. In other embodiments, ring A is pyridinyl, furanyl, pyrazinyl, pyrimidinyl, pyridazinyl, pyrrolyl, thienyl, triazinyl, or pyrazolyl. In some preferred embodiments, ring A is pyridinyl or furanyl.

In some embodiment, ring A is a bicyclic aromatic heterocyclic ring having 8- to 10-ring members comprising 1 or 2 or 3 heteroatoms selected from O, S, and N. In another embodiment, ring A is cinnolinyl, benzothienyl, benzofuryl, benzoimidazolyl, indolyl, isoindolyl, indolinyl, phthalazinyl, quinolinyl, isoquinolinyl, pyrrolopyridinyl, pyrazolopyridinyl, benzodioxolyl, benzoxazolyl, pteridinyl, purinyl, benzofurazanyl, benzothiophenyl, benzothiazolyl, benzoxazolyl, quinazolinyl, quinoxalinyl, naphthyridinyl, furopyridinyl, benzothiazolyl, or indazolyl. In some preferred embodiments, ring A is benzothiophenyl (such as benzo[b]thiophen-2-yl, benzo[b]thiophen-3-yl, benzo[b]thiophen-5-yl, or benzo[b]thiophen-6-yl) or quinolinyl (such as quinolin-2-yl, quinolin-3-yl, quinolin-4-yl, quinolin-5-yl, quinolin-6-yl, quinolin-7-yl, quinolin-8-yl) or benzodioxolyl (such as benzo[d][1,3]dioxol-5-yl).

In one embodiment, ring A is optionally substituted with one substituent $R^7$ which is independently hydrogen, halogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl.

In one preferred embodiment, ring A is quinolinyl (such as quinolin-2-yl, quinolin-3-yl, quinolin-4-yl, quinolin-5-yl, quinolin-6-yl, quinolin-7-yl, quinolin-8-yl) optionally substituted with halogen or $C_{1-8}$haloalkyl. More preferably, ring A is 6-fluoroquinolin-4-yl or 8-fluoro-quinolin-5-yl.

In one embodiment, the compound disclosed herein has one of the following configurations:
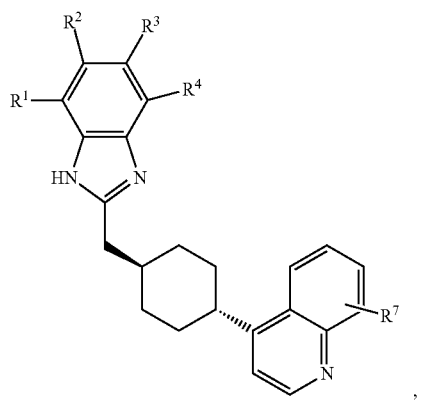
,
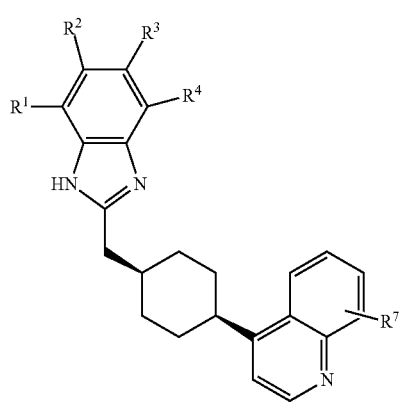
,
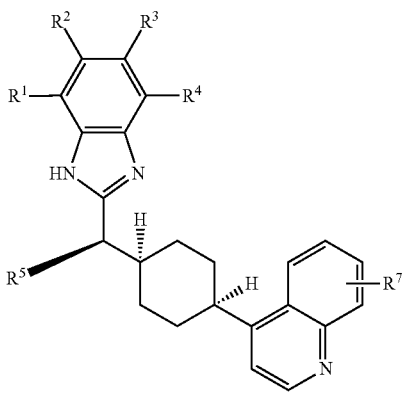
,
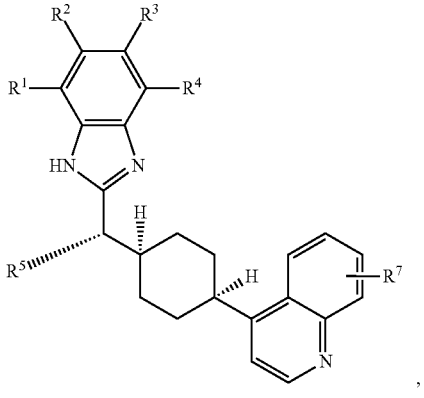
,
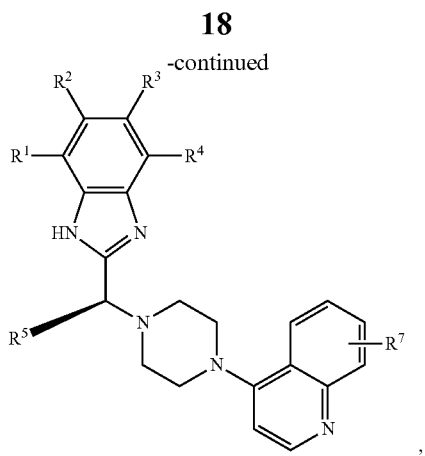
,
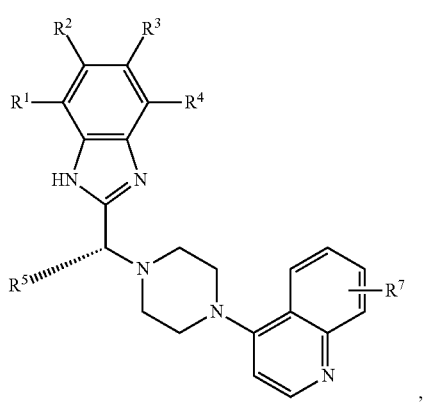
,
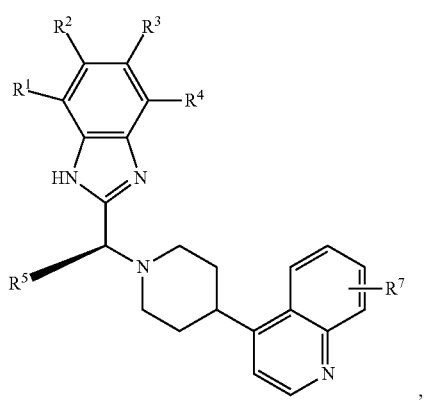
,
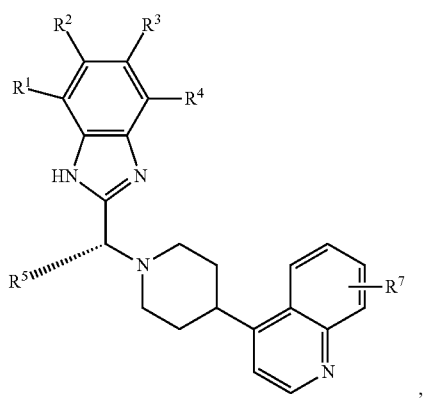
,

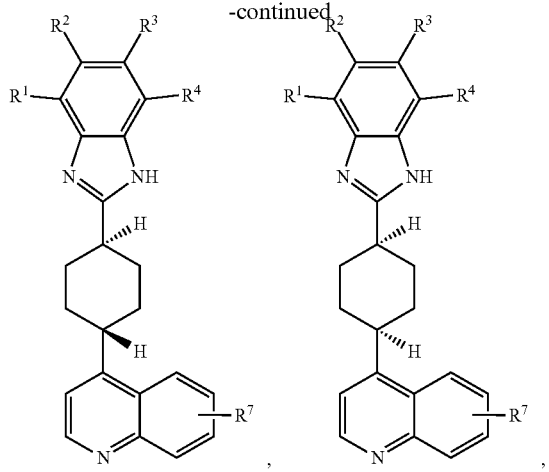
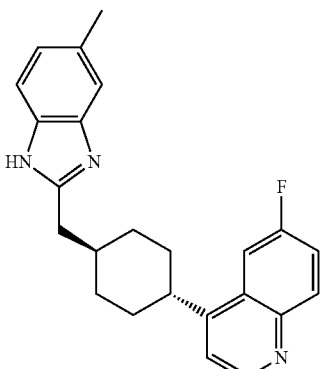
wherein $R^5$ is $C_{1-4}$alkyl, $C_{1-4}$haloalkyl, $C_{1-4}$alkoxy, or $C_{3-6}$cycloalkyl; $R^1$, $R^2$, $R^3$, $R^4$ and $R^7$ are defined as for Formula (I).
Also disclosed herein is a compound selected from the group consisting of:
Example A1a
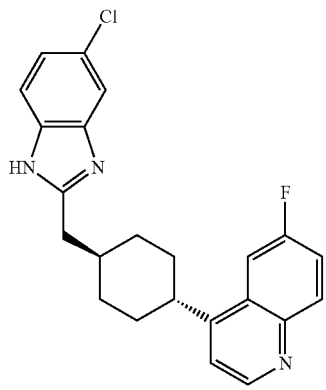 [SMILES: Fc1ccc2nccc([C@H]3CC[C@H](Cc4nc5cc(C(F)(F)F)ccc5[nH]4)CC3)c2c1]
Example A1b
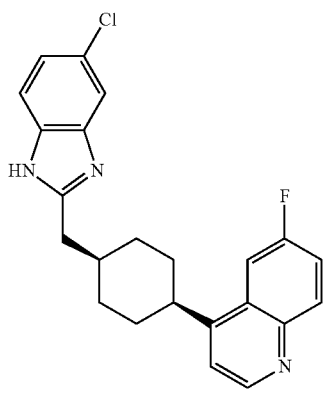
Example A2a
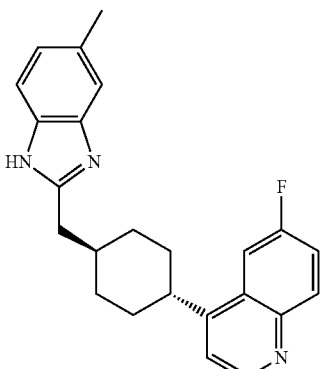
Example A2b
Example A3a
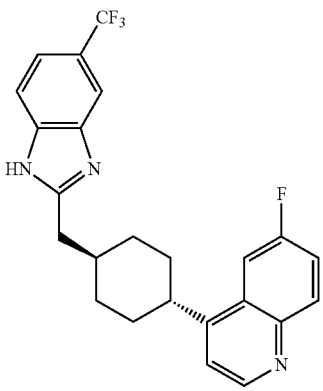
Example A3b
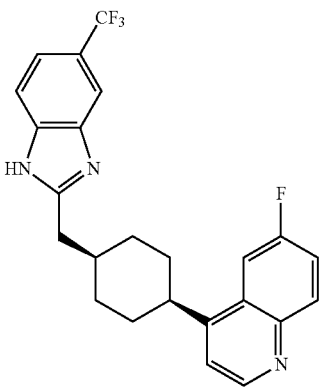 [SMILES: Fc1ccc2nccc([C@H]3CC[C@@H](Cc4nc5cc(C(F)(F)F)ccc5[nH]4)CC3)c2c1]

Example A4a
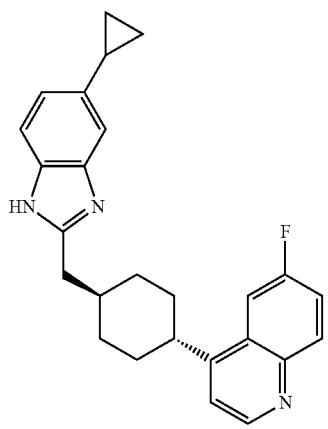 [SMILES: Fc1ccc2nccc([C@H]3CC[C@H](Cc4nc5cc(C6CC6)ccc5[nH]4)CC3)c2c1]
Example A4b
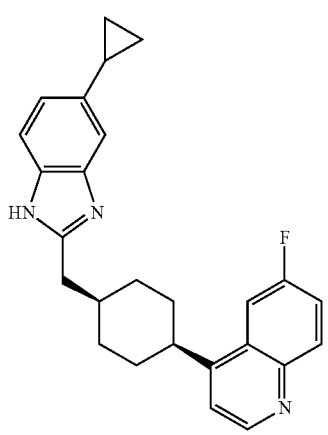 [SMILES: Fc1ccc2nccc([C@H]3CC[C@@H](Cc4nc5cc(C6CC6)ccc5[nH]4)CC3)c2c1]
Example A5a
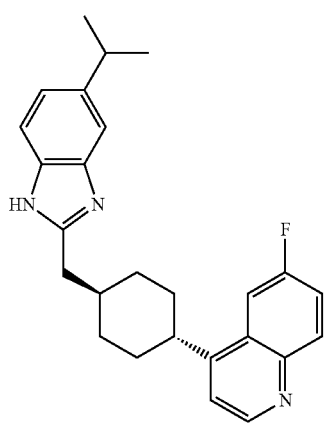 [SMILES: CC(C)c1ccc2[nH]c(C[C@H]3CC[C@H](c4ccnc5ccc(F)cc54)CC3)nc2c1]
Example A5b
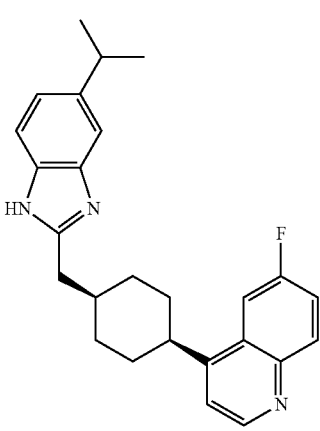
Example A6a
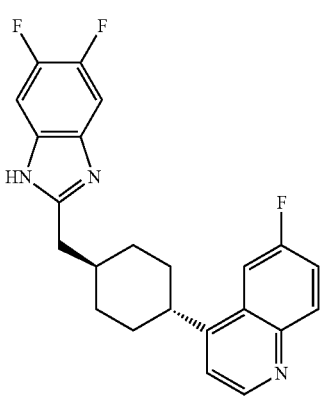
Example A6b
Example A7a
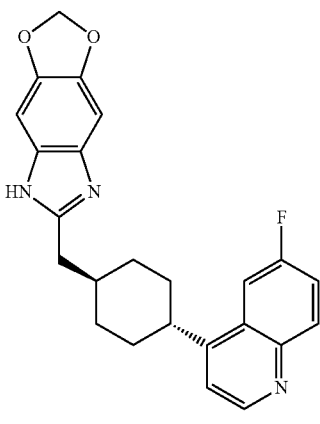

Example A7b
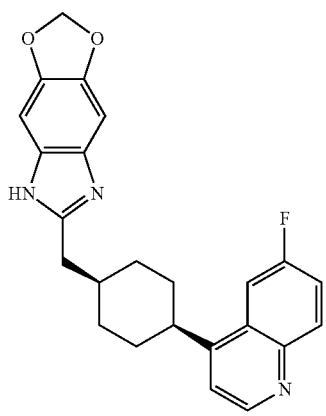
Example A8a
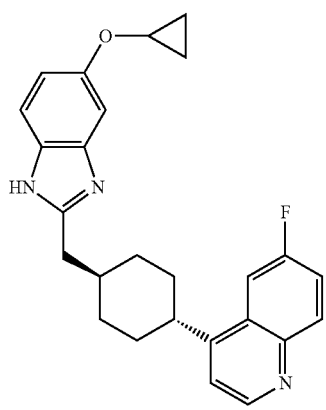
Example A8b
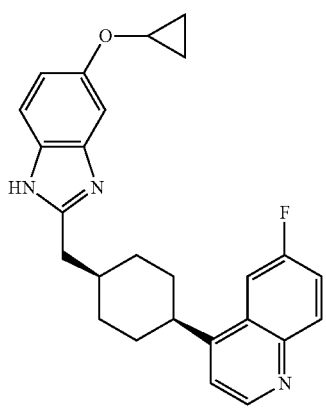
Example A9a
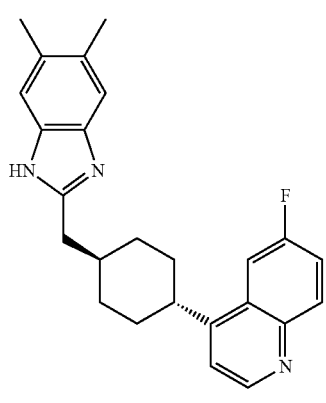
Example A9b
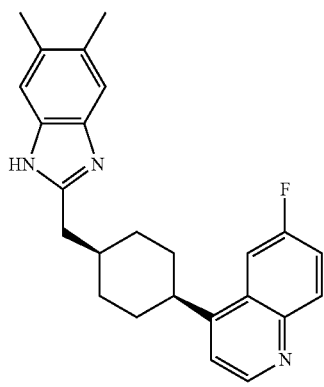
Example A10a
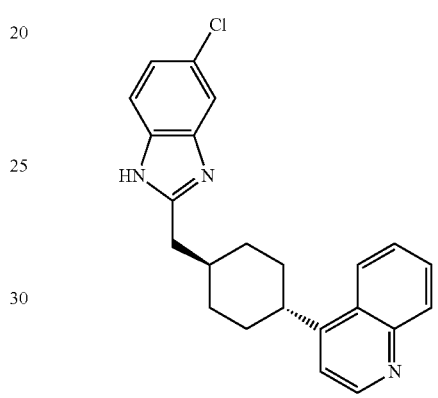
Example A10b
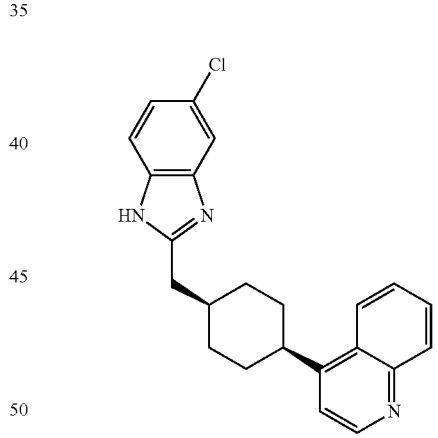
Example A11a
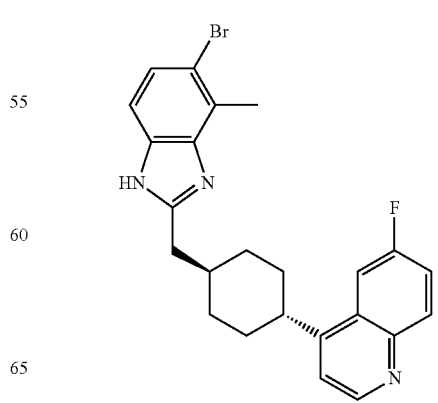

Example A11b
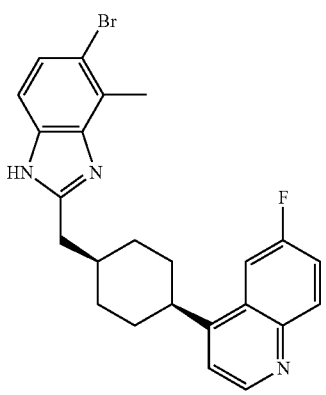
Example A12
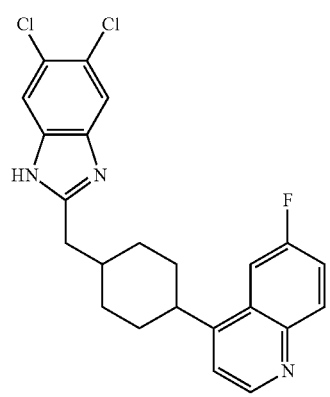
Example 13
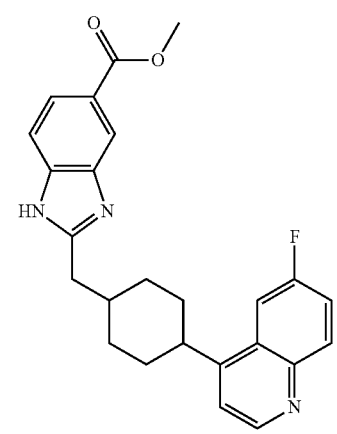
Example A14
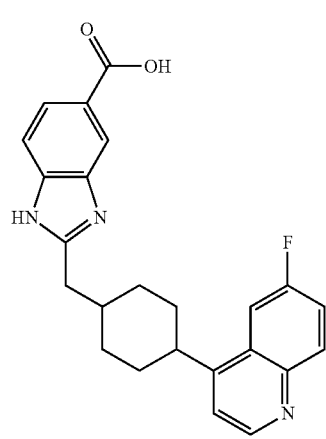
Example A15
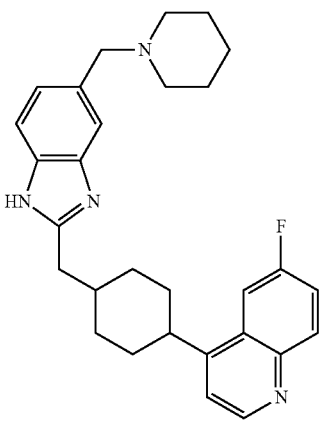
Example A16
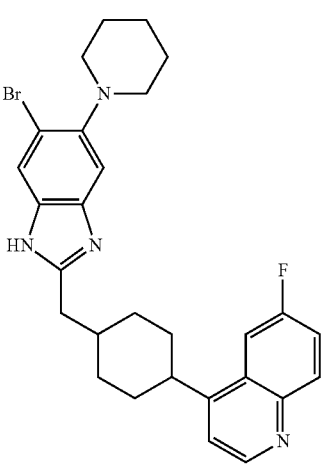
Example A17
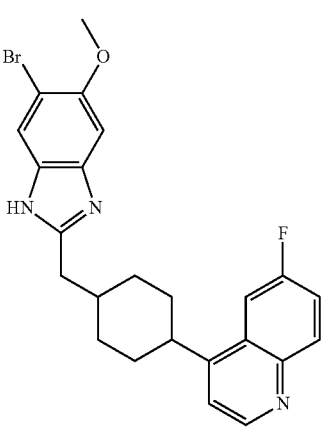

Example A18
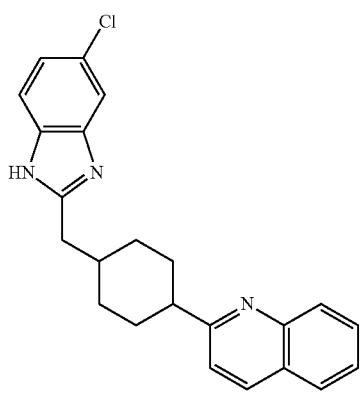
Example A19
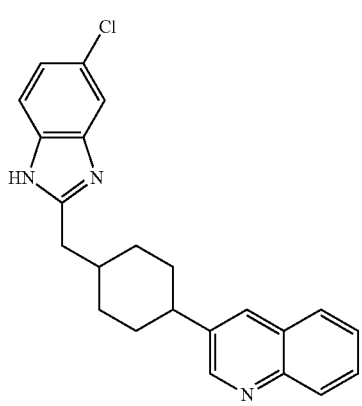
Example A20
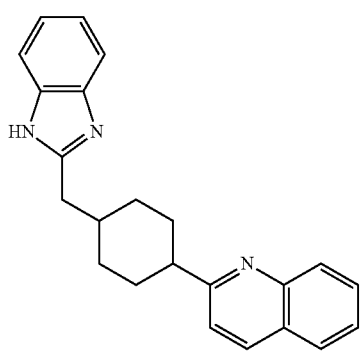
Example A21
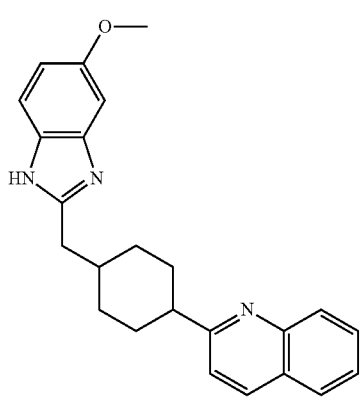
Example A22
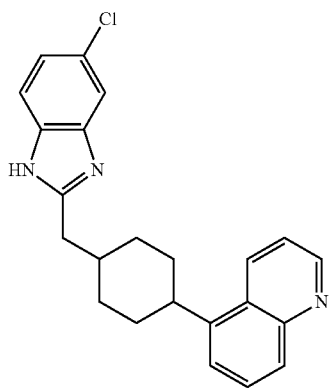
Example A23A
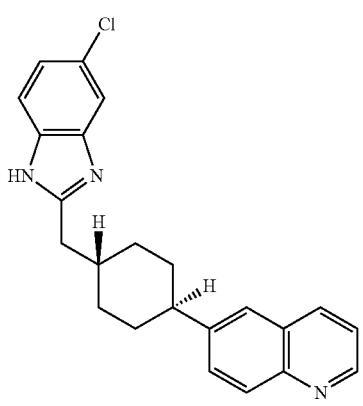
Example A23b
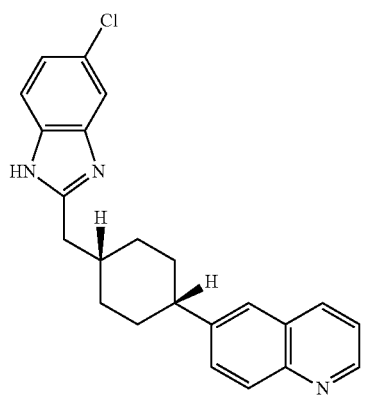
Example A24
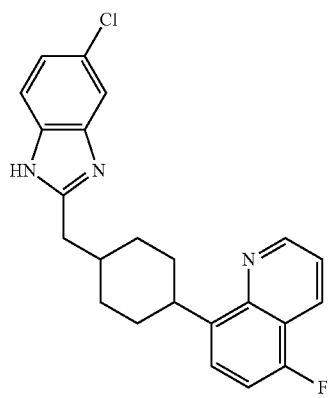

Example A25
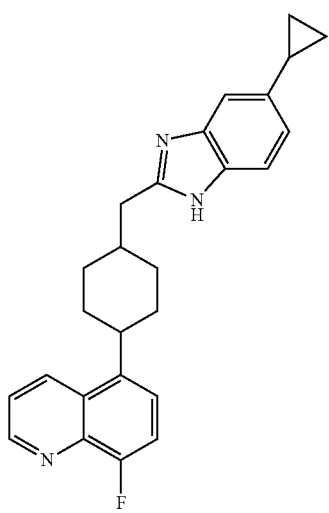
Example A26a
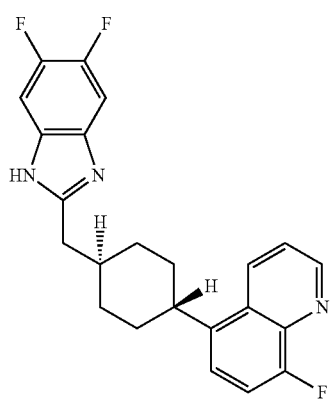
Example A26b
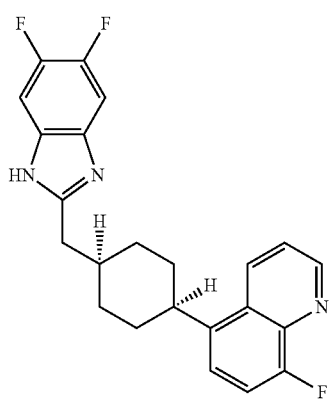
Example A27
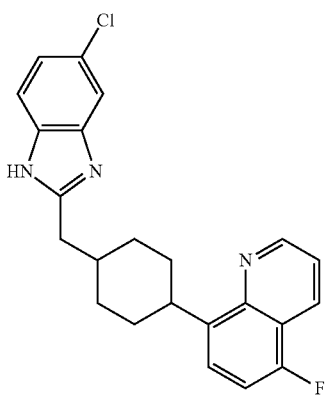
Example A28
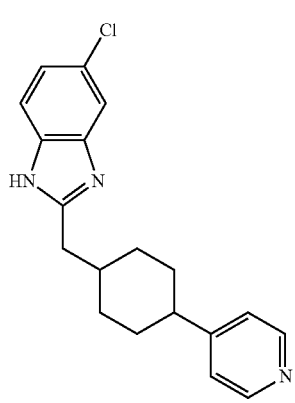
Example A29
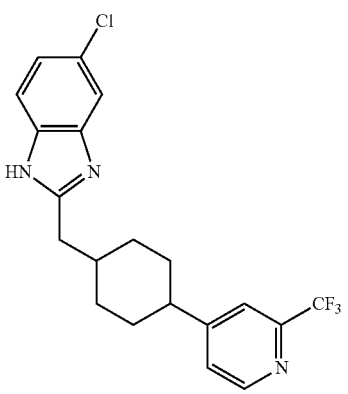
Example A30a
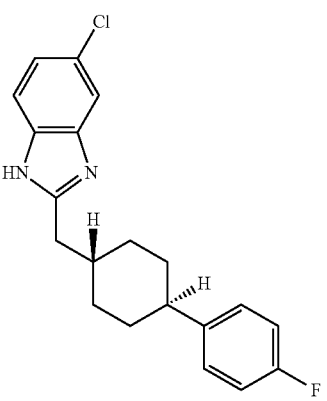

Example A30b
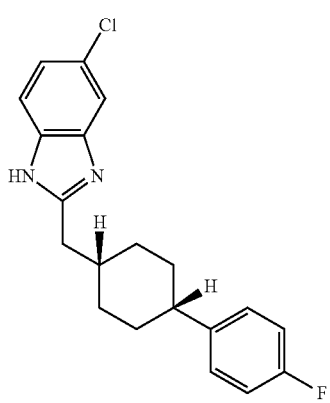
Example A31
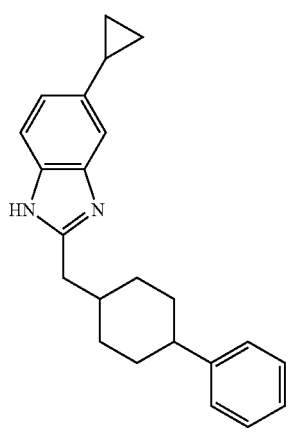
Example A32
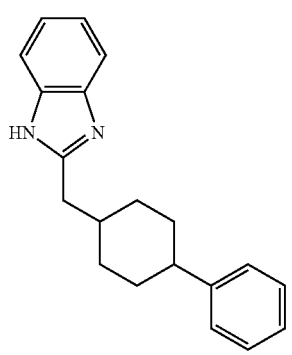
Example A33a
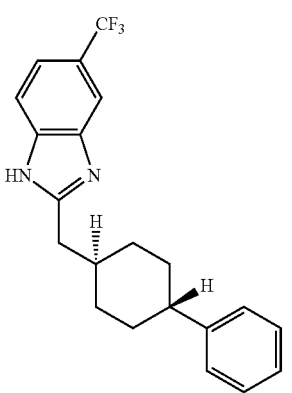
Example A33b
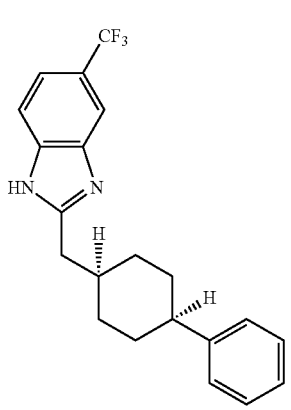
Example A34a
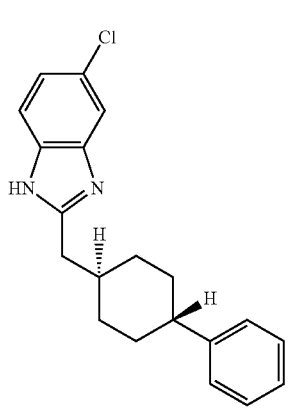
Example A34b
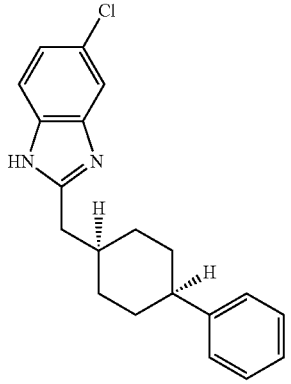
Example A35
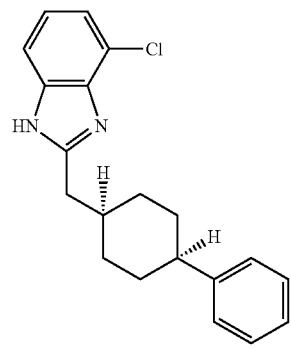

Example A36
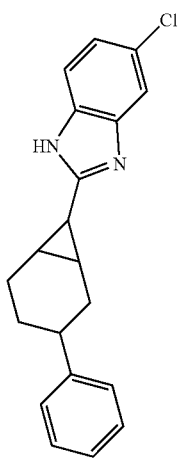
Example A37a
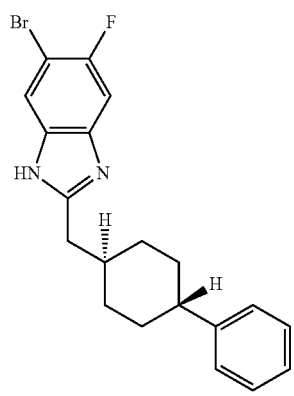
Example A37b
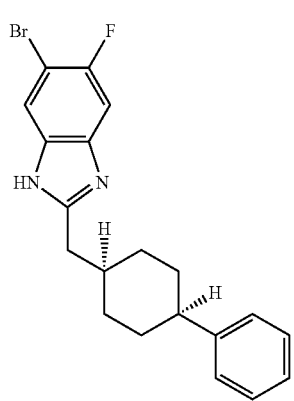
Example A38
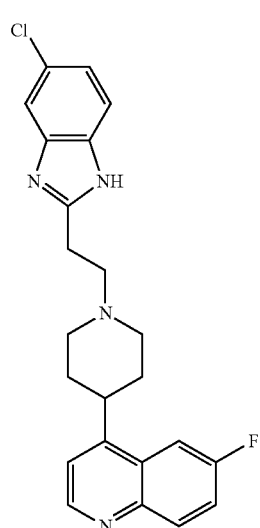
Example A39
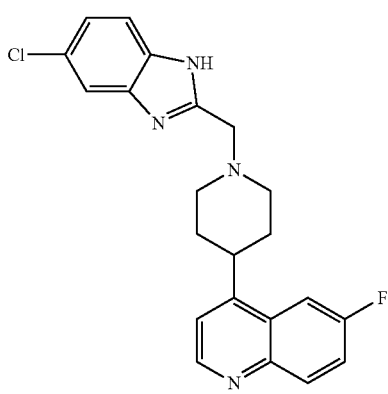
Example A40
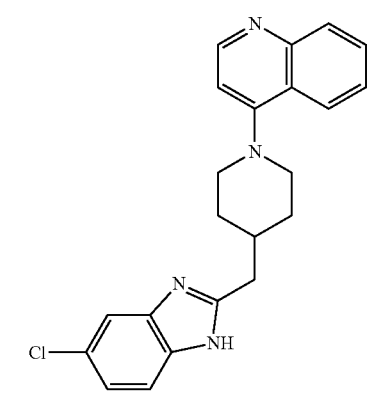
Example A41
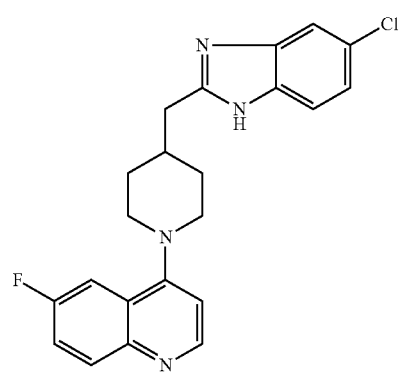

-continued
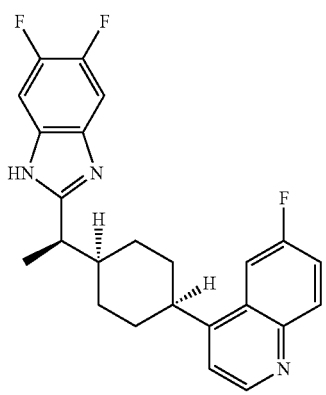
Example B1a
Example B1b
Example B1c
Example B1d
-continued
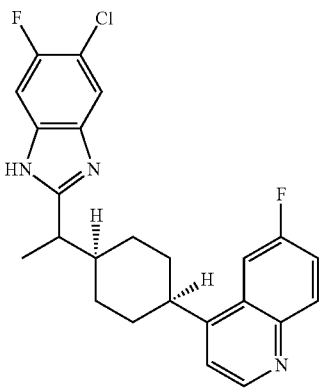
Example B2
Example B2a
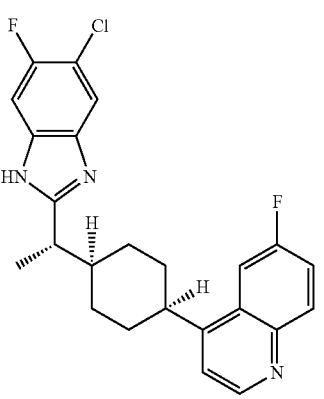
Example B2b
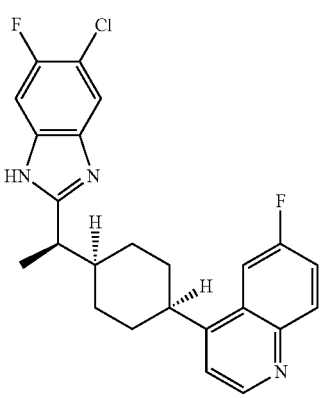
Example B3
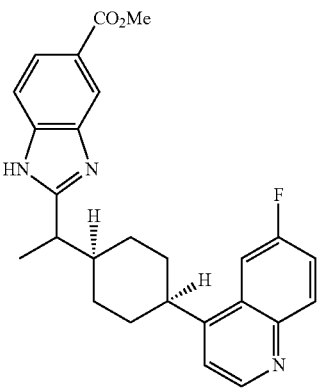

-continued
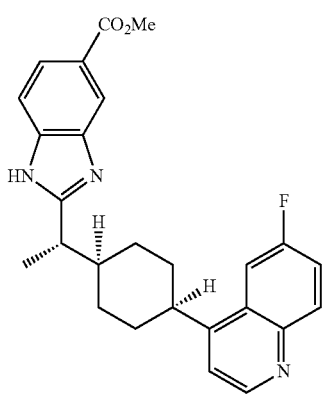
Example B3a
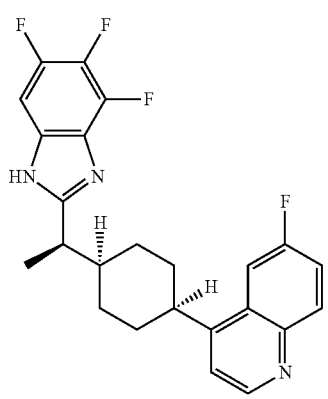
Example B6
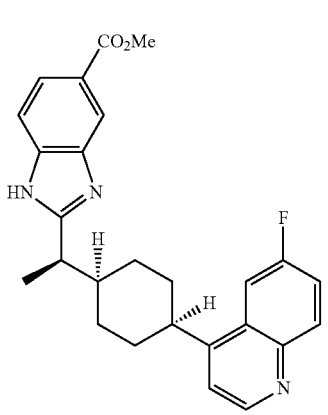
Example B3b
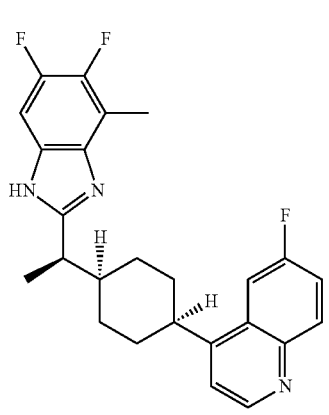
Example B7
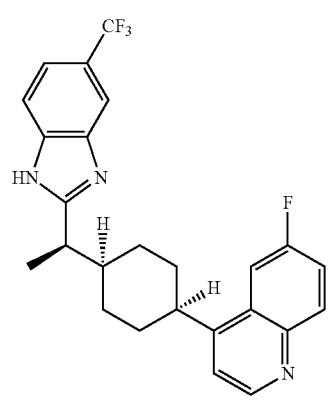
Example B4
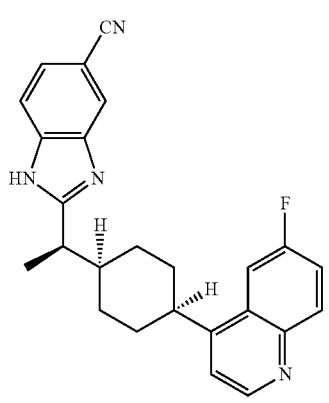
Example B8
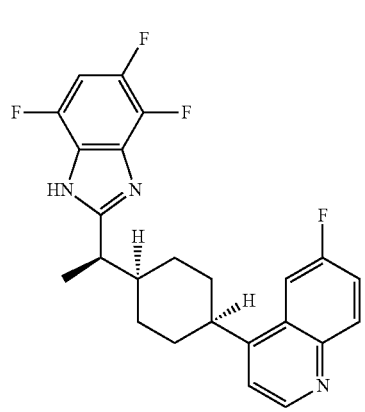
Example B5
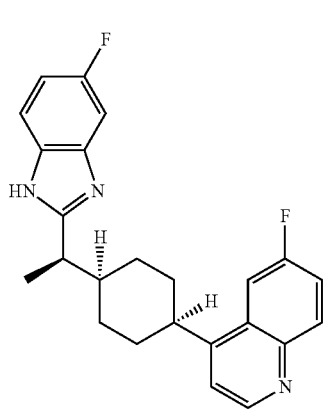
Example B9

Example B10
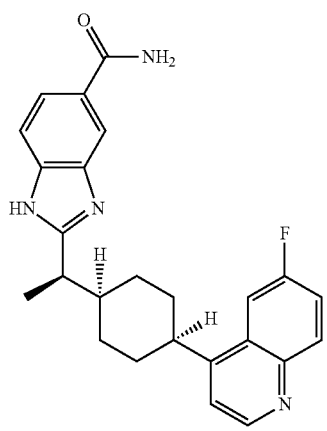
Example B11
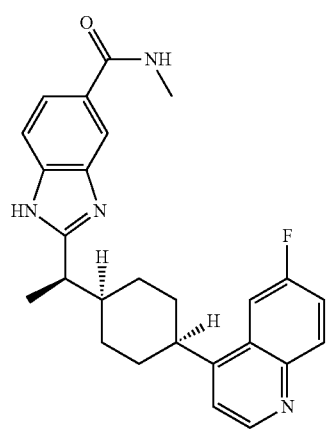
Example B12
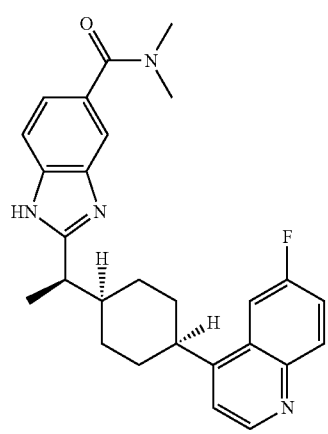
Example B13
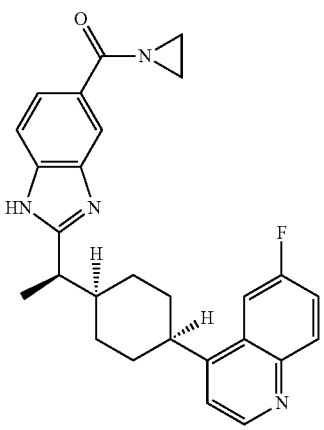
Example B14
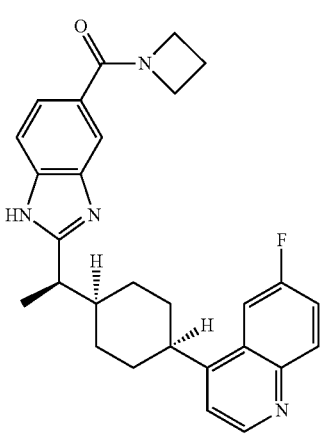
Example B15

Example B16
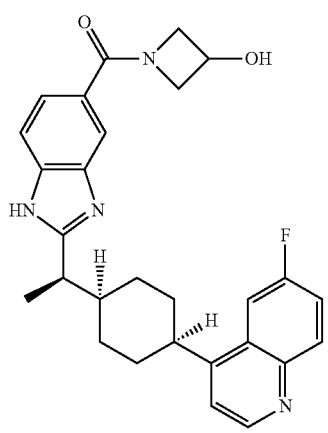
Example B17
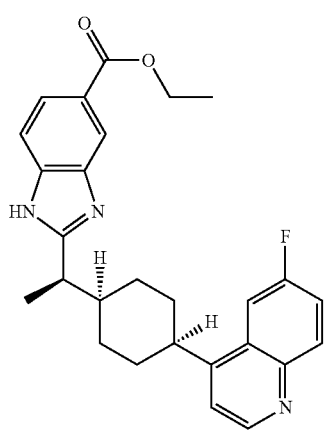
Example B18
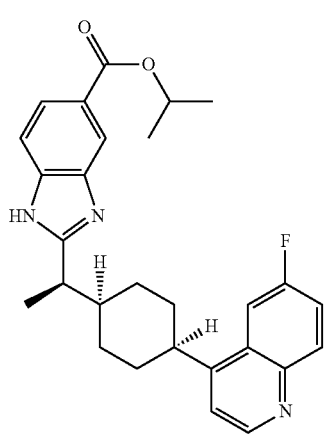
Example B19
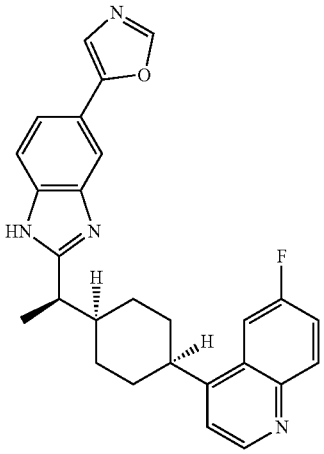
Example B20
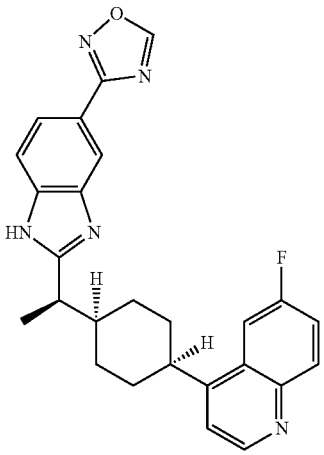
Example B21

Example B22
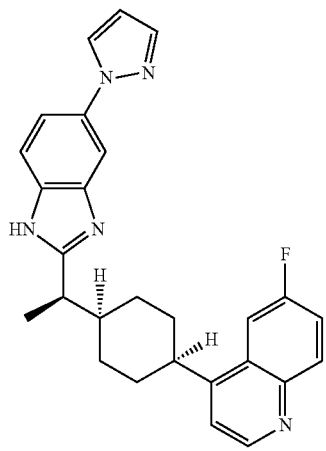
Example B23
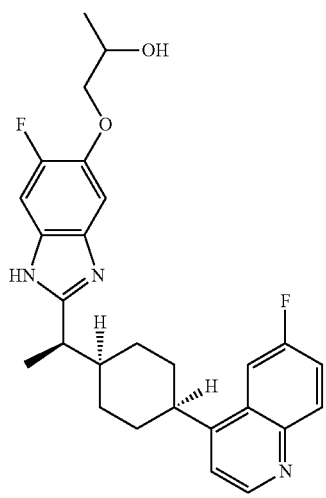
Example B24
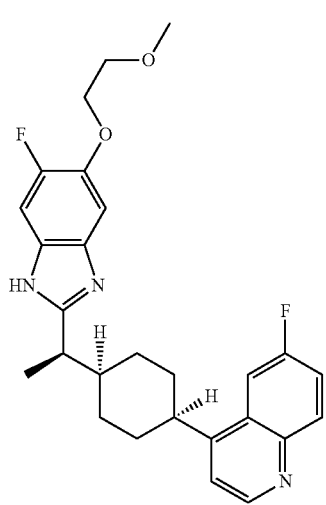
Example B25a
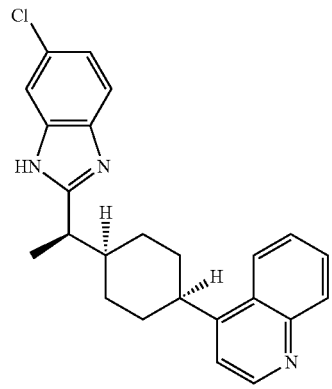
Example B25b
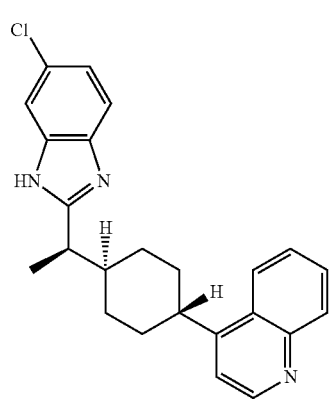
Example B26
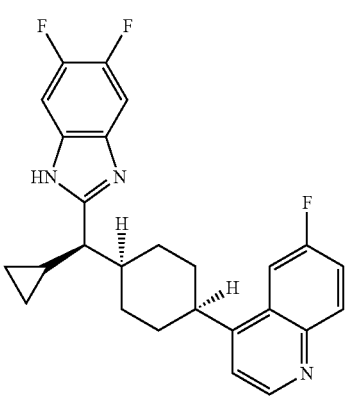
Example B27
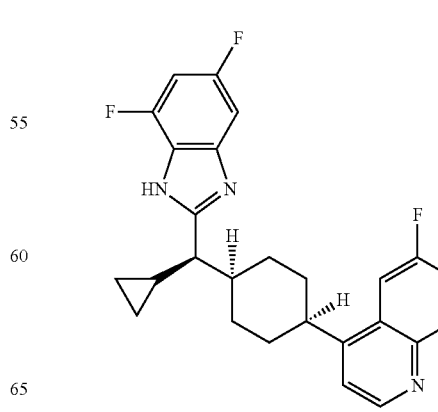

-continued
Example B28
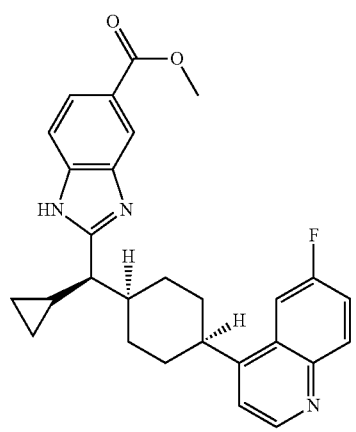
Example B29
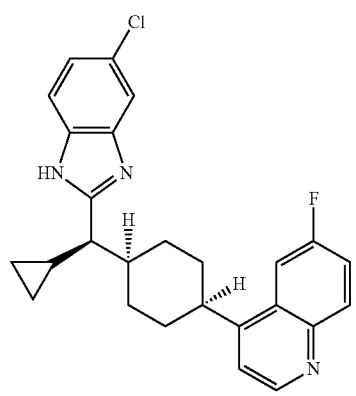
Example B30
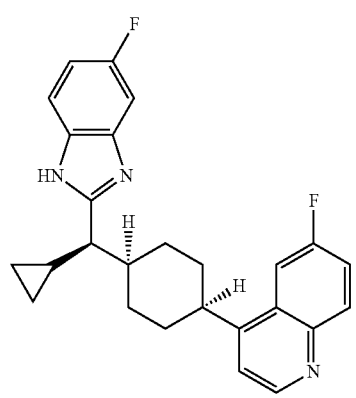
Example B31
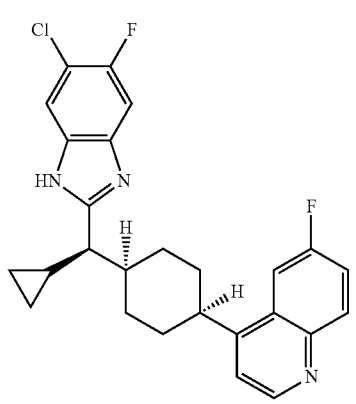
-continued
Example B32
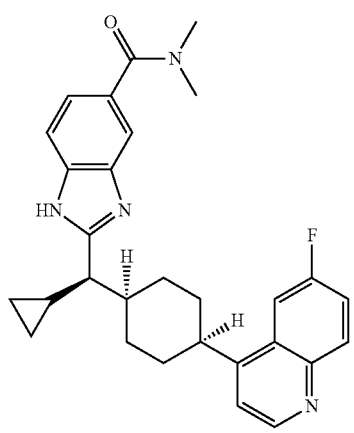
Example B33
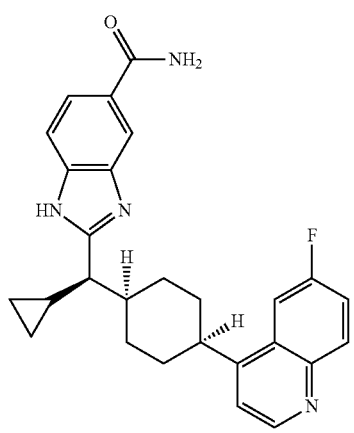
Example B34
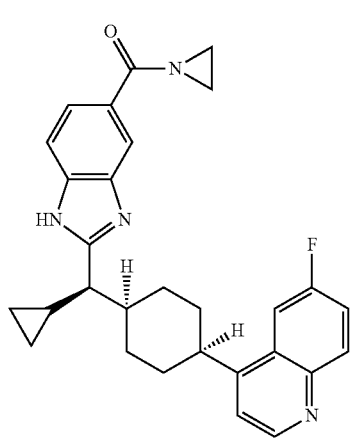

Example B35
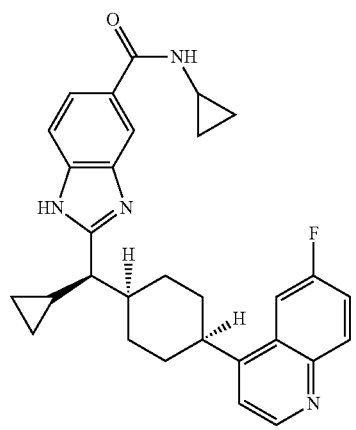
Example B36
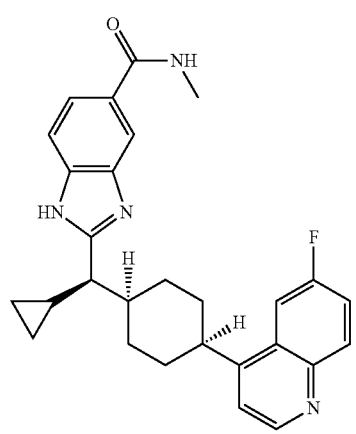
Example B37
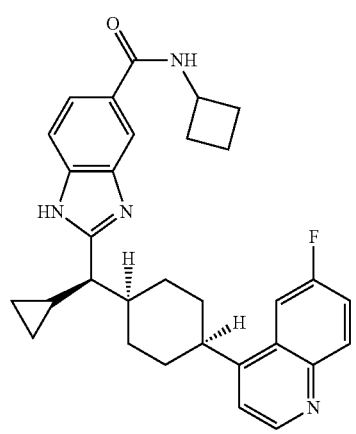
Example B38
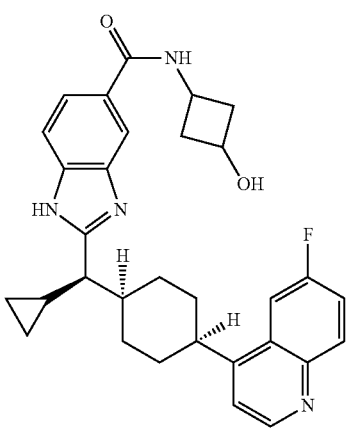
Example B39
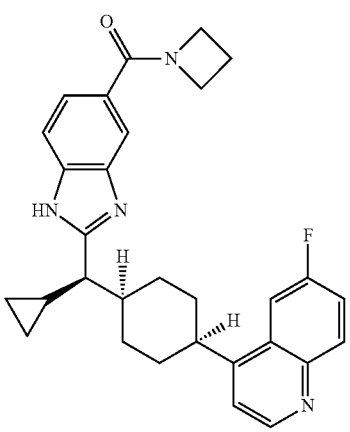
Example B40
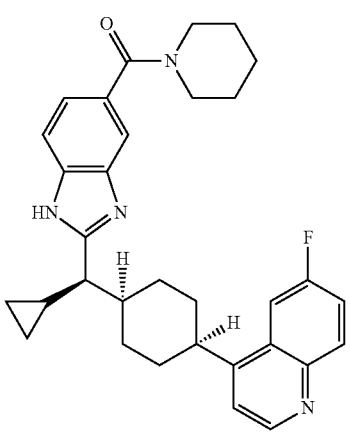

Example B41
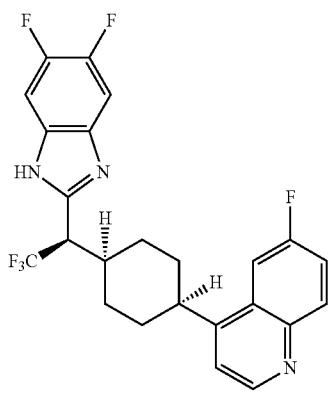
Example B42
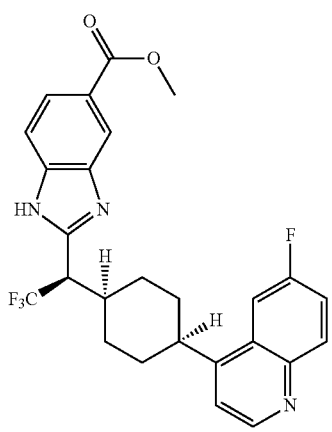
Example B43
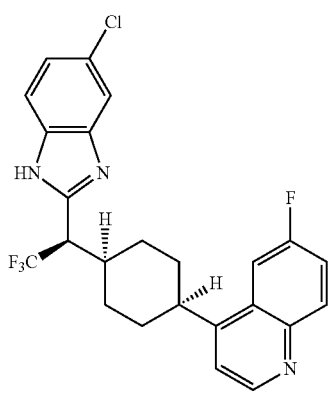
Example B44
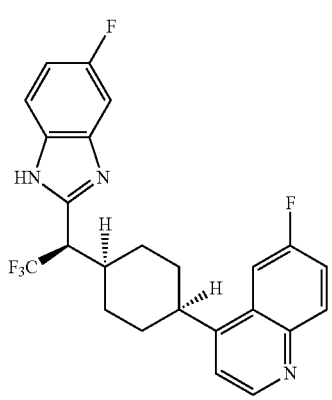
Example B45

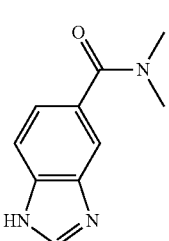
Example B46
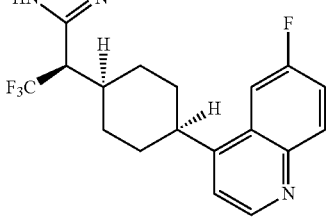
Example B47
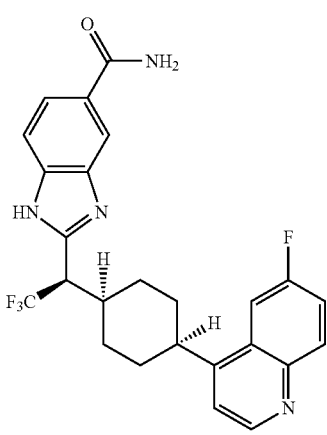

Example B48
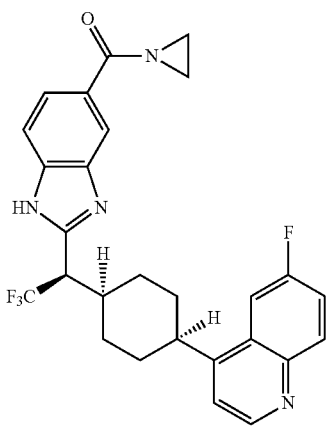
Example B49
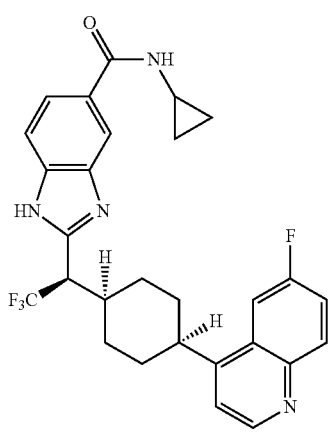
Example B50
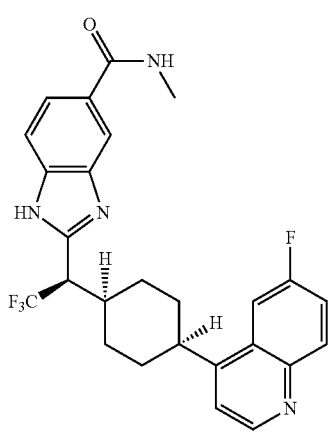
Example B51
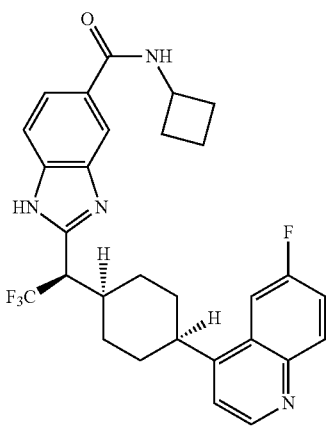
Example B52
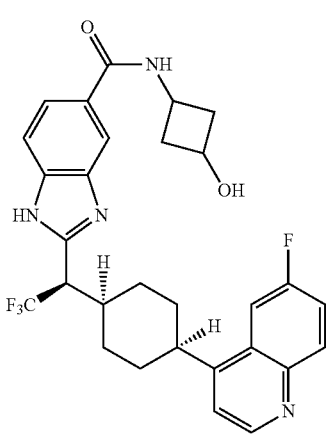
Example B53
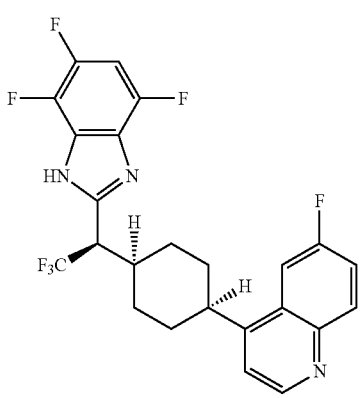
Example B54
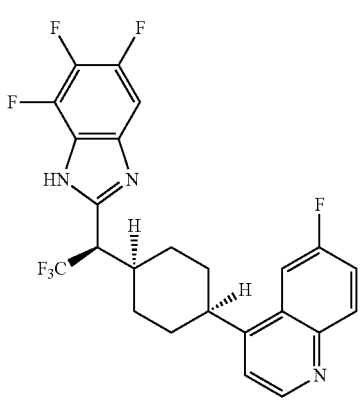

Example B55
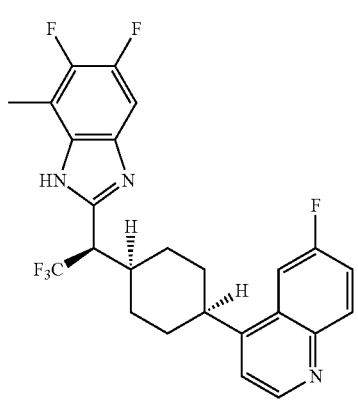
Example B56
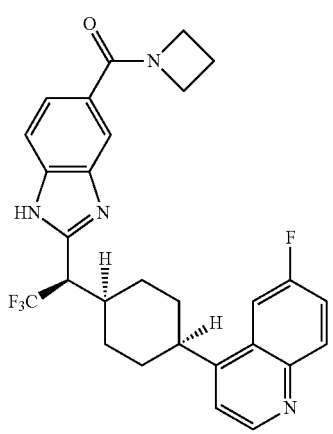
Example B57
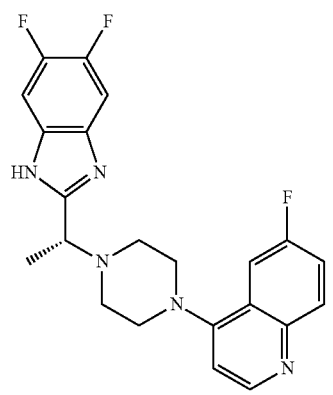
Example B58
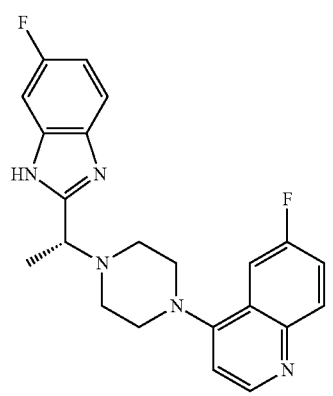
Example B59
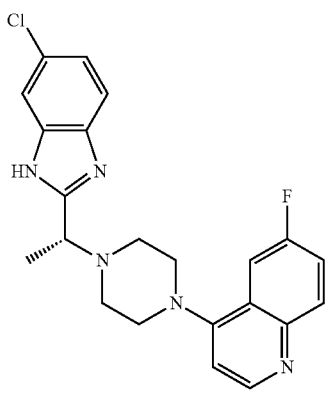
Example B60
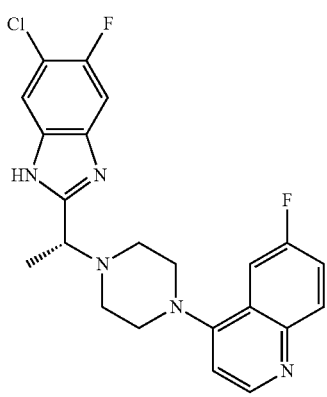
Example B61
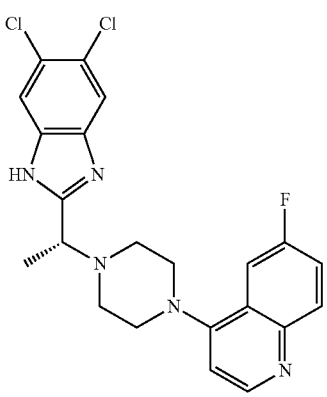
Example B62
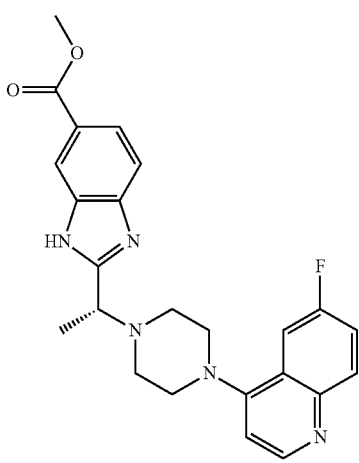

Example B63
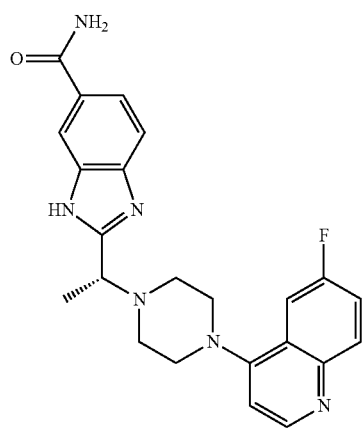
Example B64
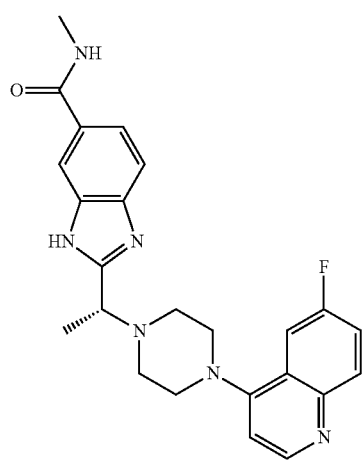
Example B65
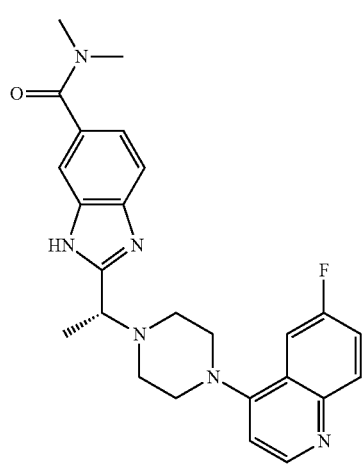
Example B66
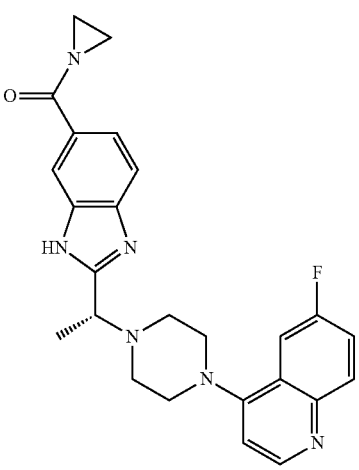
Example B67
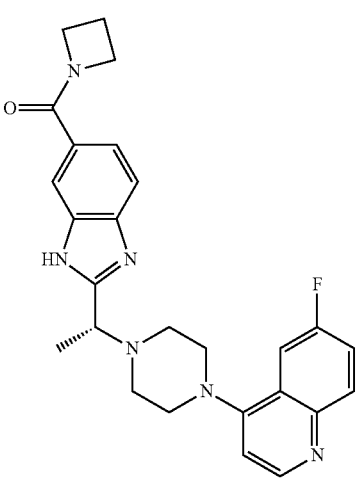
Example B68
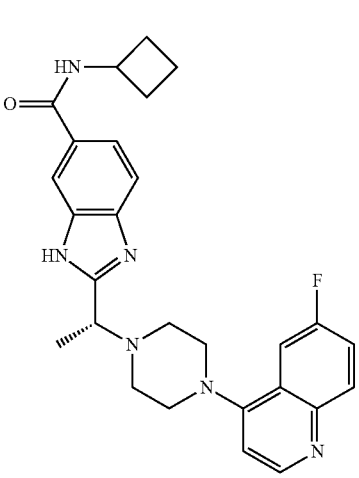

Example B69
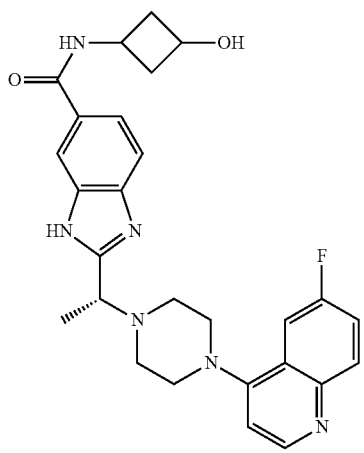
Example B70
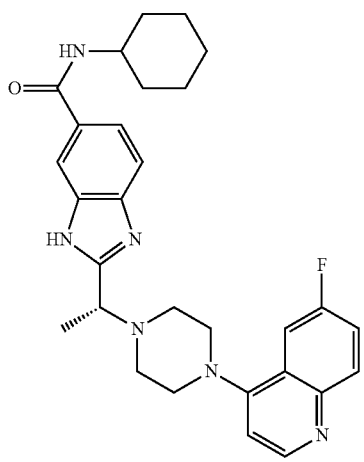
Example B71
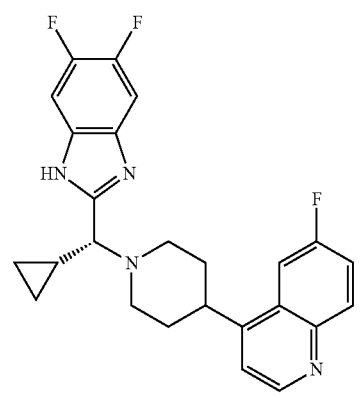
Example B72
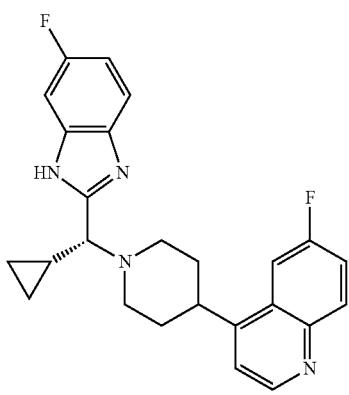
Example B73
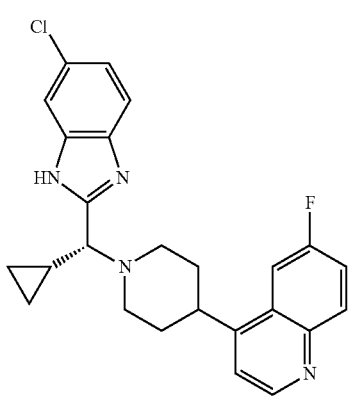
Example B74
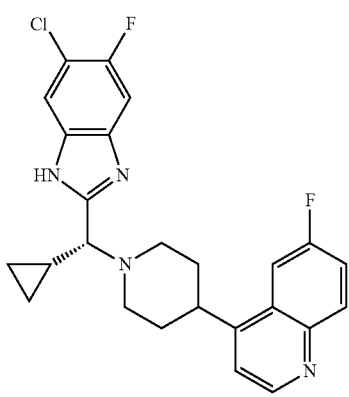
Example B75
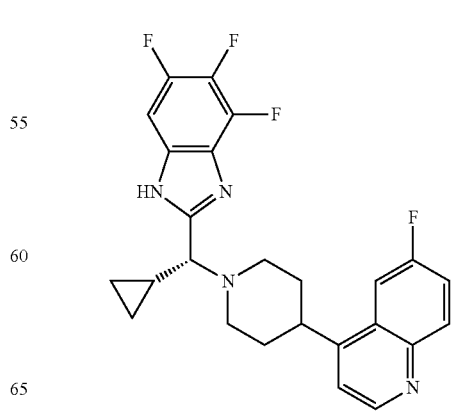

Example B76
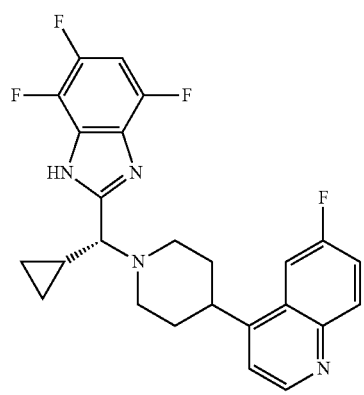
Example B77
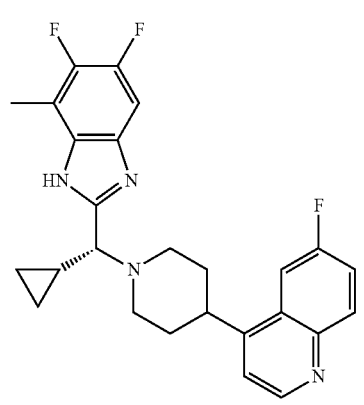
Example B78
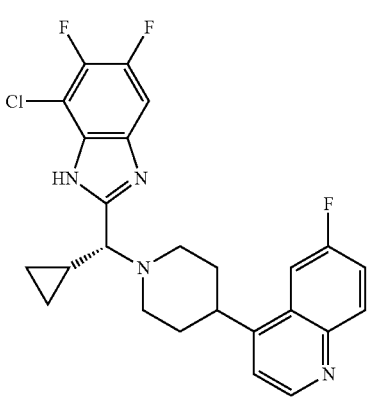
Example B79
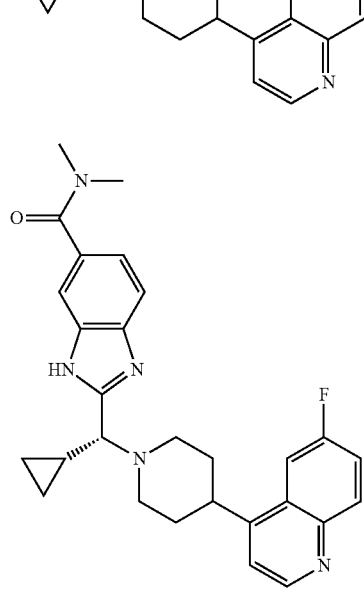
Example B80
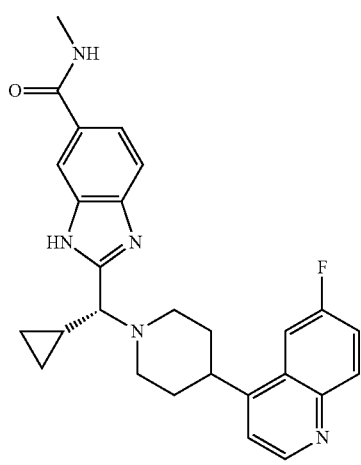
Example B81
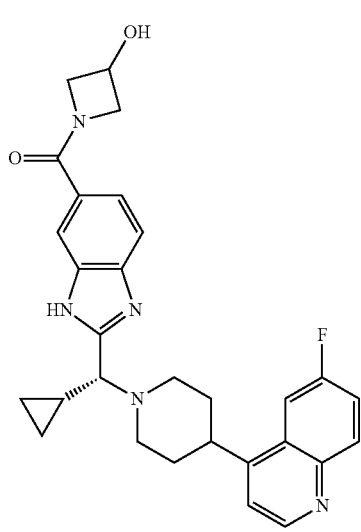
Example B82
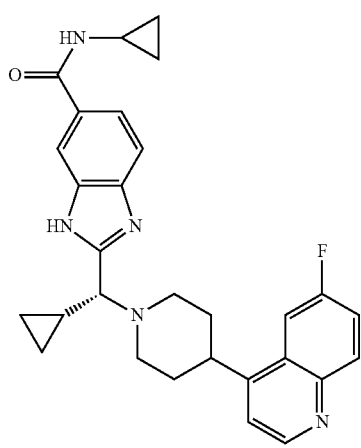

Example B83
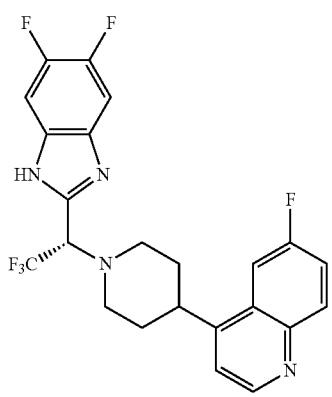
Example B84
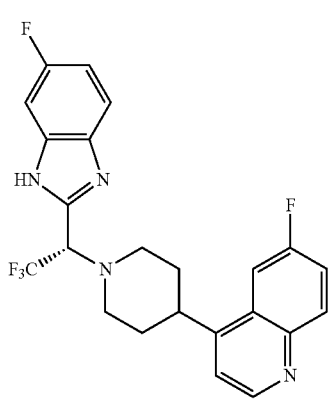
Example B85
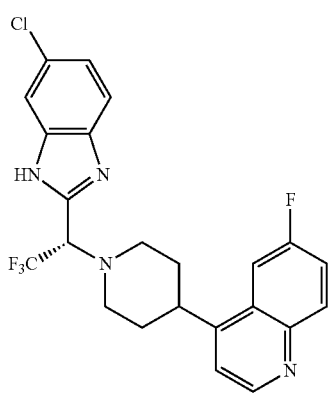
Example B86
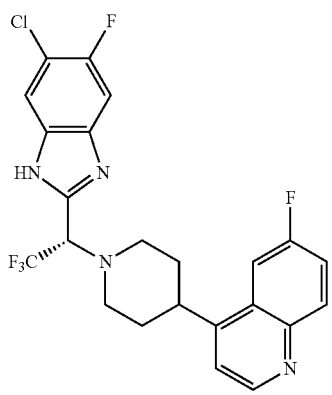
Example B87
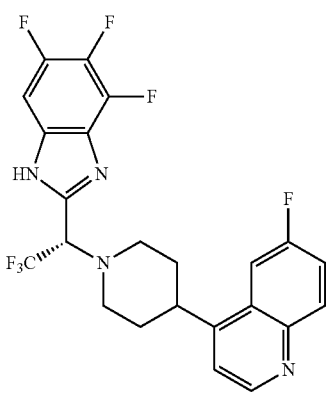
Example B88
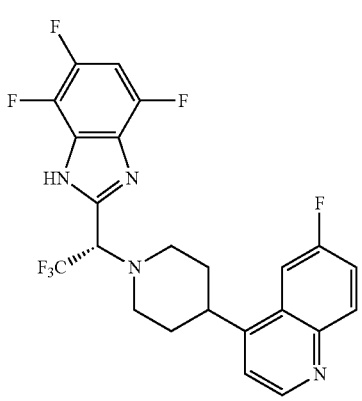
Example B89
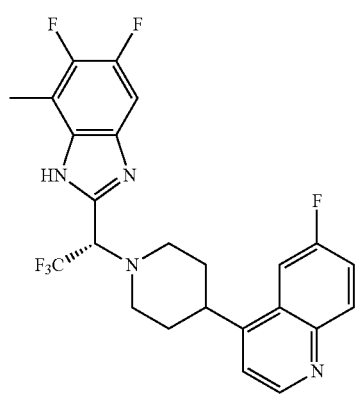
Example B90
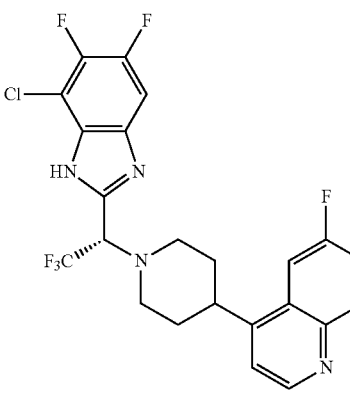

Example B91
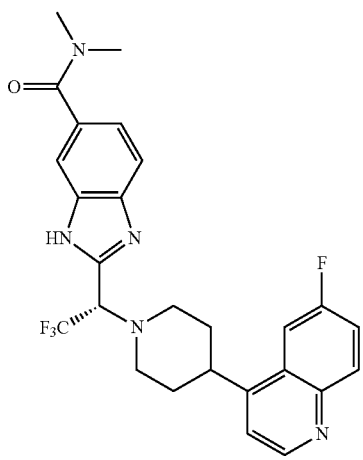
Example B92
Example B93
Example B94
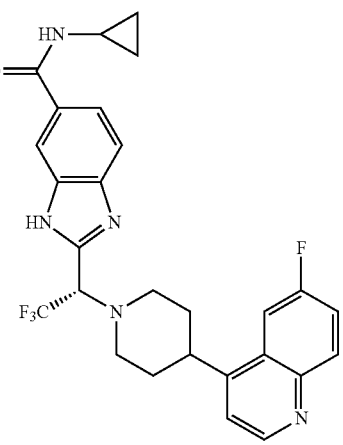
Example B95
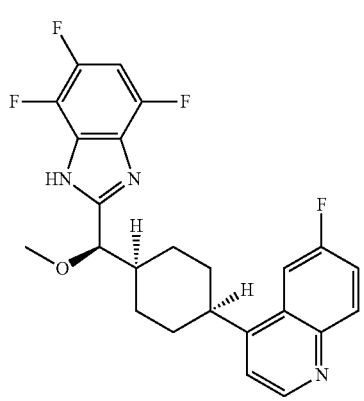
Example B96
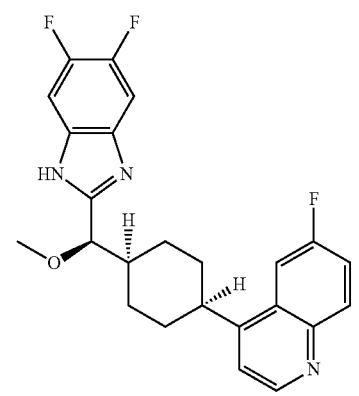
Example B97
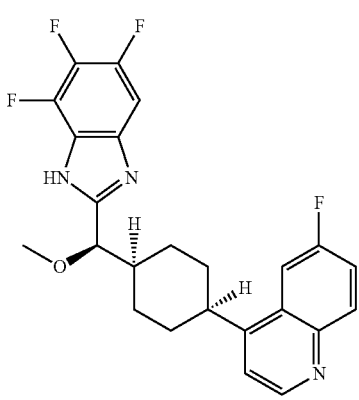

Example B98
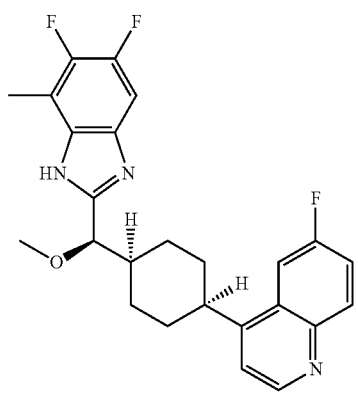
Example B99
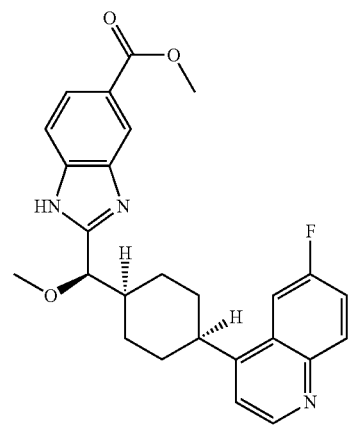
Example B100
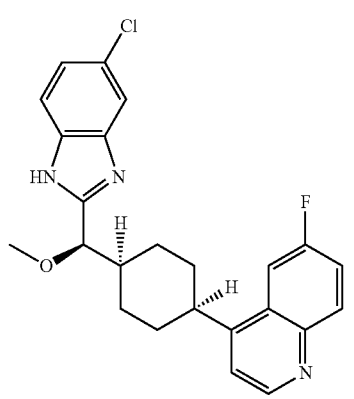
Example B101
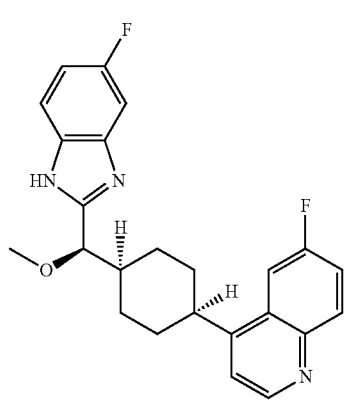
Example B102
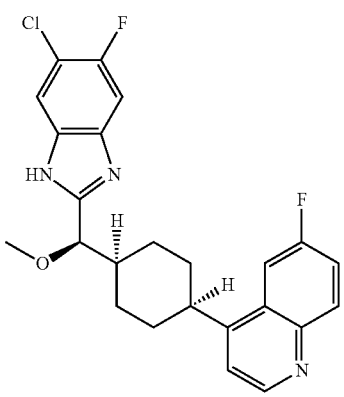
Example B103
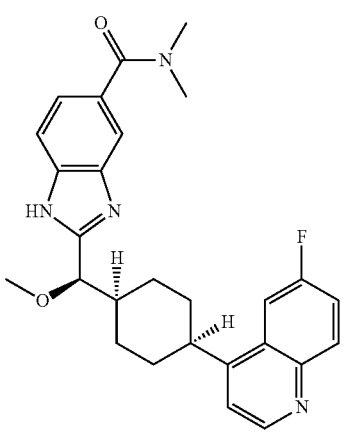
Example B104
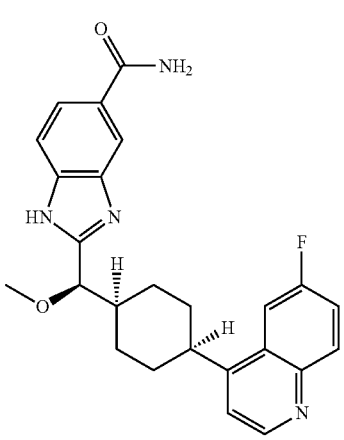

Example B105
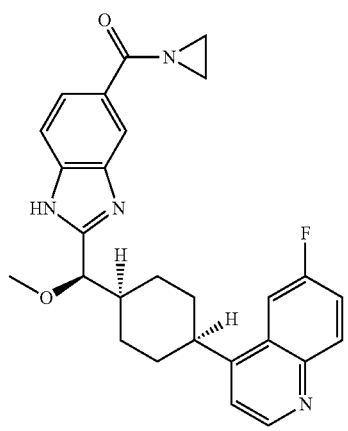
Example B106
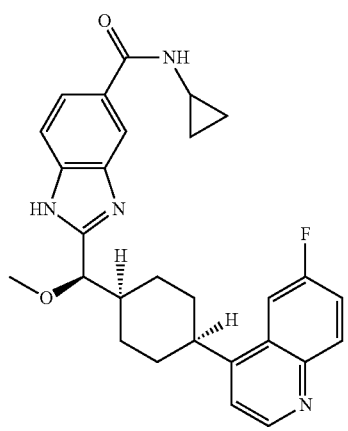
Example B107
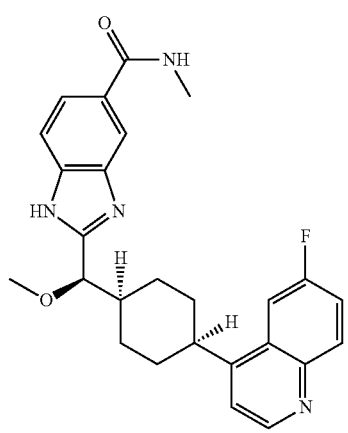
Example B108
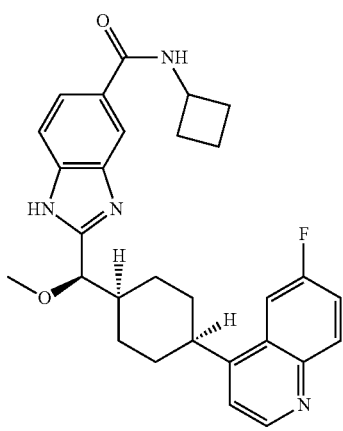
Example B109
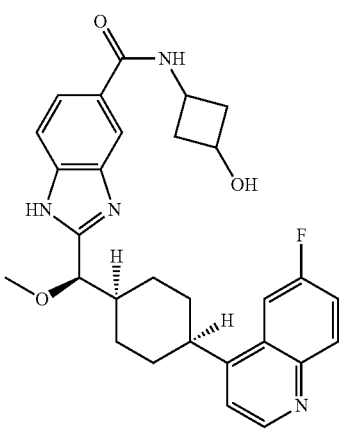
Example B110
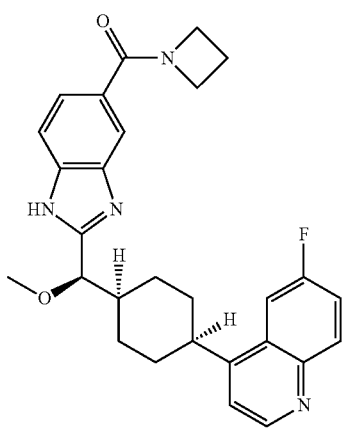

Example B111
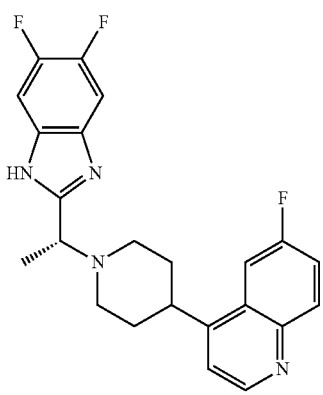
Example B112
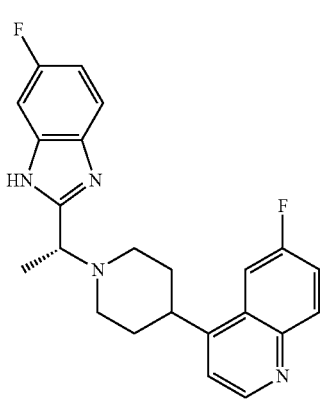
Example B113
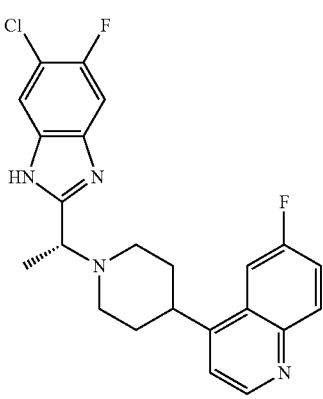
Example B114
Example B115
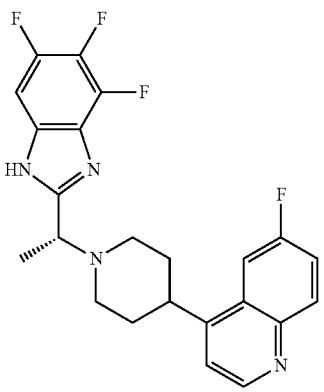
Example B116
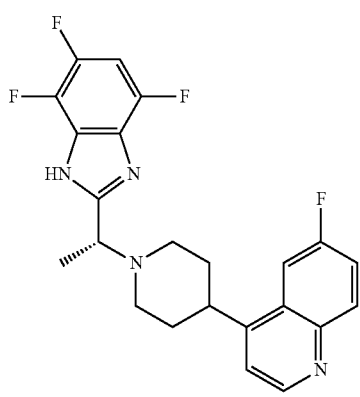
Example B117
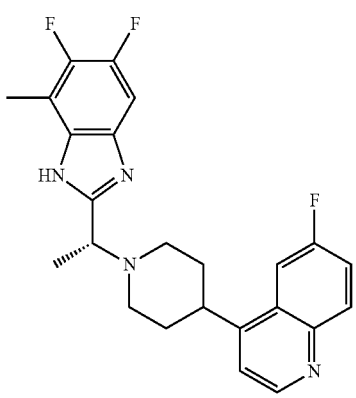
Example B118
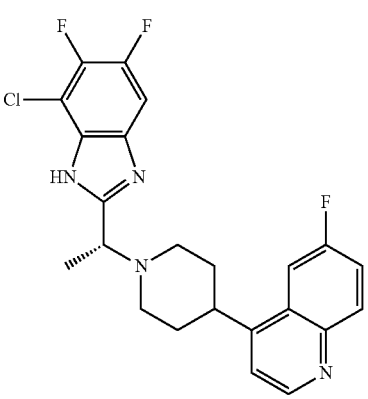

Example B119
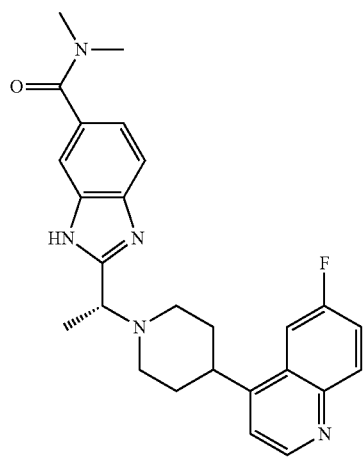
Example B122
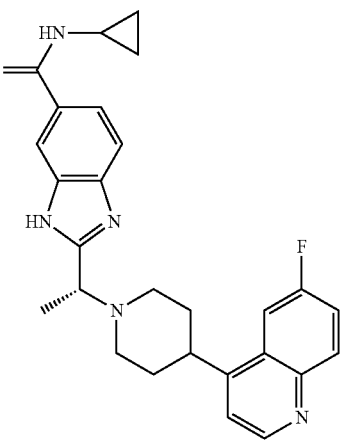
Example B123
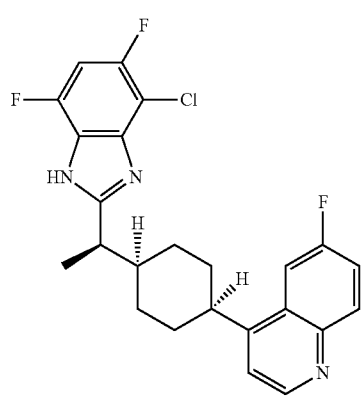
Example B120
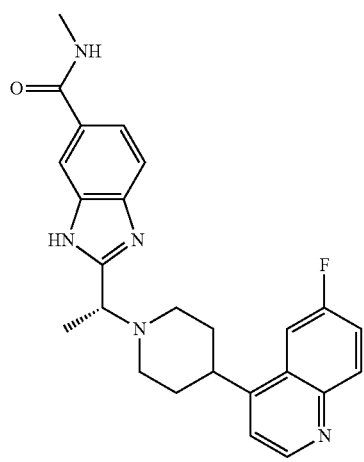
Example B124
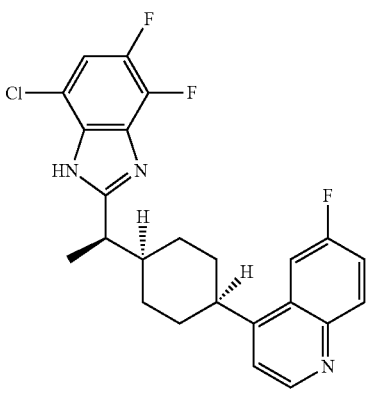
Example B121
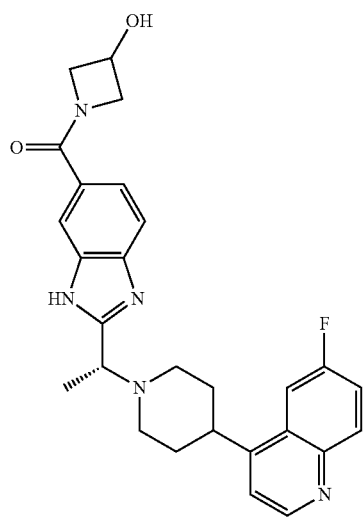
Example B125
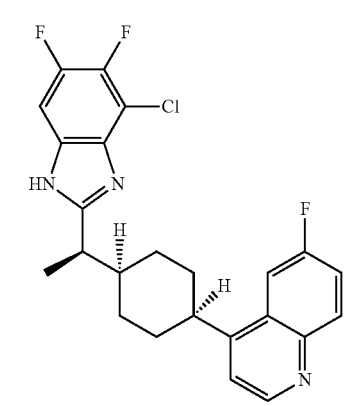

Example B126
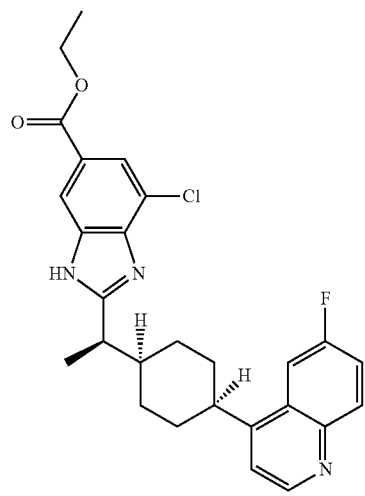
Example B127
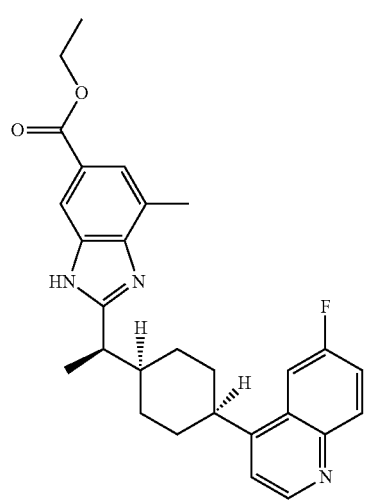
Example B128
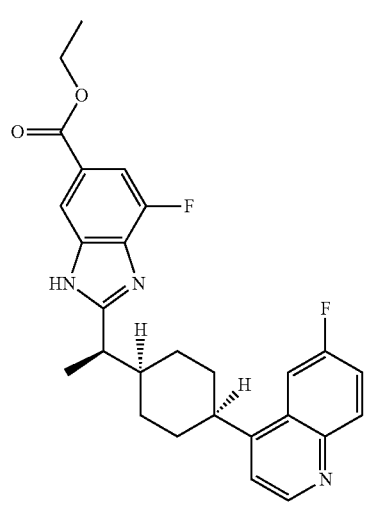
Example B129
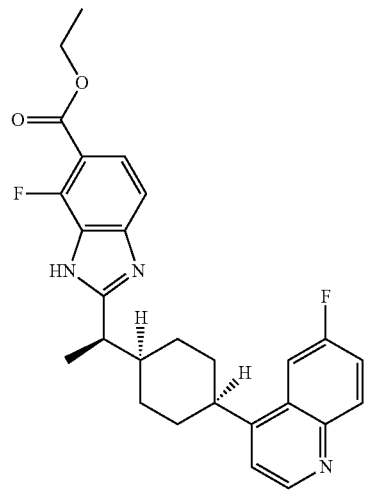
Example B130
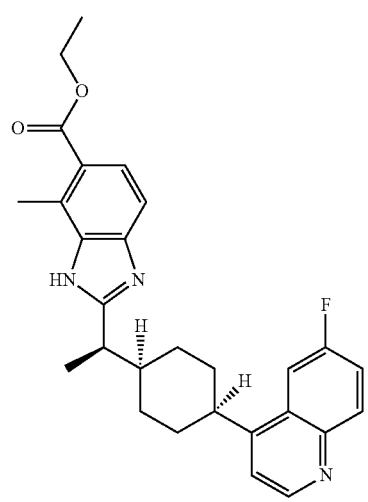
Example B131
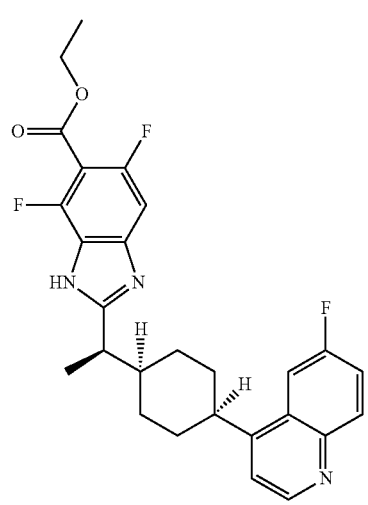

Example B132
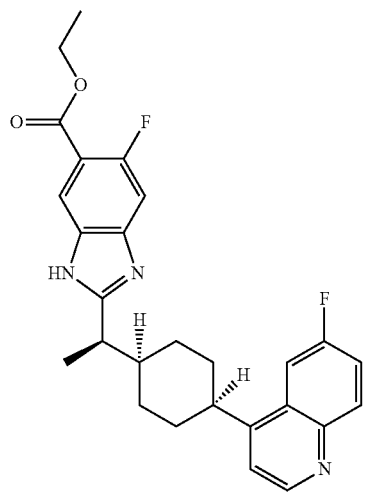
Example B133
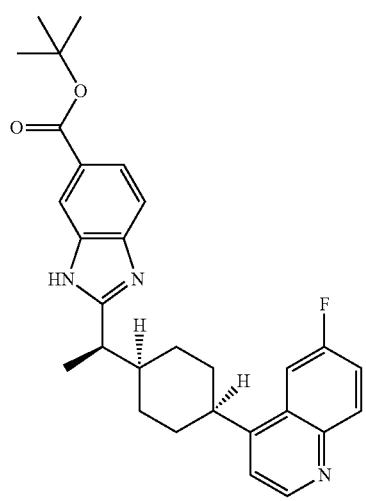
Example B134
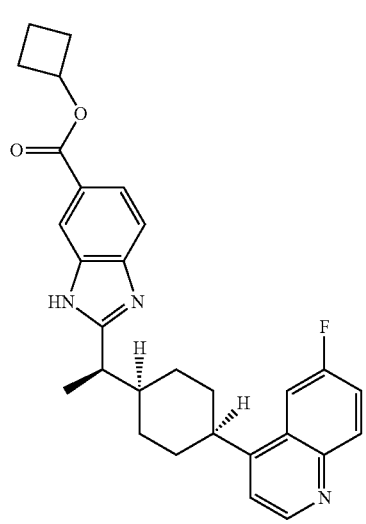
Example B135
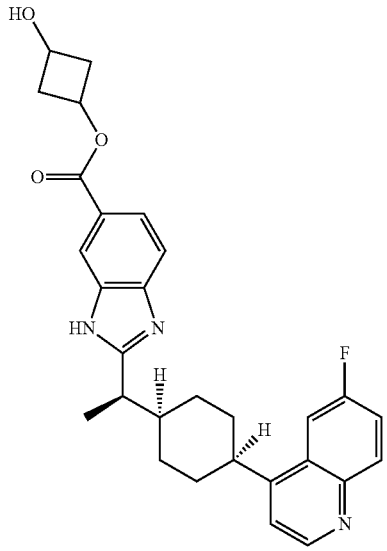
Example B136
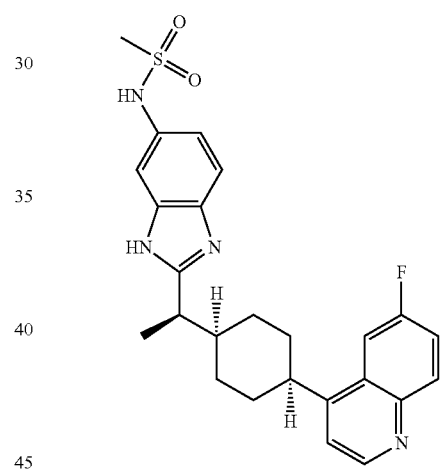
Example B137
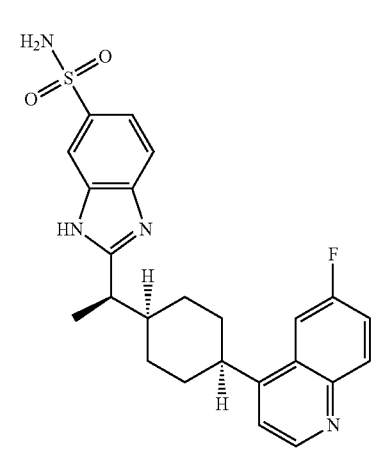

Example B138
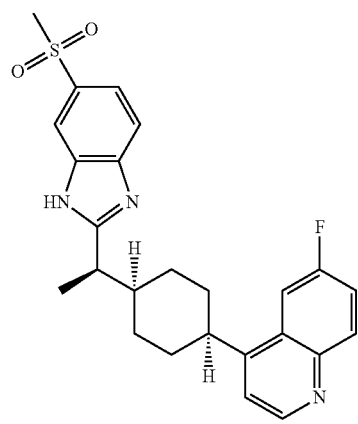
Example B141
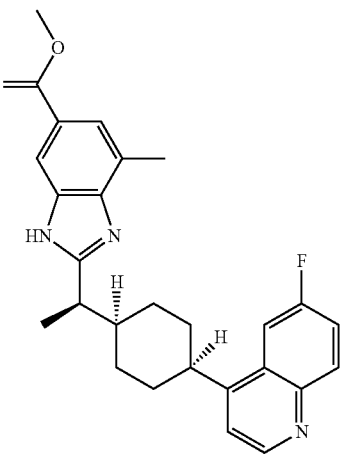
Example B139
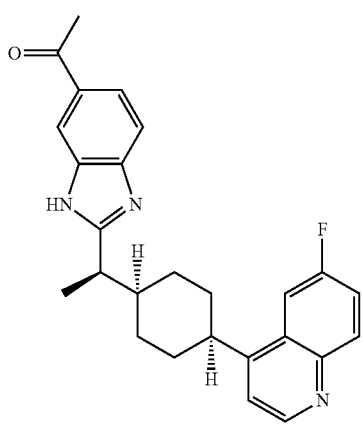
Example B142
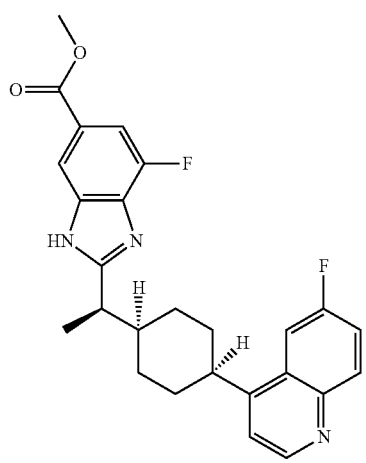
Example B140
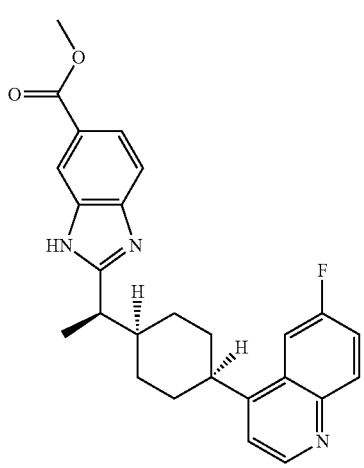
Example B143
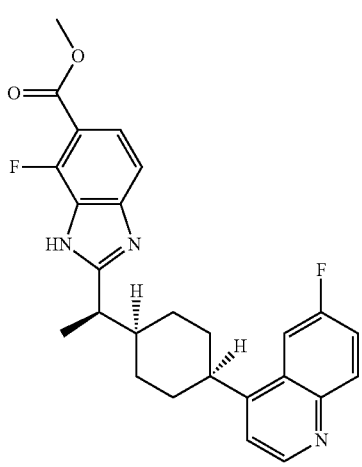

Example B144
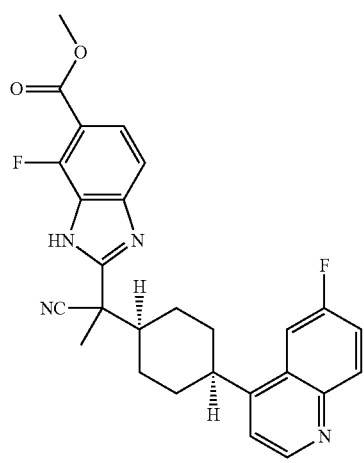
Example B147
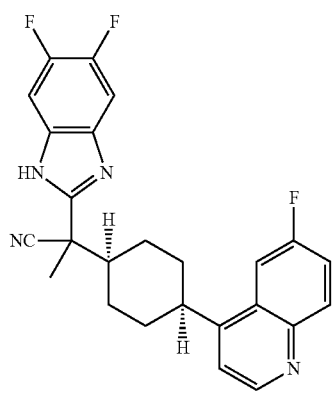
Example B145
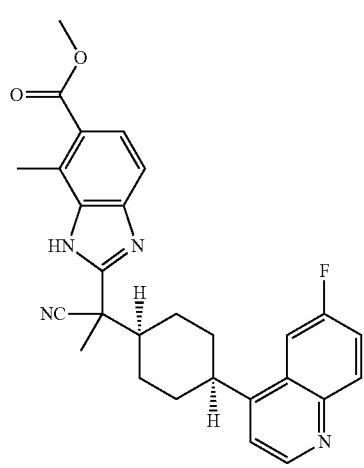
Example B148
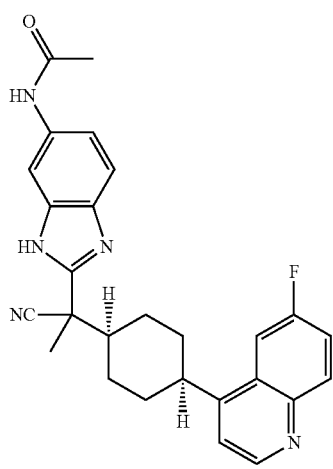
Example B146
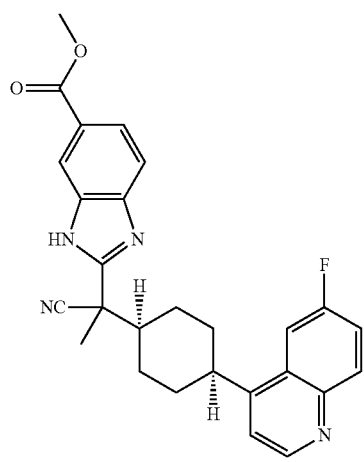
Example B149
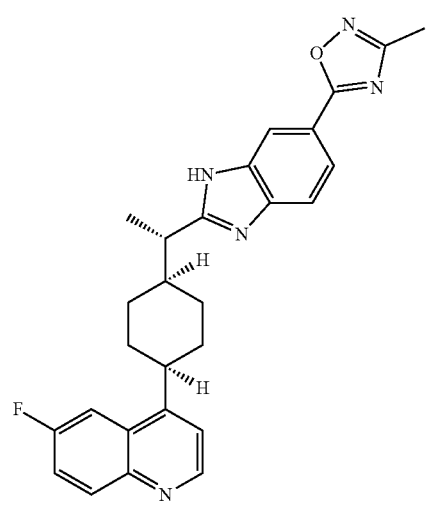

Example B150
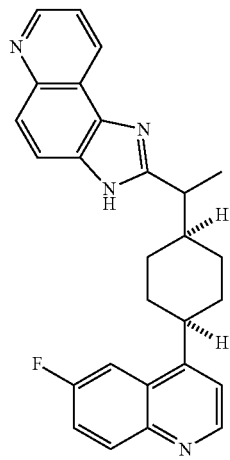
Example B151
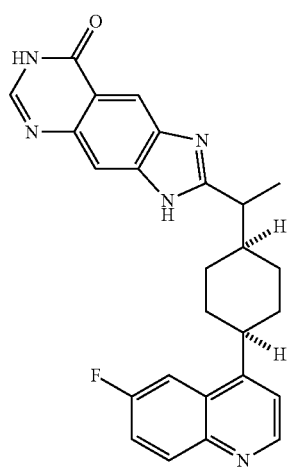
Example B152
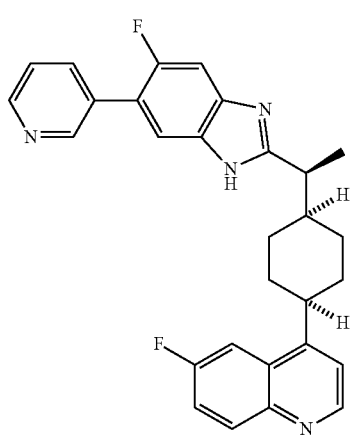
Example B153
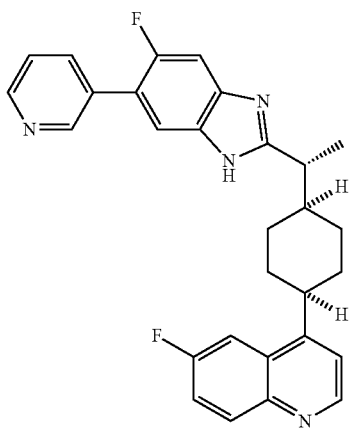
Example B154
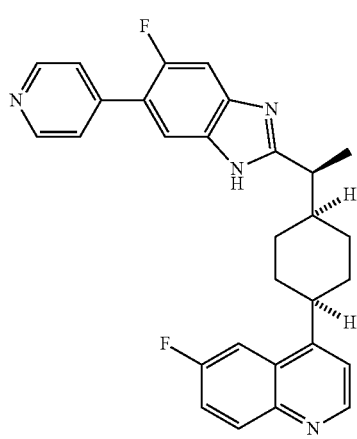
Example B155
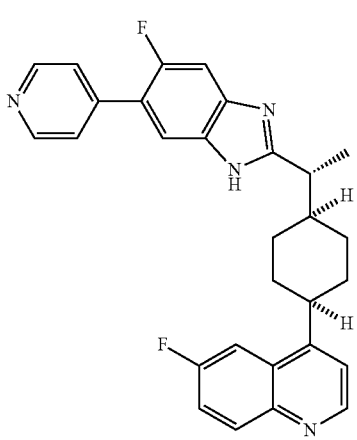

Example B156
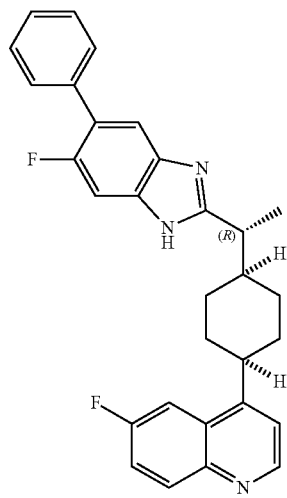
Example B157
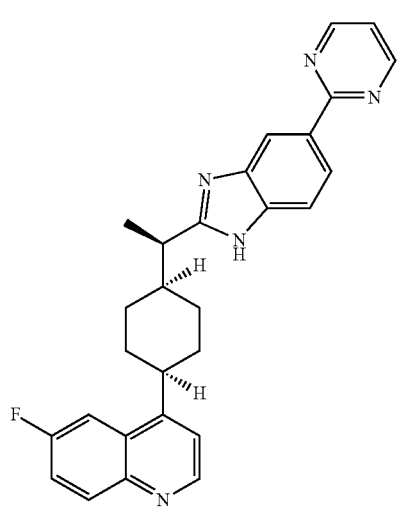
Example B158
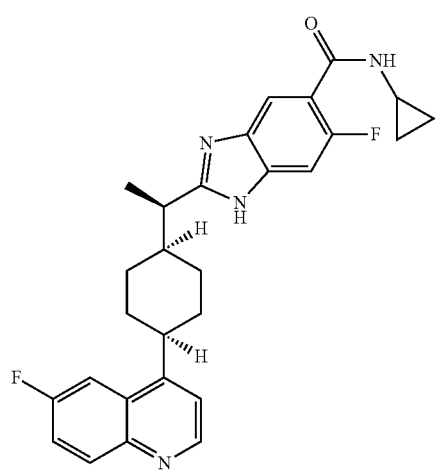
Example B159
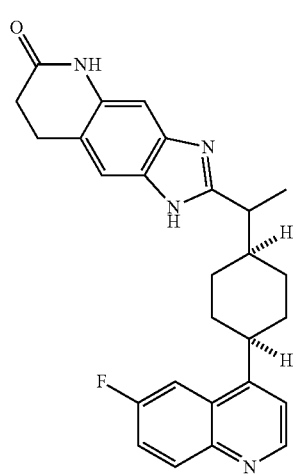
Example B160
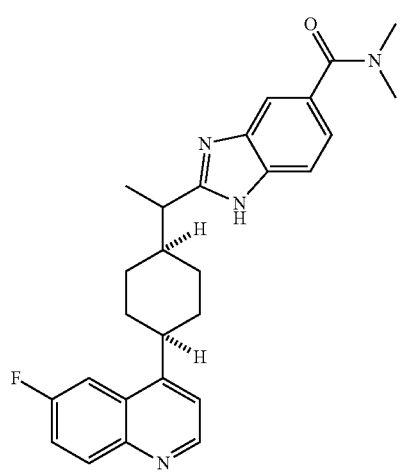
Example B161
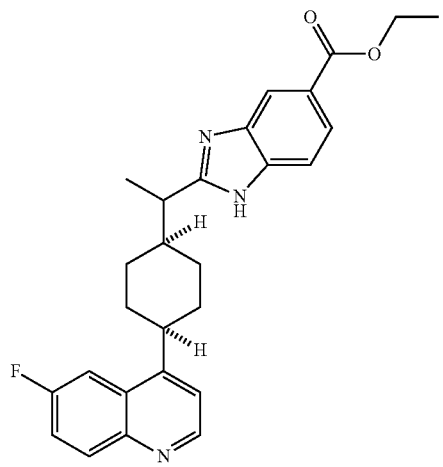

Example B163
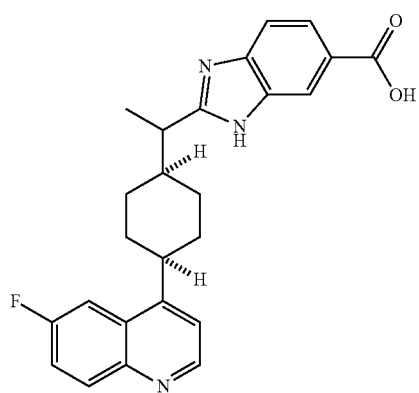
Example B164
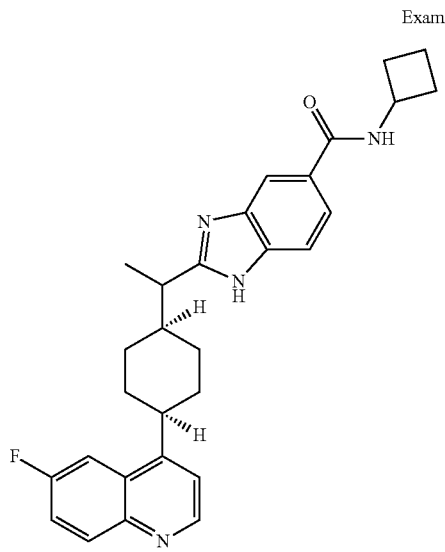
Example B165
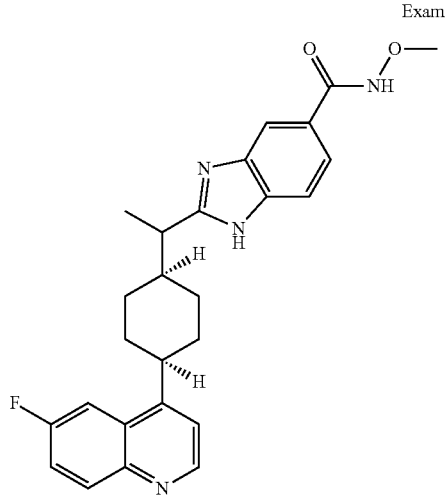
Example B166
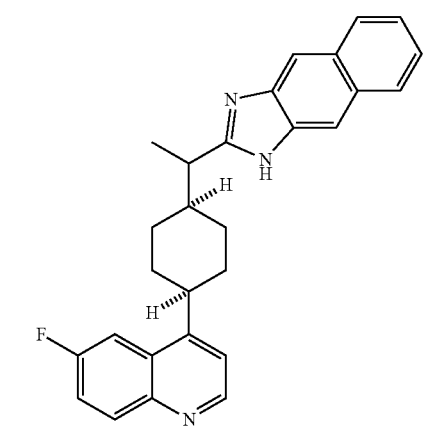
Example B167
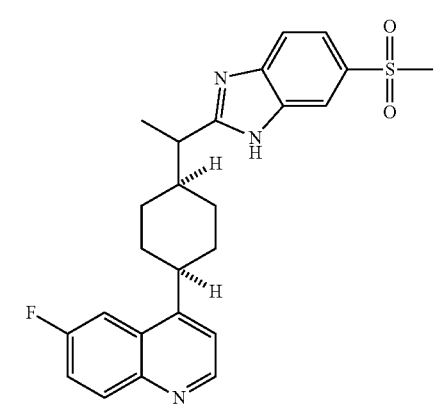
Example B168
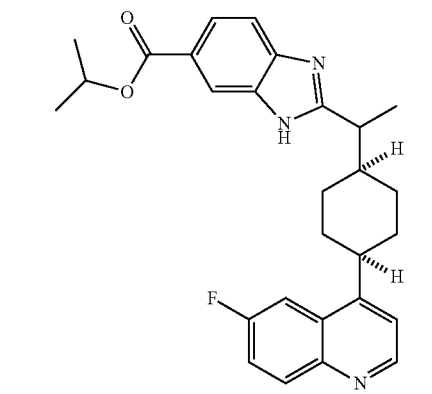
Example B169
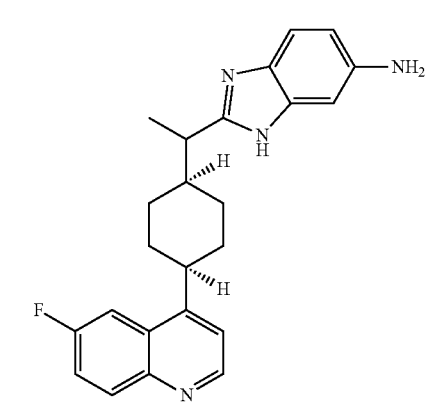

Example B170
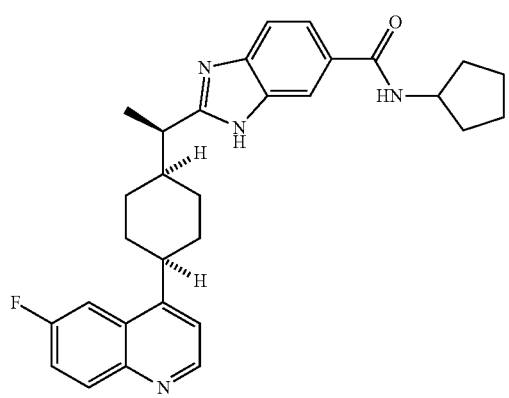
Example B171
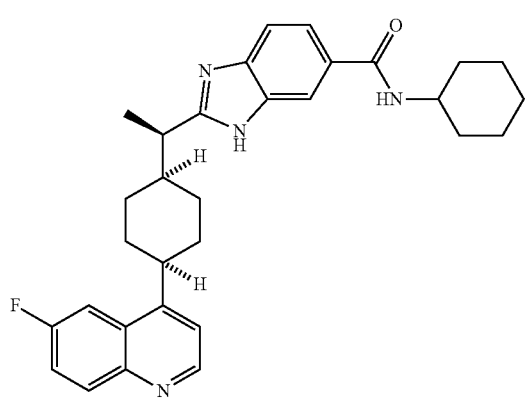
Example B172
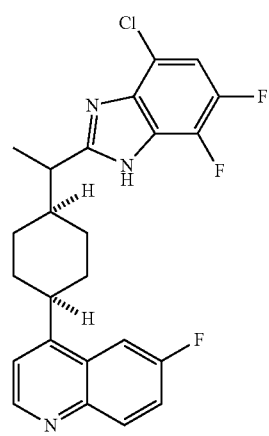
Example B173
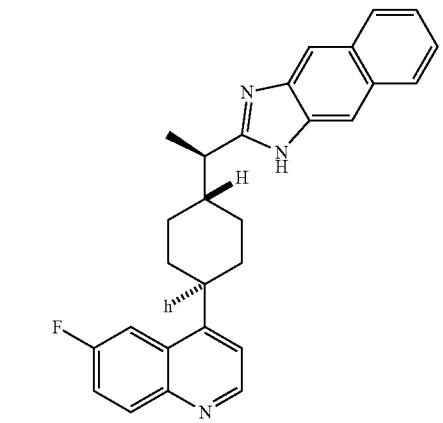
Example B174
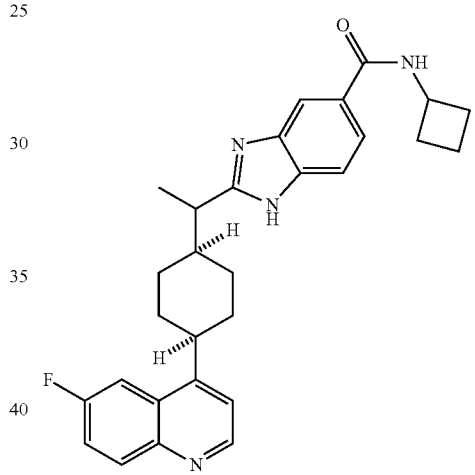
Example B175
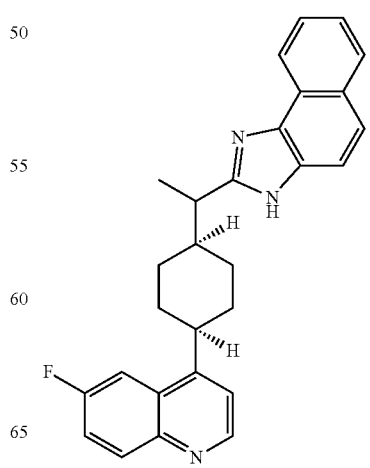

Example B176
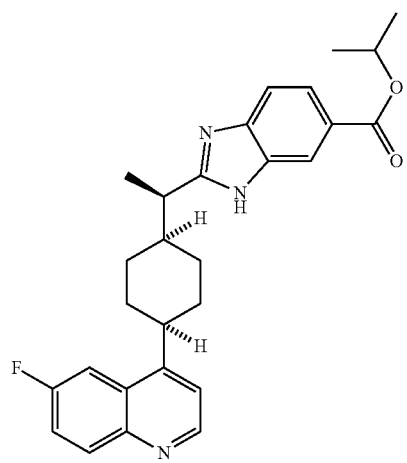
Example B177
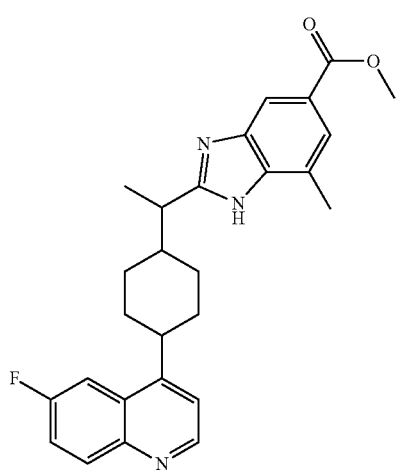
Example B178
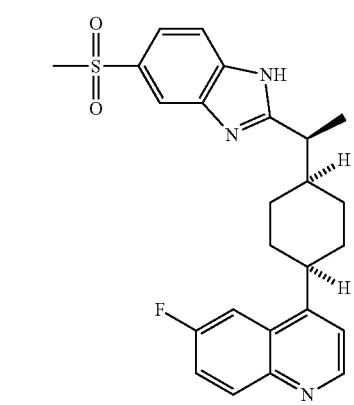
Example B179
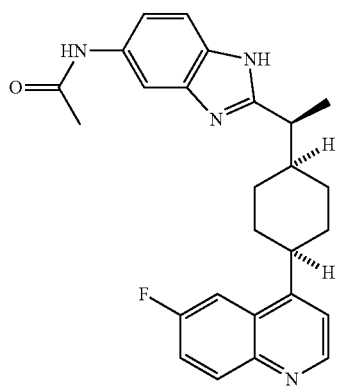
Example B180
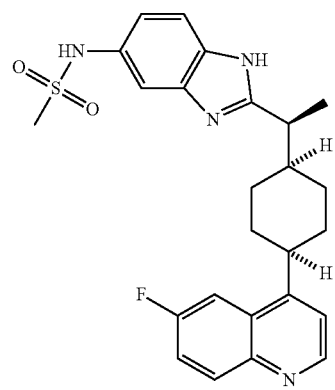
Example B181
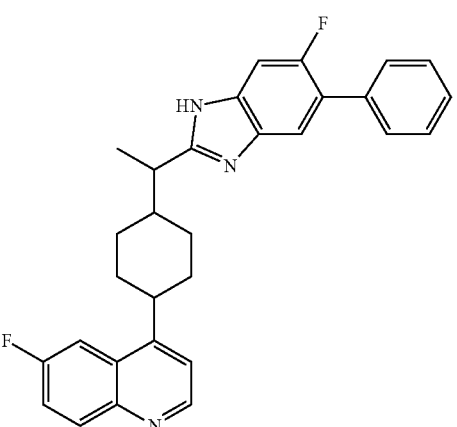
Example B182
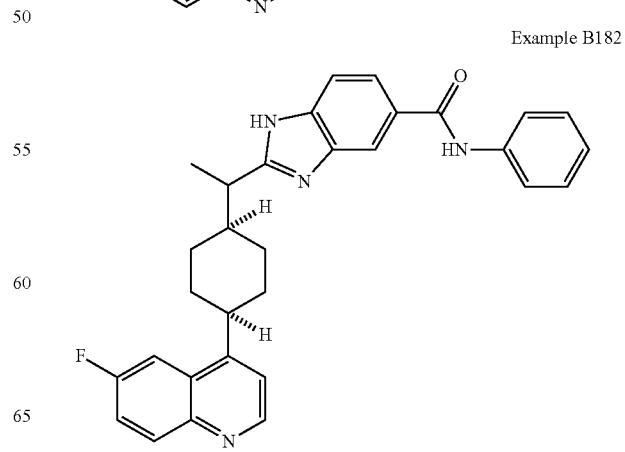

ExampleB183
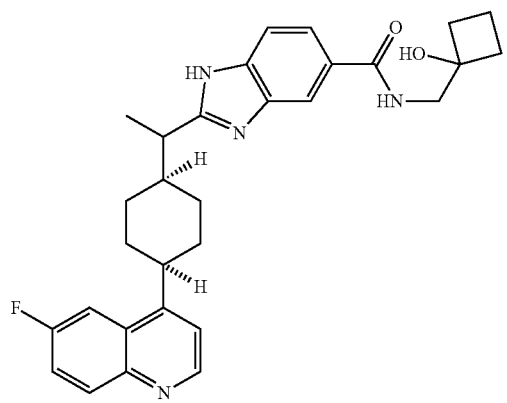
Example B184
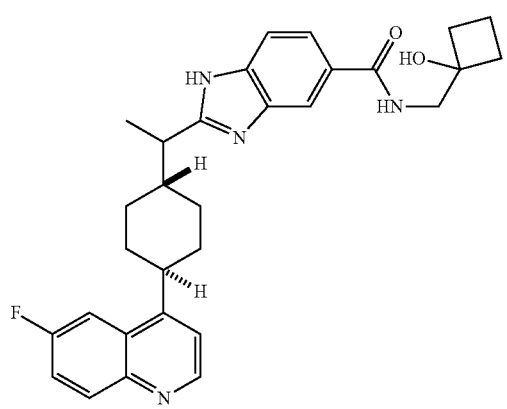
Example B185
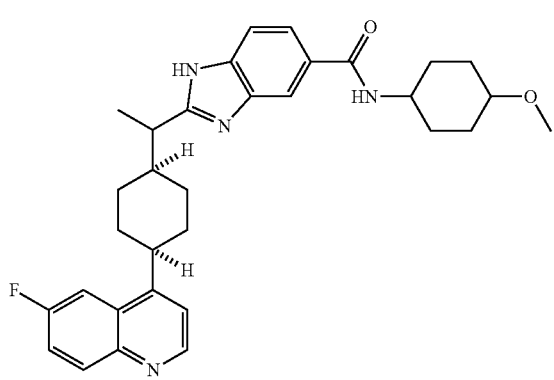
Example B186
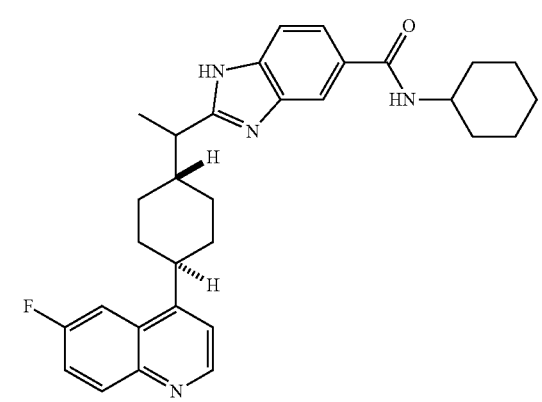
Example B187
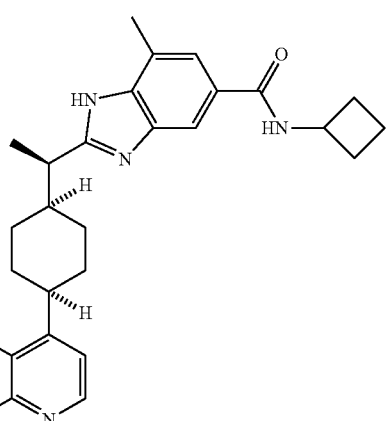
Example B188
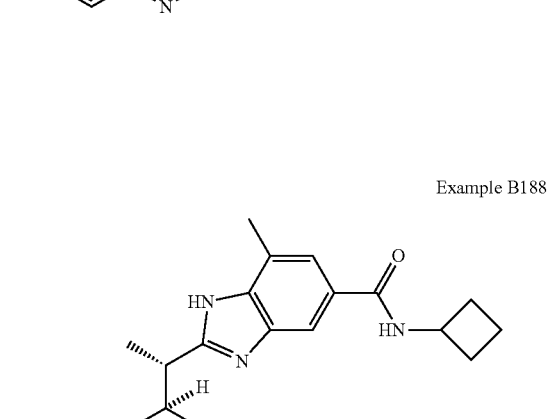
Example B189
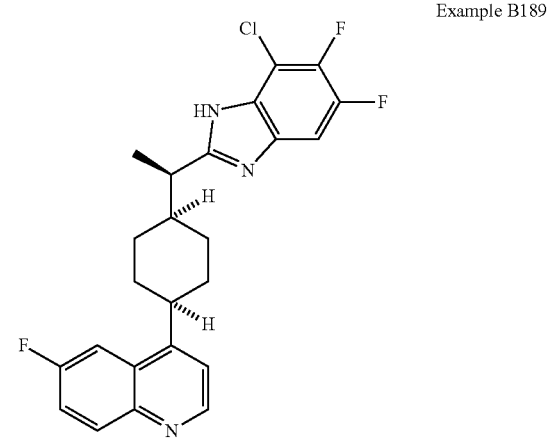

Example B190
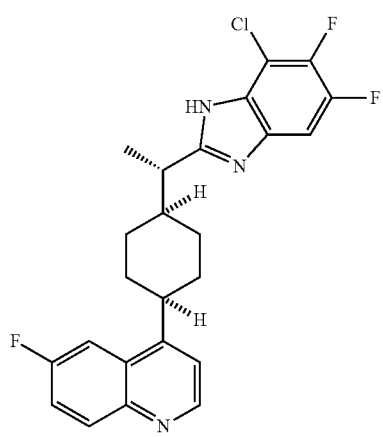
Example B191
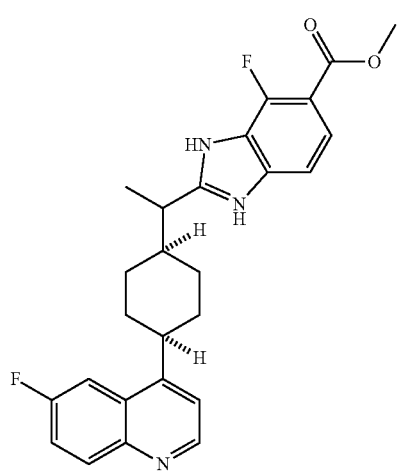
Example B192
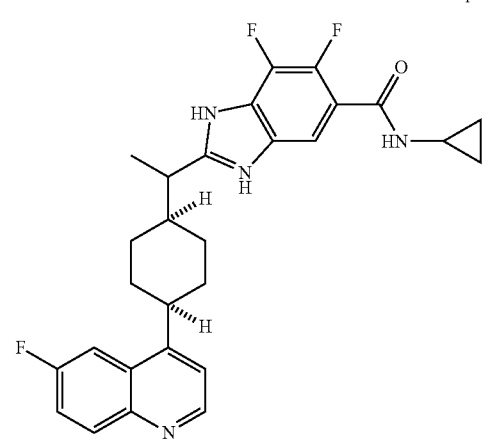
Example B193
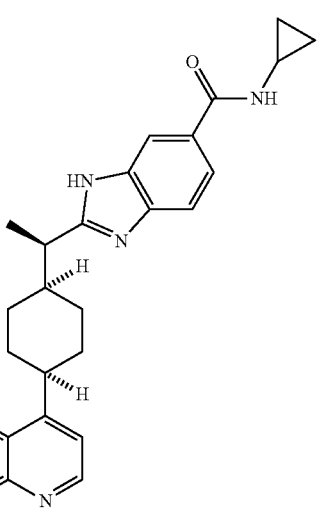
Example B194
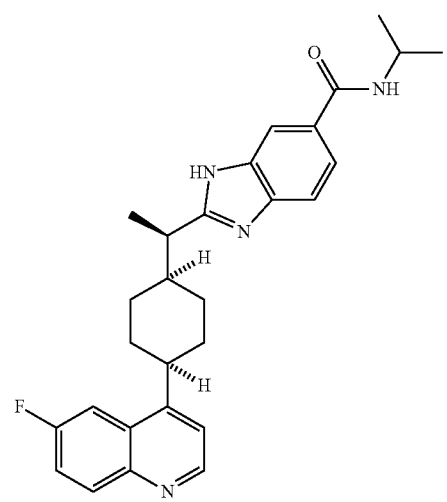
Example B195
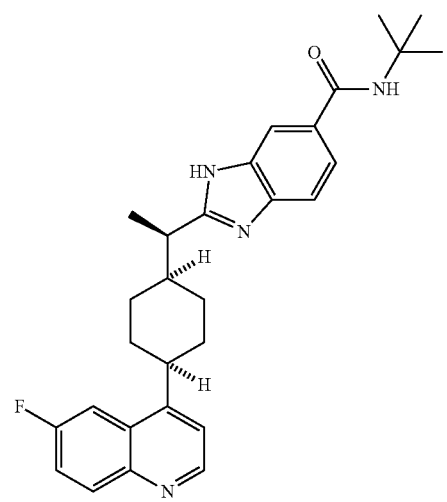

Example B196
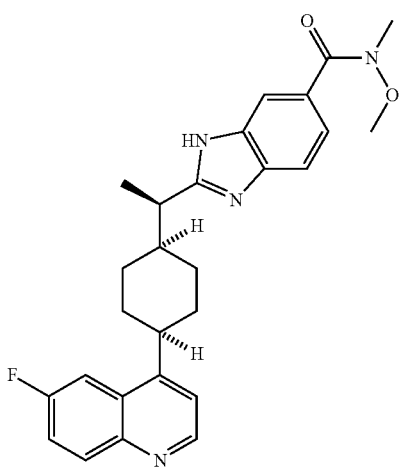
Example B197
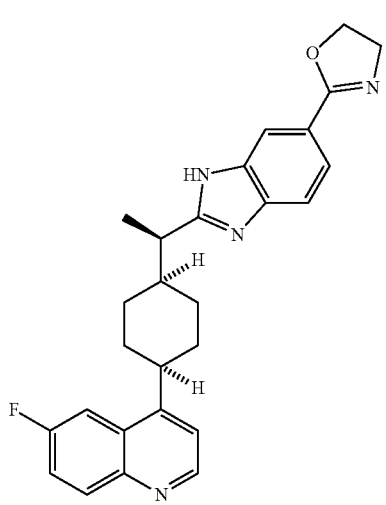
Example B198
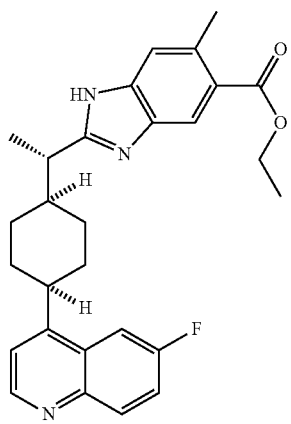
Example B199
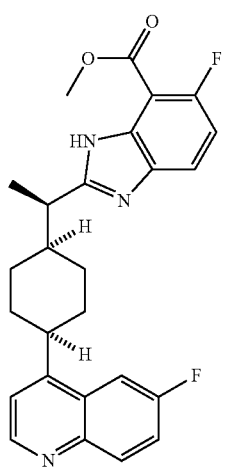
Example B200
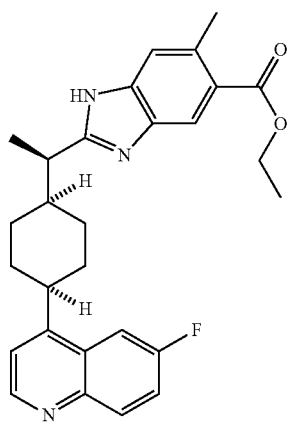
Example B201

Example B202
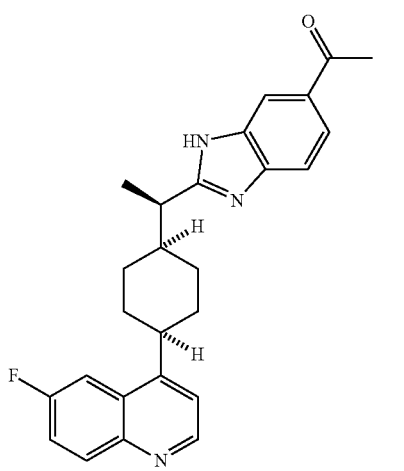
Example B203
Example B204
Example B205
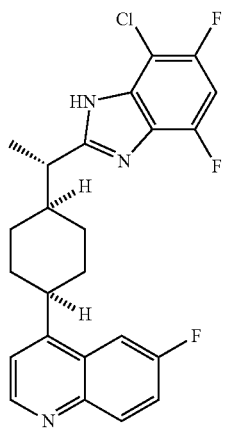
Example B206
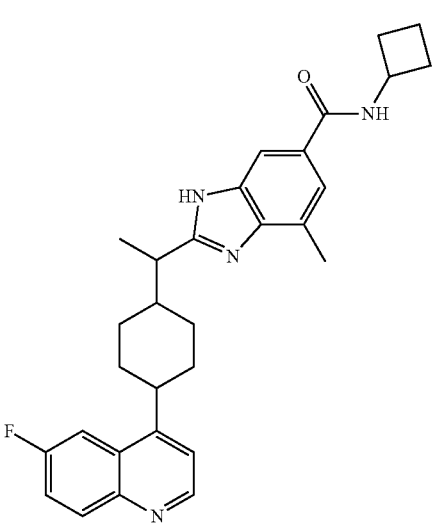
Example B207

Example B208
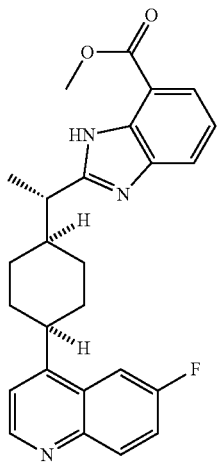
Example B210
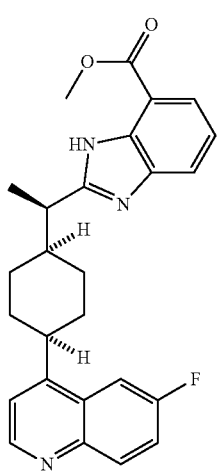
Example B211
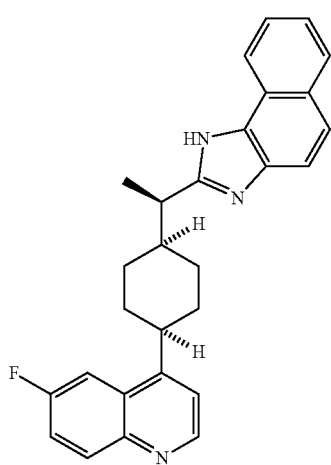
Example B212
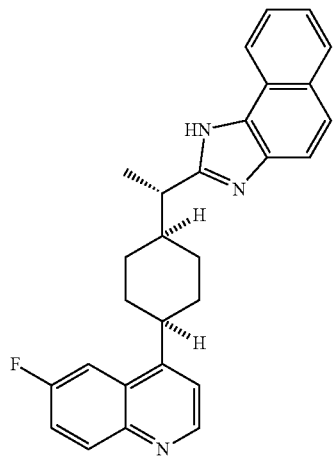
Example B213
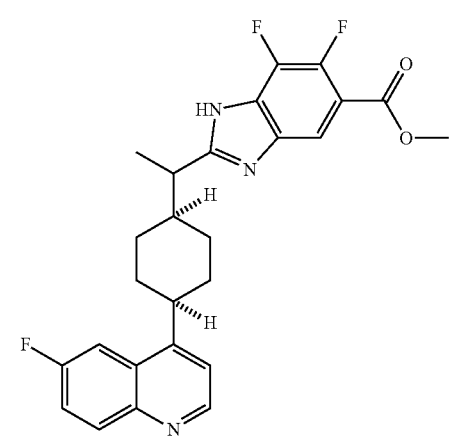
Example B214
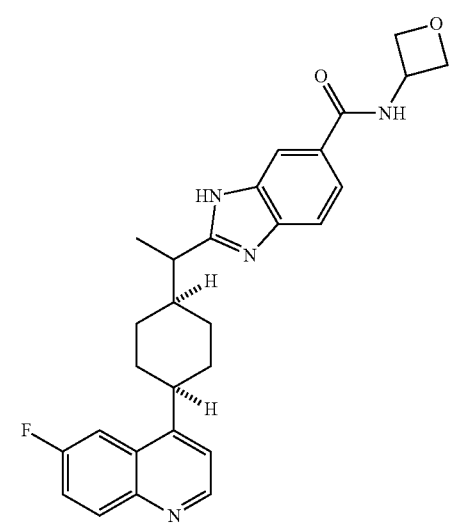

Example B215
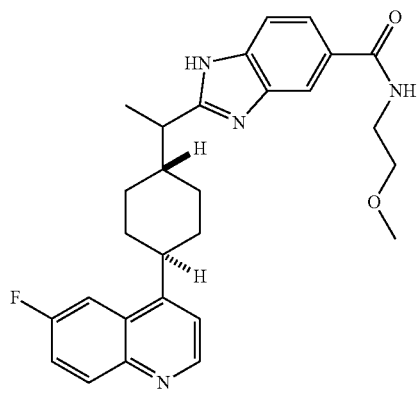
Example B216
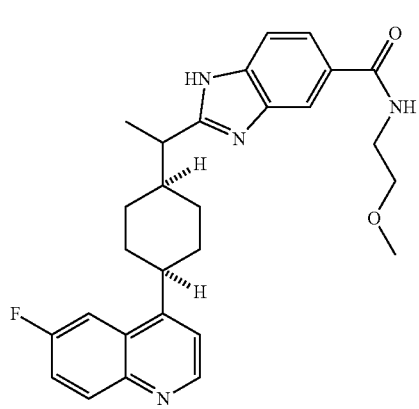
Example B217
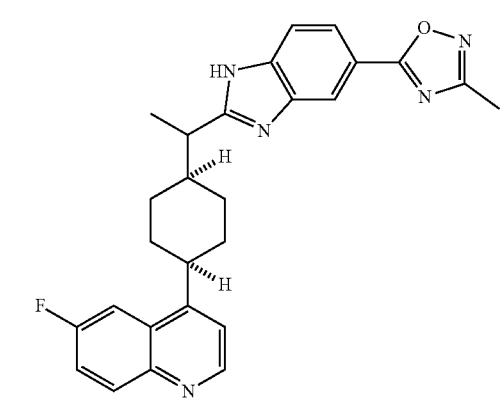
Example B218
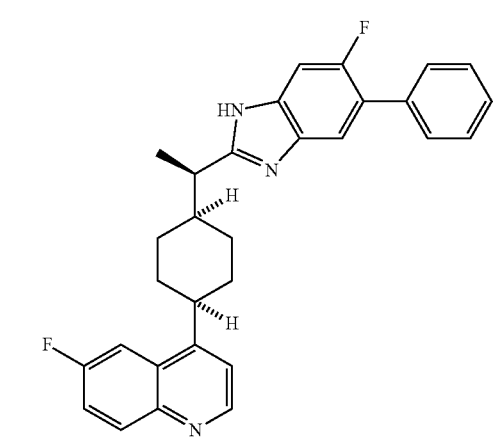
Example B219
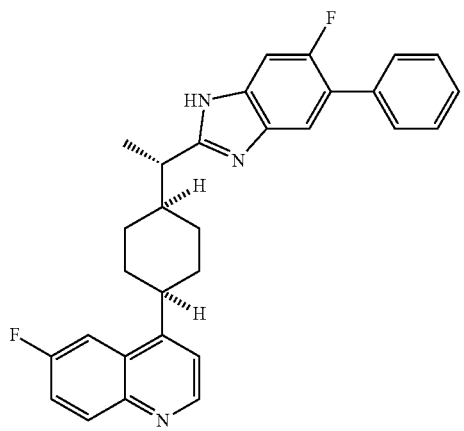
Example B220
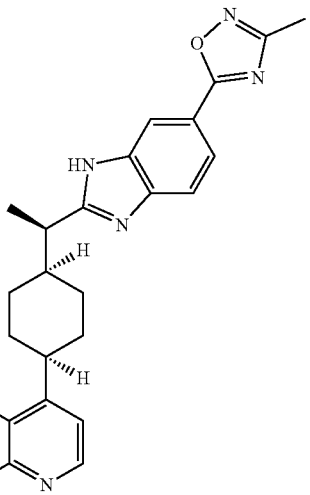
Example D1
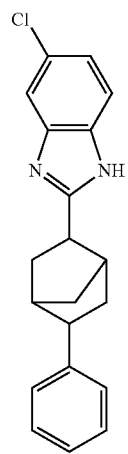

Example D2
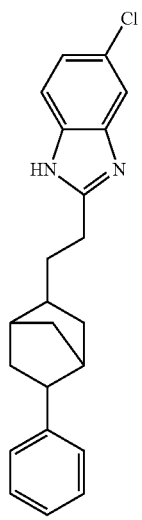
Example D3
Example D4
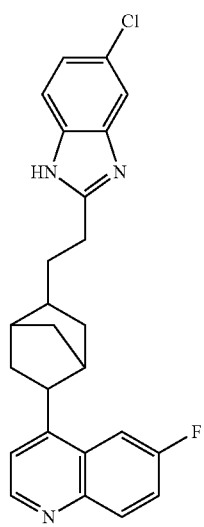
Example D5
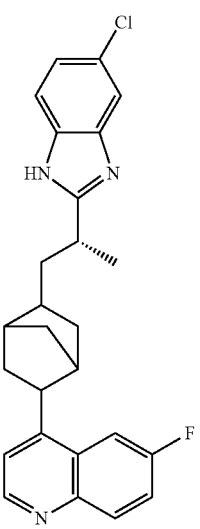
Example D6
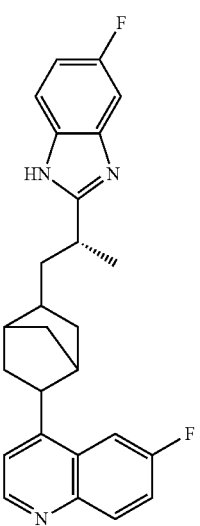
Example D7
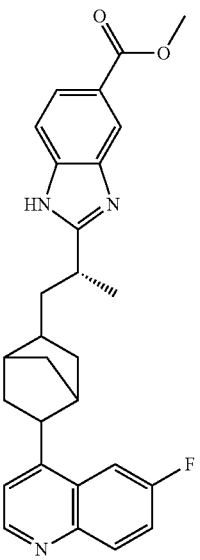

Example D8

Example D9

Example D10

Example D11

Example D12

Example D13

Example D14
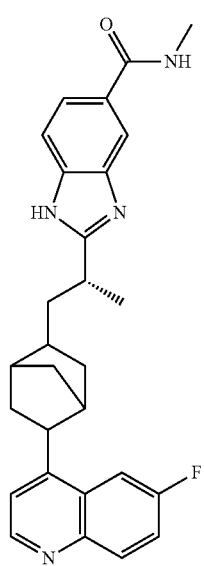
Exampl;e D15
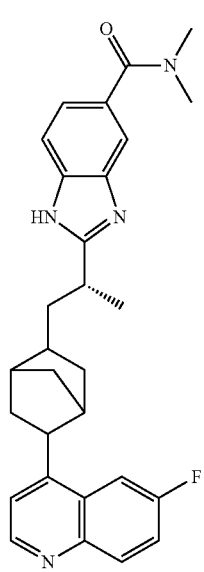
Example D16
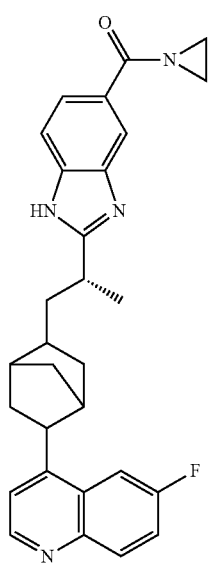
Example D17
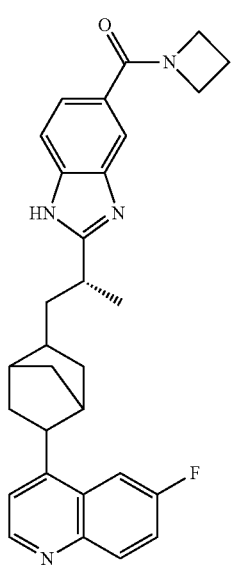
Example D18
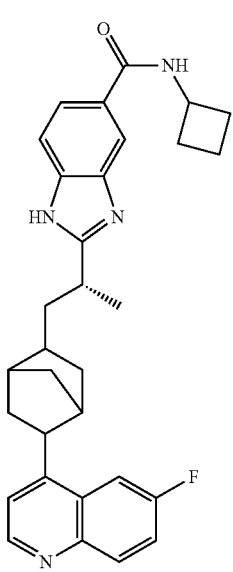
Example D19
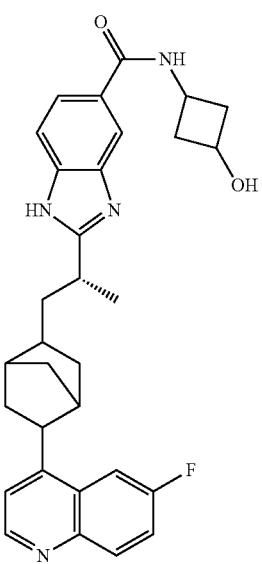

Example D20
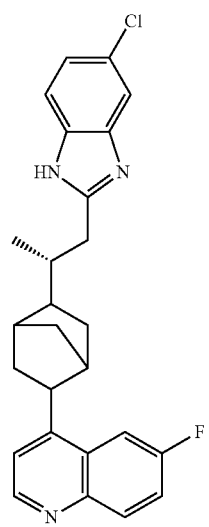
Example D21
Example D22
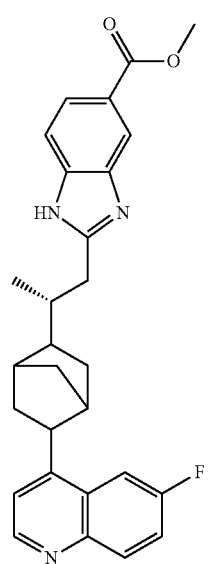
Example D23
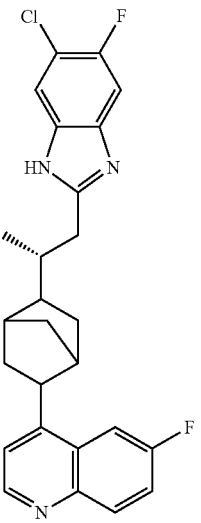
Example D24
Example D25
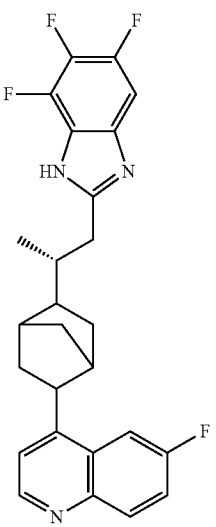

Example D26
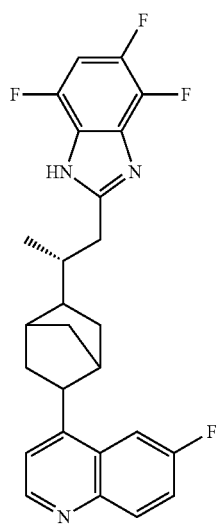
Example D27
Example D28
Example D29
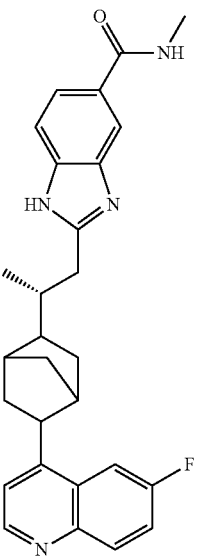
Example D30
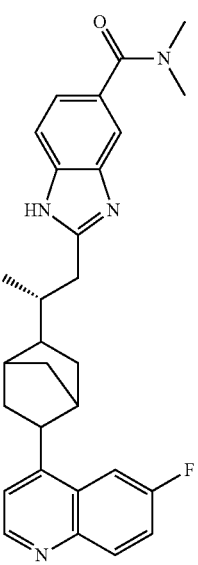
Example D31
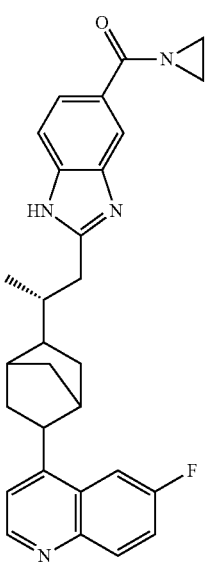

Example D32
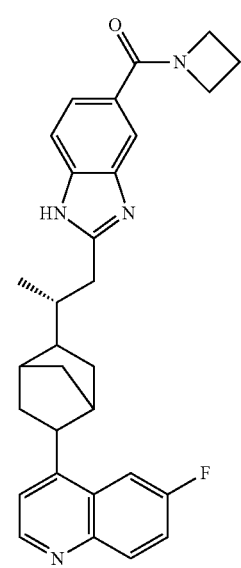
Example D33
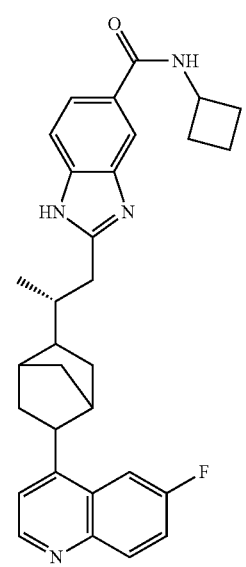
Example D34
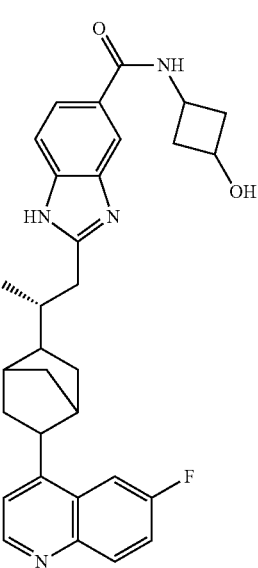
Example E1
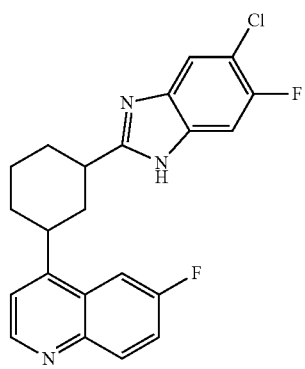
Example E2
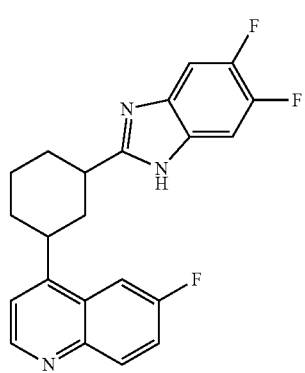
Example E3
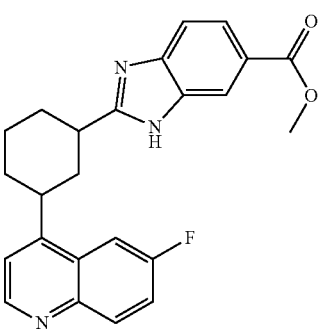
Example E4
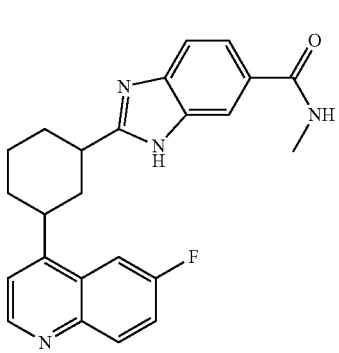

Example E5

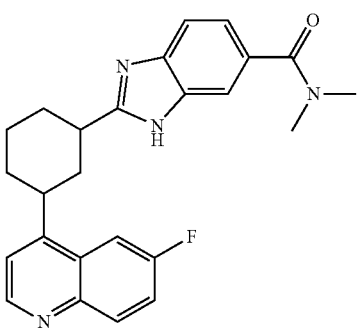

Example E6

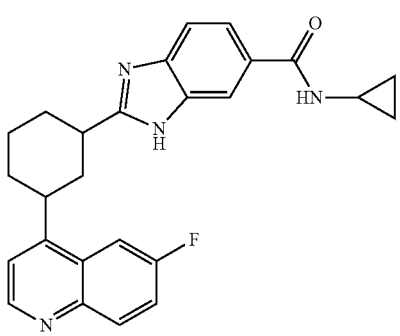

Example E7

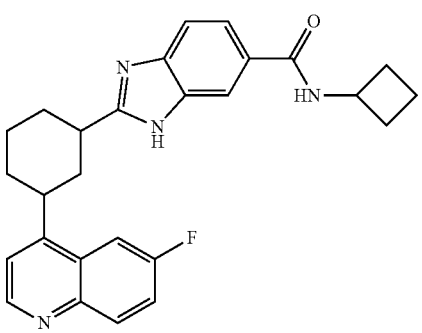

Example E8

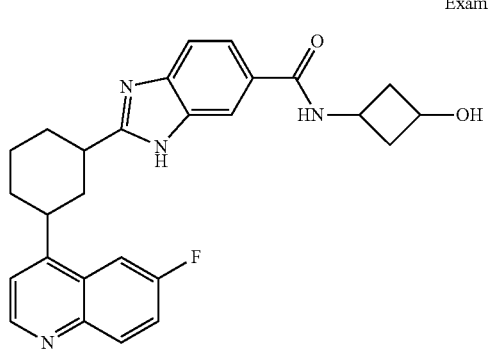

or a pharmaceutically acceptable salt thereof.

In the fourth aspect, disclosed herein is the process for preparing the compounds of formula (Ia), (Ib), (Ic), (Id), (Ie) and (If) disclosed herein.

The compounds disclosed herein, and/or the pharmaceutically acceptable salts thereof, can be synthesized from commercially available starting materials taken together with the disclosure herein.

Compounds of Formula (Ia, Ib, Ic, Id, Ie and If) may be prepared by the exemplary processes described in the working Examples, as well as relevant published literature procedures that are used by one skilled in the art. Exemplary reagents and procedures for these reactions appear hereinafter and in the working Examples. Protection and deprotection in the processes below may be carried out by procedures generally known in the art (see, for example, Greene, T. W. et al., eds., *Protecting Groups in Organic Synthesis*, 3$^{rd}$ Edition, Wiley (1999)). *General methods of organic synthesis and functional group transformations* are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Reactions, Mechanisms, and Structure*. 4$^{th}$ Edition, Wiley & Sons, New York, N.Y. (1992); Katritzky, A. R. et al., eds., *Comprehensive Organic Functional Groups Transformations*, 1$^{st}$ Edition, Elsevier Science Inc., Tarrytown, N.Y. (1995); Larock, R. C., *Comprehensive Organic Transformations*, VCH Publishers, Inc., New York, N.Y. (1989), and references therein.

Compounds of the invention (IA) may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, Wiley-Interscience, New York, 2001, or other standard texts on the topic of synthetic organic chemistry.

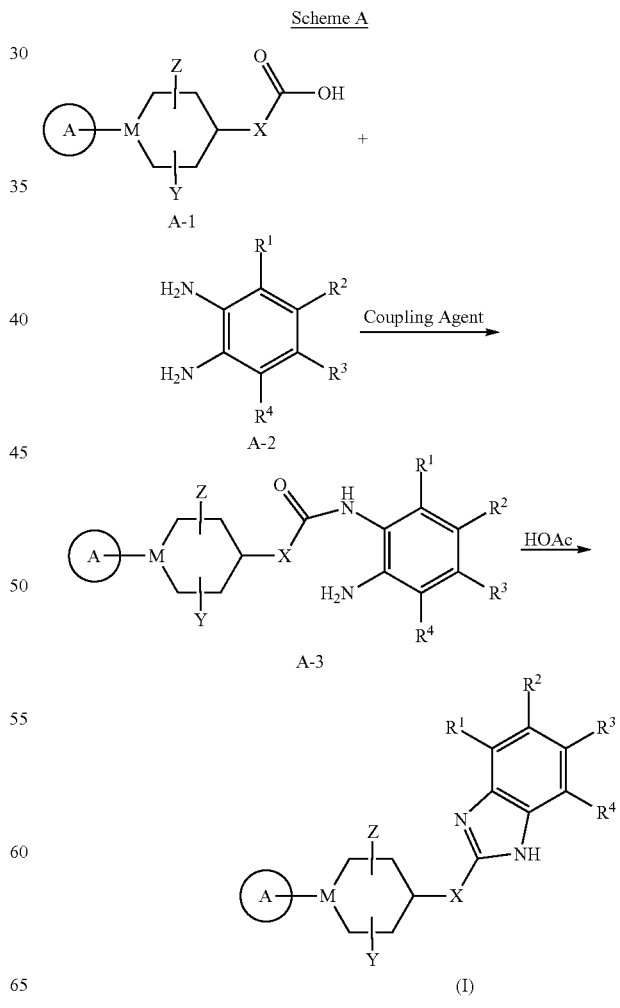

Scheme A

Compounds I can be prepared by a procedure depicted in Scheme A. The starting acid A-1 is converted into the amide A-3 through coupling with substituted benzenediamine. The amide A-3 can be cyclized into the final benzoimidazole by treatment with hot acetic acid.

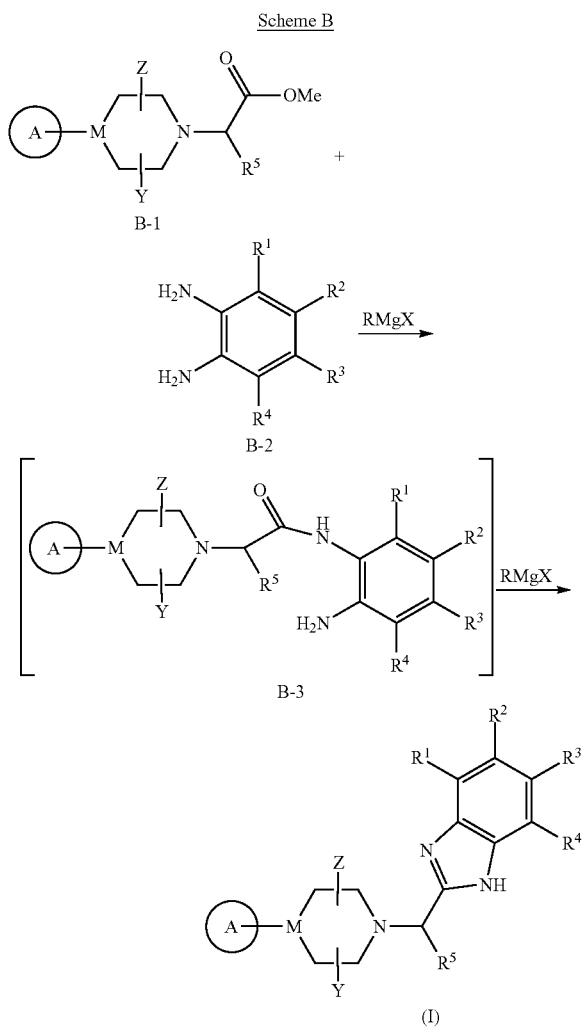

Compounds I can also be prepared by a procedure depicted in Scheme B. The starting ester B-1 is directly converted into the final benzoimidazole by treating it with substituted benzenediamine in the presence of excessive methyl magnesium bromide.

The syntheses of the starting acid and ester are described in the corresponding examples in the experimental part.

In the fifth aspect, disclosed herein is a method for treating or preventing hyperproliferative disorders, such as cancer, comprising administrating to a subject, such as a mammal or human in need thereof a pharmaceutically-effective amount of a compound selected from compounds of Formulas (Ia, Ib, Ic, Id, Ie and If), or a stereoisomer thereof, or a pharmaceutically acceptable salt thereof disclosed herein.

Also disclosed herein is a method for treating or preventing hyperproliferative disorders, such as cancer by inhibiting IDO, comprising administrating to a subject, such as a mammal or human in need thereof a pharmaceutically-effective amount of a compound selected from compounds of Formulas (Ia, b, Ic, Id, Ie and If), or a stereoisomer thereof, or a pharmaceutically acceptable salt thereof disclosed herein.

Also disclosed herein is a method for treating or preventing cancer including but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma, comprising administrating to a subject, such as a mammal or human in need thereof a pharmaceutically-effective amount of a compound selected from compounds of Formulas (Ia, Ib, Ic, Id, Ie and If), or a stereoisomer thereof, or a pharmaceutically acceptable salt thereof disclosed herein.

Also disclosed herein is a method for treating or preventing HIV/AIDS, comprising administrating to a subject, such as a mammal or human in need thereof a pharmaceutically-effective amount of a compound selected from compounds of Formulas (Ia, Ib, Ic, Id, Ie and If), or a stereoisomer thereof, or a pharmaceutically acceptable salt thereof disclosed herein.

Also disclosed herein is a method for enhancing the effectiveness of an anti-retroviral therapy, comprising administrating to a subject, such as a mammal or human in need thereof an anti-retroviral agent and a pharmaceutically-effective amount of a compound selected from compounds of Formulas (Ia, Ib, Ic, Id, Ie and If), or a stereoisomer thereof, or a pharmaceutically acceptable salt thereof disclosed herein.

Also disclosed herein is a method of treating cancer responsive to inhibition of IDO and/or TDO comprising administering to a subject, such as a mammal or human, in need of treating for the cancer a pharmaceutically-effective amount of a compound selected from compounds of (Ia, Ib, Ic, Id, Ie and If), or a stereoisomer thereof, or a pharmaceutically acceptable salt thereof disclosed herein, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

Also disclosed herein is a use of a compound selected from compounds of (Ia, Ib, Ic, Id, Ie and If), or a stereoisomer thereof, or a pharmaceutically acceptable salt thereof disclosed herein in the manufacture of a medicament for the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

Also disclosed herein is a compound selected from compounds of (Ia, Ib, Ic, Id, Ie and If), or a stereoisomer thereof, or a pharmaceutically acceptable salt thereof disclosed herein for use in the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

The compound selected from compounds of Formulas (Ia, Ib, Ic, Id, Ie and If), or a stereoisomer thereof, or a pharmaceutically acceptable salt thereof may be employed alone or in combination with at least one other therapeutic agent for treatment. In some embodiments, the compound selected from compounds of Formulas (Ia, Ib, Ic, Id, Ie and If), or a stereoisomer thereof, or a pharmaceutically acceptable salt thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-α and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); Trametinib (GSK1120212); Selumetinib (AZD6244); Binimetinib (MEK162); Pimasertib; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gammaII and calicheamicin omegaII (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin;

capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goserelin; as well as troxacitabine (a 1,3-dioxolane nucleoside cytosine analog); (iv) protein kinase inhibitors such as MEK1/2 inhibitors, for example, trametinib, selumetinib, pimasertib and GDC-0973; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER$^2$ expression inhibitors; (viii) anti-retroviral protease inhibitors, such as lopinavir, indinavir, nelfinavir, amprenavir, darunavir and atazanavir; (ix) vaccines such as gene therapy vaccines, for example, ALLOVECTIN, LEUVECTIN, and VAXID; PROLEUKIN® rIL-2; a topoisomerase 1 inhibitor such as LURTOTECAN®; ABARELIX® rmRH; (x) anti-angiogenic agents such as bevacizumab (AVASTIN®, Genentech); and (xi) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the compound selected from compounds of Formulas (IA) and/or (IB), stereoisomers thereof, and pharmaceutically acceptable salt thereofmay, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, elotuzumab, epratuzumab, erlizumab, felvizumab, fontolizumab, gemtuzumab ozogamicin, inotuzumab ozogamicin, ipilimumab, labetuzumab, lintuzumab, mpdl3280A, matuzumab, medi4736, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, Pembroluzima, pertuzumab, pexelizumab, ralivizumab, ranibizumab, reslivizumab, reslizumab, resyvizumab, rovelizumab, rupliuzumab, sibrotuzumab, siplizumab, sontuzumab, tacatuzumab tetraxetan, tadocizumab, talizumab, tefibazumab, tocilizumab, toralizumab, trastuzumab, tremelizumab, tucotuzumab celmoleukin, tucusituzumab, umavizumab, urtoxazumab, and visilizumab.

In the sixth aspect, disclosed herein is a pharmaceutical composition comprising a compound selected from compounds of Formulas (Ia, Ib, Ic, Id, Ie and If), or a stereoisomer thereof, or a pharmaceutically acceptable salt thereof disclosed herein and a pharmaceutically-acceptable excipient, e.g., a carrier, a diluent, or a adjuvant.

Also disclosed herein is a composition comprising a compound selected from compounds of Formulas (a, Ib, Ic, Id, Ie and If), or a stereoisomer thereof, or a pharmaceutically acceptable salt thereof, and at least one pharmaceutically acceptable excipient.

The composition comprising a compound selected from compounds of Formulas (IA) and/or (IB), or a stereoisomer thereof, or a pharmaceutically acceptable salt thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound selected from Formulas (Ia, Ib, Ic, Id, Ie and If), or a stereoisomer thereof, or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound selected from compounds of Formulas (Ia, Ib, Ic, Id, Ie and If), or a stereoisomer thereof, or a pharmaceutically acceptable salt thereof disclosed herein can also be administered parenterally, in sterile liquid dosage forms, such as dispersions, suspensions or solutions. Other dosages forms that can also be used to administer the compound selected from Formulas (Ia, Ib, Ic, Id, Ie and If), or a stereoisomer thereof, or a pharmaceutically acceptable salt thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, suitable oil, saline, aqueous dextrose (glucose), and related sugar solutions and glycols such as propylene glycol or polyethylene glycols can be Examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be Examples of suitable stabilizing agents. Citric acid and its salts and sodium EDTA can also be used as Examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The compound selected from compounds of Formulas (Ia, Ib, Ic, Id, Ie and If), or a stereoisomer thereof, or a pharmaceutically acceptable salt thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound selected from compounds of Formulas (Ia, Ib, Ic, Id, Ie and If), or a stereoisomer thereof, or a pharmaceutically acceptable salt thereof disclosed herein may be conveniently delivered in the form of an aerosol spray presentation from pressurized packs or nebulisers. The compound selected from compounds of Formulas (Ia, Ib, Ic, Id, Ie and If), or a stereoisomer thereof, or a pharmaceutically acceptable salt thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound selected from compounds of Formulas (Ia, Ib, Ic, Id, Ie and If), or a stereoisomer thereof, or a pharmaceutically acceptable salt thereof disclosed herein in at least one suitable propellant, selected, for example, from fluorocarbons and hydrocarbons.

For ocular administration, an ophthalmic preparation may be formulated with an appropriate weight percentage of a solution or suspension of the compound selected from compounds of Formulas (Ia, b, Ic, Id, Ie and If), or a stereoisomer thereof, or a pharmaceutically acceptable salt thereof disclosed herein in an appropriate ophthalmic vehicle, such that the compound selected from compounds of Formulas (Ia, b, Ic, Id, Ie and If), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the compound selected from compounds of Formulas (Ia, Ib, Ic, Id, Ie and If), or a stereoisomer thereof, or a pharmaceutically acceptable salt thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the compound selected from compounds of Formulas (Ia, b, Ic, Id, Ie and If), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound selected from compounds of Formulas (Ia, Ib, Ic, Id, Ie and If), or a stereoisomer thereof, or a pharmaceutically acceptable salt thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound selected from compounds of Formulas (Ia, b, Ic, Id, Ie and If), or a stereoisomer thereof, or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided a compound selected from compounds of Formulas (Ia, Ib, Ic, Id, Ie and If), or a stereoisomer thereof, or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound selected from compounds of Formulas (Ia, b, Ic, Id, Ie and If), or a stereoisomer thereof, or a pharmaceutically acceptable salt thereof are administered stepwise or in conjunction with at least one other therapeutic agent. When drugs are administered in physical combination, the dosage form and administration route should be selected depending on the compatibility of the combined drugs. Thus the term "coadministration" is understood to include the administration of at least two agents concomitantly or sequentially, or alternatively as a fixed dose combination of the at least two active components.

The compound selected from compounds of Formulas (Ia, Ib, Ic, Id, Ie and If), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

EXAMPLES

The Examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra were recorded on a Varian instrument operating at 400 MHz. $^1$H-NMR spectra were obtained using CDCl$_3$, CD$_2$Cl$_2$, CD$_3$OD, D$_2$O, d$_6$-DMSO, d$_6$-acetone or (CD$_3$)$_2$CO as solvent and tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm; d$_6$-acetone: 2.05; (CD$_3$)$_2$CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following Examples, the abbreviations below are used:
AcOH Acetic acid
Aq Aqueous
Brine Saturated aqueous sodium chloride solution
Bn Benzyl
BnBr Benzyl Bromide
Boc Tert-butyloxycarbonyl
Cbz benzyloxycarbonyl
CH$_2$Cl$_2$ Dichloromethane
DMF N,N-Dimethylformamide
Dppf 1,1''-bis(diphenylphosphino)ferrocene DBU 1,8-diazabicyclo[5.4.0]undec-7-ene
DIEA or DIPEA N,N-diisopropylethylamine
DIBAL-H Diisobutylaluminium hydride
DMAP 4-N,N-dimethylaminopyridine
DMF N,N-dimethylformamide
DMSO Dimethyl sulfoxide
EA or EtOAc Ethyl acetate
EtOH Ethanol
Et$_2$O or ether Diethyl ether
g Grams
h or hr Hour
HATU O-(7-Azabenzotriazol-1-yl)-N,N,N',N'-tetramethyluronium hexafluorophosphate
HBTU O-(7-Azabenzotriazol-1-yl)-N,N,N',N'-tetramethyluronium hexafluorophosphate
HCl Hydrochloric acid
Hex Hexane
HPLC High-performance liquid chromatography
IPA 2-propanol
i-PrOH Isopropyl alcohol
mg Milligrams
mL Milliliters
Mmol Millimole
MeCN Acetonitrile
MeOH Methanol
Min Minutes
ms or MS Mass spectrum
Na$_2$SO$_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THE Tetrahydrofuran
TLC thin layer chromatography
Ts para-toluenesulfonyl
TBS tert-butyldimethylsilyl
μL Microliters Synthesis of substituted benzo[d]imidazols Example A1a: 4-(4-((5-chloro-1H-benzo[d]imidazol-2-yl)methyl)cyclohexyl)-6-fluoroquinoline

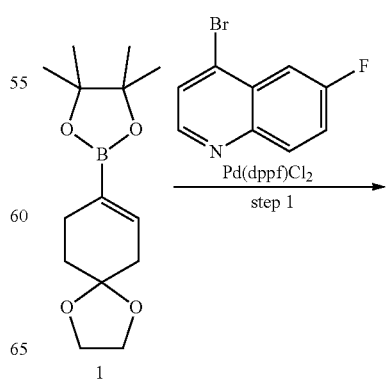

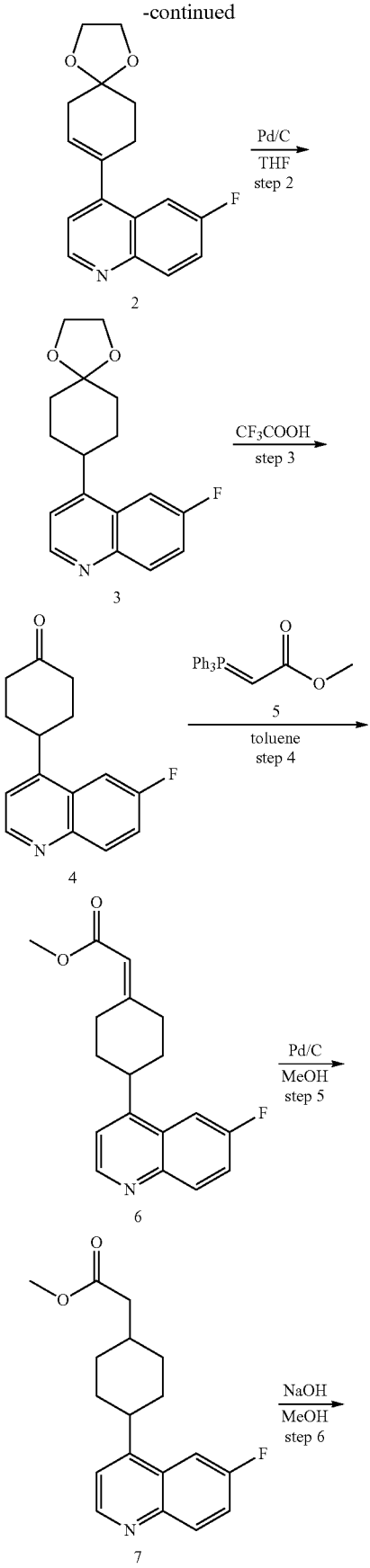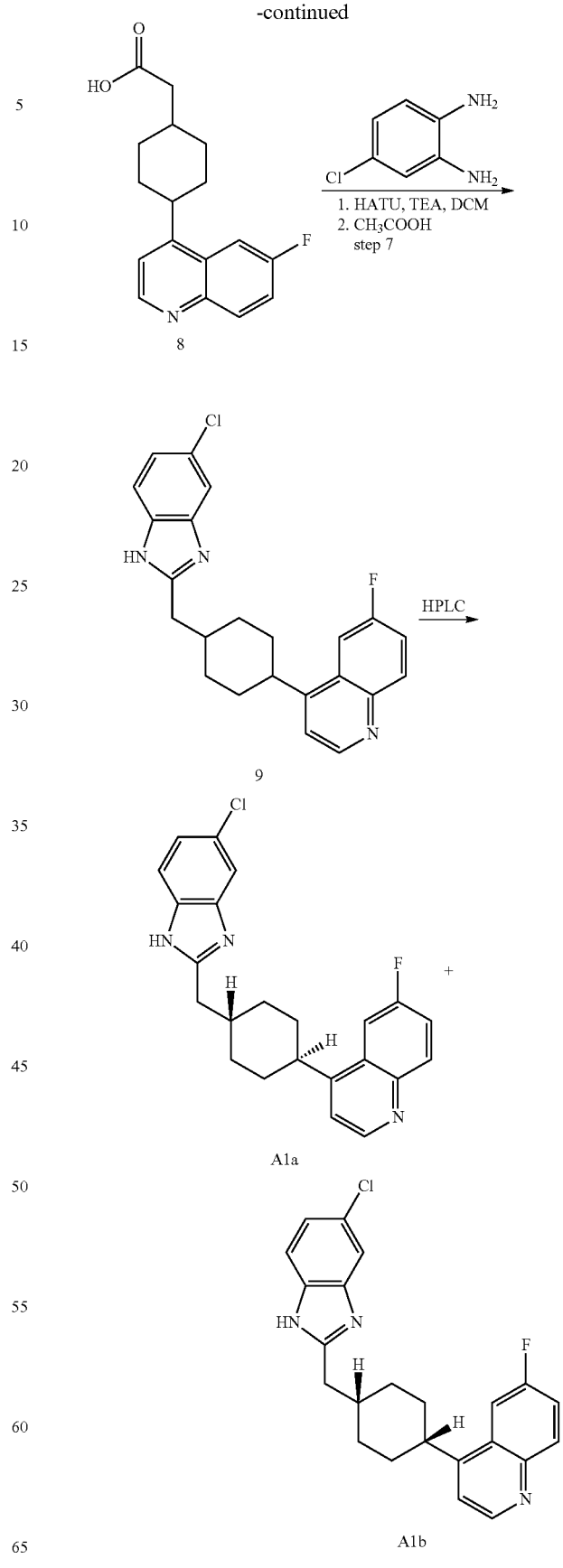

Step 1: 6-fluoro-4-(1,4-dioxaspiro[4.5]dec-7-en-8-yl)quinoline

To a solution of 4,4,5,5-tetramethyl-2-(1,4-dioxaspiro[4.5]dec-7-en-8-yl)-1,3,2-dioxaborolane (13.3 g, 50 mmol, 1.00 eq) dissolved in 1,4-dioxane (250 ml) and water (1 ml), 4-bromo-6-fluoroquinoline (11.3 g, 50 mmol, 1.00 eq), Pd(dppf)Cl$_2$ (5.50 g, 7.5 mmol, 0.15 eq) and Cs$_2$CO$_3$ (24.38 g, 75 mmol, 1.50 eq) were added. The mixture was stirred at 90° C. overnight under N$_2$. TLC showed the starting material was disappeared completely, then the solvent was evaporated under reduced pressure. The crude was purified by column chromatography on silica gel 100 g (PE/EA=4/1 to 2/1) to give the title compound (12.43 g, 87% yield) as a pale-yellow oil. $^1$H NMR (CDCl$_3$) $\delta_H$ 8.80 (d, J=4.4 Hz, 1H), 8.05-8.15 (m, 1H), 7.60-7.66 (m, 1H), 7.43-7.50 (m, 1H), 7.24 (d, J=4.4 Hz, 1H), 5.73-5.77 (m, 1H), 4.05-4.08 (m, 4H), 2.59-2.65 (m, 2H), 2.52-2.55 (m, 2H) and 1.99 (t, J=6.4 Hz, 2H).

Step 2: 6-fluoro-4-(1,4-dioxaspiro[4.5]decan-8-yl)quinoline

To a mixture of 6-fluoro-4-(1,4-dioxaspiro[4.5]dec-7-en-8-yl)quinoline (12.43 g, 44 mmol, 1.00 eq) in THF (100 ml), Pd/C (2.48 g, 20% w.t.) was added. The mixture was stirred at room temperature under one hydrogen balloon protection for 48 hours. The solution was filtered and concentrated to give the crude product (12.50 g, 100% yield), which was used for next step without further purification. $^1$H NMR (CDCl$_3$) $\delta_H$ 8.77 (d, J=4.4 Hz, 1H), 8.09-8.19 (m, 1H), 7.62-7.68 (m, 1H), 7.42-7.50 (m, 1H), 7.33 (d, J=4.8 Hz, 1H), 3.96-4.01 (m, 4H), 3.16-3.24 (m, 1H), 1.89-1.99 (m, 5H) and 1.75-1.86 (m, 3H).

Step 3: 4-(6-fluoroquinolin-4-yl)cyclohexan-1-one 6-fluoro-4-(1,4-dioxaspiro[4.5]decan-8-yl)quinoline (12.5 g, 43.5 mmol, 1.00 eq) was dissolved in CF$_3$COOH (150 ml) and the mixture was stirred at 70° C. under nitrogen protection for 48 hours. The solvent was concentrated to dryness. The crude was added to saturated Na$_2$CO$_3$ aqueous solution 300 mL and extracted with EA (200 ml×3). The organic layer was combined, dried over Na$_2$SO$_4$, filtered and concentrated to give the crude product (10.35 g), which was used for next step without further purification. $^1$H NMR (CDCl$_3$) $\delta_H$ 8.87 (d, J=4.4 Hz, 1H), 8.16-8.27 (m, 1H), 7.70-7.80 (m, 1H), 7.51-7.60 (m, 1H), 7.34 (d, J=4.4 Hz, 1H), 3.64-3.76 (m, 1H), 2.57-2.74 (m, 4H), 2.34-2.42 (m, 2H) and 2.02-2.09 (m, 2H).

Step 4: methyl 2-(4-(6-fluoroquinolin-4-yl)cyclohexylidene)acetate

To a mixture of 4-(6-fluoroquinolin-4-yl)cyclohexan-1-one (10.33 g, 43 mmol, 1.00 eq) dissolved in toluene (250 ml), compound 5 (28.4 g, 85 mmol, 2.00 eq) and TEA (8.58 g, 85 mmol, 2.00 eq) were added. And the mixture was stirred at 100° C. for overnight. Then the mixture was cooled to room temperature and concentrated to dryness. The crude product was purified by column chromatography on silica gel 100 g (PE/EA=5/1) to give a clear oil (7.00 g, 55% yield). $^1$H NMR (CDCl$_3$) $\delta_H$ 8.79-8.86 (m, 1H), 8.05-8.50 (m, 1H), 7.72-7.80 (m, 1H), 7.51-7.61 (m, 1H), 7.30-7.42 (m, 1H), 5.76 (s, 1H), 3.73 (s, 3H), 3.45-3.54 (m, 1H), 2.48-2.57 (m, 2H), 2.14-2.30 (m, 3H), 1.68-1.85 (m, 2H) and 1.24-1.29 (m, 1H).

Step 5: methyl 2-(4-(6-fluoroquinolin-4-yl)cyclohexyl)acetate

To a mixture of methyl 2-(4-(6-fluoroquinolin-4-yl)cyclohexylidene)acetate (7.00 g, 23 mmol, 1.00 eq) in MeOH (100 ml), Pd/C (2.10 g, w.t. 30%) was added. The mixture was stirred at room temperature under hydrogen (one balloon) for 45 hours. The solution was filtered and concentrated to dryness. The crude product (5.40 g, 76% yield) was used for next step without further purification. $^1$H NMR (CDCl$_3$) $\delta_H$ 8.76-8.85 (m, 1H), 8.04-8.17 (m, 1H), 7.60-7.69 (m, 1H), 7.42-7.49 (m, 1H), 7.26-7.32 (m, 1H), 3.70 (s, 3H), 3.07-3.19 (m, 1H), 2.24-2.45 (m, 2H), 1.96-2.05 (m, 3H), 1.74-1.85 (m, 2H), 1.52-1.72 (m, 2H) and 1.21-1.43 (m, 2H).

Step 6: 2-(4-(6-fluoroquinolin-4-yl)cyclohexyl)acetic acid

To a mixture of methyl 2-(4-(6-fluoroquinolin-4-yl)cyclohexyl)acetate (5.40 g, 18 mmol, 1.00 eq) in MeOH (20 ml), NaOH (2 N, 10 mL, 1.10 eq) was added. The mixture was stirred at room temperature for 2 hours. The solvent was concentrated to 10 ml and extracted with EA (20 ml×3) to remove the impurities. The water layer was concentrated to 5 ml. The water layer was neutralized with 1 N HCl to make the PH to 7. Then some white solid was precipitated, filtered and washed with water (1 ml) to get a white solid (2.94 g, 57% yield). $^1$H NMR (DMSO-d$_6$) $\delta_H$ 12.04 (s, 1H), 8.78-8.84 (m, 1H), 8.05-8.11 (m, 1H), 7.93-8.00 (m, 1H), 7.63-7.70 (m, 1H), 7.44-7.55 (m, 1H), 3.24-3.31 (m, 1H), 2.40-2.47 (m, 1H), 2.17-2.20 (m, 1H), 1.90-1.95 (m, 4H), 1.50-1.75 (m, 4H) and 1.31-1.38 (m, 1H).

Step 7: 4-((1r,4r)-4-((5-chloro-1H-benzo[d]imidazol-2-yl)methyl)cyclohexyl)-6-fluoroquinoline and 4-((1s,4s)-4-((5-chloro-1H-benzo[d]imidazol-2-yl)methyl)cyclohexyl)-6-fluoroquinoline

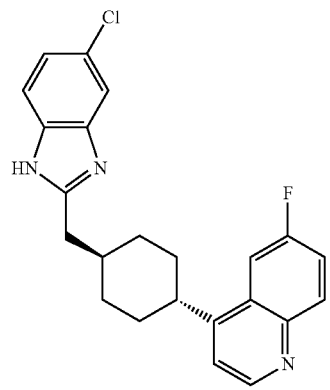

A1a

-continued

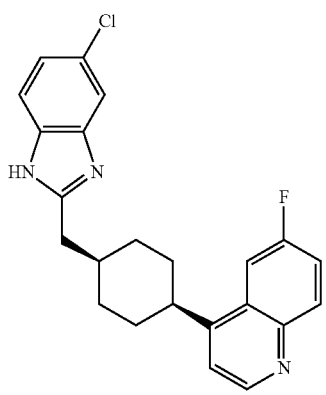

A1b

To a mixture of 2-(4-(6-fluoroquinolin-4-yl)cyclohexyl)acetic acid (0.57 g, 2 mmol, 1.00 eq) in DCM (20 ml), 4-chlorobenzene-1,2-diamine (0.28 g, 2 mmol, 1.00 eq), HATU (0.76 g, 2 mmol, 1.00 eq) and TEA (0.40 g, 4 mmol, 2.00 eq) were added. The mixture was stirred at room temperature overnight. The solvent was extracted with saturated NH$_4$Cl aqueous solution (50 ml×3). The organic layer was dried over Na$_2$SO$_4$, filtered and concentrated to dryness. The crude was dissolved in CH$_3$COOH (20 ml) and stirred at 100° C. for 2 hours. Then the mixture was concentrated to dryness. The crude product was added to saturated Na$_2$CO$_3$ aqueous solution 50 mL and extracted with DCM (40 ml×3). The organic layer was combined, dried over Na$_2$SO$_4$, filtered and concentrated to dryness. The crude product was purified by pre-HPLC to give the desired two compounds: A1a (123 mg, 16% yield): $^1$H NMR (DMSO-d$_6$) δ$_H$ 8.81 (d, J=4.4 Hz, 1H), 8.04-8.12 (m, 1H), 7.95-8.02 (m, 1H), 7.59-7.72 (m, 2H), 7.55 (m, J=8.8 Hz, 1H), 7.41-7.47 (m, 1H), 7.17-7.25 (m, 1H), 3.28-3.37 (m, 1H), 2.85 (d, J=7.2 Hz, 2H), 1.95-2.06 (m, 1H), 1.80-1.95 (m, 4H) and 1.33-1.64 (m, 4H). A1b (287 mg, 36% yield): $^1$H NMR (CDCl$_3$) δ$_H$ 8.78 (d, J=4.4 Hz, 1H), 8.06-8.14 (m, 1H), 7.56-7.64 (m, 2H), 7.52 (d, J=8.4 Hz, 1H), 7.41-7.49 (m, 1H), 7.18-7.26 (m, 2H), 3.06-3.17 (m, 1H), 2.95 (d, J=6.8 Hz, 2H), 1.90-2.14 (m, 5H), 1.49-1.64 (m, 2H) and 1.30-1.46 (m, 2H).

Compounds A2 to A37 were prepared in a procedure similar to Example A1a.

Example A2a: 6-fluoro-4-((1r,4r)-4-((5-methyl-1H-benzo[d]imidazol-2-yl)methyl)cyclohexyl)quinoline

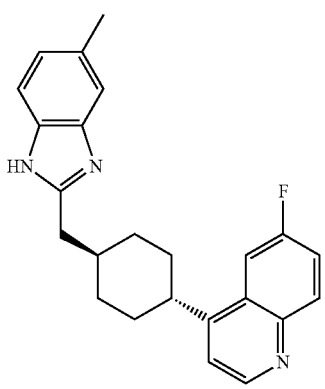

$^1$H NMR (DMSO-d6) δ 12.29 (s, 1H), 8.80 (d, J=4.8 Hz, 1H), 8.08 (dd, J=9.2, 6.0 Hz, 1H), 7.99 (dd, J=10.8, 2.4 Hz, 1H), 7.70-7.62 (m, 2H), 7.44 (d, J=4.4 Hz, 2H), 7.29 (d, J=8.0 Hz, 1H), 7.02 (t, J=7.4 Hz, 2H), 6.92 (d, J=7.2 Hz, 1H), 2.80 (d, J=3.2 Hz, 3H), 2.05-1.95 (m, 2H), 1.91-1.84 (m, 6H), 1.62-1.63 (m, 4H), 1.48-1.39 (m, 4H), MS (ESI) m/e [M+1]+ 374.

Example A2b: 6-fluoro-4-((1s,4s)-4-((5-methyl-1H-benzo[d]imidazol-2-yl)methyl)cyclohexyl)quinoline

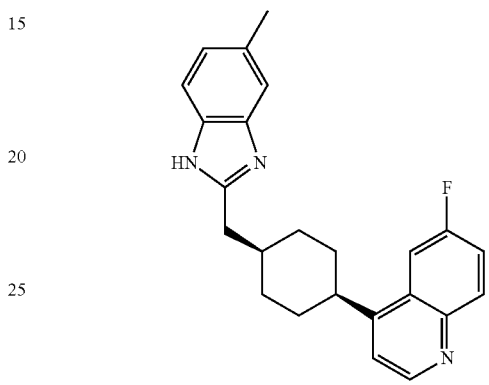

$^1$H NMR (DMSO-d6) δ 12.16 (s, 1H), 8.87 (d, J=4.4 Hz, 1H), 8.10 (dd, J=9.2, 5.6 Hz, 1H), 7.99 (dd, J=10.8, 2.8 Hz, 1H), 7.67 (td, J=8.4, 2.4 Hz, 1H), 7.59 (d, J=4.8 Hz, 1H), 7.29 (d, J=6.8 Hz, 1H), 7.00 (t, J=7.6 Hz, 1H), 6.91 (d, J=7.2 Hz, 1H), 3.02 (d, J=8.0 Hz, 2H), 2.51-2.49 (m, 4H), 1.91-1.82 (m, 5H), 1.68 (d, J=8.5 Hz, 5H), MS (ESI) m/e [M+1]+ 374.

Example A3a: 6-fluoro-4-((1s,4s)-4-((5-(trifluoromethyl)-1H-benzo[d]imidazol-2-yl)methyl)cyclohexyl)quinoline

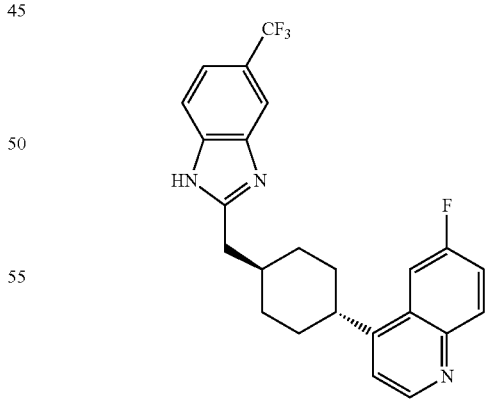

$^1$H NMR (DMSO-d6) δ 12.68 (s, 1H), 8.87 (d, J=4.4 Hz, 1H), 8.10 (dd, J=9.2, 6.0 Hz, 1H), 7.99 (dd, J=10.8, 2.4 Hz, 1H), 7.90 (s, 1H), 7.81-7.62 (m, 3H), 7.59 (d, J=4.4 Hz, 1H), 7.45 (t, J=8.4 Hz, 1H), 3.45-3.35 (m, 1H), 3.09 (d, J=8.0 Hz, 2H), 1.89-1.86 (m, 4H), 1.71-1.65 (m, 4H), MS (ESI) m/e [M+1]+ 428;

Example A3b: 6-fluoro-4-((1r,4r)-4-((5-(trifluoromethyl)-1H-benzo[d]imidazol-2-yl)methyl)cyclohexyl)quinoline

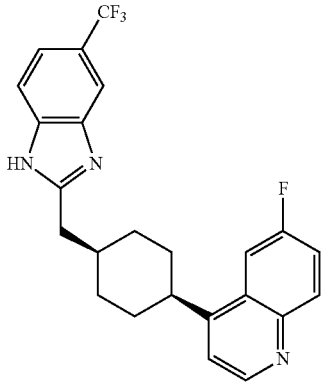

¹H NMR (DMSO-d6) δ 8.81 (d, J=4.4 Hz, 1H), 8.09 (dd, J=9.2, 6.0 Hz, 1H), 7.99 (dd, J=10.8, 2.4 Hz, 1H), 7.88 (s, 1H), 7.75-7.61 (m, 2H), 7.50-7.45 (m, 2H), 3.39-3.29 (m, 1H), 2.87 (d, J=7.2 Hz, 2H), 2.03 (s, 1H), 1.88 (t, J=13.8 Hz, 4H), 1.62-1.54 (m, 2H), 1.49-1.40 (m, 2H), MS (ESI) m/e [M+1]+ 428.

Example A4a: 4-((1r,4r)-4-((5-cyclopropyl-1H-benzo[d]imidazol-2-yl)methyl)cyclohexyl)-6-fluoroquinoline

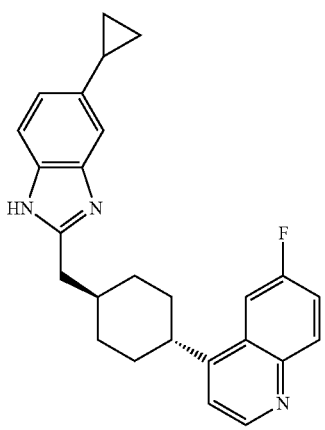

¹H NMR (400 MHz, DMSO-d) δH 12.12 (s, 1H), 8.80 (d, J=4.4 Hz, 1H), 8.08 (dd, J=9.2, 6.0 Hz, 1H), 7.98 (dd, J=10.8, 2.8 Hz, 1H), 7.68-7.63 (m, 1H), 7.44 (d, J=4.4 Hz, 1H), 7.34 (d, J=8.2 Hz, 1H), 7.15 (s, 1H), 6.87 (d, J=7.6 Hz, 1H), 3.33-3.31 (m, 1H), 2.76 (d, J=7.2 Hz, 2H), 2.02-1.82 (m, 5H), 1.62-1.33 (m, 5H), 0.91-0.85 (m, 2H), 0.68-0.61 (m, 2H). [M+H]⁺=400.2.

Example A4b: 4-((1s,4s)-4-((5-cyclopropyl-1H-benzo[d]imidazol-2-yl)methyl)cyclohexyl)-6-fluoroquinoline

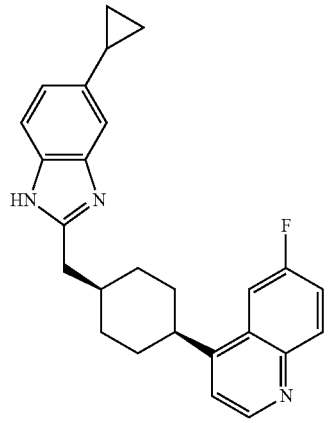

1H NMR (400 MHz, DMSO-d) δ$_H$ 12.06 (s, 1H), 8.86 (d, J=4.4 Hz, 1H), 8.10 (dd, J=9.2, 6.0 Hz, 1H), 7.98 (dd, J=10.8, 2.4 Hz, 1H), 7.73-7.64 (m, 1H), 7.58 (d, J=4.4 Hz, 1H), 7.34 (d, J=8.0 Hz, 1H), 7.15 (s, 1H), 6.86 (d, J=8.4 Hz, 1H), 3.38 (br, 1H), 2.99 (d, J=8.0 Hz, 2H), 2.02-1.95 (m, 1H), 1.86-1.84 (m, 4H), 1.71-1.59 (m, 4H), 1.42-1.33 (m, 1H), 0.93-0.85 (m, 2H), 0.66-0.63 (m, 2H). [M+H]⁺=400.2.

Example A5a: 6-fluoro-4-((1r,4r)-4-((5-isopropyl-1H-benzo[d]imidazol-2-yl)methyl)cyclohexyl)quinoline ¹H NMR (400 MHz, DMSO-d) δ$_H$ 12.16 (s, 1H), 8.80 (d, J=4.8 Hz, 1H), 8.10-7.97 (m, 2H), 7.68-7.64 (m, 1H), 7.45-7.27 (m, 3H), 7.02 (d, J=8.4 Hz, 1H), 3.33 (br, 1H), 3.01-2.95 (m, 1H), 2.77 (d, J=6.8 Hz, 2H), 1.99-1.84 (m, 5H), 1.61-1.43 (m, 4H), 1.24 (d, J=6.8 Hz, 6H). [M+H]+=402.2.

Example A5b: 6-fluoro-4-((1s,4s)-4-((5-isopropyl-1H-benzo[d]imidazol-2-yl)methyl)cyclohexyl)quinoline

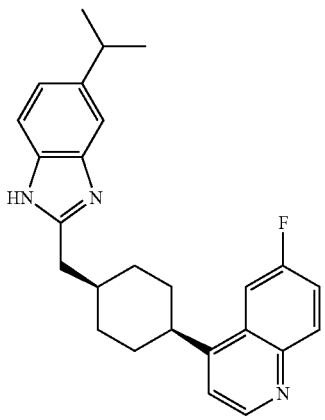 [SMILES: CC(C)c1ccc2[nH]c(C[C@H]3CC[C@@H](c4ccnc5ccc(F)cc54)CC3)nc2c1]

¹H NMR (400 MHz, DMSO-d) δ$_H$ 12.06 (s, 1H), 8.86 (d, J=4.4 Hz, 1H), 8.12-8.06 (m, 1H), 7.98 (d, J=10.8 Hz, 1H), 7.71-7.65 (m, 1H), 7.58 (d, J=4.4 Hz, 1H), 7.37 (br, 2H), 7.01 (d, J=8.4 Hz, 1H), 3.39 (br, 1H), 3.03-2.89 (m, 3H), 2.44 (br, 1H), 1.87-1.85 (m, 4H), 1.69-1.64 (m, 4H), 1.24 (d, J=6.4 Hz, 6H). [M+H]+=402.2.

Example A6a: 4-((1r,4r)-4-((5,6-difluoro-1H-benzo[d]imidazol-2-yl)methyl)cyclohexyl)-6-fluoroquinoline

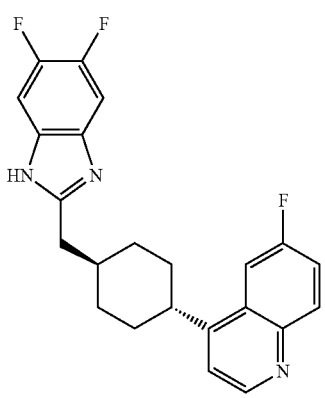 [SMILES: Fc1ccc2nccc([C@H]3CC[C@H](Cc4nc5cc(F)c(F)cc5[nH]4)CC3)c2c1]

¹H NMR (400 MHz, DMSO-d6): δ$_H$ 12.44 (s, 1H), 8.78 (d, J=4.8 Hz, 1H), 8.06 (dd, J=9.2, 6.0 Hz, 1H), 7.96 (dd, J=11.2, 2.8 Hz, 1H), 7.70-7.32 (m, 4H), 3.31-3.29 (m, 1H), 2.76 (d, J=6.8 Hz, 2H), 2.00-1.78 (m, 5H), 1.59-1.34 (m, 4H). [M+H]+=396.1

Example A6b: 4-((1s,4s)-4-((5,6-difluoro-1H-benzo[d]imidazol-2-yl)methyl)cyclohexyl)-6-fluoroquinoline

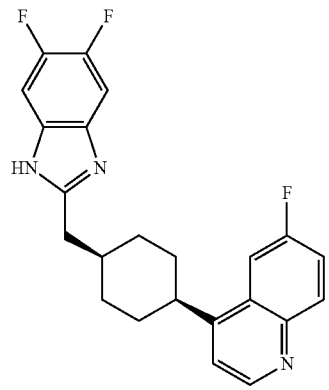 [SMILES: Fc1ccc2nccc([C@H]3CC[C@@H](Cc4nc5cc(F)c(F)cc5[nH]4)CC3)c2c1]

¹H NMR (400 MHz, DMSO-d6): δ$_H$ 12.44 (s, 1H), 8.84 (d, J=4.4 Hz, 1H), 8.08 (dd, J=9.2, 5.6 Hz, 1H), 7.97 (dd, J=11.2, 2.8 Hz, 1H), 7.70-7.45 (m, 4H), 3.36-3.33 (m, 1H), 3.00 (d, J=8.0 Hz, 2H), 2.42 (br, 1H), 1.86-1.82 (m, 4H), 1.70-1.59 (m, 4H). [M+H]+=396.1

Example A7a: 6-(((1r,4r)-4-(6-fluoroquinolin-4-yl)cyclohexyl)methyl)-5H-[1,3]dioxolo[4',5':4,5]benzo[1,2-d]imidazole

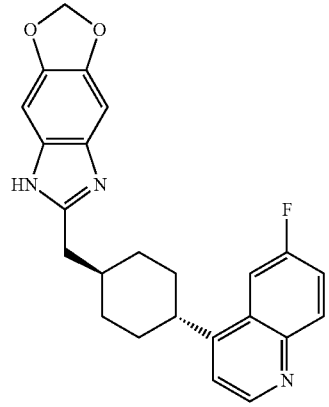 [SMILES: Fc1ccc2nccc([C@H]3CC[C@H](Cc4nc5cc6c(cc5[nH]4)OCO6)CC3)c2c1]

¹H NMR (400 MHz, DMSO-d) δH 12.21 (s, 1H), 8.78 (s, 1H), 8.06 (br, 1H), 7.96 (d, J=10.8 Hz, 1H), 7.64 (br, 1H), 7.42 (s, 1H), 7.00 (s, 2H), 5.94 (s, 2H), 3.27-3.19 (br, 1H), 2.71-2.69 (m, 2H), 1.96-1.75 (m, 5H), 1.56-1.36 (m, 4H). [M+H]+=404.1.

Example A7b: 6-(((1s,4s)-4-(6-fluoroquinolin-4-yl)cyclohexyl)methyl)-5H-[1,3]dioxolo[4',5':4,5]benzo[1,2-d]imidazole

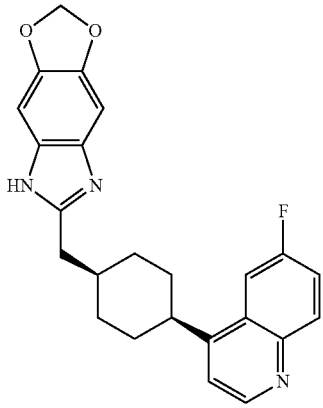 [SMILES: Fc1ccc2nccc([C@H]3CC[C@@H](Cc4nc5cc6c(cc5[nH]4)OCO6)CC3)c2c1]

¹H NMR (400 MHz, DMSO-d) δ$_H$ 12.03 (s, 1H), 8.86 (s, 1H), 8.12-8.06 (m, 1H), 7.98 (d, J=10.8 Hz, 1H), 7.70-7.62 (m, 1H), 7.58-7.56 (m, 1H), 7.04-6.97 (m, 2H), 5.95 (d, J=3.6 Hz, 2H), 3.38 (br, 1H), 2.95-2.92 (m, 2H), 2.40 (br, 1H), 1.88-1.61 (m, 8H). [M+H]+=404.1.

Example A8a: 4-((1r,4r)-4-((5-cyclopropoxy-1H-benzo[d]imidazol-2-yl)methyl)cyclohexyl)-6-fluoroquinoline

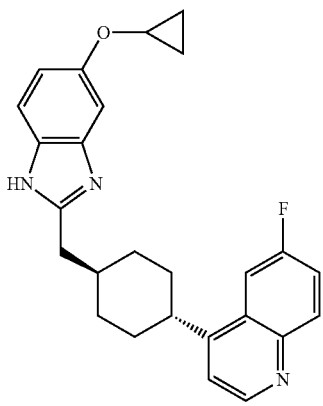 [SMILES: Fc1ccc2nccc([C@H]3CC[C@H](Cc4nc5cc(OC6CC6)ccc5[nH]4)CC3)c2c1]

¹H NMR (400 MHz, DMSO-d) δ$_H$ 12.04 (s, 1H), 8.80 (s, 1H), 8.17-7.88 (m, 2H), 7.71-7.66 (m, 1H), 7.45-7.11 (m, 3H), 6.78 (br, 1H), 3.83 (br, 1H), 3.31 (br, 1H), 2.75 (s, 2H), 1.91-1.84 (m, 5H), 1.58-1.40 (m, 4H), 0.77-0.66 (m, 4H). [M+H]+=416.2.

Example A8b: 4-((1s,4s)-4-((5-cyclopropoxy-1H-benzo[d]imidazol-2-yl)methyl)cyclohexyl)-6-fluoroquinoline

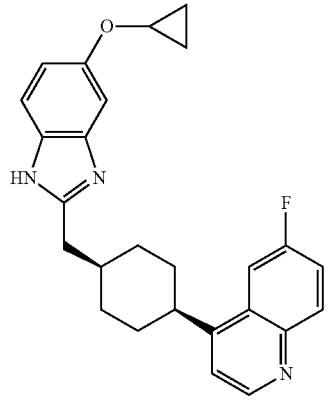 [SMILES: Fc1ccc2nccc([C@H]3CC[C@@H](Cc4nc5cc(OC6CC6)ccc5[nH]4)CC3)c2c1]

¹H NMR (400 MHz, DMSO-d) δ$_H$ 12.05 (s, 1H), 8.87 (s, 1H), 8.15-7.99 (m, 2H), 7.68-7.58 (m, 2H), 7.48-7.08 (m, 2H), 6.77 (s, 1H), 3.83 (s, 1H), 3.39 (s, 1H), 2.98 (s, 2H), 2.43 (s, 1H), 1.87 (s, 4H), 1.69-1.65 (m, 4H), 0.77-0.66 (m, 4H). [M+H]+=416.2.

Example A9a: 4-((1r,4r)-4-((5,6-dimethyl-1H-benzo[d]imidazol-2-yl)methyl)cyclohexyl)-6-fluoroquinoline

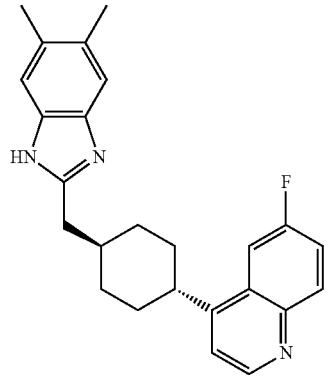 [SMILES: Cc1cc2nc(C[C@H]3CC[C@H](c4ccnc5ccc(F)cc54)CC3)[nH]c2cc1C]

¹H NMR (DMSO-d6) δ 11.91 (s, 1H), 8.80 (d, J=4.4 Hz, 1H), 8.08 (dd, J=9.2, 5.6 Hz, 1H), 7.98 (dd, J=11.2, 2.8 Hz, 1H), 7.66 (td, J=8.4, 2.8 Hz, 1H), 7.44 (d, J=4.4 Hz, 1H), 7.29 (s, 1H), 7.17 (s, 1H), 3.30 (s, 1H), 2.73 (d, J=7.2 Hz, 2H), 2.28 (d, J=6.0 Hz, 6H), 1.92-1.79 (m, 5H), 1.61-1.52 (m, 2H), 1.45-1.36 (m, 2H), MS (ESI) m/e [M+1]+ 388;

Example A9b: 4-((1s,4s)-4-((5,6-dimethyl-1H-benzo[d]imidazol-2-yl)methyl)cyclohexyl)-6-fluoroquinoline

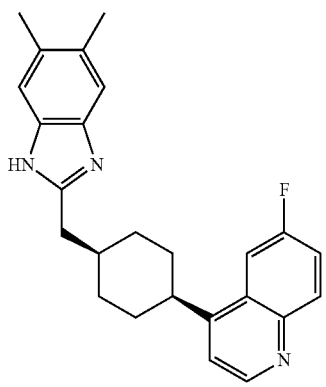 [SMILES: Cc1cc2nc(C[C@H]3CC[C@@H](c4ccnc5ccc(F)cc54)CC3)[nH]c2cc1C]

$^1$H NMR (DMSO-d6) δ 12.31 (s, 1H), 8.86 (d, J=4.4 Hz, 1H), 8.10 (dd, J=9.2, 6.0 Hz, 1H), 7.98 (dd, J=10.8, 2.4 Hz, 1H), 7.67 (td, J=8.8, 2.8 Hz, 1H), 7.57 (d, J=4.8 Hz, 1H), 7.26 (s, 2H), 3.45-3.46 (m, 2H), 3.00 (d, J=8.0 Hz, 3H), 2.29 (s, 7H), 1.86-1.84 (m, 4H), 1.73-1.58 (m, 5H), MS (ESI) m/e [M+1]+ 388;

Example A10a: 4-((1r,4r)-4-((5-chloro-1H-benzo[d]imidazol-2-yl)methyl)cyclohexyl)quinoline

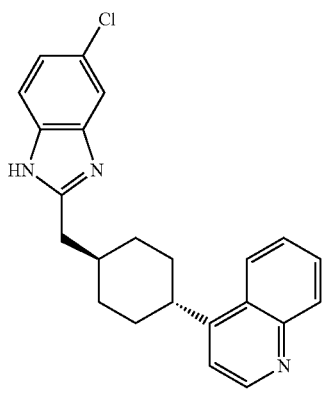 [SMILES: Clc1ccc2[nH]c(C[C@H]3CC[C@H](c4ccnc5ccccc54)CC3)nc2c1]

$^1$H NMR (400 MHz, DMSO-d$_6$) δ$_H$ 12.44 (s, 1H), 8.81 (d, J=4.4 Hz, 1H), 8.22 (d, J=8.4 Hz, 1H), 8.01 (d, J=8.4 Hz, 1H), 7.74 (t, J=7.6 Hz, 1H), 7.62 (t, J=7.6 Hz, 1H), 7.46-7.56 (m, 1H), 7.40 (t, J=4.0 Hz, 1H), 7.11-7.18 (m, 1H), 3.36-3.45 (m, 1H), 2.80 (d, J=7.2 Hz, 2H), 1.95-2.08 (m, 1H), 1.83-1.96 (m, 4H), 1.53-1.65 (m, 2H) and 1.33-1.45 (m, 2H).

Example A10b: 4-((1s,4s)-4-((5-chloro-1H-benzo[d]imidazol-2-yl)methyl)cyclohexyl)quinoline

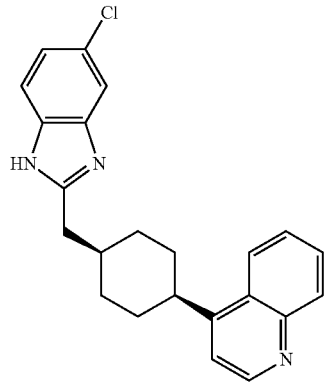 [SMILES: Clc1ccc2[nH]c(C[C@H]3CC[C@@H](c4ccnc5ccccc54)CC3)nc2c1]

$^1$H NMR (400 MHz, DMSO-d$_6$) δ$_H$ 12.46 (s, 1H), 8.87 (d, J=4.8 Hz, 1H), 8.23 (d, J=8.8 Hz, 1H), 8.03 (d, J=8.4 Hz, 1H), 7.75 (t, J=8.0 Hz, 1H), 7.63 (t, J=8.0 Hz, 1H), 7.42-7.59 (m, 3H), 7.09-7.18 (m, 1H), 3.43-3.52 (m, 1H), 3.03 (d, J=8.0 Hz, 2H), 2.43-2.51 (m, 1H), 1.90-1.95 (m, 4H) and 1.60-1.75 (m, 4H).

Example A11a: 4-((1r,4r)-4-((5-bromo-4-methyl-1H-benzo[d]imidazol-2-yl)methyl)cyclohexyl)-6-fluoroquinoline $^1$H NMR (DMSO-d$_6$) δ$_H$ 12.37 (s, 1H), 8.80 (d, J=4.0 Hz, 1H), 8.06-8.10 (m, 1H), 7.96-8.00 (m, 1H), 7.63-7.73 (m, 2H), 7.44 (d, J=4.0 Hz, 1H), 7.27-7.30 (m, 1H), 2.80 (d, J=7.6 Hz, 2H), 2.55 (s, 3H), 1.83-1.99 (m, 4H), 1.52-1.66 (m, 3H), and 1.34-1.48 (m, 3H). [M+H]$^+$=452.

Example A1b: 4-((1s,4s)-4-((5-bromo-4-methyl-1H-benzo[d]imidazol-2-yl)methyl)cyclohexyl)-6-fluoroquinoline

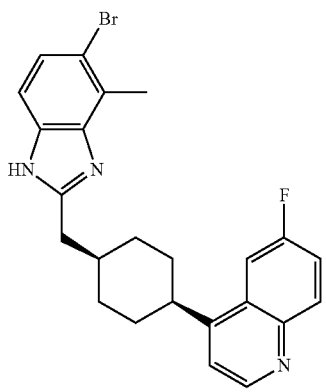 [SMILES: Cc1c(Br)ccc2[nH]c(C[C@H]3CC[C@@H](c4ccnc5ccc(F)cc54)CC3)nc12]

¹H NMR (DMSO-d₆) δ_H 12.36 (s, 1H), 8.87 (d, J=4.0 Hz, 1H), 8.08-8.12 (m, 1H), 7.97-8.01 (m, 1H), 7.64-7.70 (m, 1H), 7.59 (d, J=4.0 Hz, 1H), 7.25-7.26 (m, 2H), 303 (d, J=8.4 Hz, 2H), 2.54 (s, 3H), 1.85-1.88 (m, 4H), and 1.64-1.71 (m, 6H). [M+H]⁺=452.

Example A12: 4-(4-((5,6-dichloro-1H-benzo[d]imidazol-2-yl)methyl)cyclohexyl)-6-fluoroquinoline

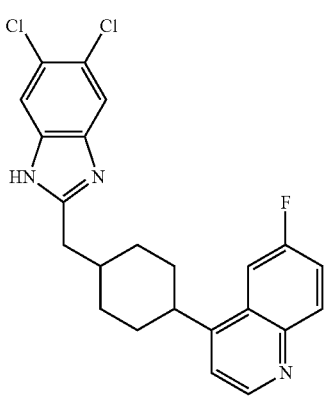 [SMILES: Fc1ccc2nccc(C3CCC(Cc4nc5cc(Cl)c(Cl)cc5[nH]4)CC3)c2c1]

¹H NMR (400 MHz, DMSO-d₆) δ_H 8.85 (d, J=4.4 Hz, 1H), 8.05-8.13 (m, 1H), 7.93-8.01 (m, 1H), 7.63-7.75 (m, 3H), 7.55 (s, 1H), 3.03 (d, J=7.6 Hz, 2H), 2.31-2.47 (m, 2H), 1.77-1.93 (m, 4H), 1.58-1.73 (m, 4H).

Example A13: methyl 2-((4-(6-fluoroquinolin-4-yl)cyclohexyl)methyl)-1H-benzo[d]imidazole-5-carboxylate

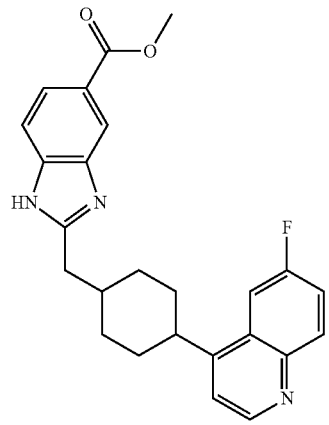 [SMILES: COC(=O)c1ccc2[nH]c(CC3CCC(c4ccnc5ccc(F)cc45)CC3)nc2c1]

¹H NMR (400 MHz, CDCl₃) δ_H 8.80 (d, J=4.4 Hz, 1H), 8.33 (s, 1H), 8.13 (dd, J=9.2, 5.6 Hz, 1H), 8.00 (d, J=8.8 Hz, 1H), 7.60-7.67 (m, 2H), 7.49 (t, J=8.0 Hz, 1H), 7.43 (d, J=4.4 Hz, 1H), 3.92 (s, 3H), 3.24 (d, J=8.0 Hz, 3H), 2.64 (s, 1H), 1.66-1.97 (m, 8H).

Example A14: 2-((4-(6-fluoroquinolin-4-yl)cyclohexyl)methyl)-1H-benzo[d]imidazole-5-carboxylic acid

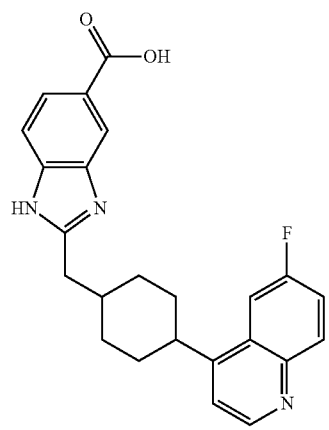 [SMILES: O=C(O)c1ccc2[nH]c(CC3CCC(c4ccnc5ccc(F)cc45)CC3)nc2c1]

¹H NMR (400 MHz, DMSO-d₆) δ_H 12.11 (s, 1H), 8.86 (d, J=4.4 Hz, 1H), 8.10 (dd, J=9.2, 6.0 Hz, 1H), 7.88-8.04 (m, 2H), 7.62-7.77 (m, 2H), 7.59 (d, J=4.4 Hz, 1H), 7.17-7.35 (m, 1H), 3.00 (d, J=7.8 Hz, 2H), 2.53-2.54 (m, 2H), 1.81-1.97 (m, 4H), 1.59-1.76 (m, 4H).

Example A15: 6-fluoro-4-(4-((5-(piperidin-1-ylmethyl)-1H-benzo[d]imidazol-2-yl)methyl)cyclohexyl)quinoline

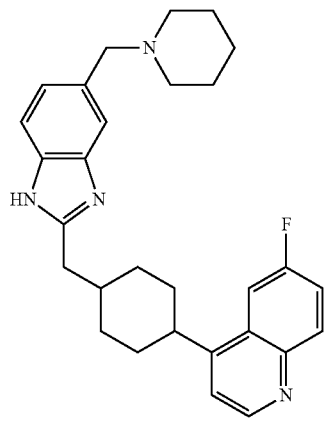 [SMILES: Fc1ccc2nccc(C3CCC(Cc4nc5cc(CN6CCCCC6)ccc5[nH]4)CC3)c2c1]

¹H NMR (DMSO-d₆) δ_H 12.10 (s, 1H), 8.85 (s, 1H), 8.05-8.10 (m, 1H), 7.94-7.96 (m, 1H), 7.61-7.68 (m, 2H), 7.51-7.53 (m, 1H), 7.28-7.37 (m, 1H), 6.99-7.03 (m, 1H), 4.18-4.23 (m, 2H), 23.36-3.48 (m, 3H), 3.00 (d, J=6.4 Hz, 2H), 2.36-2.38 (m, 2H), 1.83-1.85 (m, 4H), 1.58-1.68 (m, 5H), and 1.35-1.51 (m, 6H). [M+H]⁺=457.

Example A16: 4-(4-((6-bromo-5-(piperidin-1-yl)-1H-benzo[d]imidazol-2-yl)methyl)cyclohexyl)-6-fluoroquinoline

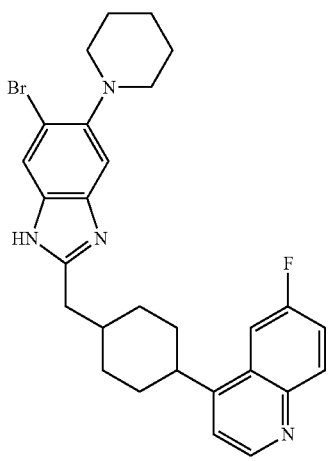 [SMILES: Fc1ccc2nccc(C3CCC(Cc4nc5cc(N6CCCCC6)c(Br)cc5[nH]4)CC3)c2c1]

¹H NMR (DMSO-d₆) δ_H 12.25 (s, 1H), 8.86 (d, J=4.4 Hz, 1H), 8.08-8.12 (m, 1H), 7.97-8.00 (m, 1H), 7.65-7.70 (m, 2H), 7.58 (d, J=4.4 Hz, 1H), 7.20-7.22 (m, 1H), 3.39-3.49 (m, 2H), 2.99 (d, J=7.6 Hz, 2H), 2.86-2.88 (m, 4H), 1.83-1.90 (m, 4H), 1.62-1.69 (m, 8H), and 1.53-1.54 (m, 2H). [M+H]⁺=521.

Example A17: 4-(4-((6-bromo-5-methoxy-1H-benzo[d]imidazol-2-yl)methyl)cyclohexyl)-6-fluoroquinoline

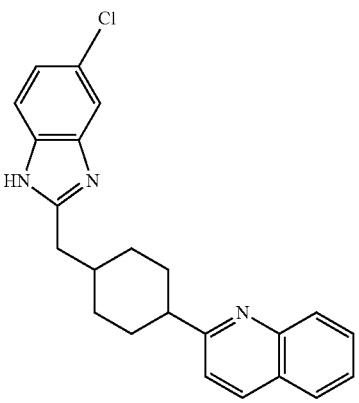 [SMILES: Cl ; Cc1ccc2[nH]c(CC3CCC(c4ccc5ccccc5n4)CC3)nc2c1]

¹H NMR (DMSO-d₆) δ_H 12.24 (s, 1H), 8.86 (d, J=4.0 Hz, 1H), 8.08-8.12 (m, 1H), 7.96-8.01 (m, 1H), 7.62-7.73 (m, 2H), 7.58 (d, J=4.0 Hz, 1H), 7.10 (s, 1H), 3.86 (s, 3H), 3.38-3.40 (m, 1H), 3.00 (d, J=8.0 Hz, 2H), 2.40-2.43 (m, 1H), 1.81-1.89 (m, 4H), and 1.63-1.70 (m, 4H). [M+H]⁺=468.

Example A18: 2-(4-((5-chloro-1H-benzo[d]imidazol-2-yl)methyl)cyclohexyl)quinoline ¹H NMR (400 MHz, DMSO-d₆) δ_H 12.39 (s, 1H), 8.25 (d, J=8.4 Hz, 1H), 7.91 (t, J=7.2 Hz, 2H), 7.70 (t, J=7.2 Hz, 1H), 7.35-7.60 (m, 4H), 7.13 (d, J=8.4 Hz, 1H), 2.85 (t, J=11.6 Hz, 1H), 2.87 (d, J=7.2 Hz, 1H), 1.79-2.03 (m, 5H), 1.59-1.73 (m, 2H) and 1.19-1.32 (m, 2H).

Example A19: 3-(4-((5-chloro-1H-benzo[d]imidazol-2-yl)methyl)cyclohexyl)quinoline

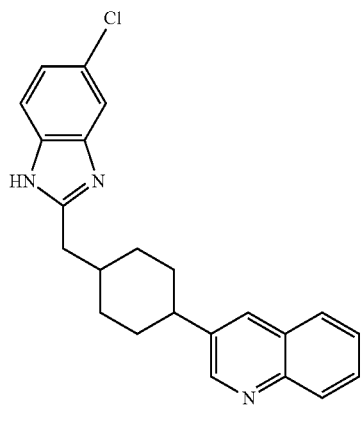 [SMILES: Cl ; Cc1ccc2[nH]c(CC3CCC(c4cnc5ccccc5c4)CC3)nc2c1]

¹H NMR (400 MHz, DMSO-d₆) δ_H 12.46 (s, 1H), 8.84 (s, 1H), 8.13 (s, 1H), 7.88-8.00 (m, 2H), 7.69 (t, J=7.6 Hz, 1H), 7.52-7.62 (m, 2H), 7.45-7.52 (d, J=8.4 Hz, 1H), 7.15 (d, J=8.4 Hz, 1H), 2.70-2.82 (m, 3H), 1.90-1.99 (m, 5H), 1.52-1.64 (m, 2H) and 1.22-1.34 (m, 2H).

Example A20: 2-(4-((1H-benzo[d]imidazol-2-yl)methyl)cyclohexyl)quinoline

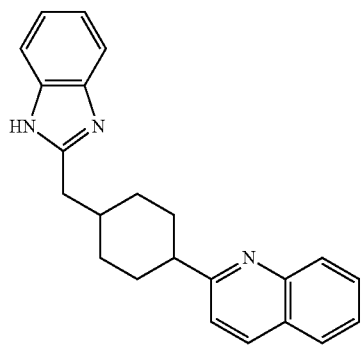 [SMILES: c1ccc2nc(C3CCC(Cc4nc5ccccc5[nH]4)CC3)ccc2c1]

¹H NMR (400 MHz, CDCl₃) δ_H 8.09 (d, J=8.4 Hz, 1H), 8.02 (d, J=8.4 Hz, 1H), 7.77 (d, J=8.0 Hz, 1H), 7.66 (t, J=7.2 Hz, 1H), 7.57-7.63 (m, 2H), 7.48 (t, J=7.2 Hz, 1H), 7.24-7.29 (m, 4H), 2.83-2.97 (m, 3H), 1.88-2.12 (m, 5H), 1.59-1.74 (m, 2H), 1.20-1.35 (m, 2H).

Example A21: 2-(4-((5-methoxy-1H-benzo[d]imidazol-2-yl)methyl)cyclohexyl)quinoline

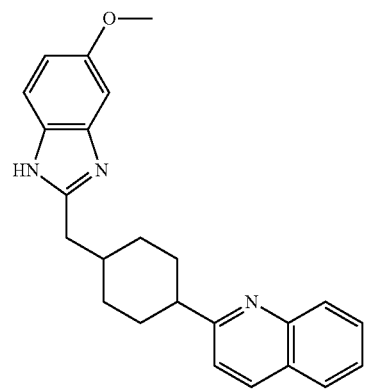 [SMILES: COc1ccc2[nH]c(CC3CCC(c4ccc5ccccc5n4)CC3)nc2c1]

¹H NMR (400 MHz, DMSO-d₆) δ_H 12.03 (s, 1H), 8.26 (d, J=8.0 Hz, 1H), 7.82-8.04 (m, 2H), 7.64-7.76 (m, 1H), 7.41-7.58 (m, 2H), 7.29-7.39 (m, 1H), 6.99 (s, 1H), 6.66-6.81 (m, 1H), 3.77 (s, 4H), 2.79-2.91 (m, 1H), 2.65-2.77 (m, 2H), 1.76-2.06 (m, 6H), 1.52-1.76 (m, 2H), 1.12-1.34 (m, 2H).

Example A22: 5-(4-((5-chloro-1H-benzo[d]imidazol-2-yl)methyl)cyclohexyl)quinoline

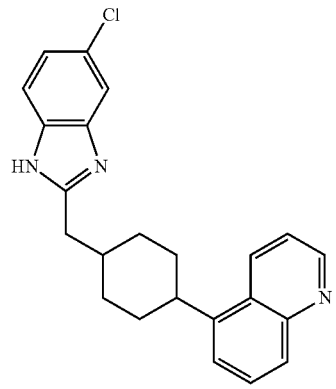 [SMILES: Clc1ccc2[nH]c(CC3CCC(c4cccc5ncccc45)CC3)nc2c1]

Example A23a: 6-((1r,4r)-4-((5-chloro-1H-benzo[d]imidazol-2-yl)methyl)cyclohexyl)quinoline

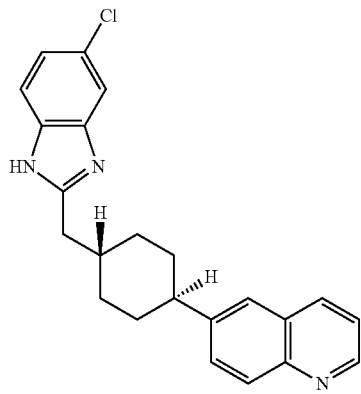

¹H NMR (DMSO-d6) δ 12.41 (d, J=16.4 Hz, 1H), 8.83 (s, 1H), 8.28 (d, J=8.4 Hz, 1H), 7.93 (d, J=8.4 Hz, 1H), 7.76 (s, 1H), 7.67 (d, J=8.4 Hz, 1H), 7.59-7.53 (m, 1H), 7.49-7.43 (m, 2H), 7.14 (t, J=8.8 Hz, 1H), 2.77 (d, J=6.8 Hz, 2H), 2.73-2.65 (m, 1H), 1.93-1.83 (m, 5H), 1.56 (dd, J=24.4, 12.4 Hz, 2H), 1.30-1.24 (m, 3H), MS (ESI) m/e [M+1]+ 376;

Example A23b: 6-((1s,4s)-4-((5-chloro-1H-benzo[d]imidazol-2-yl)methyl)cyclohexyl)quinoline

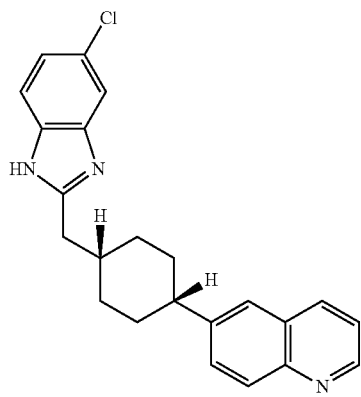 [SMILES: Clc1ccc2[nH]c(C[C@H]3CC[C@@H](c4ccc5ncccc5c4)CC3)nc2c1]

¹H NMR (DMSO-d6) δ 12.44 (s, 1H), 8.84 (dd, J=4, 1.6 Hz, 1H), 8.32 (d, J=16 Hz, 1H), 7.97 (d, J=8.4 Hz, 1H), 7.85 (s, 1H), 7.75 (dd, J=8.8, 1.6 Hz, 1H), 7.58-7.42 (m, 3H), 7.14 (dd, J=8.4, 2.0 Hz, 1H), 2.99 (d, J=8.0 Hz, 2H), 2.83-2.77 (m, 1H), 2.44-2.32 (m, 1H), 2.00-1.85 (m, 2H), 1.73-1.59 (m, 6H), MS (ESI) m/e [M+1]+ 376;

Example A24: 8-(4-((5-chloro-1H-benzo[d]imidazol-2-yl)methyl)cyclohexyl)-5-fluoroquinoline

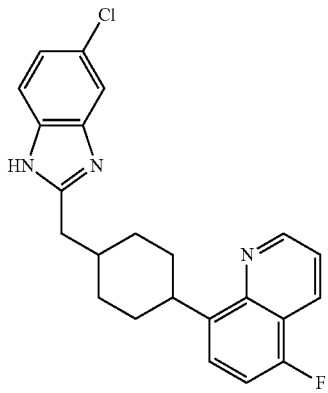 [SMILES: Fc1ccc(C2CCC(Cc3nc4cc(Cl)ccc4[nH]3)CC2)c2ncccc12]

Example A25: 5-(4-((5-cyclopropyl-1H-benzo[d]imidazol-2-yl)methyl)cyclohexyl)-8-fluoroquinoline

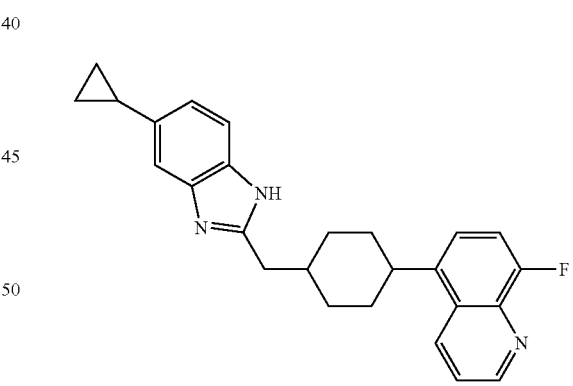

¹H NMR (DMSO-d6) δ 12.03 (d, J=17.2 Hz, 1H), 8.98-8.90 (m, 1H), 8.66 (d, J=7.6 Hz, 1H), 7.69-7.62 (m, 1H), 7.60-7.56 (m, 1H), 7.55-7.42 (m, 1H), 7.39-7.36 (m, 1H), 7.21-7.09 (m, 1H), 6.85-6.83 (m, 1H), 3.33-3.31 (m, 3H), 2.99-2.74 (m, 3H), 2.05-1.76 (m, 7H), 1.73-1.49 (m, 4H), 1.40-1.37 (m, 1H), 0.96-0.86 (m, 2H), 0.68-0.60 (m, 2H), MS (ESI) m/e [M+1]+ 400;

Example A26a: 5-((1r,4r)-4-((5,6-difluoro-1H-benzo[d]imidazol-2-yl)methyl)cyclohexyl)-8-fluoroquinoline

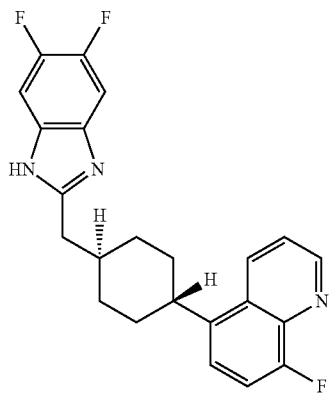 [SMILES: Fc1cc2nc(C[C@H]3CC[C@H](c4ccc(F)c5ncccc54)CC3)[nH]c2cc1F]

¹H NMR (DMSO-d6) δ 12.45 (s, 1H), 8.95 (dd, J=4.0, 1.6 Hz, 1H), 8.65 (d, J=8.8 Hz, 1H), 7.65 (dd, J=8.8, 4.4 Hz, 1H), 7.61-7.42 (m, 4H), 3.31-3.26 (m, 1H), 2.78 (d, J=6.8 Hz, 2H), 2.00-1.93 (m, 1H), 1.89-1.83 (m, 4H), 1.62-1.53 (m, 2H), 1.43-1.34 (m, 2H), MS (ESI) m/e [M+1]+ 396;

Example A26b: 5-((1s,4s)-4-((5,6-difluoro-1H-benzo[d]imidazol-2-yl)methyl)cyclohexyl)-8-fluoroquinoline

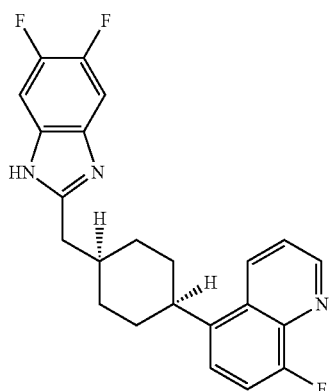

¹H NMR (DMSO-d6) δ 12.46 (s, 1H), 8.96 (d, J=4.0 Hz, 1H), 8.66 (d, J=8.4 Hz, 1H), 7.66 (dd, J=8.8, 4.0 Hz, 1H), 7.58 (d, J=8.0 Hz, 3H), 7.52-7.48 (m, 2H), 3.33-3.30 (m, 1H), 3.01 (d, J=8.0 Hz, 2H), 2.47-2.39 (m, 1H), 1.86-1.83 (m, 4H), 1.69-1.66 (m, 4H), MS (ESI) m/e [M+1]+ 396;

Example A27: 8-(4-((5-chloro-1H-benzo[d]imidazol-2-yl)methyl)cyclohexyl)-5-fluoroquinoline

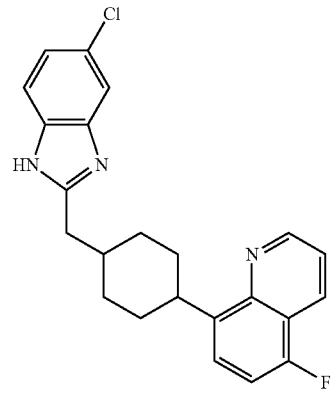 [SMILES: Fc1ccc(C2CCC(Cc3nc4cc(Cl)ccc4[nH]3)CC2)c2ncccc12]

Example A28: 5-chloro-2-((4-(pyridin-4-yl)cyclohexyl)methyl)-1H-benzo[d]imidazole

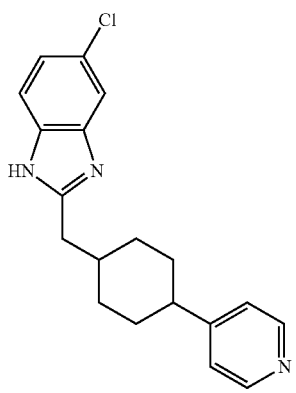 [SMILES: Clc1ccc2[nH]c(CC3CCC(c4ccncc4)CC3)nc2c1]

Example A29: 5-chloro-2-((4-(2-(trifluoromethyl)pyridin-4-yl)cyclohexyl)methyl)-1H-benzo[d]imidazole

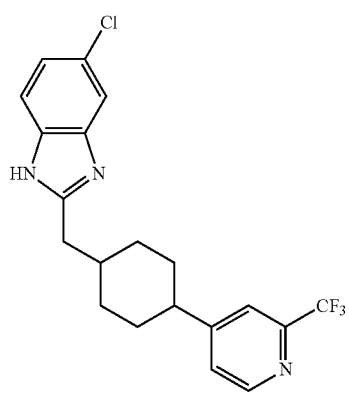 [SMILES: FC(F)(F)c1cc(C2CCC(Cc3nc4cc(Cl)ccc4[nH]3)CC2)ccn1]

Example A30a: 5-chloro-2-(((1r,4r)-4-(4-fluorophenyl)cyclohexyl)methyl)-1H-benzo[d]imidazole

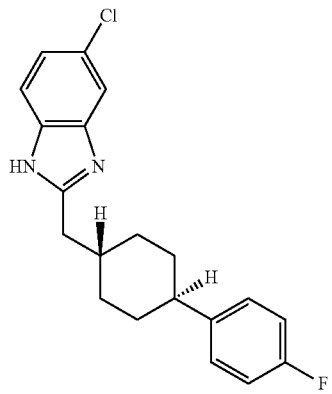 [SMILES: Fc1ccc([C@H]2CC[C@H](Cc3nc4cc(Cl)ccc4[nH]3)CC2)cc1]

$^1$H NMR (DMSO-d6) δ 12.38 (s, 1H), 7.56-7.48 (m, 2H), 7.25-7.23 (m, 2H), 7.16-7.00 (m, 3H), 2.73 (d, J=6.8 Hz, 2H), 1.78 (d, J=10.8 Hz, 5H), 1.41 (q, J=11.6 Hz, 2H), 1.23-1.14 (m, 2H), MS (ESI) m/e [M+1]+ 343;

Example A30b: 5-chloro-2-(((1s,4s)-4-(4-fluorophenyl)cyclohexyl)methyl)-1H-benzo[d]imidazole

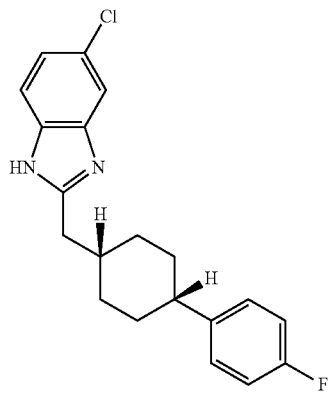 [SMILES: Fc1ccc([C@H]2CC[C@@H](Cc3nc4cc(Cl)ccc4[nH]3)CC2)cc1]

$^1$H NMR (DMSO-d6) 12.39 (s, 1H), 7.58-7.43 (m, 2H), 7.35-7.30 (m, 2H), 7.14-7.10 (m, 3H), 2.95 (d, J=7.6 Hz, 2H), 2.58 (t, J=12.2 Hz, 1H), 2.34 (s, 1H), 1.80-1.72 (m, 3H), 1.65-1.57 (m, 6H), MS (ESI) m/e [M+1]+ 343;

Example A31: 5-cyclopropyl-2-((4-phenylcyclohexyl)methyl)-1H-benzo[d]imidazole

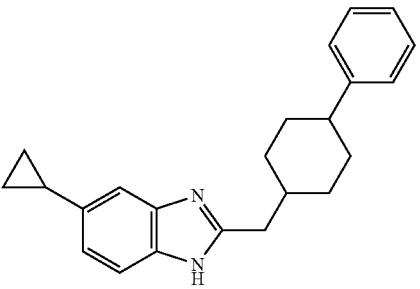 [SMILES: c1ccc(C2CCC(Cc3nc4cc(C5CC5)ccc4[nH]3)CC2)cc1]

$^1$H NMR (CDCl3) δ$_H$ 7.48 (d, J=8.4 Hz, 1H), 7.33 (s, 1H), 7.19-7.21 (m, 4H), 7.03-7.11 (m, 2H), 3.17-3.20 (m, 2H), 2.45-2.51 (m, 2H), 1.87-1.92 (m, 1H), 1.70-1.77 (m, 2H), 1.56-1.63 (m, 4H), 1.45-1.49 (m, 2H), 0.91-0.97 (m, 2H), and 0.59-0.64 (m, 2H). MS (ESI) m/e [M+H]$^+$=331.

Example A32: 2-((4-phenylcyclohexyl)methyl)-1H-benzo[d]imidazole

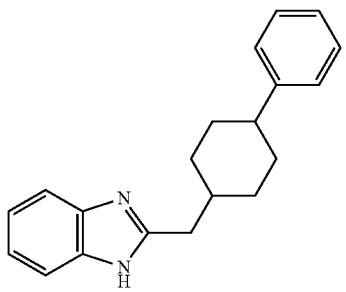 [SMILES: c1ccc(C2CCC(Cc3nc4ccccc4[nH]3)CC2)cc1]

$^1$H NMR (DMSO-d$_6$) δ$_H$ 7.55-7.57 (m, 2H), 7.30-7.34 (m, 4H), 7.18-7.24 (m, 3H), 3.04 (d, J=7.6 Hz, 2H), 2.58-2.67 (m, 3H), 2.32-2.39 (m, 1H), 1.75-1.82 (m, 2H), and 1.54-1.68 (m, 6H). MS (ESI) m/e [M+H]$^+$=291.

Example A33a: 2-(((1r,4r)-4-phenylcyclohexyl)methyl)-5-(trifluoromethyl)-1H-benzo[d]imidazole

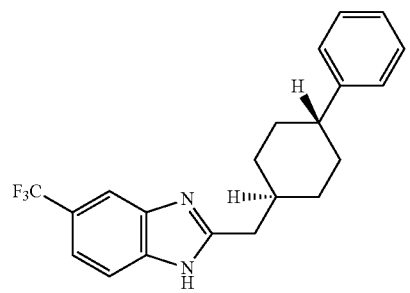 [SMILES: FC(F)(F)c1ccc2[nH]c(C[C@H]3CC[C@H](c4ccccc4)CC3)nc2c1]

$^1$H NMR (DMSO-d$_6$) δ$_H$ 7.85 (s, 1H), 7.67 (d, J=8.0 Hz, 1H), 7.44-7.48 (m, 1H), 7.11-7.29 (m, 5H), 2.81 (d, J=7.2 Hz, 2H), 2.44-2.49 (m, 1H), 1.91-1.96 (m, 1H), 1.78-1.82 (m, 4H), 1.40-1.50 (m, 2H), and 1.16-1.27 (m, 2H). MS (ESI) m/e [M+H]=359.

Example A33b: 2-(((1s,4s)-4-phenylcyclohexyl)methyl)-5-(trifluoromethyl)-1H-benzo[d]imidazole

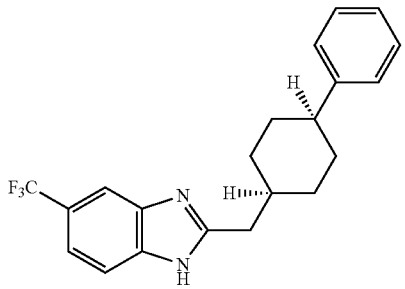 [SMILES: FC(F)(F)c1ccc2[nH]c(C[C@H]3CC[C@@H](c4ccccc4)CC3)nc2c1]

$^1$H NMR (DMSO-d$_6$) δ$_H$ 12.69 (s, 1H), 7.84 (s, 1H), 7.66 (d, J=8.4 Hz, 1H), 7.43-7.47 (m, 1H), 7.29-7.34 (m, 4H), 7.16-7.21 (m, 1H), 3.02 (d, J=8.0 Hz, 2H), 2.54-2.58 (m, 1H), 2.36-2.40 (m, 1H), 1.76-1.85 (m, 2H), and 1.54-1.68 (m, 6H). MS (ESI) m/e [M+H]$^+$=359.

Example A34a: 5-chloro-2-(((1r,4r)-4-phenylcyclohexyl)methyl)-1H-benzo[d]imidazole

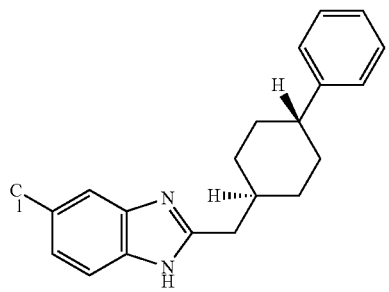 [SMILES: Clc1ccc2[nH]c(C[C@H]3CC[C@H](c4ccccc4)CC3)nc2c1]

$^1$H NMR (DMSO-d$_6$) δ$_H$ 7.46-7.53 (m, 2H), 7.45-7.48 (m, 1H), 7.12-7.29 (m, 6H), 2.73 (d, J=8.0 Hz, 2H), 2.47-2.52 (m, 1H), 1.77-1.91 (m, 5H), 1.42-1.46 (m, 2H), and 1.18-1.24 (m, 2H). MS (ESI) m/e [M+H]$^+$=325

Example A34b: 5-chloro-2-(((1s,4s)-4-phenylcyclohexyl)methyl)-1H-benzo[d]imidazole

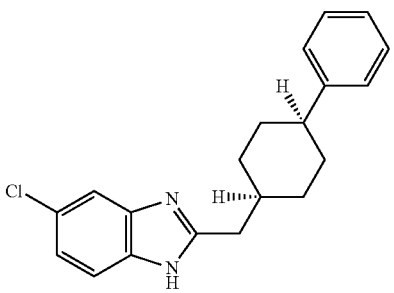 [SMILES: Clc1ccc2[nH]c(C[C@H]3CC[C@@H](c4ccccc4)CC3)nc2c1]

$^1$H NMR (DMSO-d$_6$) δ$_H$ 7.60 (s, 1H), 7.53 (d, J=8.0 Hz, 1H), 7.26-7.32 (m, 4H), 7.17-7.22 (m, 2H), 3.01 (d, J=8.0 Hz, 2H), 2.55-2.60 (m, 1H), 2.31-2.38 (m, 1H), 1.66-1.77 (m, 2H), and 1.53-1.63 (m, 6H). MS (ESI) m/e [M+H]$^+$=325.

Example A35: 4-chloro-2-(((1s,4s)-4-phenylcyclohexyl)methyl)-1H-benzo[d]imidazole

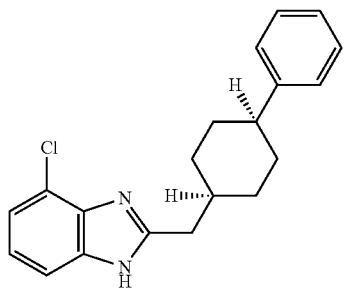 [SMILES: Clc1cccc2[nH]c(C[C@H]3CC[C@@H](c4ccccc4)CC3)nc12]

$^1$H NMR (DMSO-d$_6$) δ$_H$ 12.67 (s, 1H), 7.45 (d, J=7.6 Hz, 1H), 7.28-7.34 (m, 4H), 7.11-7.22 (m, 3H), 3.00 (d, J=8.0 Hz, 2H), 2.54-2.61 (m, 1H), 2.37-2.39 (m, 1H), 1.76-1.87 (m, 2H), and 1.53-1.68 (m, 6H). MS (ESI) m/e [M+H]$^+$=325.

Example A36: 5-chloro-2-(3-phenylbicyclo[4.1.0]heptan-7-yl)-1H-benzo[d]imidazole

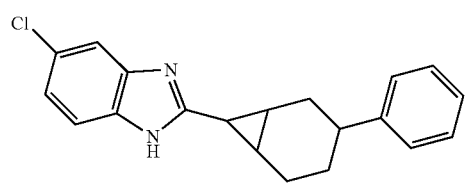 [SMILES: Clc1ccc2[nH]c(C3C4CCC(c5ccccc5)CC43)nc2c1]

$^1$H NMR (400 MHz, CDCl3) δ 7.53-7.52 (m, 1H), 7.41 (d, J=8.8 Hz, 1H), 7.24-7.19 (m, 2H), 7.17-7.15 (m, 2H), 7.07-6.99 (m, 2H), 2.40-2.00 (m, 8H), 1.98-1.78 (m, 2H), 1.71-1.46 (m, 3H), and 1.40-1.20 (m, 3H). MS (ESI) m/e [M+1]$^+$=323.

Example A37a: 6-bromo-5-fluoro-2-(((1r,4r)-4-phenylcyclohexyl)methyl)-1H-benzo[d]imidazole

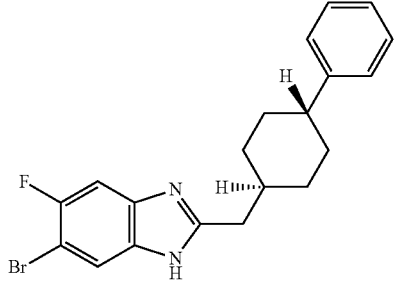 [SMILES: Fc1cc2nc(C[C@H]3CC[C@H](c4ccccc4)CC3)[nH]c2cc1Br]

$^1$H NMR (DMSO-d$_6$) δ$_H$ 12.57 (s, 1H), 7.78-7.79 (d, J=6.4 Hz, 1H), 7.50-7.52 (d, J=9.2 Hz, 1H), 7.13-7.26 (m, 5H), 2.73-2.75 (d, J=7.6 Hz, 2H), 2.43-2.50 (m, 1H), 1.86-1.96 (m, 1H), 1.77-1.80 (d, J=11.6 Hz, 4H), 1.38-1.49 (m, 2H), and 1.14-1.25 (m, 2H). MS (ESI) m/e[M+1]$^+$=387.

Example A37b: 6-bromo-5-fluoro-2-(((1s,4s)-4-phenylcyclohexyl)methyl)-1H-benzo[d]imidazole

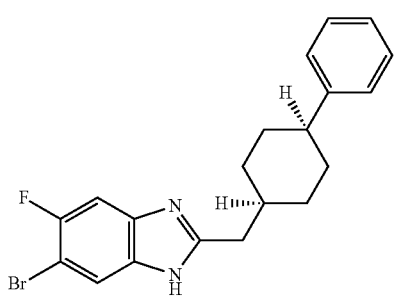 [SMILES: Fc1cc2nc(C[C@H]3CC[C@@H](c4ccccc4)CC3)[nH]c2cc1Br]

$^1$H NMR (DMSO-d$_6$) $\delta_H$ 12.58 (s, 1H), 7.78-7.80 (d, J=6.4 Hz, 1H), 7.50-7.52 (d, J=9.6 Hz, 1H), 7.28-7.33 (m, 4H), 7.16-7.20 (m, 1H), 2.94-2.96 (d, J=8.0 Hz, 2H), 2.51-2.61 (m, 1H), 2.30-2.37 (m, 1H), 1.73-1.83 (m, 2H), and 1.54-1.66 (m, 6H). MS (ESI) m/e[M+1]$^+$=387.

Example A38: 4-(1-(2-(5-chloro-1H-benzo[d]imidazol-2-yl)ethyl)piperidin-4-yl)-6-fluoroquinoline

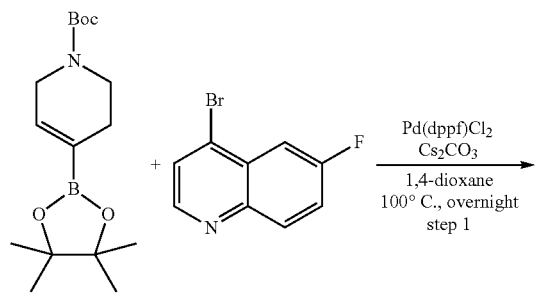
Pd(dppf)Cl$_2$
Cs$_2$CO$_3$
1,4-dioxane
100° C., overnight
step 1

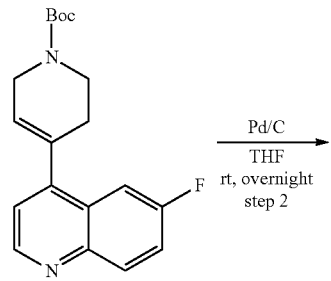
Pd/C
THF
rt, overnight
step 2

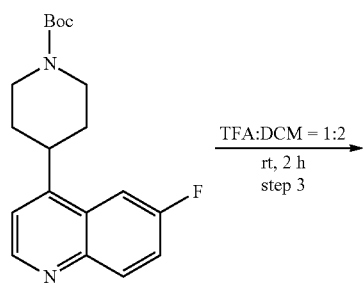
TFA:DCM = 1:2
rt, 2 h
step 3

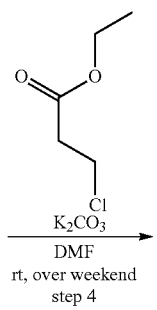
K$_2$CO$_3$
DMF
rt, over weekend
step 4

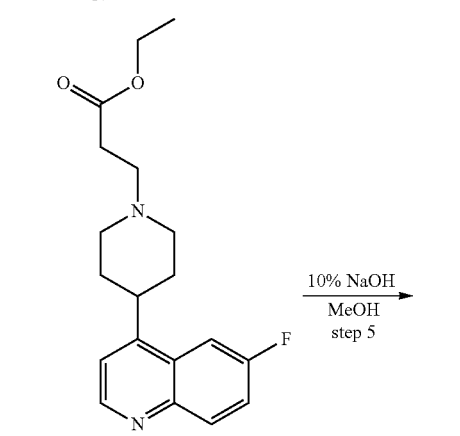
10% NaOH
MeOH
step 5

HATU, TEA
r.t. 2 h
step 6

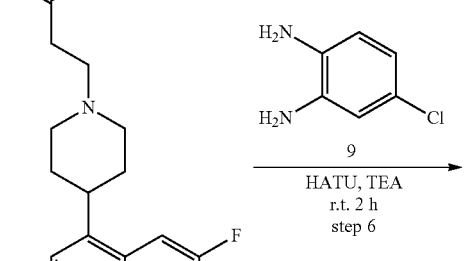
CF$_3$COOH
80° C., 3 h
step 7

-continued

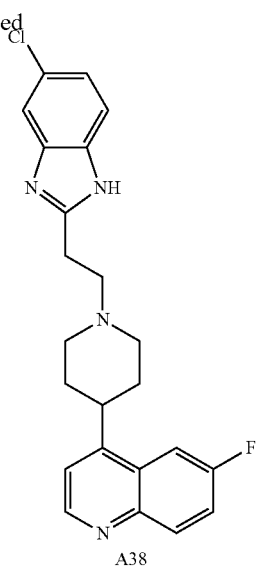

A38

Step 1: tert-butyl 4-(6-fluoroquinolin-4-yl)-3,6-dihydropyridine-1(2H)-carboxylate A mixture of tert-butyl 4-(4,4,5,5-tetramethyl-1,3,2-dioxaborolan-2-yl)-3,6-dihydropyridine-1(2H)-carboxylate (3.1 g, 0.01 mol), 4-bromo-6-fluoroquinoline (2.24 g, 0.01 mol), $Cs_2CO_3$ (6.51 g, 0.02 mol), and $Pd(dppf)Cl_2$ (731 mg, 0.001 mol) in 1,4-dioxane was stirred overnight at 100° C. under $N_2$. After determined the reaction to be complete by LCMS and TLC, the reaction was cooled to r.t. The solvent was removed under vacuo. The residue was purified by silica gel column (PE:EA=2:1) to afford desired product 3.42 g as yellow oil. $[M+1]^+$ 329.

Step 2: tert-butyl 4-(6-fluoroquinolin-4-yl)piperidine-1-carboxylate

To a solution of tert-butyl 4-(6-fluoroquinolin-4-yl)-3,6-dihydropyridine-1(2H)-carboxylate (3.42 g, 1.04 mmol) in THF (25 mL) was added Pd/C (684 mg, 20%). The mixture was stirred overnight under 4 atm of $H_2$ at r.t. After determined the reaction to be complete by LCMS, the solid was filtered and the filtrate was concentrated to give the crude product (3.45 g) as a yellow oil, which was used for the next step without further purification. $[M+1]^+$ 331.

Step 3: 6-fluoro-4-(piperidin-4-yl)quinoline

To a solution of tert-butyl 4-(6-fluoroquinolin-4-yl)piperidine-1-carboxylate (1 g, 3.00 mmol) in DCM (10 ml) was added TFA (5 ml). The mixture was stirred for 2 h at r.t. After determined the reaction to be complete by LCMS, the solvent was removed under vacuo. The residue was added to 50 ml DCM, and washed with saturated aqueous of $NaHCO_3$ (30 mL×2), the organic layer was combined and washed with brine (40 mL×1), dried over $Na_2SO_4$, filtered and concentrated to afford desired product 560 mg as yellow oil. $[M+1]^+$ 231.

Step 4: ethyl 3-(4-(6-fluoroquinolin-4-yl)piperidin-1-yl)propanoate

To a solution of 6-fluoro-4-(piperidin-4-yl)quinoline (560 mg, 2.43 mmol) in DMF (10 ml), were added $K_2CO_3$ (840 mg, 6.09 mmol), ethyl 3-chloropropanoate (497 mg, 3.65 mmol). The mixture was stirred over weekend at r.t. After determined the reaction to be complete by LCMS, the mixture was added to $H_2O$ (80 ml), extracted with EA (80 mL×2). The organic layer was combined and washed with brine (100 mL×1), dried over $Na_2SO_4$, filtered and concentrated to give the crude product (850 mg) as a yellow solid. $[M+1]^+$ 331.

Step 5: 3-(4-(6-fluoroquinolin-4-yl)piperidin-1-yl)propanoic acid

To a solution of ethyl 3-(4-(6-fluoroquinolin-4-yl)piperidin-1-yl)propanoate (1.49 g, 4.5 mmol) in MeOH (10 ml) was added NaOH (10%, 10 ml). The mixture was stirred for 2 h at r.t. After determined the reaction to be complete by LCMS, MeOH was removed under vacuo. The pH value of residue aqueous layer was adjusted to 5~6 with HCl (12M), and the aqueous layer was extracted with DCM (50 mL×2), EA (50 mL×2). The organic layer was combined and washed with brine (100 mL×1), dried over $Na_2SO_4$, filtered and concentrated to afford desired crude product 850 mg as off-white solid. [M+1]303.

Step 6: N-(2-amino-4-chlorophenyl)-3-(4-(6-fluoroquinolin-4-yl)piperidin-1-yl)propenamide A mixture of 3-(4-(6-fluoroquinolin-4-yl)piperidin-1-yl) propanoic acid (850 mg, 2.81 mmol) and HATU (1.28 g, 3.38 mmol) in DCM (10 mL) was stirred for 10 mins under $N_2$ at r.t. Then 4-chlorobenzene-1,2-diamine (399 mg, 2.81 mmol) and TEA (568 mg, 5.62 mmol) were added. The mixture was stirred for 2 h at r.t. After determined the reaction to be complete by LCMS, the reaction mixture was extracted with DCM (30 mL×2). The organic layer was combined and washed with brine (50 mL×1), dried over $Na_2SO_4$, filtered and concentrated to give a crude product 1.14 g as red solid, which was used for the next step without further purification. $[M+1]^+$ 427.

Step 7: 4-(1-(2-(5-chloro-1H-benzo[d]imidazol-2-yl)ethyl)piperidin-4-yl)-6-fluoroquinoline

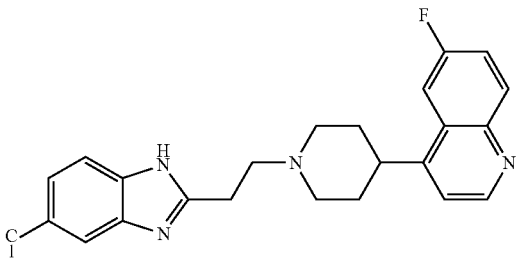 [SMILES: Fc1ccc2nccc(C3CCN(CCc4nc5cc(Cl)ccc5[nH]4)CC3)c2c1]

A solution of N-(2-amino-4-chlorophenyl)-3-(4-(6-fluoroquinolin-4-yl)piperidin-1-yl)propenamide (880 mg crude, 2.05 mmol) in $CH_3COOH$ (15 mL) was stirred for 3 h at 80° C. After determined the reaction to be complete by LCMS, the reaction mixture was concentrated in vacuo to remove the solvent, and the residue was purified by prep-HPLC, to afford desired product 105.14 mg as white solid. $^1$H NMR (DMSO-$d_6$) δ 12.36 (s, 1H), 8.81 (d, J=4.0 Hz, 1H), 8.05 (m, 2H), 7.68 (t, J=8.0 Hz, 1H), 7.50 (m, 3H), 7.15 (d, J=8.0 Hz, 1H), 3.15-2.97 (m, 4H), 3.15-2.83 (m, 7H), 2.34 (t, J=10.0

Hz, 2H), 1.92-1.70 (m, 5H), [M+1]⁺ 409. Compound A39 was prepared in a procedure similar to Example A38.

Example A39: 4-(1-((5-chloro-1H-benzo[d]imidazol-2-yl)methyl)piperidin-4-yl)-6-fluoroquinoline

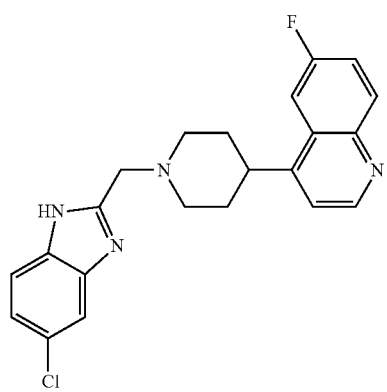 [SMILES: Fc1ccc2nccc(C3CCN(Cc4nc5cc(Cl)ccc5[nH]4)CC3)c2c1]

¹H NMR (DMSO-d₆) δ 12.57 (s, 1H), 8.88 (d, J=4.0 Hz, 1H), 8.15 (dd, J=8.0, 4.0 Hz, 1H), 8.07 (dd, J=12.0, 2.0 Hz, 1H), 7.77-7.48 (m, 4H), 7.28-7.16 (m, 1H), 3.90 (s, 2H), 3.43 (s, 1H), 3.08 (d, J=8.0 Hz, 2H), 2.51 (s, 2H), 2.00-1.80 (m, 4H), [M+1]⁺ 395.

Example A40: 4-(4-((5-chloro-1H-benzo[d]imidazol-2-yl)methyl)piperidin-1-yl)quinoline

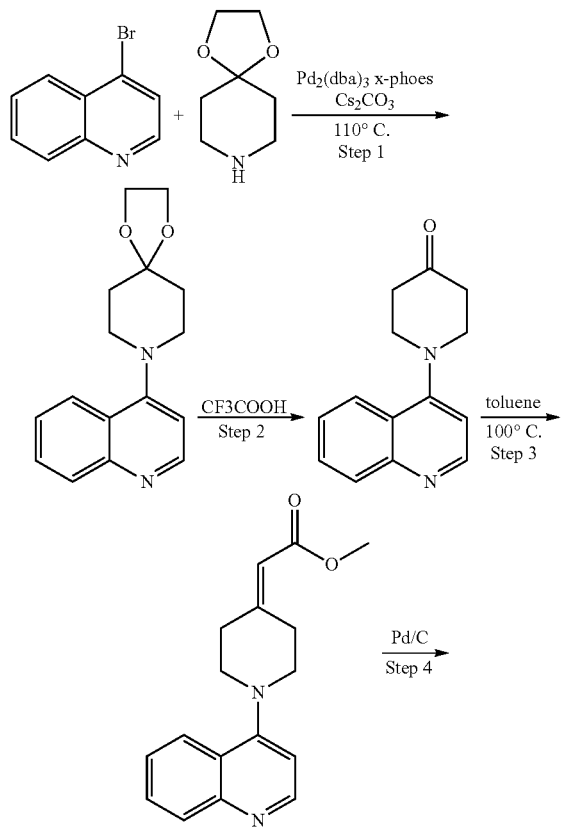

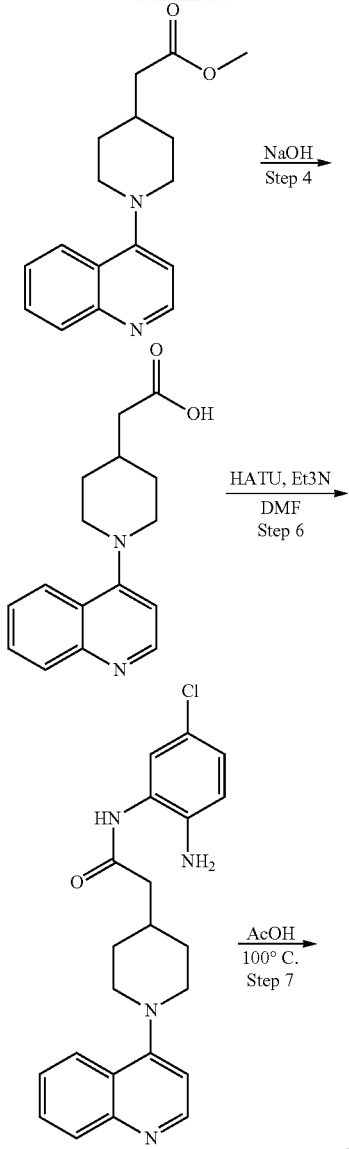

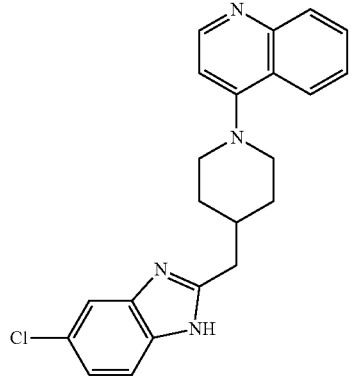

Step 1: Synthesis of 8-(quinolin-4-yl)-1,4-dioxa-8-azaspiro[4.5]decane

To a solution of 1,4-dioxa-8-azaspiro[4.5]decane (10 g, 70 mmol) in toluene (150 ml) were added 4-bromoquinoline (15.2 g, 73.5 mmol), Pd₂(dba)₃ (6.4 g, 7 mmol), x-phos (6.7 g, 14 mmol) and Cs$_2$CO$_3$(57 g, 175 mmol). The mixture was stirred for 3 days at 110° C. under N$_2$. The solid was filtered and the filtrate was purified by column chromatography on silica, eluting with EA:PE=1:1 to 1: 0 to give 8-(quinolin-4-yl)-1,4-dioxa-8-azaspiro[4.5]decane (10.8 g). MS (EST) m/e [M+H]$^+$=271.

Step 2: 1-(quinolin-4-yl)piperidin-4-one

A solution of 8-(quinolin-4-yl)-1,4-dioxa-8-azaspiro[4.5] decane (10.8 g, 40 mmol) in CF$_3$COOH (20 ml) was stirred overnight at 50° C. The solvent was removed under vacuo, the residue was adjusted to the pH>7 with Na$_2$CO$_3$(aq.) then extracted with EA (50 ml×3). The organic layer was dried over Na$_2$SO$_4$, filtered and concentrated to give 1-(quinolin-4-yl)piperidin-4-one (9.6 g) which was used in next step without further purification. MS (ESI) m/e [M+H]$^+$=227.

Step 3: methyl 2-(1-(quinolin-4-yl)piperidin-4-ylidene)acetate

To a solution of 1-(quinolin-4-yl)piperidin-4-one (9.6 g, 42.5 mmol) in toluene (60 ml) were added methoxycarbonylmethylene-triphenylphosphorane (15.6 g, 46.8 mmol) and Et$_3$N (8.6 g, 85 mmol). The mixture was stirred overnight at 100° C. under N$_2$. The mixture was purified by column chromatography on silica, eluting with EA:PE=1:1 to give methyl 2-(1-(quinolin-4-yl)piperidin-4-ylidene)acetate (5.7 g). MS (ESI) m/e [M+H]$^+$=283.

Step 4: methyl 2-(1-(quinolin-4-yl)piperidin-4-yl)acetate

To a solution of methyl 2-(1-(quinolin-4-yl)piperidin-4-ylidene)acetate (5.7 g, 20 mmol) in MeOH (60 ml) was added Pd/C (2.3 g). The mixture was stirred for 7 days at r.t. under H$_2$(4 atm). The solid was filtered and the filtrate was concentrated under vacuo to give methyl 2-(1-(quinolin-4-yl)piperidin-4-yl)acetate (5 g) which was used in next step without further purification. MS (ESI) m/e [M+H]$^+$=285.

Step 5: 2-(1-(quinolin-4-yl)piperidin-4-yl)acetic acid

To a solution of methyl 2-(1-(quinolin-4-yl)piperidin-4-yl)acetate (5 g, 17.5 mmol) in MeOH (50 ml) and H$_2$O (10 ml) was added NaOH (1.4 g, 35 mmol). The mixture was stirred for 2 h at r.t. The solvent was removed under vacuo. The residue was acidified by HCl (1N, aq.) to the pH=7. The solid was filtered and dried to give 2-(1-(quinolin-4-yl) piperidin-4-yl)acetic acid (1.4 g). MS (ESI) m/e [M+H]$^+$=271.

Step 6: N-(2-amino-5-chlorophenyl)-2-(1-(quinolin-4-yl)piperidin-4-yl)acetamide

To a solution of 2-(1-(quinolin-4-yl)piperidin-4-yl)acetic acid (1.4 g, 5.2 mmol) in DMF (30 ml) were added 4-chlorobenzene-1,2-diamine (744 mg, 5.2 mmol), HATU (2.0 g, 5.2 mmol) and Et$_3$N (1.1 g, 10.4 mmol). The mixture was stirred overnight at r.t. To the mixture was added H$_2$O (20 ml). The solid was filtered and dried to give N-(2-amino-5-chlorophenyl)-2-(1-(quinolin-4-yl)piperidin-4-yl)acetamide (600 mg). MS (ESI) m/e [M+H]$^+$=395.

Step 7: 4-(4-((5-chloro-1H-benzo[d]imidazol-2-yl) methyl)piperidin-1-yl)quinoline

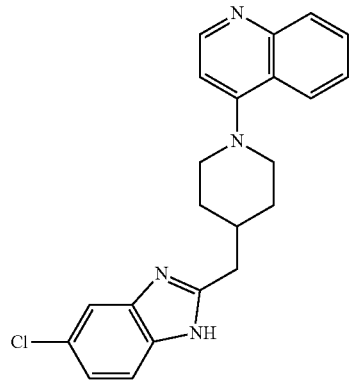 [SMILES: Clc1ccc2[nH]c(CC3CCN(c4ccnc5ccccc45)CC3)nc2c1]

A solution of N-(2-amino-5-chlorophenyl)-2-(1-(quinolin-4-yl)piperidin-4-yl)acetamide (600 mg, 1.52 mmol) in CH$_3$COOH (20 ml) was stirred overnight at 100° C. under N$_2$. The solvent was removed under vacuo, the residue was adjusted to the pH>7 with Na$_2$CO$_3$(aq.) then extracted with EA (50 ml×3). The organic layer was dried over Na$_2$SO$_4$, filtered and concentrated to give crude product which was further purified by column chromatography on silica, eluting with EA:PE=1:1 to give 4-(4-((5-chloro-1H-benzo[d]imidazol-2-yl)methyl)piperidin-1-yl)quinoline (300 mg). $^1$H NMR (DMSO-d$_6$)$_6$) 12.45 (s, 1H), 8.66 (d, J=4.8 Hz, 1H), 7.91-7.99 (m, 2H), 7.65-7.70 (m, 1H), 7.44-7.59 (m, 3H), 7.12-7.17 (m, 1H), 6.96 (d, J=4.8 Hz, 1H), 3.52-3.56 (m, 2H), 2.73-2.89 (m, 4H), 2.09-2.12 (m, 1H), 1.83-1.87 (m, 2H), and 1.58-1.67 (m, 2H). [M+H]$^+$=377.

Example A41: 4-(4-((5-chloro-1H-benzo[d]imidazol-2-yl)methyl)piperidin-1-yl)-6-fluoroquinoline

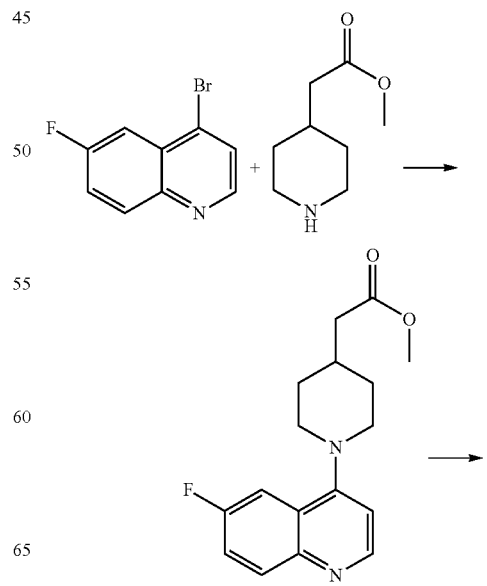

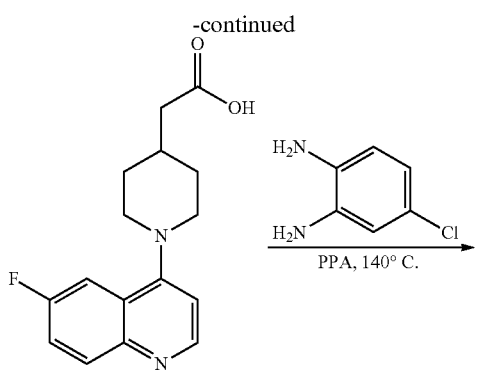

Step 1: methyl 2-(1-(6-fluoroquinolin-4-yl)piperidin-4-ylacetate

To a solution of 4-bromo-6-fluoroquinoline (4.5 g, 20 mmol) in DMF (60 mL) were added methyl 2-(piperidin-4-yl)acetate (3.77 g, 24 mmol), Cs₂CO₃ (9.8 g, 30 mmoL), Pd(dba)₂ (1.8 g, 2 mmol) and S-Phos (0.4 g, 1 mmol). Warmed to 100° C. and stirred for 5 hours under N₂. The reaction was then quenched with H₂O (150 mL) and extracted with EA (100 mL). Separated the organic phase and washed with brine (150 mL). Concentrated and used for next step directly without further purification.

Step 2: 2-(1-(6-fluoroquinolin-4-yl)piperidin-4-yl)acetic acid

To a solution of methyl 2-(1-(6-fluoroquinolin-4-yl)piperidin-4-yl)acetate (8 g, 26.5 mmol) in THF/MeOH/H₂O (2:2:1, 100 mL) was added LiOH.H₂O (1.3 g, 0.03 mol). Stirred at 20-30° C. for 5 hours. Evaporated the organic solution, added H₂O (50 mL) and EA (50 mL), separated the aqueous phase and extracted with EA (50 mL*2). The aqueous phase was adjusted pH to 6~7 with HCl (4N). Extracted with EA (50 mL*2). Combined the organic phase and concentrated to 5~10 mL. Filtered and washed the filter cake with EA (5 mL). Dried the filter cake under reduced pressure to give product 3 g as yellow solid. ¹H NMR (400 MHz, DMSO-d6): δ$_H$ 12.13 (s, 1H), 8.67 (d, J=4.8 Hz, 1H), 8.02 (dd, J=9.2, 5.6 Hz, 1H), 7.64-7.56 (m, 2H), 7.02 (d, J=4.8 Hz, 1H), 3.47 (d, J=12.0 Hz, 2H), 2.81 (t, J=11.2 Hz, 2H), 2.29 (d, J=6.8 Hz, 2H), 1.95-1.85 (m, 3H), 1.58-1.49 (m, 2H).

Step 3: 4-(4-((5-chloro-1H-benzo[d]imidazol-2-yl)methyl)piperidin-1-yl)-6-fluoroquinoline

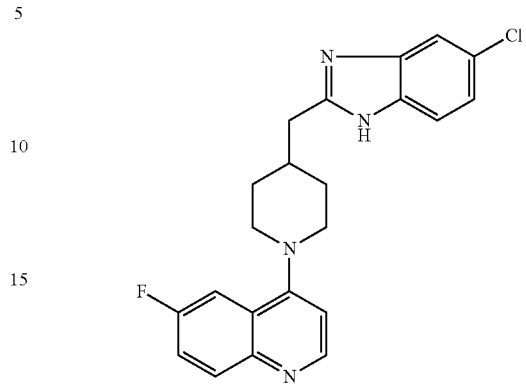

To a mixture of 2-(1-(6-fluoroquinolin-4-yl)piperidin-4-yl)acetic acid (0.14 g, 0.5 mmol) and 4-chlorobenzene-1,2-diamine (0.08 g, 0.6 mmol) was added PPA (10 mL). The mixture was stirred at 140° C. for 4 hours. The reaction was then quenched with H₂O (50 mL) and EA (50 mL). The pH value of the solution was adjusted to 8~9 with NaOH solution. Concentrated the organic phase and purified by pre-HPLC. ¹H NMR (400 MHz, DMSO-d6): δ$_H$ 12.44 (br, 1H), 8.66 (d, J=4.8 Hz, 1H), 8.03-7.99 (m, 1H), 7.76-7.30 (m, 4H), 7.15 (d, J=8.0 Hz, 1H), 7.02 (d, J=4.8 Hz, 1H), 3.49 (d, J=12.0 Hz, 2H), 2.91-2.75 (m, 4H), 2.11 (s, 1H), 1.86-1.83 (m, 2H), 1.67-1.58 (m, 2H). [M+H]⁺=395.1

Example B1a: 4-((1S,4s)-4-((R)-1-(5,6-difluoro-1H-benzo[d]imidazol-2-yl)ethyl)cyclohexyl)-6-fluoroquinoline

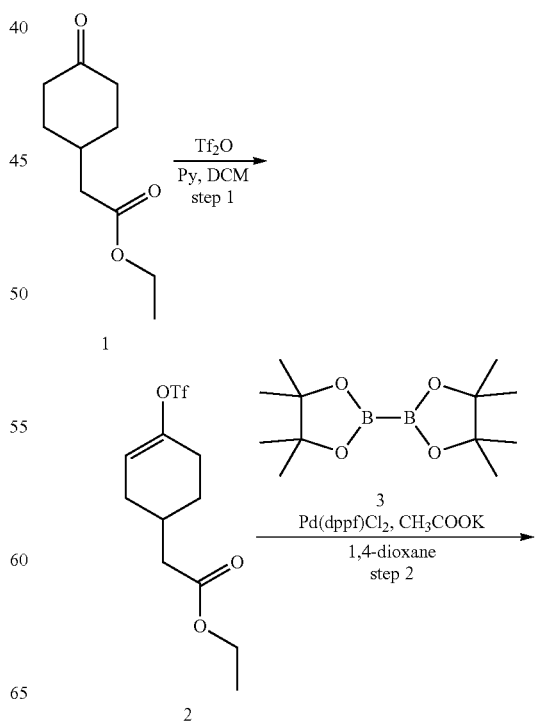

165
-continued
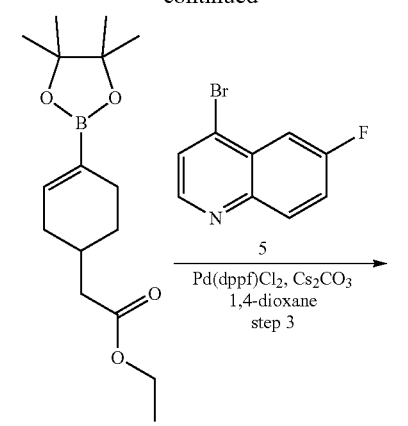
3
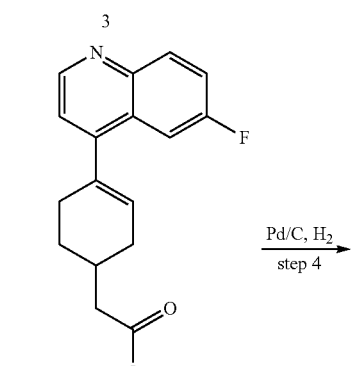
6
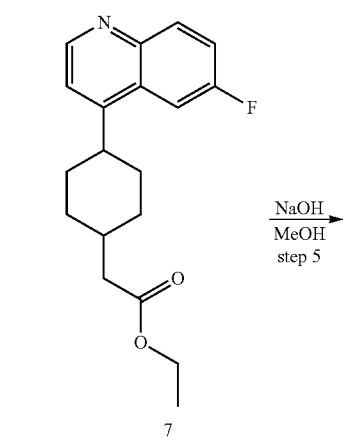
7
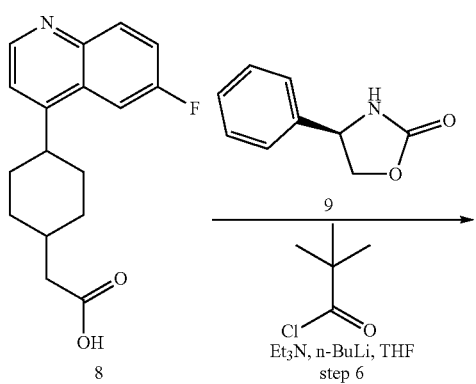
8
166
-continued
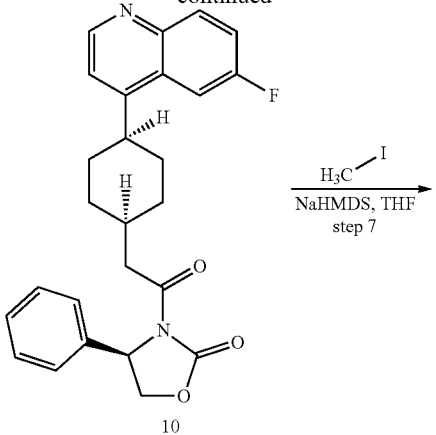
10
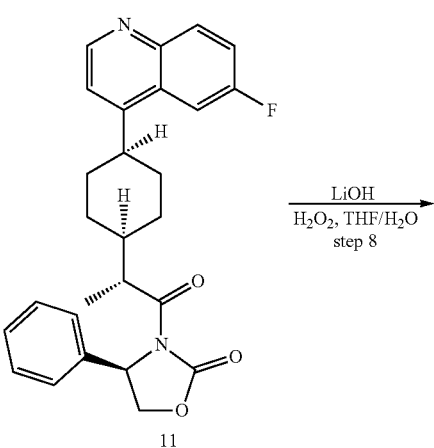
11
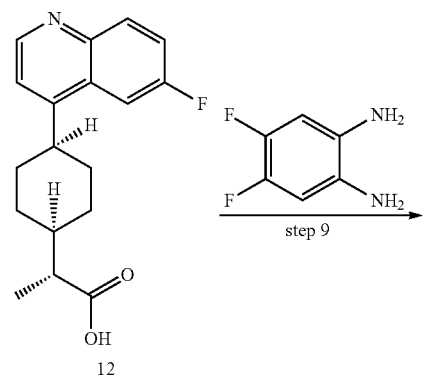
12
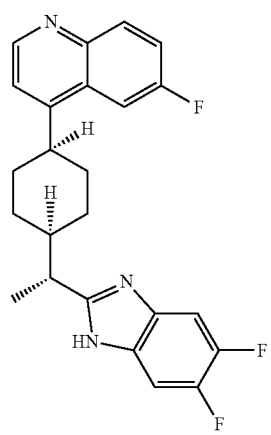

Step 1: ethyl 2-(4-(((trifluoromethyl)sulfonyl)oxy)cyclohex-3-en-1-yl)acetate

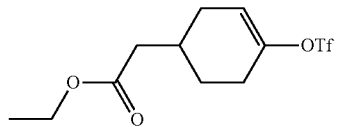 [SMILES: CCOC(=O)CC1CC=C(OS(=O)(=O)C(F)(F)F)CC1]

To a solution of compound ethyl 2-(4-oxocyclohexyl)acetate (18.4 g, 100 mmol, 1.00 eq) dissolved in DCM (250 ml) were added pyridine (9.48 g, 120 mmol, 1.20 eq) and Tf$_2$O (42.15 g, 150 mmol, 1.50 eq). The mixture was stirred at room temperature for overnight. The solution was washed with water 400 ml, saturated ammonium chloride 400 ml and brine 400 ml. The organic layer was combined, dried over Na$_2$SO$_4$, filtered and concentrated to dryness. The crude (30.32 g, 95% yield) was used for next step without further purification. $^1$H NMR (CDCl$_3$) $\delta_H$ 5.72 (s, 1H), 4.15 (q, J=7.2 Hz, 2H), 2.39-2.51 (m, 1H), 2.28-2.38 (m, 4H), 2.08-2.21 (m, 1H), 1.87-1.98 (m, 2H), 1.45-1.57 (m, 1H) and 1.27 (t, J=7.2 Hz, 3H).

Step 2: ethyl 2-(4-(4,4,5,5-tetramethyl-1,3,2-dioxaborolan-2-yl)cyclohex-3-en-1-yl)acetate

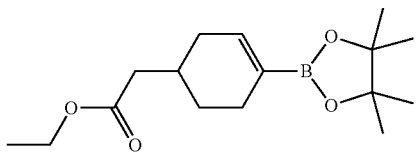 [SMILES: CCOC(=O)CC1CC=C(B2OC(C)(C)C(C)(C)O2)CC1]

To a mixture of ethyl 2-(4-(((trifluoromethyl)sulfonyl)oxy)cyclohex-3-en-1-yl)acetate (30.3 g, crude, 96 mmol, 1.00 eq) dissolved in 1,4-dioxane (400 ml), 4,4,4',4',5,5,5',5'-octamethyl-2,2'-bi(1,3,2-dioxaborolane) (26.8 g, 106 mmol, 1.10 eq), CH$_3$COOK (38.02 g, 192 mmol, 2.00 eq) and Pd(dppf)Cl$_2$ (14.04 g, 19.2 mmol, 0.20 eq) were added. The mixture was stirred at 95° C. under nitrogen protection for 18 hours. The solution was filtered and concentrated to dryness. The crude (12.50 g, 100% yield) was filtered through the silica gel pad and washed with PE/EA=6:1. The filtrate was concentrated to dryness to give a black oil (33.2 g, 112.3% yield) which was used in next step without further purification. $^1$H NMR (CDCl$_3$) $\delta_H$ 6.51 (s, 1H), 4.13 (q, J=7.2 Hz, 3H), 1.99-2.40 (m, 9H), 1.68-1.94 (m, 3H) and 1.18-1.26 (m, 12H).

Step 3: ethyl 2-(4-(6-fluoroquinolin-4-yl)cyclohex-3-en-1-yl)acetate

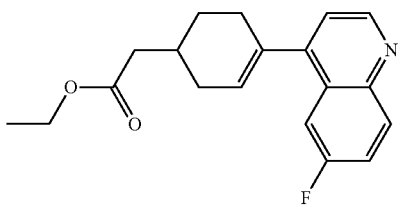 [SMILES: CCOC(=O)CC1CC=C(c2ccnc3ccc(F)cc23)CC1]

Ethyl 2-(4-(4,4,5,5-tetramethyl-1,3,2-dioxaborolan-2-yl)cyclohex-3-en-1-yl)acetate (33.02 g, 110 mmol, 1.10 eq) was dissolved in 1,4-dioxane (450 ml) and was added with 4-bromo-6-fluoroquinoline (22.5 g 100 mmol, 1.00 eq), Cs$_2$CO$_3$ (65 g, 200 mmol, 2.00 eq) and Pd(dppf)Cl$_2$ (14.62 g, 20 mmol, 0.20 eq). The mixture was stirred at 95° C. under nitrogen protection for 18 hours. The solution was filtered and concentrated to dryness. The crude was purified by column chromatography on silica gel 200 g (PE/EA=10/1 to 4/1) to give a clear oil (12.02 g, 34.8% yield). $^1$H NMR (CDCl$_3$) $\delta_H$ 8.80 (d, J=4.4 Hz, 1H), 8.15 (dd, J=9.2, 5.6 Hz, 1H), 7.62 (dd, J=10.0, 2.8 Hz, 1H), 7.49 (m, 1H), 7.21 (d, J=4.4 Hz, 1H), 5.81-5.87 (m, 1H), 4.19 (q, J=7.2 Hz, 2H), 2.23-2.57 (m, 6H), 1.95-2.04 (m, 2H), 1.53-1.65 (m, 1H) and 1.30 (t, J=7.2 Hz, 3H).

Step 4: ethyl 2-(4-(6-fluoroquinolin-4-yl)cyclohexyl)acetate

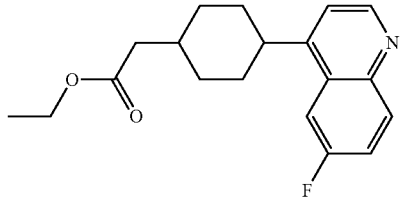 [SMILES: CCOC(=O)CC1CCC(c2ccnc3ccc(F)cc23)CC1]

To a mixture of ethyl 2-(4-(6-fluoroquinolin-4-yl)cyclohex-3-en-1-yl)acetate (12.02 g, 38 mmol, 1.00 eq) dissolved in MeOH (50 ml) was added Pd/C (2.4 g, w.t. 20%). And the mixture was stirred at room temperature under one hydrogen balloon for overnight. Then the mixture was filtered and concentrated to dryness. The crude was purified by column chromatography on silica gel 150 g (PE/EA=10/1 to 2/1) to give a pale yellow oil (8.51 g, 70.3% yield). $^1$H NMR (CDCl$_3$) $\delta_H$ 8.77-8.86 (m, 1H), 8.15 (dd, J=9.2, 5.6 Hz, 1H), 7.66 (dd, J=10.4, 2.4 Hz, 1H), 7.44-7.52 (m, 1H), 7.28-7.38 (m, 1H), 4.16 (q, J=7.2 Hz, 2H), 3.07-3.32 (m, 1H), 2.45-2.53 (m, 2H), 1.92-2.10 (m, 3H), 1.53-1.89 (m, 6H) and 1.28 (t, J=7.2, 4.0 Hz, 3H).

Step 5: 2-(4-(6-fluoroquinolin-4-yl)cyclohexyl)acetic acid

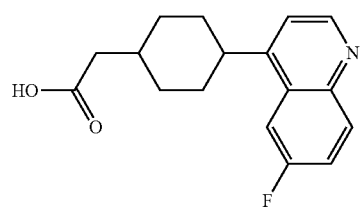 [SMILES: O=C(O)CC1CCC(c2ccnc3ccc(F)cc23)CC1]

To a mixture of ethyl 2-(4-(6-fluoroquinolin-4-yl)cyclohexyl)acetate (8.51 g, 27 mmol, 1.00 eq) dissolved in MeOH (20 ml) and water (20 ml) was added NaOH (1.61 g, 40.5 mmol, 1.50 eq). The mixture was stirred at room temperature for 2 hours. The solvent was concentrated to 20 ml and extracted with EA (20 mL×3) to remove the impurities. The water layer was concentrated to 5 ml. The water layer was neutralized with 1N HCl to make the PH to 7. Then the mixture was added to water 200 ml and extracted with DCM/MeOH (20/1, 400 ml×3). The organics was dried over Na$_2$SO$_4$, filtered and concentrated to give crude product, which was recrystilazed in water to give product (7.74 g). $^1$H NMR (DMSO-d$_6$) δ$_H$ 8.84 (t, J=4.4 Hz, 1H), 8.11-8.25 (m, 1H), 7.66 (dd, J=10.4, 2.4 Hz, 1H), 7.44-7.54 (m, 1H), 7.28-7.40 (m, 1H), 3.09-3.32 (m, 1H), 2.31-2.64 (m, 3H), 1.96-2.10 (m, 2H), 1.72-1.91 (m, 4H), 1.56-1.69 (m, 1H) and 1.29-1.45 (m, 1H).

Step 6: (R)-3-(2-((1s,4S)-4-(6-fluoroquinolin-4-yl)cyclohexyl)acetyl)-4-phenyloxazolidin-2-one

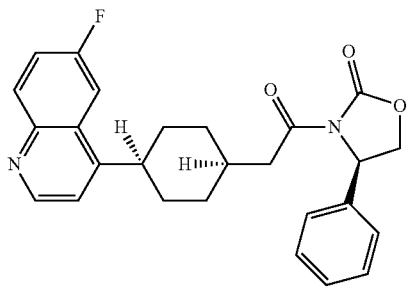

To a flask # a were added 2-(4-(6-fluoroquinolin-4-yl)cyclohexyl)acetic acid (7.74 g, 27 mmol, 1.00 eq), THF (250 ml) and TEA (8.5 ml, 2.00 eq). The mixture was stirred at −78° C. for 0.5 hours. Pivaloyl chloride (3.5 ml, 1.95 eq) was added to the flask dropwised under nitrogen protection. Then the mixture was warmed to 0° C. and stirred for 1 hour.

To a flask # b were added (R)-4-phenyloxazolidin-2-one (3.55 g, 29 mmol, 1.10 eq) and THF (60 ml). The solution was cooled to −78° C. before the careful addition of n-BuLi (1.6 N, 34 ml, 2.00 eq). And the mixture was stirred at −78° C. for 0.5 hour.

Flask # a was then cooled to −78° C. and the contents of Flask # b were added to Flask # a via cannula over the course of 15 minutes. After addition was completed, the cold bath was removed, and the reaction was stirred for 3 hours at room temperature. The reaction was quenched with saturated ammonium chloride solution 500 ml and extracted with EA (500 ml×3). The organic layer was combined, dried over Na$_2$SO$_4$, filtered and concentrated to dryness. The crude was purified by column chromatography on silica gel 100 g (PE/EA=4/1 to 1/1) to give product as a white solid, which was slurried in 2-methoxy-2-methylpropane to give product as cis-product, and the mother liquid was cis and trans mixture. Cis-product $^1$H NMR (CDCl$_3$) δ$_H$ 8.77-8.86 (m, 1H), 8.24 (s, 1H), 7.66 (dd, J=10.2, 2.4 Hz, 1H), 7.51 (t, J=8.4 Hz, 1H), 7.28-7.45 (m, 6H), 5.47 (dd, J=8.8, 3.6 Hz, 1H), 4.68-4.79 (m, 2H), 4.26-4.35 (m, 2H), 2.93-3.27 (m, 2H), 2.41-2.56 (m, 1H), 1.89-2.01 (m, 2H), 1.67-1.84 (m, 4H), 1.47-1.63 (m, 1H), 1.28-1.39 (m, 1H).

Step 7: (R)-3-((R)-2-((1s,4S)-4-(6-fluoroquinolin-4-yl)cyclohexyl)propanoyl)-4-phenyloxazolidin-2-one

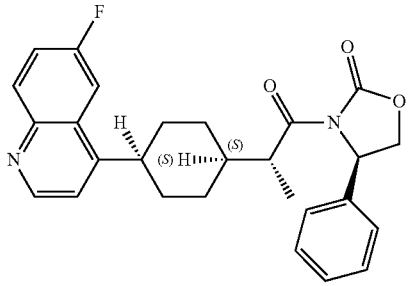

To a solution of NaHMDS (1.0 N, 14 ml, 2.00 eq) was added (R)-3-(2-((s,4S)-4-(6-fluoroquinolin-4-yl)cyclohexyl)acetyl)-4-phenyloxazolidin-2-one (3.55 g, 8 mmol, 1.00 eq) in THF 80 ml at −78° C. The mixture was warmed to −20° C. and stirred for 1 hour. Then the mixture was cooled to −78° C. and added iodomethane (7.50 g, 3.3 ml, 5.00 eq). The mixture was stirred at this temperature for 2 hours and quenched with saturated ammonium chloride solution 100 ml and extracted with EA (100 ml×3). The organic layer was combined, dried over Na$_2$SO$_4$, filtered and concentrated to dryness. The crude was purified by column chromatography on silica gel 100 g (PE/EA=4/1 to 1/1) to give product (2.11 g, 41% yield) as a pale yellow solid. $^1$H NMR (CDCl$_3$) δ$_H$ 8.77-8.85 (m, 1H), 8.09-8.18 (m, 1H), 7.62-7.70 (m, 1H), 7.44-7.50 (m, 1H), 7.29-7.44 (m, 6H), 5.38-5.52 (m, 2H), 4.91-5.00 (m, 1H), 4.66-4.79 (m, 2H), 4.16-4.38 (m, 2H), 2.10-2.20 (m, 1H), 1.86-2.03 (m, 2H), 1.65-1.83 (m, 4H), 1.45-1.64 (m, 1H), 1.12 (t, J=7.2 Hz, 2H).

Step 8: (R)-2-((1s,4S)-4-(6-fluoroquinolin-4-yl)cyclohexyl)propanoic acid

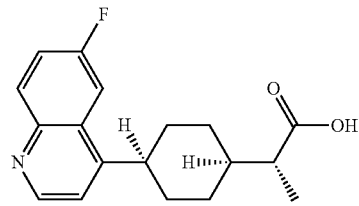

To a solution of (R)-3-((R)-2-((1s,4S)-4-(6-fluoroquinolin-4-yl)cyclohexyl)propanoyl)-4-phenyloxazolidin-2-one (2.71 g, 6 mmol, 1.00 eq) dissolved in THF (40 ml) and water (10 ml) was added H$_2$O (5 ml) dropwised at 0° C. The mixture was stirred at 0° C. for 1 hour. Then the mixture was added with LiOH (2 N, 6 ml, 2.00 eq) and stirred at room temperature for 4 hours. Progress was followed by LC/MS and the mixture was carefully quenched at 0° C. by the addition of saturated Na$_2$SO$_3$ once starting material had been consumed. The PH was adjusted to 5~6 with 1N HCl and then the mixture was extracted with DCM/MeOH (40/1, 50 ml x 4). The organics was dried over Na$_2$SO$_4$, filtered and concentrated to dryness get a pale yellow solid (1.02 g, not pure, 55% yield). $^1$H NMR (CDCl$_3$) δ$_H$ 8.82 (d, J=4.6 Hz, 1H), 8.11-8.20 (m, 1H), 7.63-7.72 (m, 1H), 7.45-7.53 (m, 1H), 7.27-7.33 (m, 1H), 3.12-3.33 (m, 1H), 2.34-2.49 (m, 1H), 1.57-2.14 (m, 9H), 1.20-1.29 (m, 3H).

Step 9: 4-((1S,4s)-4-((R)-1-(5,6-difluoro-1H-benzo[d]imidazol-2-yl)ethyl)cyclohexyl)-6-fluoroquinoline

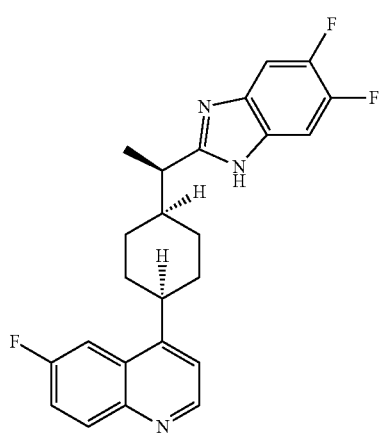

To a solution of (R)-2-((1s,4S)-4-(6-fluoroquinolin-4-yl)cyclohexyl)propanoic acid (0.2 g, 0.66 mmol) in DMF (10 mL), HATU (0.3 g, 0.8 mmol), DIEA (0.5 mL) were added at room temperature. Then 4,5-difluorobenzene-1,2-diamine (0.14 g, 0.8 mmol) was added. The mixture was stirred at 20-30° C. for 48 hours. The reaction was then quenched with H₂O (50 mL), Extracted with EA (50 mL), Separated the organic phase and washed with brine (100 mL). Concentrated the organic phase to give the crude product (R)—N-(2-amino-4,5-difluorophenyl)-2-((1s,4S)-4-(6-fluoroquinolin-4-yl)cyclohexyl)propanamide, which was used to the next step without further purification.

A solution of (R)—N-(2-amino-4,5-difluorophenyl)-2-((1s,4S)-4-(6-fluoroquinolin-4-yl)cyclohexyl)propanamide in HOAc (20 mL) was stirred at 100° C. for 18 hours. The solvent was evaporated. The crude residue was dissolved with EA (50 mL) and washed with saturated NaHCO₃ solution (50 mL). Separated the organic phase and purified by pre-HPLC to give the title compound. ¹H NMR (400 MHz, DMSO-d) $d_H$ 12.45 (s, 1H), 8.86 (d, J=4.4 Hz, 1H), 8.09 (dd, J=9.2, 6.0 Hz, 1H), 7.98 (dd, J=10.8, 2.4 Hz, 1H), 7.71-7.62 (m, 1H), 7.58-7.40 (m, 3H), 3.45-3.38 (m, 2H), 2.16-1.99 (m, 2H), 1.94-1.46 (m, 7H), 1.33 (d, J=6.8 Hz, 3H). [M+H]⁺=409.9.

Example B1b: 4-((1R,4s)-4-((S)-1-(5,6-difluoro-1H-benzo[d]imidazol-2-yl)ethyl)cyclohexyl)-6-fluoroquinoline

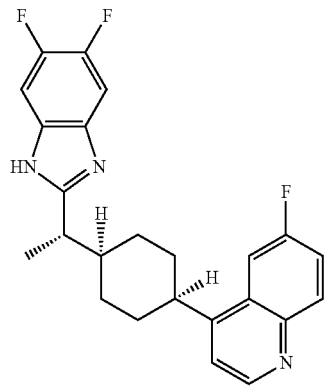 [SMILES: C[C@H](c1nc2cc(F)c(F)cc2[nH]1)[C@H]1CC[C@@H](c2ccnc3ccc(F)cc32)CC1]

Example B1c: 4-((1R,4r)-4-((R)-1-(5,6-difluoro-1H-benzo[d]imidazol-2-yl)ethyl)cyclohexyl)-6-fluoroquinoline

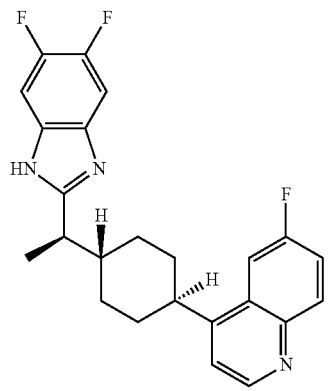 [SMILES: C[C@@H](c1nc2cc(F)c(F)cc2[nH]1)[C@H]1CC[C@H](c2ccnc3ccc(F)cc32)CC1]

Example B1d: 4-((1S,4r)-4-((S)-1-(5,6-difluoro-1H-benzo[d]imidazol-2-yl)ethyl)cyclohexyl)-6-fluoroquinoline

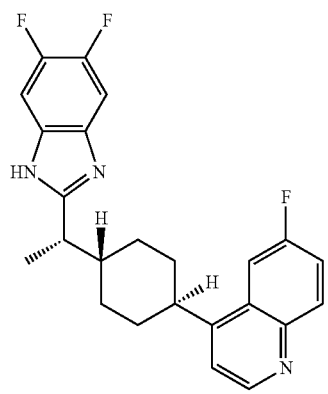 [SMILES: C[C@H](c1nc2cc(F)c(F)cc2[nH]1)[C@H]1CC[C@H](c2ccnc3ccc(F)cc32)CC1]

Example B2: 4-((1S,4s)-4-((R)-1-(5-chloro-6-fluoro-1H-benzo[d]imidazol-2-yl)ethyl)cyclohexyl)-6-fluoroquinoline

Step 2: 4-((1S,4s)-4-((R)-1-(5-chloro-6-fluoro-1H-benzo[d]imidazol-2-yl)ethyl)cyclohexyl)-6-fluoroquinoline

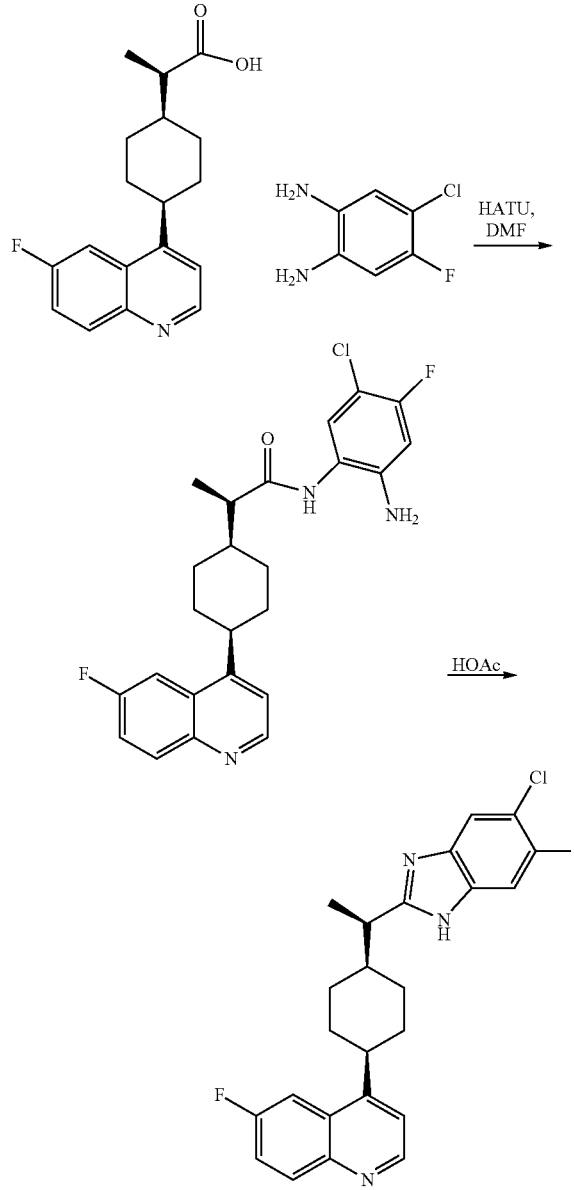

A solution of (R)—N-(2-amino-5-chloro-4-fluorophenyl)-2-((1s,4S)-4-(6-fluoroquinolin-4-yl)cyclohexyl)propanamide in HOAc (20 mL) was stirred at 80° C. for 18 hours. The solvent was evaporated. The crude residue was dissolved with EA (50 mL) and washed with saturated NaHCO₃ solution (50 mL). Separated the organic phase and purified by pre-HPLC to give the title compound. ¹H NMR (400 MHz, DMSO-d) $\delta_H$ 12.52 (d, J=13.6 Hz, 1H), 8.86 (d, J=4.4 Hz, 1H), 8.09 (dd, J=9.2, 6.0 Hz, 1H), 7.98 (d, J=11.2 Hz, 1H), 7.75-7.45 (m, 4H), 3.41-3.38 (m, 2H), 2.17-1.96 (m, 2H), 1.95-1.51 (m, 7H), 1.33 (d, J=6.8 Hz, 3H). [M+H]⁺=425.8.

Example B2a and B2b: 4-((1R,4s)-4-((S)-1-(5-chloro-6-fluoro-1H-benzo[d]imidazol-2-yl)ethyl)cyclohexyl)-6-fluoroquinoline and 4-((1S,4s)-4-((R)-1-(5-chloro-6-fluoro-1H-benzo[d]imidazol-2-yl)ethyl)cyclohexyl)-6-fluoroquinoline

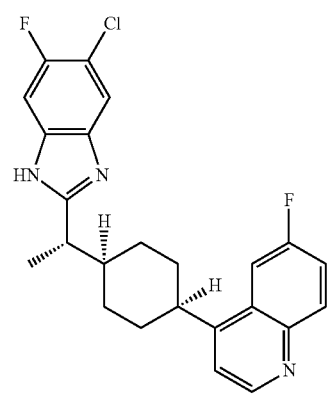

Fast isomer in CHIRALPAK IC HPLC
Eluting reagent: Hex(0.1%IPAmine):EtOH = 90:10

Step 1: (R)—N-(2-amino-5-chloro-4-fluorophenyl)-2-((1s,4S)-4-(6-fluoroquinolin-4-yl)cyclohexyl)propanamide To a solution of (R)-2-((1s,4S)-4-(6-fluoroquinolin-4-yl)cyclohexyl)propanoic acid (0.36 g, 01.2 mmol) in DMF (10 mL) were added HATU (0.54 g, 1.4 mmol), DIEA (0.5 mL) at room temperature. 4-chloro-5-fluorobenzene-1,2-diamine (0.23 g, 1.4 mmol) was added. The mixture was stirred at 50° C. for 18 hours. The reaction was then quenched with H₂O (50 mL), extracted with EA (50 mL*2), and the the organic phase was separated and washed with brine (100 mL). The organic phase was concentrated for next step directly without further purification.

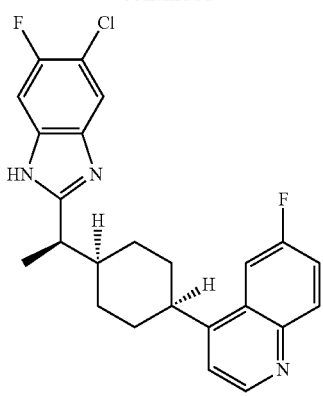

Slow isomer in CHIRALPAL IC HPLC
Eluting reagent: Hex(0.1%IPAmine):EtOH = 90:10

Each enantiomer of racemic B2a and B2b was separated using preparative HPLC on a CHIRALPAK IC with Hex:EtOH=90:10 as an eluent. The first one enantiomer eluted at the retention time of 3.414 min, B2a (3.81 mg), $^1$H NMR (MeOH-d6) $\delta_H$ 8.78 (d, J=4.8 Hz, 1H), 8.07 (dd, J=9.2, 5.6 Hz, 1H), 7.87 (dd, J=10.8, 2.8 Hz, 1H), 7.66-7.49 (m, 3H), 7.35 (br, 1H), 3.51-3.37 (m, 2H), 2.18-2.16 (m, 2H), 2.02-1.54 (m, 7H), 1.43 (d, J=6.8 Hz, 3H). [M+H]$^+$=425.8. And the other enantiomer eluted at the retention time of 3.881 min, B2b (43.63 mg), $^1$H NMR (MeOH-d6) $\delta_H$ 8.68 (d, J=4.8 Hz, 1H), 7.97 (dd, J=9.2, 5.6 Hz, 1H), 7.76 (dd, J=10.8, 2.8 Hz, 1H), 7.59-7.39 (m, 3H), 7.26 (br, 1H), 3.45-3.29 (m, 2H), 2.07-1.84 (m, 2H), 1.97-1.54 (m, 7H), 1.33 (d, J=6.8 Hz, 3H). [M+H]$^+$=425.8.

Example B3: methyl 2-(1-(4-(6-fluoroquinolin-4-yl)cyclohexyl)ethyl)-1H-benzo[d]imidazole-5-carboxylate

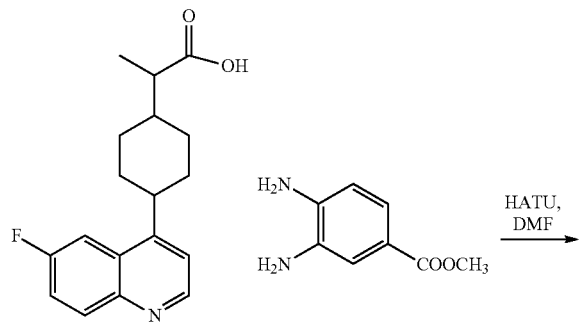

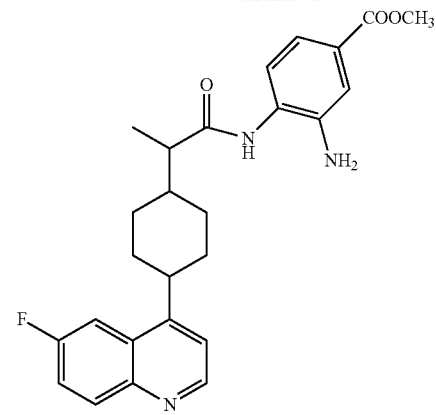

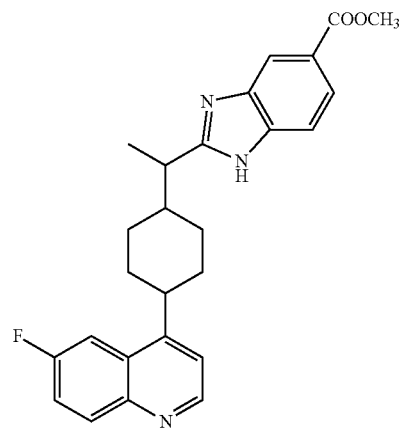

Step 1: methyl 3-amino-4-(2-(4-(6-fluoroquinolin-4-yl)cyclohexyl)propanamido)benzoate To a solution of (R)-2-((1s,4S)-4-(6-fluoroquinolin-4-yl)cyclohexyl)propanoic acid (0.2 g, 0.66 mmol) in DMF (10 mL) were added HATU (0.3 g, 0.8 mmol), DIEA (0.5 mL) at room temperature. Methyl 3,4-diaminobenzoate (0.13 g, 0.8 mmol) was added. The mixture was stirred at 50° C. for 18 hours. The reaction was then quenched with H$_2$O (50 mL), extracted with EA (50 mL*2), separated the organic phase and washed with brine (100 mL). Concentrated the organic phase for next step directly without further purification.

Step 2: methyl 2-(1-(4-(6-fluoroquinolin-4-yl)cyclohexyl)ethyl)-1H-benzo[d]imidazole-5-carboxylate

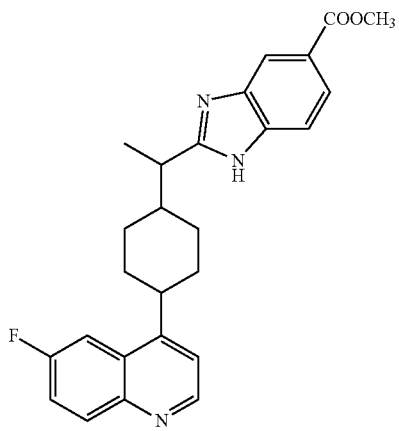 [SMILES: COC(=O)c1ccc2[nH]c(C(C)C3CCC(c4ccnc5ccc(F)cc45)CC3)nc2c1]

A solution of methyl 3-amino-4-(2-(4-(6-fluoroquinolin-4-yl)cyclohexyl)propanamido)benzoate in HOAc (20 mL) was stirred at 100° C. for 18 hours. The solvent was evaporated. The crude residue was dissolved with EA (50 mL) and washed with saturated NaHCO₃ solution (50 mL). Separated the organic phase and purified by pre-HPLC to give the title compound. ¹H NMR (400 MHz, DMSO-d) $\delta_H$ 12.60 (d, J=4.4 Hz, 1H), 8.86 (d, J=4.4 Hz, 1H), 8.19-7.93 (m, 3H), 7.78-7.76 (m, 1H), 7.71-7.50 (m, 3H), 3.86 (d, J=1.6 Hz, 3H), 3.45-3.40 (m, 2H), 2.21-2.01 (m, 2H), 1.93-1.54 (m, 7H), 1.36 (d, J=6.0 Hz, 3H). [M+H]⁺=431.9.

Example B3a and B3b: methyl 2-((S)-1-((1s,4R)-4-(6-fluoroquinolin-4-yl)cyclohexyl)ethyl)-1H-benzo[d]imidazole-5-carboxylate and methyl 2-((R)-1-((1s,4S)-4-(6-fluoroquinolin-4-yl)cyclohexyl)ethyl)-1H-benzo[d]imidazole-5-carboxylate

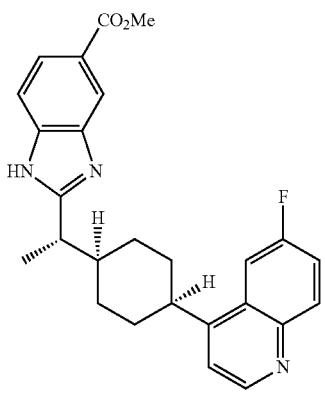

Fast isomer in CHIRALPAK IC HPLC
Eluting reagent: Hex(0.1%DEA):EtOH = 70:30

-continued

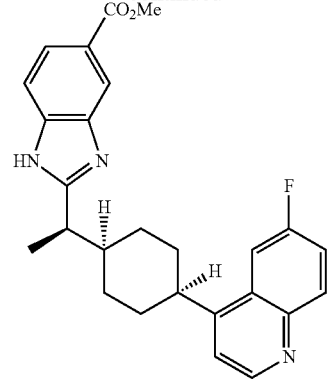

Slow isomer in CHIRALPAL IC HPLC
Eluting reagent: Hex(0.1%DEA):EtOH = 70:30

Each enantiomer of racemic B3a and B3b was separated using preparative HPLC on a CHIRALPAK IC with Hex:EtOH=70:30 as an eluent. The first one enantiomer eluted at the retention time of 1.534 min, B3a (7.65 mg). ¹H NMR (MeOH-d6) δH 8.68 (d, J=4.8 Hz, 1H), 8.13 (s, 1H), 7.97 (dd, J=9.2, 5.6 Hz, 1H), 7.83-7.75 (m, 2H), 7.53-7.42 (m, 3H), 3.82 (s, 3H), 3.45-3.31 (m, 2H), 2.15-2.07 (m, 2H), 1.95-1.54 (m, 7H), 1.36 (d, J=6.8 Hz, 3H). [M+H]⁺=431.8. And the other enantiomer eluted at the retention time of 2.048 min, B3b: (37.58 mg). ¹H NMR (MeOH-d6) $\delta_H$ 8.77 (d, J=4.4 Hz, 1H), 8.26-8.05 (m, 2H), 7.94-7.81 (m, 2H), 7.61-7.55 (m, 3H), 3.91 (s, 3H), 3.55-3.37 (m, 2H), 2.28-2.13 (m, 2H), 2.01-1.68 (m, 7H), 1.45 (d, J=6.8 Hz, 3H). [M+H]⁺=431.8.

Example B4 6-fluoro-4-((1S,4s)-4-((R)-1-(5-(trifluoromethyl)-1H-benzo[d]imidazol-2-yl)ethyl)cyclohexyl)quinoline

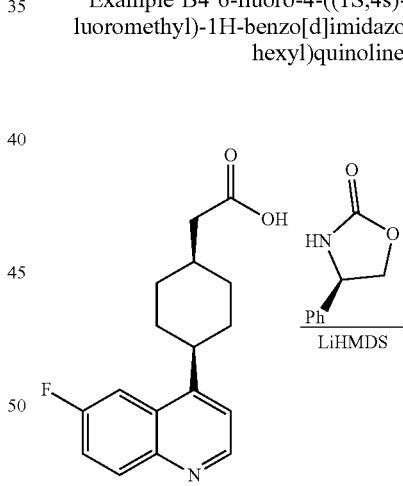

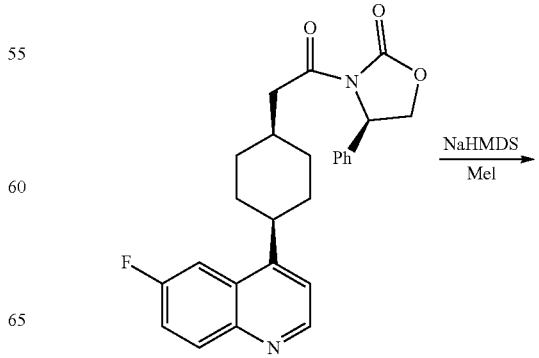

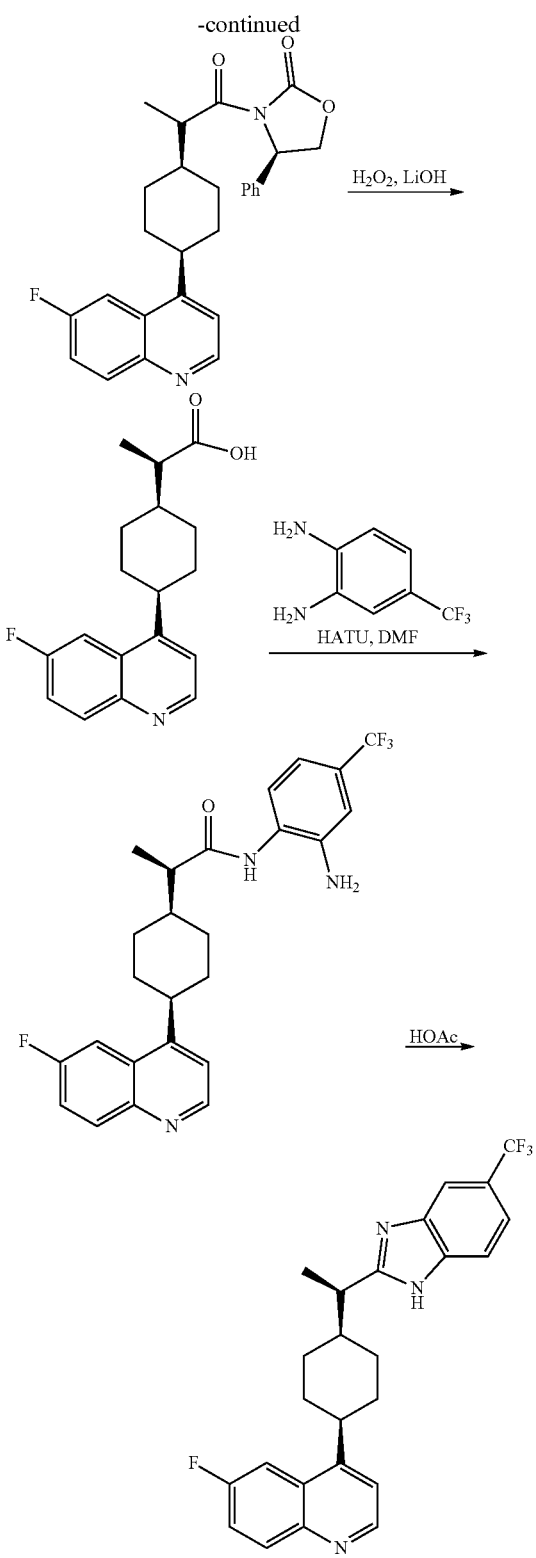

Step 1: (R)-3-(2-((1s,4S)-4-(6-fluoroquinolin-4-yl)cyclohexyl)acetyl)-4-phenyloxazolidin-2-one To a solution of 2-((1s,4s)-4-(6-fluoroquinolin-4-yl)cyclohexyl)acetic acid in THF (35 mL) was added TEA (3.1 mL). Cooled to 0° C. and added TMAcCl (1.7 mL). Stirred at 0° C. for 30 min. To another flask were added (R)-4-phenyloxazolidin-2-one (2.4 g, 14.7 mmol) and THE (70 mL). Cooled to 0° C. and added LiHMDS (11.3 mL, 1.3 eq). The reaction mixture was added into the first flask slowly at 0° C. The mixture was stirred at 20-30° C. for 2 hours. Poured the mixture into sat. NH$_4$Cl solution (150 mL), extracted with EA (100 mL*3). Combined the organic phase and washed with brine (100 mL). Concentrated the organic phase and purified by column chromatography on silica gel. The crude oil was slurry with MTBE to give product (3.3 g) as white solid.

Step 2: (R)-3-((S)-2-((1s,4R)-4-(6-fluoroquinolin-4-yl)cyclohexyl)propanoyl)-4-phenyloxazolidin-2-one To a solution of (R)-3-(2-((1s,4S)-4-(6-fluoroquinolin-4-yl)cyclohexyl)acetyl)-4-phenyloxazolidin-2-one (4.1 g, 9.5 mmol) in THF (40 mL) was added NaHMDS (5.7 mL, 11.4 mmol) at −40° C. The mixture was stirred at −40° C. for 10 min. Me (2.0 g, 14.2 mmol) was added slowly and stirred at −40° C. for 2 hours. The mixture was quenched with sat. NH$_4$Cl solution (80 mL) and extracted with EA (50 mL*3). Combined the organic phase and washed with brine (100 mL). Concentrated the organic phase and purified by column chromatography on silica gel to give product (3.3 g) as white solid.

Step 3: (R)-2-((1s,4S)-4-(6-fluoroquinolin-4-yl)cyclohexyl)propanoic acid

To a solution of (R)-3-((S)-2-((1s,4R)-4-(6-fluoroquinolin-4-yl)cyclohexyl)propanoyl)-4-phenyloxazolidin-2-one (2.9 g, 6.5 mmol) in THE (21.6 mL) were added H$_2$O (2.9 mL), LiOH.H$_2$O (0.4 g, 10.6 mmol) in H$_2$O (6.7 mL) at 0° C. The mixture was stirred at 20-30° C. for 18 hours. The reaction mixture was cooled to 0° C. and added sat. NaHSO$_3$ solution (8.8 mL). Evaporated the organic phase and added HOAc (1.2 mL) and EA (20 mL). Separated the organic phase and extracted the aqueous phase with EA (20 mL*2). Combined the organic phase and concentrated. Crystallized with MeCN (14 mL) and washed the filter cake with MeCN (10 mL). Dried the filter cake under reduced pressure to give product (1.6 g) as white solid. $^1$H NMR (400 MHz, DMSO-d6) $\delta_H$: 12.11 (d, J=3.2 Hz, 1H), 8.82 (s, 1H), 8.15-7.89 (m, 2H), 7.82-7.42 (m, 2H), 3.39 (br, 1H), 2.72 (br, 1H), 1.83-1.68 (m, 9H), 1.10 (br, 3H).

Step 4: (R)—N-(2-amino-4-(trifluoromethyl)phenyl)-2-((1s,4S)-4-(6-fluoroquinolin-4-yl)cyclohexyl)propanamide To a solution of (R)-2-((1s,4S)-4-(6-fluoroquinolin-4-yl)cyclohexyl)propanoic acid (0.2 g, 0.66 mmol) in DMF (10 mL) were added HATU (0.3 g, 0.8 mmol), DIEA (0.5 mL) at room temperature. 4-(trifluoromethyl)benzene-1,2-diamine (0.14 g, 0.8 mmol) was added. The mixture was stirred at 50° C. for 18 hours. The reaction was then quenched with H$_2$O (50 mL), Extracted with EA (50 mL*2), Separated the organic phase and washed with brine (100 mL). Concentrated the organic phase for next step directly without further purification.

Step 5: 6-fluoro-4-((1S,4s)-4-((R)-1-(5-(trifluoromethyl)-1H-benzo[d]imidazol-2-yl)ethyl)cyclohexyl)quinoline

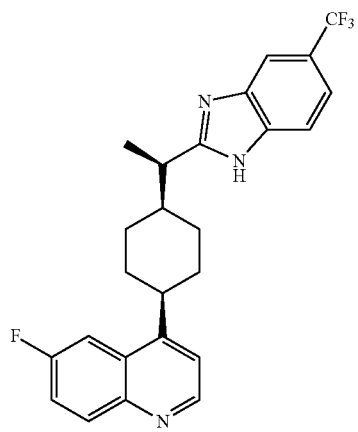 [SMILES: C[C@@H](c1nc2cc(C(F)(F)F)ccc2[nH]1)[C@H]1CC[C@@H](c2ccnc3ccc(F)cc32)CC1]

A solution of (R)—N-(2-amino-4-(trifluoromethyl)phenyl)-2-((1s,4S)-4-(6-fluoroquinolin-4-yl)cyclohexyl)propanamide in HOAc (20 mL) was stirred at 80° C. for 18 hours. The solvent was evaporated. The crude residue was dissolved with EA (50 mL) and washed with saturated NaHCO₃ solution (50 mL). Separated the organic phase and purified by pre-HPLC to give the title compound.

¹H NMR (400 MHz, DMSO-d) δ$_H$ 12.66 (s, 1H), 8.85 (d, J=4.4 Hz, 1H), 8.10 (dd, J=9.2, 6.0 Hz, 1H), 7.98 (dd, J=11.2, 2.4 Hz, 1H), 7.85 (s, 1H), 7.68-7.64 (m, 2H), 7.57-756 (m, 1H), 7.44 (d, J=8.4 Hz, 1H), 3.51-3.41 (m, 2H), 2.16-2.05 (m, 2H), 1.96-1.49 (m, 7H), 1.37 (d, J=6.8 Hz, 3H). [M+H]⁺=441.8.

Compounds B5 to B148 were prepared in a procedure similar to Example B1a.

Example B5: 6-fluoro-4-((1S,4s)-4-((R)-1-(4,6,7-trifluoro-1H-benzo[d]imidazol-2-yl)ethyl)cyclohexyl)quinoline

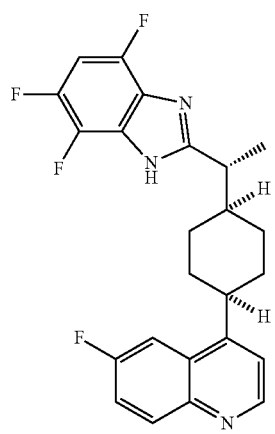 [SMILES: C[C@@H](c1nc2c(F)cc(F)c(F)c2[nH]1)[C@H]1CC[C@@H](c2ccnc3ccc(F)cc32)CC1]

¹H NMR (400 MHz, DMSO-d6) δ$_H$ 13.07-13.36 (m, 1H), 8.84 (d, J=4.4 Hz, 1H), 8.08 (dd, J=9.2, 6.0 Hz, 1H), 7.96 (dd, J=10.8, 2.4 Hz, 1H), 7.61-7.69 (m, J=9.2, 2.4 Hz, 1H), 7.56 (d, J=4.4 Hz, 1H), 7.16-7.32 (m, 1H), 3.35-3.47 (m, 2H), 2.11-2.21 (m, 1H), 1.98-2.07 (m, J=12.8 Hz, 1H), 1.81-1.92 (m, 2H), 1.69-1.80 (m, 2H), 1.49-1.69 (m, 2H), 1.34 (d, J=6.8 Hz, 3H), 1.08-1.18 (m, 1H).

Example B6: 6-fluoro-4-((1S,4s)-4-((R)-1-(4,5,6-trifluoro-1H-benzo[d]imidazol-2-yl)ethyl)cyclohexyl)quinoline

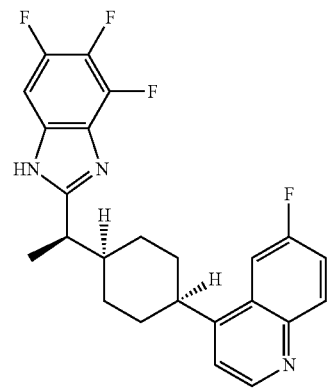

Example B7: 4-((1S,4s)-4-((R)-1-(5,6-difluoro-4-methyl-1H-benzo[d]imidazol-2-yl)ethyl)cyclohexyl)-6-fluoroquinoline

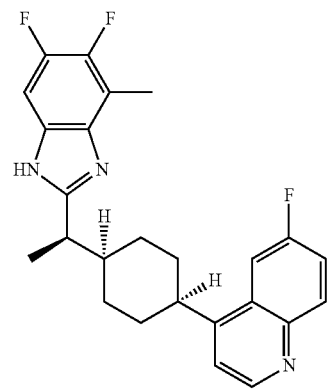

Example B8: 2-((S)-1-((1s,4R)-4-(6-fluoroquinolin-4-yl)cyclohexyl)ethyl)-1H-benzo[d]imidazole-6-carbonitrile

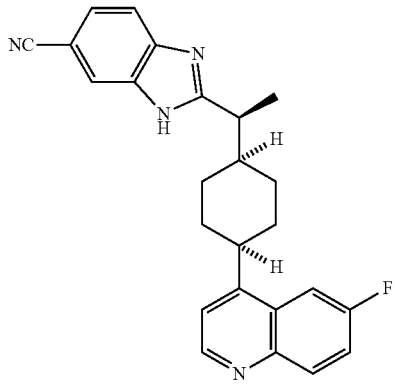 [SMILES: C[C@H](c1nc2ccc(C#N)cc2[nH]1)[C@H]1CC[C@@H](c2ccnc3ccc(F)cc32)CC1]

¹H NMR (400 MHz, DMSO-d6) δH 12.85 (s, 1H), 8.87 (d, J=4.4 Hz, 1H), 8.10 (m, 1H), 8.05 (s, 1H), 7.98 (m, 1H), 7.67 (m, 2H), 7.55 (m, 2H), 3.47 (m, 2H), 2.16 (m, 1H), 2.05 (m, 1H), 1.88 (m, 2H), 1.79 (m, 2H), 1.65 (m, 1H), 1.56 (m, 1H), 1.37 (d, J=6.8 Hz, 3H), 1.15 (m, 1H).

Example B9: 6-fluoro-4-((1S,4s)-4-((R)-1-(5-fluoro-1H-benzo[d]imidazol-2-yl)ethyl)cyclohexyl)quinoline

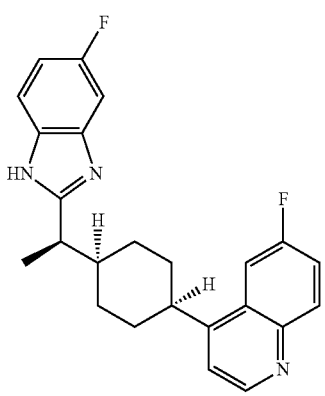 [SMILES: C[C@@H](c1nc2cc(F)ccc2[nH]1)[C@H]1CC[C@@H](c2ccnc3ccc(F)cc32)CC1]

Example B10: 2-((R)-1-((1s,4S)-4-(6-fluoroquinolin-4-yl)cyclohexyl)ethyl)-1H-benzo[d]imidazole-5-carboxamide

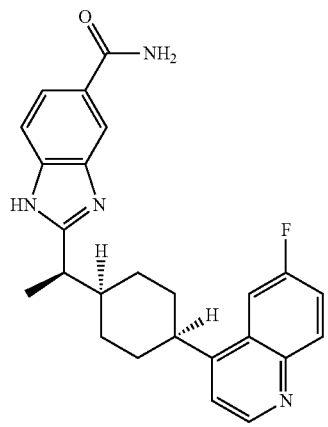 [SMILES: C[C@@H](c1nc2cc(C(N)=O)ccc2[nH]1)[C@H]1CC[C@@H](c2ccnc3ccc(F)cc32)CC1]

Example B11: 2-(1-((1s,4s)-4-(6-fluoroquinolin-4-yl)cyclohexyl)ethyl)-N-methyl-1H-benzo[d]imidazole-5-carboxamide

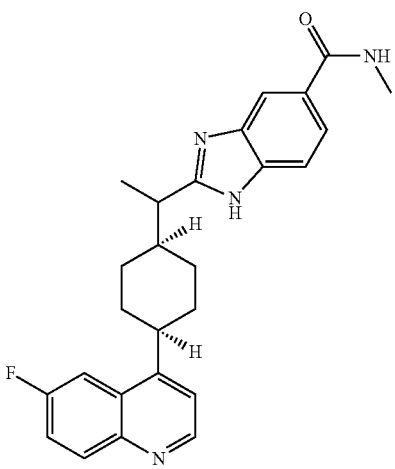 [SMILES: CNC(=O)c1ccc2[nH]c(C(C)[C@H]3CC[C@@H](c4ccnc5ccc(F)cc54)CC3)nc2c1]

¹H NMR (400 MHz, cd3od) δ_H 8.79 (d, J=4.7 Hz, 1H), 8.09-8.06 (m, 2H), 7.89-7.86 (m, 1H), 7.77-7.46 (m, 4H), 3.56-3.39 (m, 2H), 2.94 (s, 3H), 2.28-2.14 (m, 2H), 2.00-1.90 (m, 4H), 1.78-1.69 (m, 2H), 1.47-1.45 (m, 3H), 1.31 (d, J=12.1 Hz, 1H).

Example B12: 2-((R)-1-((1s,4S)-4-(6-fluoroquinolin-4-yl)cyclohexyl)ethyl)-N,N-dimethyl-1H-benzo[d]imidazole-5-carboxamide

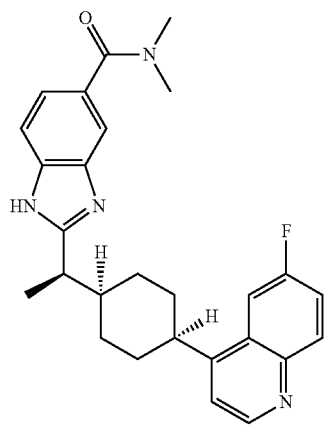 [SMILES: C[C@@H](c1nc2cc(C(=O)N(C)C)ccc2[nH]1)[C@H]1CC[C@@H](c2ccnc3ccc(F)cc32)CC1]

Example B14: N-cyclopropyl-2-((R)-1-((1s,4S)-4-(6-fluoroquinolin-4-yl)cyclohexyl)ethyl)-1H-benzo[d]imidazole-5-carboxamide

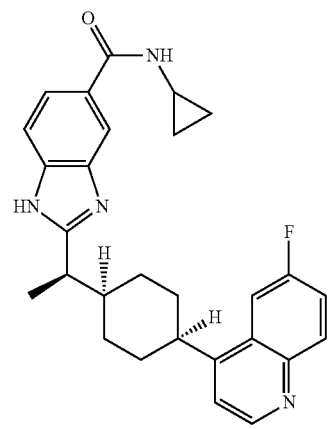

Example B13: aziridin-1-yl(2-((R)-1-((1s,4S)-4-(6-fluoroquinolin-4-yl)cyclohexyl)ethyl)-1H-benzo[d]imidazol-5-yl)methanone

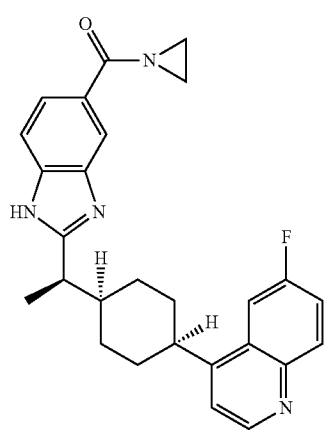 [SMILES: C[C@@H](c1nc2cc(C(=O)N3CC3)ccc2[nH]1)[C@H]1CC[C@@H](c2ccnc3ccc(F)cc32)CC1]

Example B15: azetidin-1-yl(2-((R)-1-((1s,4S)-4-(6-fluoroquinolin-4-yl)cyclohexyl)ethyl)-1H-benzo[d]imidazol-5-yl)methanone

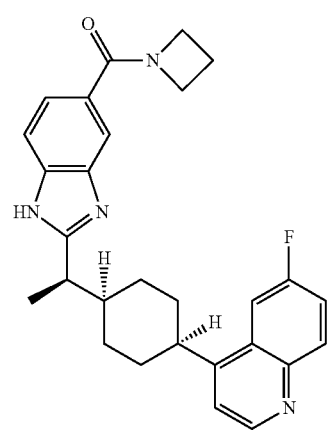 [SMILES: C[C@@H](c1nc2cc(C(=O)N3CCC3)ccc2[nH]1)[C@H]1CC[C@@H](c2ccnc3ccc(F)cc32)CC1]

Example B16: (2-((R)-1-((1s,4S)-4-(6-fluoroquinolin-4-yl)cyclohexyl)ethyl)-1H-benzo[d]imidazol-5-yl)(3-hydroxyazetidine-1-yl)methanone

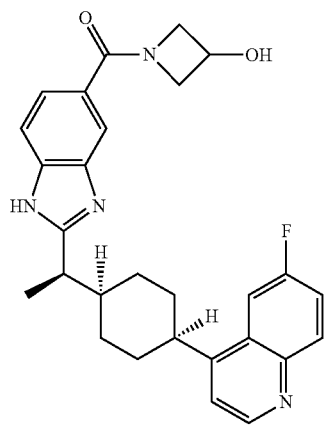 [SMILES: C[C@@H](c1nc2cc(C(=O)N3CC(O)C3)ccc2[nH]1)[C@H]1CC[C@@H](c2ccnc3ccc(F)cc32)CC1]

Example B17: ethyl 2-((R)-1-((1s,4S)-4-(6-fluoroquinolin-4-yl)cyclohexyl)ethyl)-1H-benzo[d]imidazole-5-carboxylate

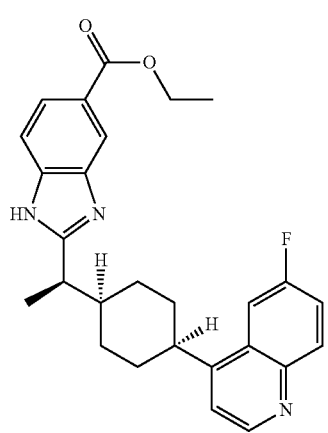 [SMILES: CCOC(=O)c1ccc2[nH]c([C@H](C)[C@H]3CC[C@@H](c4ccnc5ccc(F)cc54)CC3)nc2c1]

Example B18: isopropyl 2-((R)-1-((1s,4S)-4-(6-fluoroquinolin-4-yl)cyclohexyl)ethyl)-1H-benzo[d]imidazole-5-carboxylate

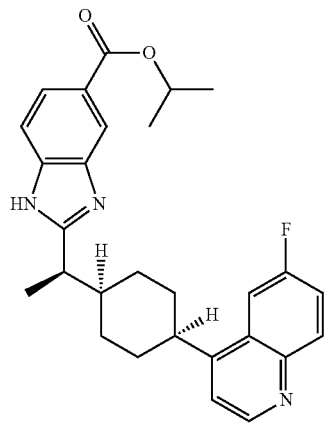 [SMILES: CC(C)OC(=O)c1ccc2[nH]c([C@H](C)[C@H]3CC[C@@H](c4ccnc5ccc(F)cc54)CC3)nc2c1]

Example B19: 5-(2-((R)-1-((1s,4S)-4-(6-fluoroquinolin-4-yl)cyclohexyl)ethyl)-1H-benzo[d]imidazol-5-yl)oxazole

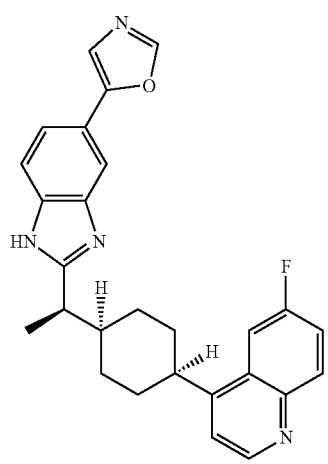 [SMILES: C[C@@H](c1nc2cc(-c3cnco3)ccc2[nH]1)[C@H]1CC[C@@H](c2ccnc3ccc(F)cc32)CC1]

Example B20: 6-((R)-1-((1s,4S)-4-(6-fluoroquinolin-4-yl)cyclohexyl)ethyl)-5H-[1,3]dioxolo[4',5':4,5]benzo[1,2-d]imidazole
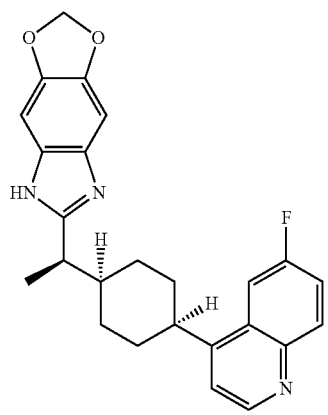 [SMILES: C[C@@H](c1nc2cc3c(cc2[nH]1)OCO3)[C@H]1CC[C@@H](c2ccnc3ccc(F)cc32)CC1]
Example B21: 3-(2-((R)-1-((1s,4S)-4-(6-fluoroquinolin-4-yl)cyclohexyl)ethyl)-1H-benzo[d]imidazol-5-yl)-1,2,4-oxadiazole
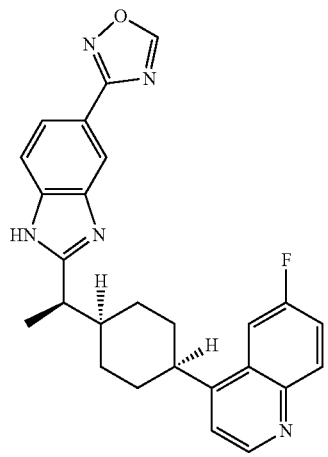 [SMILES: C[C@@H](c1nc2cc(-c3ncon3)ccc2[nH]1)[C@H]1CC[C@@H](c2ccnc3ccc(F)cc32)CC1]
Example B22: 4-((1S,4s)-4-((R)-1-(5-(1H-pyrazol-1-yl)-1H-benzo[d]imidazol-2-yl)ethyl)cyclohexyl)-6-fluoroquinoline
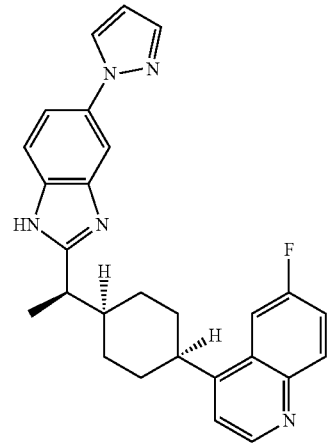 [SMILES: C[C@@H](c1nc2cc(-n3cccn3)ccc2[nH]1)[C@H]1CC[C@@H](c2ccnc3ccc(F)cc32)CC1]
Example B23: 1-((6-fluoro-2-((R)-1-((1s,4S)-4-(6-fluoroquinolin-4-yl)cyclohexyl)ethyl)-1H-benzo[d]imidazol-5-yl)oxy)propan-2-ol
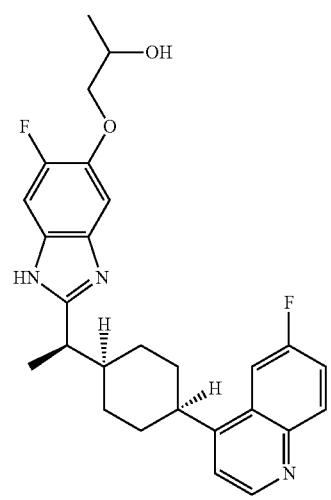

Example B24: 6-fluoro-4-((1S,4s)-4-((R)-1-(6-fluoro-5-(2-methoxyethoxy)-1H-benzo[d]imidazol-2-yl)ethyl)cyclohexyl)quinoline

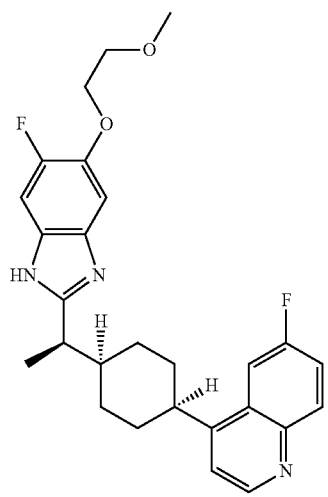 [SMILES: COCCOc1cc2nc([C@H](C)[C@H]3CC[C@@H](c4ccnc5ccc(F)cc54)CC3)[nH]c2cc1F]

Example B25a and B25b: (S)-3-(4-(1-(6-chloro-1H-benzo[d]imidazol-2-yl)ethyl)cyclohexyl)quinoline or (R)-3-(4-(1-(6-chloro-1H-benzo[d]imidazol-2-yl)ethyl)cyclohexyl)quinoline

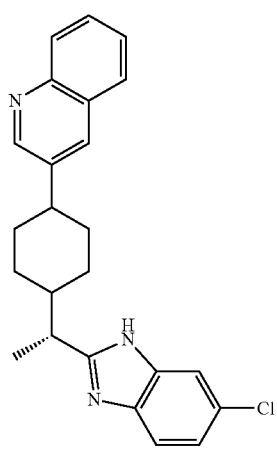

Example B25a

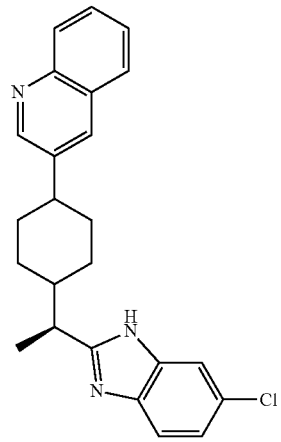

Example B25b

Example B25a $^1$H NMR (400 MHz, DMSO-d6) δ$_H$ 12.39 (s, 1H), 8.82 (d, J=2.0 Hz, 1H), 8.11 (m, 1H), 7.96 (d, J=8.4 Hz, 1H), 7.91 (d, J=7.6 Hz, 1H), 7.68 (m, 1H), 7.54 (m, 3H), 7.15 (dd, J=8.4, 2.0 Hz, 1H), 2.90 (m, 1H), 2.69 (m, 1H), 1.98 (d, J=11.2 Hz, 2H), 1.85 (m, 2H), 1.57 (m, 3H), 1.36 (d, J=7.2 Hz, 3H), 1.23 (m, 3H).

Example B25b $^1$H NMR (400 MHz, DMSO-d6) δ$_H$ 12.41 (s, 1H), 8.89 (d, J=2.0 Hz, 1H), 8.22 (s, 1H), 7.98 (dd, J=12.0, 8.4 Hz, 2H), 7.70 (t, J=7.2 Hz, 1H), 7.56 (m, 3H), 7.14 (dd, J=8.4, 1.6 Hz, 1H), 3.36 (m, 1H), 2.88 (m, 1H), 2.05 (m, 1H), 1.93 (m, 3H), 1.76 (m, 2H), 1.61 (m, 1H), 1.45 (m, 1H), 1.33 (d, J=6.8 Hz, 3H), 1.16 (m, 1H).

Example B26: 4-((1S,4s)-4-((R)-cyclopropyl(5,6-difluoro-1H-benzo[d]imidazol-2-yl)methyl)cyclohexyl)-6-fluoroquinoline

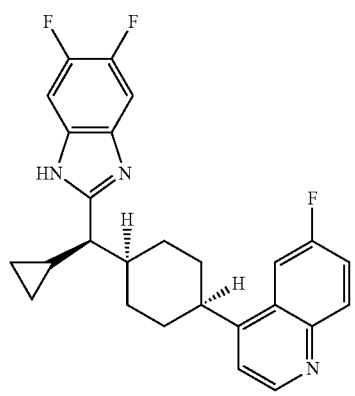 [SMILES: Fc1ccc2nccc([C@H]3CC[C@@H]([C@H](c4nc5cc(F)c(F)cc5[nH]4)C4CC4)CC3)c2c1]

Example B27: 4-((1S,4s)-4-((R)-cyclopropyl(5,7-difluoro-1H-benzo[d]imidazol-2-yl)methyl)cyclohexyl)-6-fluoroquinoline

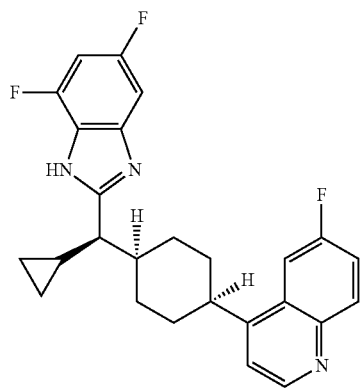 [SMILES: Fc1cc(F)c2[nH]c([C@H](C3CC3)[C@H]3CC[C@@H](c4ccnc5ccc(F)cc54)CC3)nc2c1]

Example B28: methyl 2-((R)-cyclopropyl((1s,4S)-4-(6-fluoroquinolin-4-yl)cyclohexyl)methyl)-1H-benzo[d]imidazole-5-carboxylate

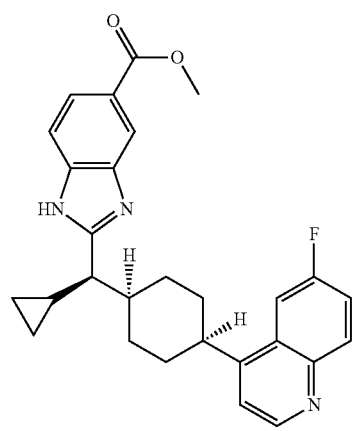 [SMILES: COC(=O)c1ccc2[nH]c([C@H](C3CC3)[C@H]3CC[C@@H](c4ccnc5ccc(F)cc54)CC3)nc2c1]

Example B29: 4-((1S,4s)-4-((R)-(5-chloro-1H-benzo[d]imidazol-2-yl)(cyclopropyl)methyl)cyclohexyl)-6-fluoroquinoline

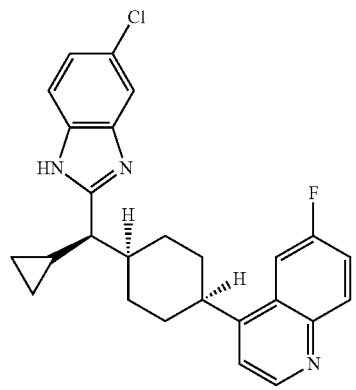 [SMILES: Fc1ccc2nccc([C@H]3CC[C@@H]([C@H](c4nc5cc(Cl)ccc5[nH]4)C4CC4)CC3)c2c1]

Example B30: 4-((1S,4s)-4-((R)-cyclopropyl(5-fluoro-1H-benzo[d]imidazol-2-yl)methyl)cyclohexyl)-6-fluoroquinoline

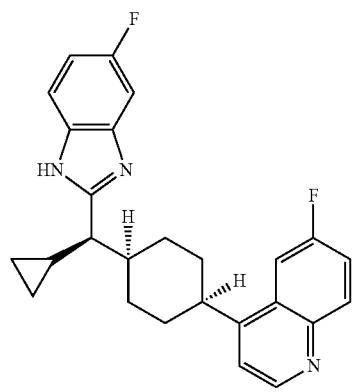 [SMILES: Fc1ccc2[nH]c([C@H](C3CC3)[C@H]3CC[C@@H](c4ccnc5ccc(F)cc54)CC3)nc2c1]

Example B31: 4-((1S,4s)-4-((R)-(6-chloro-5-fluoro-1H-benzo[d]imidazol-2-yl)(cyclopropyl)methyl)cyclohexyl)-6-fluoroquinoline

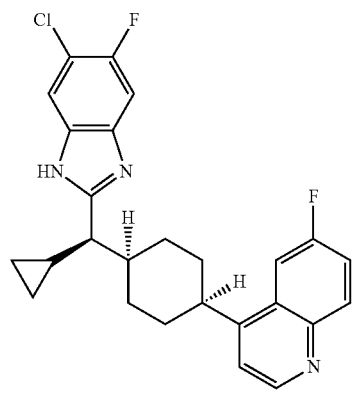 [SMILES: Fc1ccc2nccc([C@H]3CC[C@@H]([C@H](c4nc5cc(F)c(Cl)cc5[nH]4)C4CC4)CC3)c2c1]

Example B32: 2-((R)-cyclopropyl((1s,4S)-4-(6-fluoroquinolin-4-yl)cyclohexyl)methyl)-N,N-dimethyl-1H-benzo[d]imidazole-5-carboxamide Example B34: aziridin-1-yl(2-((R)-cyclopropyl((1s,4S)-4-(6-fluoroquinolin-4-yl)cyclohexyl)methyl)-1H-benzo[d]imidazol-5-yl)methanone

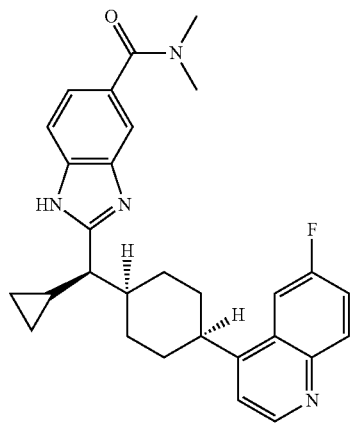 [SMILES: CN(C)C(=O)c1ccc2[nH]c([C@H](C3CC3)[C@H]3CC[C@@H](c4ccnc5ccc(F)cc54)CC3)nc2c1]

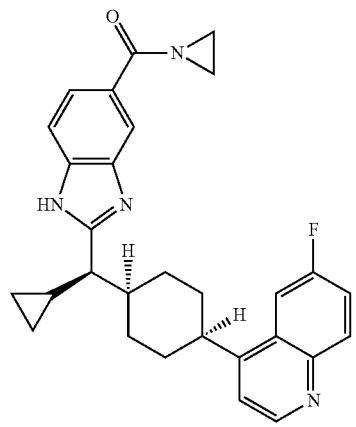

Example B33: 2-((R)-cyclopropyl((1s,4S)-4-(6-fluoroquinolin-4-yl)cyclohexyl)methyl)-1H-benzo[d]imidazole-5-carboxamide Example B35: N-cyclopropyl-2-((R)-cyclopropyl((1s,4S)-4-(6-fluoroquinolin-4-yl)cyclohexyl)methyl)-1H-benzo[d]imidazole-5-carboxamide

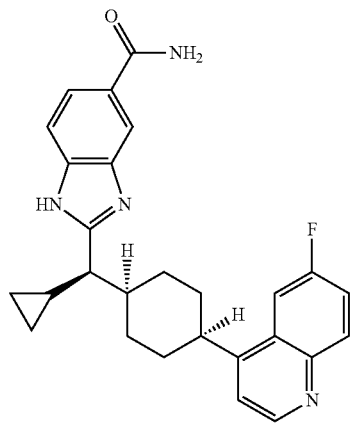 [SMILES: NC(=O)c1ccc2[nH]c([C@H](C3CC3)[C@H]3CC[C@@H](c4ccnc5ccc(F)cc54)CC3)nc2c1]

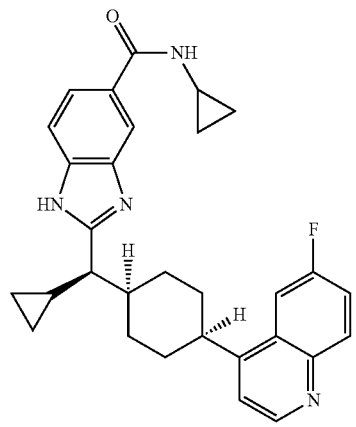 [SMILES: O=C(NC1CC1)c1ccc2[nH]c([C@H](C3CC3)[C@H]3CC[C@@H](c4ccnc5ccc(F)cc54)CC3)nc2c1]

Example B36: 2-((R)-cyclopropyl((1s,4S)-4-(6-fluoroquinolin-4-yl)cyclohexyl)methyl)-N-methyl-1H-benzo[d]imidazole-5-carboxamide Example B38: 2-((R)-cyclopropyl((1s,4S)-4-(6-fluoroquinolin-4-yl)cyclohexyl)methyl)-N-(3-hydroxycyclobutyl)-1H-benzo[d]imidazole-5-carboxamide

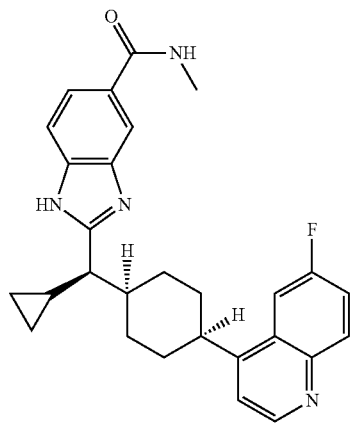 [SMILES: CNC(=O)c1ccc2[nH]c([C@H](C3CC3)[C@H]3CC[C@@H](c4ccnc5ccc(F)cc54)CC3)nc2c1]

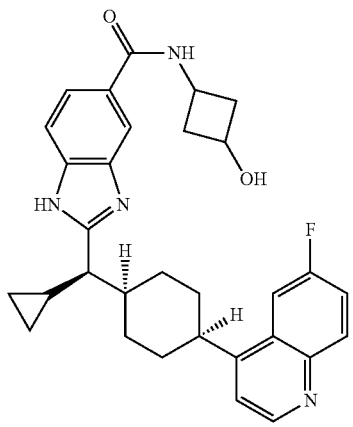

Example B37: N-cyclobutyl-2-((R)-cyclopropyl((1s,4S)-4-(6-fluoroquinolin-4-yl)cyclohexyl)methyl)-1H-benzo[d]imidazole-5-carboxamide Example B39: azetidin-1-yl(2-(R)-cyclopropyl((1s,4S)-4-(6-fluoroquinolin-4-yl)cyclohexyl)methyl)-1H-benzo[d]imidazol-5-yl)methanone

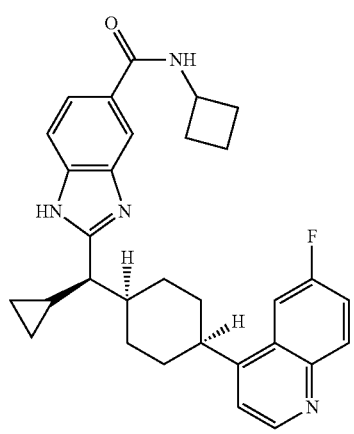 [SMILES: O=C(NC1CCC1)c1ccc2[nH]c([C@H](C3CC3)[C@H]3CC[C@@H](c4ccnc5ccc(F)cc54)CC3)nc2c1]

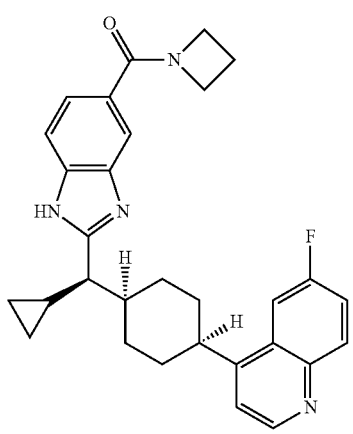 [SMILES: O=C(c1ccc2[nH]c([C@H](C3CC3)[C@H]3CC[C@@H](c4ccnc5ccc(F)cc54)CC3)nc2c1)N1CCC1]

Example B40: (2-((R)-cyclopropyl((1s,4S)-4-(6-fluoroquinolin-4-yl)cyclohexyl)methyl)-1H-benzo[d]imidazol-5-yl)(piperidin-1-yl)methanone

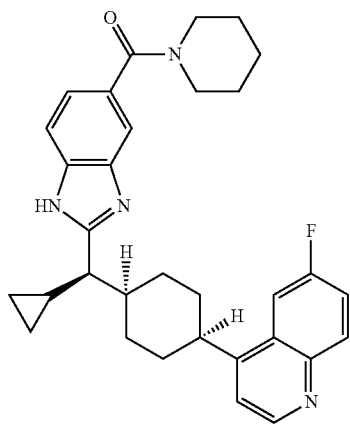 [SMILES: O=C(c1ccc2[nH]c([C@H](C3CC3)[C@H]3CC[C@@H](c4ccnc5ccc(F)cc54)CC3)nc2c1)N1CCCCC1]

Example B41: 4-((1S,4s)-4-((R)-1-(5,6-difluoro-1H-benzo[d]imidazol-2-yl)-2,2,2-trifluoroethyl)cyclohexyl)-6-fluoroquinoline

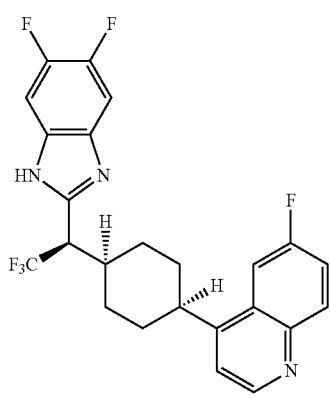 [SMILES: Fc1ccc2nccc([C@H]3CC[C@@H]([C@H](c4nc5cc(F)c(F)cc5[nH]4)C(F)(F)F)CC3)c2c1]

Example B42: methyl 2-((R)-2,2,2-trifluoro-1-((1s,4S)-4-(6-fluoroquinolin-4-yl)cyclohexyl)ethyl)-1H-benzo[d]imidazole-5-carboxylate

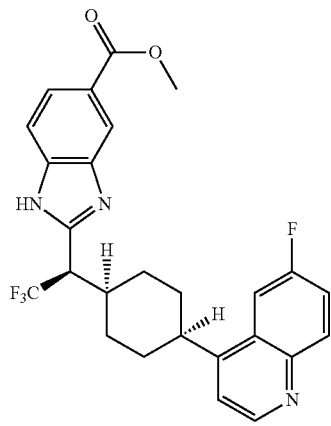 [SMILES: COC(=O)c1ccc2[nH]c([C@@H]([C@H]3CC[C@@H](c4ccnc5ccc(F)cc54)CC3)C(F)(F)F)nc2c1]

Example B43: 4-((1S,4s)-4-((R)-1-(5-chloro-H-benzo[d]imidazol-2-yl)-2,2,2-trifluoroethyl)cyclohexyl)-6-fluoroquinoline

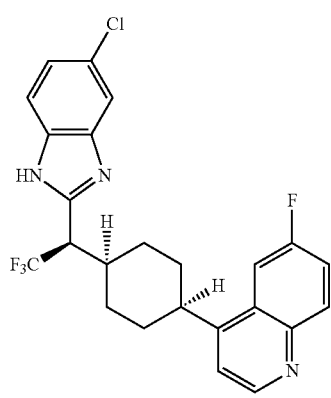 [SMILES: Fc1ccc2nccc([C@H]3CC[C@@H]([C@H](c4nc5cc(Cl)ccc5[nH]4)C(F)(F)F)CC3)c2c1]

Example B44: 6-fluoro-4-((1S,4s)-4-((R)-2,2,2-trifluoro-1-(5-fluoro-1H-benzo[d]imidazol-2-yl)ethyl)cyclohexyl)quinoline

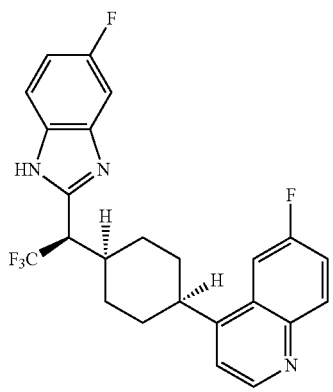 [SMILES: Fc1ccc2[nH]c([C@@H]([C@H]3CC[C@@H](c4ccnc5ccc(F)cc54)CC3)C(F)(F)F)nc2c1]

Example B45: 4-((1S,4s)-4-((R)-1-(6-chloro-5-fluoro-H-benzo[d]imidazol-2-yl)-2,2,2-trifluoroethyl)cyclohexyl)-6-fluoroquinoline

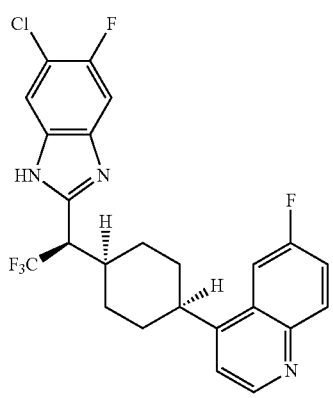 [SMILES: Fc1ccc2nccc([C@H]3CC[C@@H]([C@H](c4nc5cc(F)c(Cl)cc5[nH]4)C(F)(F)F)CC3)c2c1]

Example B46: N,N-dimethyl-2-((R)-2,2,2-trifluoro-1-((1s,4S)-4-(6-fluoroquinolin-4-yl)cyclohexyl)ethyl)-1H-benzo[d]imidazole-5-carboxamide

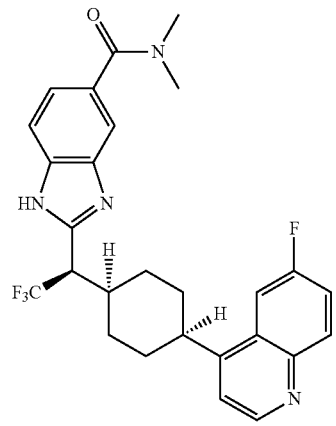

Example B47: 2-((R)-2,2,2-trifluoro-1-((1s,4S)-4-(6-fluoroquinolin-4-yl)cyclohexyl)ethyl)-1H-benzo[d]imidazole-5-carboxamide

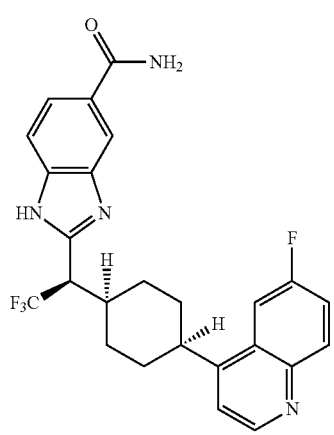 [SMILES: NC(=O)c1ccc2[nH]c([C@@H]([C@H]3CC[C@@H](c4ccnc5ccc(F)cc54)CC3)C(F)(F)F)nc2c1]

Example B48: aziridin-1-yl(2-((R)-2,2,2-trifluoro-1-((1s,4S)-4-(6-fluoroquinolin-4-yl)cyclohexyl)ethyl)-1H-benzo[d]imidazol-5-yl)methanone

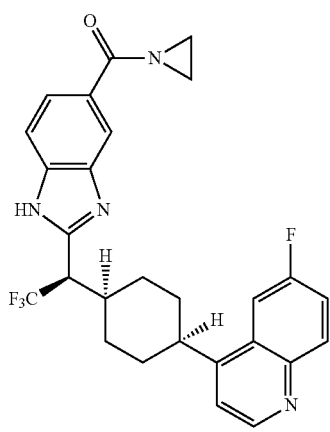 [SMILES: O=C(c1ccc2[nH]c([C@@H]([C@H]3CC[C@@H](c4ccnc5ccc(F)cc54)CC3)C(F)(F)F)nc2c1)N1CC1]

Example B49: N-cyclopropyl-2-((R)-2,2,2-trifluoro-1-((1s,4S)-4-(6-fluoroquinolin-4-yl)cyclohexyl)ethyl)-1H-benzo[d]imidazole-5-carboxamide

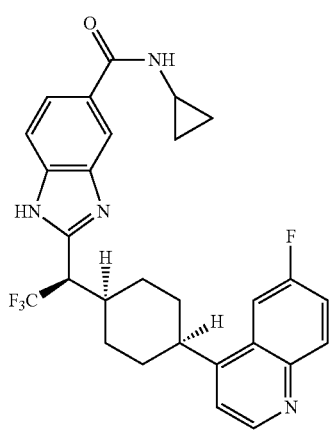 [SMILES: O=C(NC1CC1)c1ccc2[nH]c([C@@H]([C@H]3CC[C@@H](c4ccnc5ccc(F)cc54)CC3)C(F)(F)F)nc2c1]

Example B50: N-methyl-2-((R)-2,2,2-trifluoro-1-((1s,4S)-4-(6-fluoroquinolin-4-yl)cyclohexyl)ethyl)-1H-benzo[d]imidazole-5-carboxamide

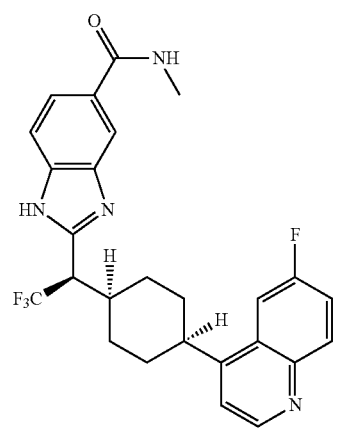 [SMILES: CNC(=O)c1ccc2[nH]c([C@@H]([C@H]3CC[C@@H](c4ccnc5ccc(F)cc54)CC3)C(F)(F)F)nc2c1]

Example B51: N-cyclobutyl-2-((R)-2,2,2-trifluoro-1-((1s,4S)-4-(6-fluoroquinolin-4-yl)cyclohexyl)ethyl)-1H-benzo[d]imidazole-5-carboxamide

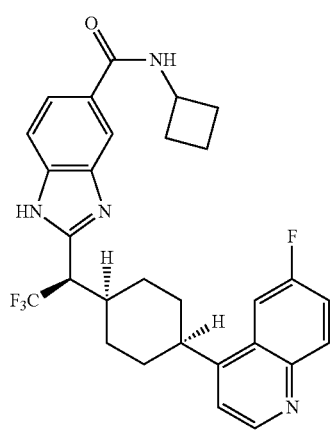

Example B52: N-(3-hydroxycyclobutyl)-2-((R)-2,2,2-trifluoro-1-((1s,4S)-4-(6-fluoroquinolin-4-yl)cyclohexyl)ethyl)-1H-benzo[d]imidazole-5-carboxamide

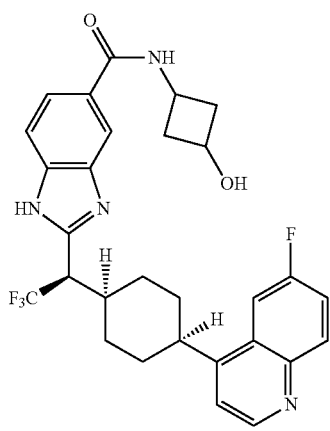 [SMILES: O=C(NC1CC(O)C1)c1ccc2[nH]c([C@@H]([C@H]3CC[C@@H](c4ccnc5ccc(F)cc54)CC3)C(F)(F)F)nc2c1]

Example B53: 6-fluoro-4-((1S,4s)-4-((R)-2,2,2-trifluoro-1-(4,6,7-trifluoro-1H-benzo[d]imidazol-2-yl)ethyl)cyclohexyl)quinoline

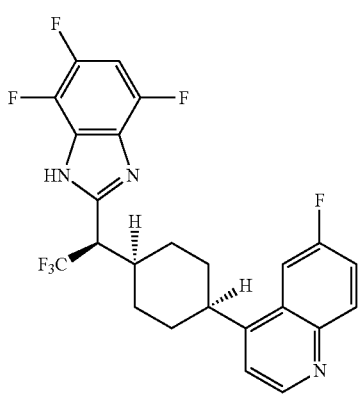 [SMILES: Fc1ccc2nccc([C@H]3CC[C@@H]([C@H](c4nc5c(F)cc(F)c(F)c5[nH]4)C(F)(F)F)CC3)c2c1]

Example B54: 6-fluoro-4-((1S,4s)-4-((R)-2,2,2-trifluoro-1-(5,6,7-trifluoro-1H-benzo[d]imidazol-2-yl)ethyl)cyclohexyl)quinoline

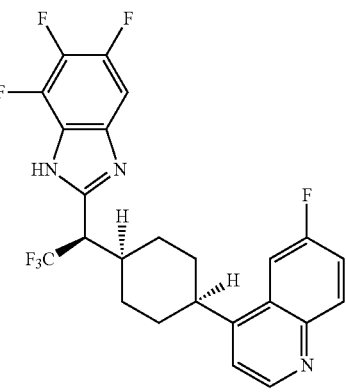

Example B55: 4-((1S,4s)-4-((R)-1-(5,6-difluoro-7-methyl-1H-benzo[d]imidazol-2-yl)-2,2,2-trifluoroethyl)cyclohexyl)-6-fluoroquinoline

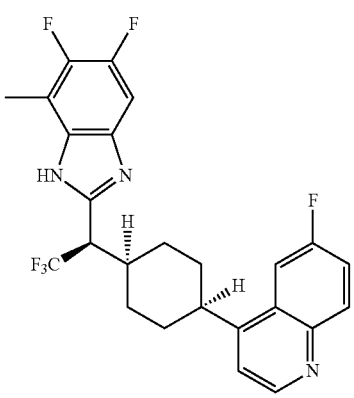 [SMILES: Cc1c(F)c(F)cc2nc([C@@H]([C@H]3CC[C@@H](c4ccnc5ccc(F)cc54)CC3)C(F)(F)F)[nH]c12]

Example B56: azetidin-1-yl(2-((R)-2,2-trifluoro-1-((1s,4S)-4-(6-fluoroquinolin-4-yl)cyclohexyl)ethyl)-1H-benzo[d]imidazol-5-yl)methanone Example B58: (R)-6-fluoro-4-(4-(1-(6-fluoro-1H-benzo[d]imidazol-2-yl)ethyl)piperazin-1-yl)quinoline

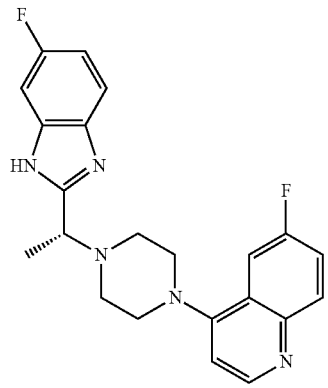

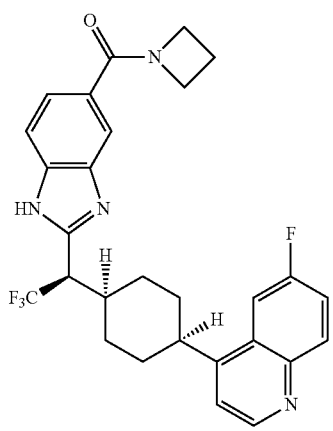 [SMILES: O=C(c1ccc2[nH]c([C@@H]([C@H]3CC[C@@H](c4ccnc5ccc(F)cc54)CC3)C(F)(F)F)nc2c1)N1CCC1]

Example B59: (R)-4-(4-(1-(6-chloro-1H-benzo[d]imidazol-2-yl)ethyl)piperazin-1-yl)-6-fluoroquinoline

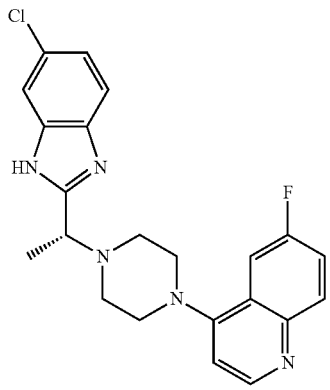

Example B57: (R)-4-(4-(1-(5,6-difluoro-1H-benzo[d]imidazol-2-yl)ethyl)piperazin-1-yl)-6-fluoroquinoline Example B60: (R)-4-(4-(1-(6-chloro-5-fluoro-1H-benzo[d]imidazol-2-yl)ethyl)piperazin-1-yl)-6-fluoroquinoline

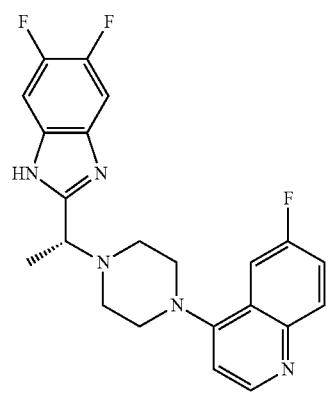 [SMILES: C[C@H](c1nc2cc(F)c(F)cc2[nH]1)N1CCN(c2ccnc3ccc(F)cc23)CC1]

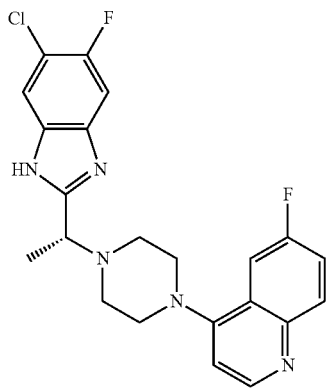 [SMILES: C[C@H](c1nc2cc(F)c(Cl)cc2[nH]1)N1CCN(c2ccnc3ccc(F)cc23)CC1]

Example B61: (R)-4-(4-(1-(5,6-dichloro-1H-benzo[d]imidazol-2-yl)ethyl)piperazin-1-yl)-6-fluoroquinoline
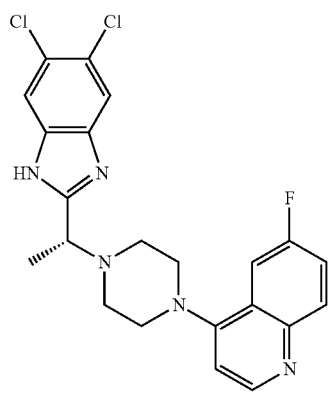 [SMILES: C[C@H](c1nc2cc(Cl)c(Cl)cc2[nH]1)N1CCN(c2ccnc3ccc(F)cc23)CC1]
Example B62: methyl (R)-2-(1-(4-(6-fluoroquinolin-4-yl)piperazin-1-yl)ethyl)-1H-benzo[d]imidazole-6-carboxylate
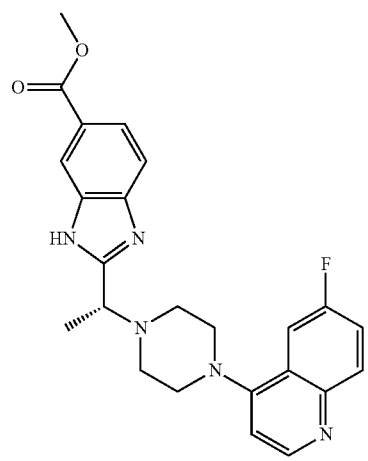 [SMILES: COC(=O)c1ccc2nc([C@@H](C)N3CCN(c4ccnc5ccc(F)cc45)CC3)[nH]c2c1]
Example B63: (R)-2-(1-(4-(6-fluoroquinolin-4-yl)piperazin-1-yl)ethyl)-1H-benzo[d]imidazole-6-carboxamide
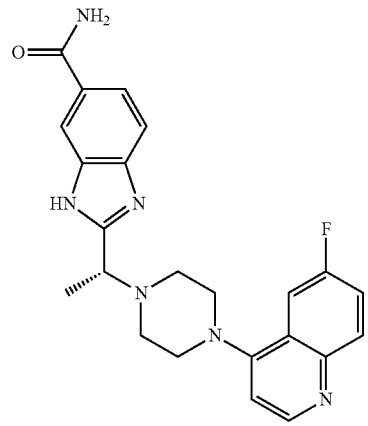 [SMILES: C[C@H](c1nc2ccc(C(N)=O)cc2[nH]1)N1CCN(c2ccnc3ccc(F)cc23)CC1]
Example B64: (R)-2-(1-(4-(6-fluoroquinolin-4-yl)piperazin-1-yl)ethyl)-N-methyl-1H-benzo[d]imidazole-6-carboxamide
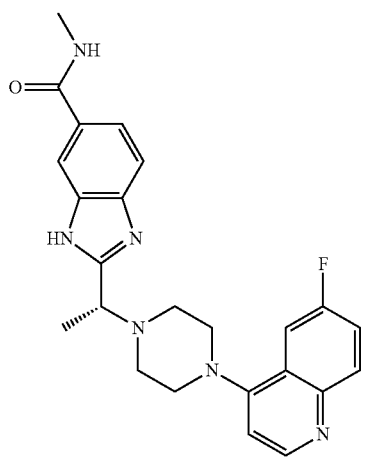 [SMILES: CNC(=O)c1ccc2nc([C@@H](C)N3CCN(c4ccnc5ccc(F)cc45)CC3)[nH]c2c1]

Example B65: (R)-2-(1-(4-(6-fluoroquinolin-4-yl)piperazin-1-yl)ethyl)-N,N-dimethyl-1H-benzo[d]imidazole-6-carboxamide

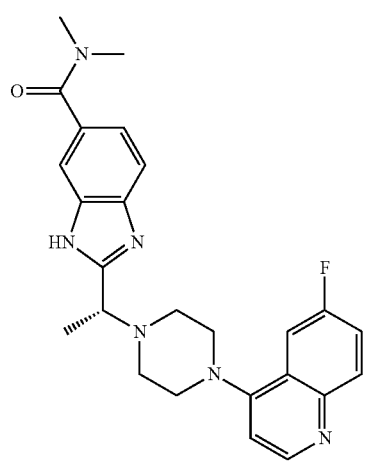 [SMILES: C[C@H](c1nc2ccc(C(=O)N(C)C)cc2[nH]1)N1CCN(c2ccnc3ccc(F)cc23)CC1]

Example B66: (R)-aziridin-1-yl(2-(1-(4-(6-fluoroquinolin-4-yl)piperazin-1-yl)ethyl)-1H-benzo[d]imidazol-6-yl)methanone

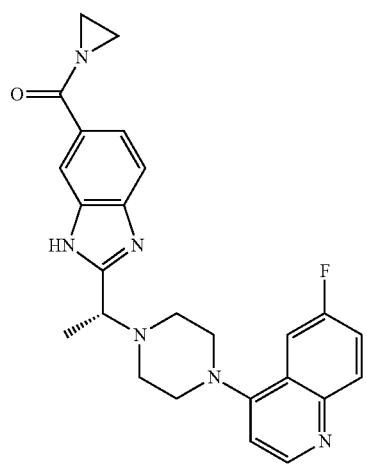 [SMILES: C[C@H](c1nc2ccc(C(=O)N3CC3)cc2[nH]1)N1CCN(c2ccnc3ccc(F)cc23)CC1]

Example B67: (R)-azetidin-1-yl(2-(1-(4-(6-fluoroquinolin-4-yl)piperazin-1-yl)ethyl)-1H-benzo[d]imidazol-6-yl)methanone

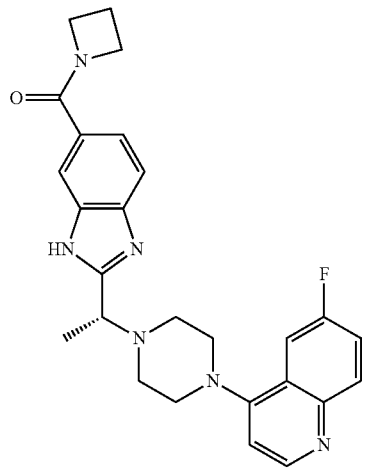 [SMILES: C[C@H](c1nc2ccc(C(=O)N3CCC3)cc2[nH]1)N1CCN(c2ccnc3ccc(F)cc23)CC1]

Example B68: (R)—N-cyclobutyl-2-(1-(4-(6-fluoroquinolin-4-yl)piperazin-1-yl)ethyl)-1H-benzo[d]imidazole-6-carboxamide

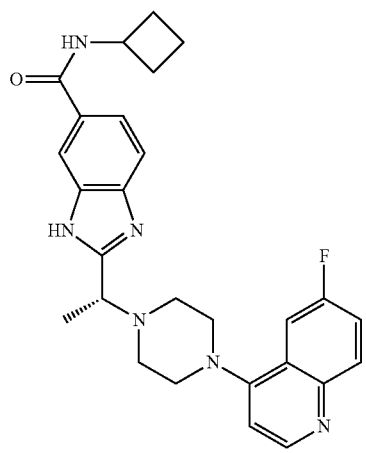 [SMILES: C[C@H](c1nc2ccc(C(=O)NC3CCC3)cc2[nH]1)N1CCN(c2ccnc3ccc(F)cc23)CC1]

Example B69: (R)-2-(1-(4-(6-fluoroquinolin-4-yl)piperazin-1-yl)ethyl)-N-(3-hydroxycyclobutyl)-1H-benzo[d]imidazole-6-carboxamide

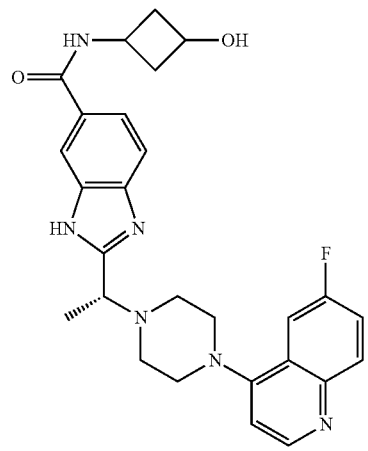 [SMILES: C[C@H](c1nc2ccc(C(=O)NC3CC(O)C3)cc2[nH]1)N1CCN(c2ccnc3ccc(F)cc23)CC1]

Example B70: (R)—N-cyclohexyl-2-(1-(4-(6-fluoroquinolin-4-yl)piperazin-1-yl)ethyl)-1H-benzo[d]imidazole-6-carboxamide

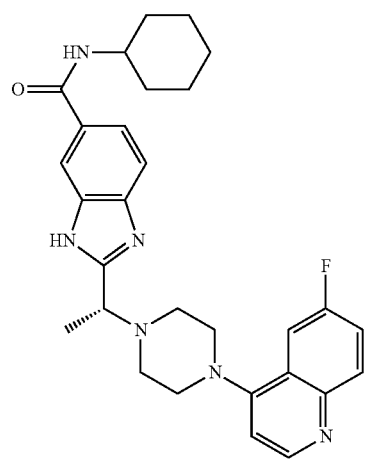 [SMILES: C[C@H](c1nc2ccc(C(=O)NC3CCCCC3)cc2[nH]1)N1CCN(c2ccnc3ccc(F)cc23)CC1]

Example B71: (R)-4-(1-(cyclopropyl(5,6-difluoro-1H-benzo[d]imidazol-2-yl)methyl)piperidin-4-yl)-6-fluoroquinoline

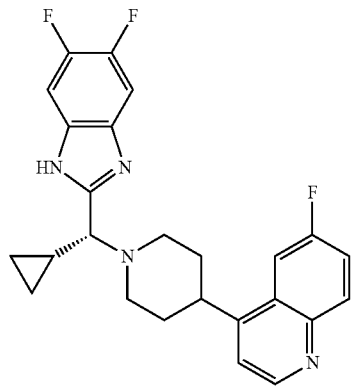 [SMILES: Fc1ccc2nccc(C3CCN([C@@H](c4nc5cc(F)c(F)cc5[nH]4)C4CC4)CC3)c2c1]

Example B72: (R)-4-(1-(cyclopropyl(6-fluoro-1H-benzo[d]imidazol-2-yl)methyl)piperidin-4-yl)-6-fluoroquinoline

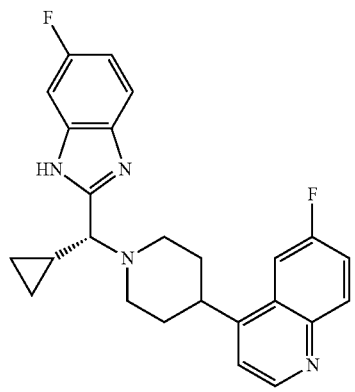 [SMILES: Fc1ccc2nc([C@@H](C3CC3)N3CCC(c4ccnc5ccc(F)cc45)CC3)[nH]c2c1]

Example B73: (R)-4-(1-((6-chloro-1H-benzo[d]imidazol-2-yl)(cyclopropyl)methyl)piperidin-4-yl)-6-fluoroquinoline

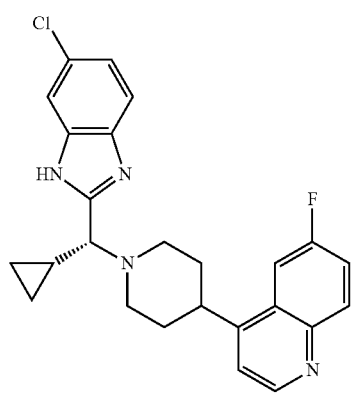 [SMILES: Fc1ccc2nccc(C3CCN([C@@H](c4nc5ccc(Cl)cc5[nH]4)C4CC4)CC3)c2c1]

Example B74: (R)-4-(1-((6-chloro-5-fluoro-1H-benzo[d]imidazol-2-yl)(cyclopropyl)methyl)piperidin-4-yl)-6-fluoroquinoline

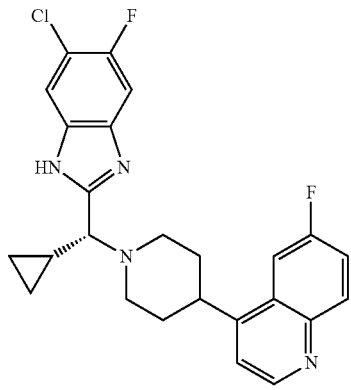 [SMILES: Fc1ccc2nccc(C3CCN([C@@H](c4nc5cc(F)c(Cl)cc5[nH]4)C4CC4)CC3)c2c1]

Example B75: (R)-4-(1-(cyclopropyl(4,5,6-trifluoro-1H-benzo[d]imidazol-2-yl)methyl)piperidin-4-yl)-6-fluoroquinoline

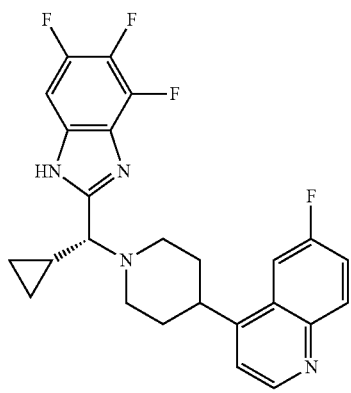 [SMILES: Fc1ccc2nccc(C3CCN([C@@H](c4nc5c(F)c(F)c(F)cc5[nH]4)C4CC4)CC3)c2c1]

Example B76: (R)-4-(1-(cyclopropyl(4,6,7-trifluoro-1H-benzo[d]imidazol-2-yl)methyl)piperidin-4-yl)-6-fluoroquinoline

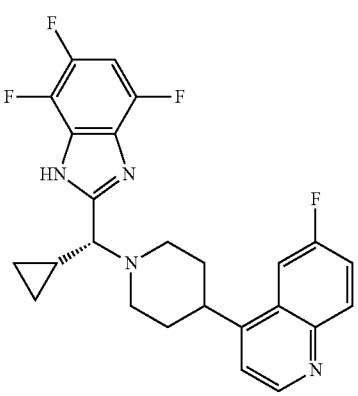 [SMILES: Fc1ccc2nccc(C3CCN([C@@H](c4nc5c(F)cc(F)c(F)c5[nH]4)C4CC4)CC3)c2c1]

Example B77: (R)-4-(1-(cyclopropyl(5,6-difluoro-7-methyl-1H-benzo[d]imidazol-2-yl)methyl)piperidin-4-yl)-6-fluoroquinoline

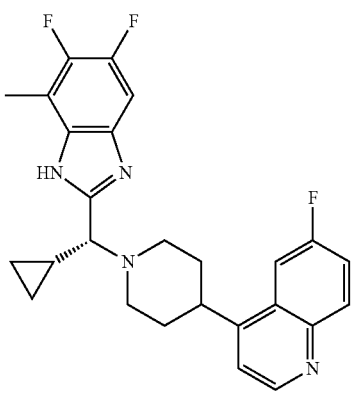 [SMILES: Cc1c(F)c(F)cc2nc([C@@H](C3CC3)N3CCC(c4ccnc5ccc(F)cc45)CC3)[nH]c12]

Example B78: (R)-4-(1-((7-chloro-5,6-difluoro-1H-benzo[d]imidazol-2-yl)(cyclopropyl)methyl)piperidin-4-yl)-6-fluoroquinoline

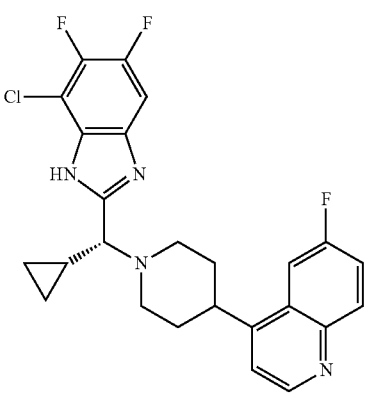 [SMILES: Fc1ccc2nccc(C3CCN([C@@H](c4nc5cc(F)c(F)c(Cl)c5[nH]4)C4CC4)CC3)c2c1]

Example B79: (R)-2-(cyclopropyl(4-(6-fluoroquinolin-4-yl)piperidin-1-yl)methyl)-N,N-dimethyl-1H-benzo[d]imidazole-6-carboxamide

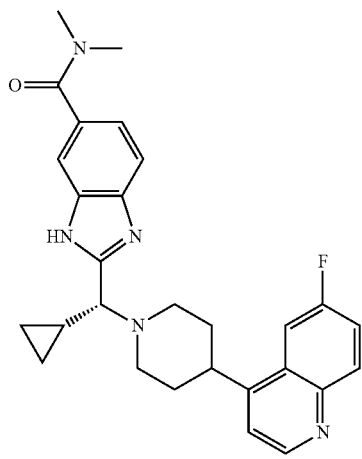 [SMILES: CN(C)C(=O)c1ccc2nc([C@@H](C3CC3)N3CCC(c4ccnc5ccc(F)cc45)CC3)[nH]c2c1]

Example B80: (R)-2-(cyclopropyl(4-(6-fluoroquinolin-4-yl)piperidin-1-yl)methyl)-N-methyl-1H-benzo[d]imidazole-6-carboxamide

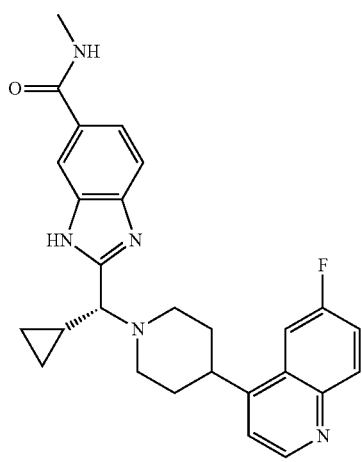 [SMILES: CNC(=O)c1ccc2nc([C@@H](C3CC3)N3CCC(c4ccnc5ccc(F)cc45)CC3)[nH]c2c1]

Example B81: (R)-(2-(cyclopropyl(4-(6-fluoroquinolin-4-yl)piperidin-1-yl)methyl)-1H-benzo[d]imidazol-6-yl)(3-hydroxyazetidin-1-yl)methanone

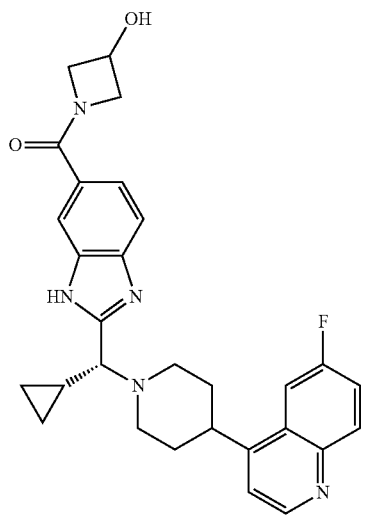 [SMILES: O=C(c1ccc2nc([C@@H](C3CC3)N3CCC(c4ccnc5ccc(F)cc45)CC3)[nH]c2c1)N1CC(O)C1]

Example B82: (R)—N-cyclopropyl-2-(cyclopropyl(4-(6-fluoroquinolin-4-yl)piperidin-1-yl)methyl)-1H-benzo[d]imidazole-6-carboxamide

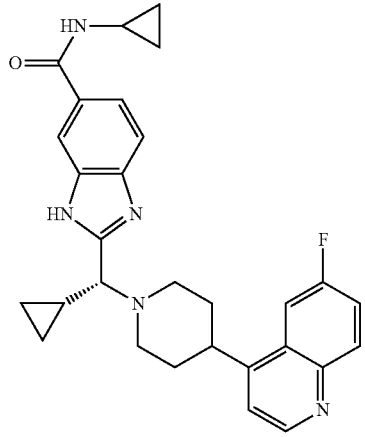 [SMILES: O=C(NC1CC1)c1ccc2nc([C@@H](C3CC3)N3CCC(c4ccnc5ccc(F)cc45)CC3)[nH]c2c1]

Example B83: (S)-4-(1-(1-(5,6-difluoro-1H-benzo[d]imidazol-2-yl)-2,2,2-trifluoroethyl)piperidin-4-yl)-6-fluoroquinoline

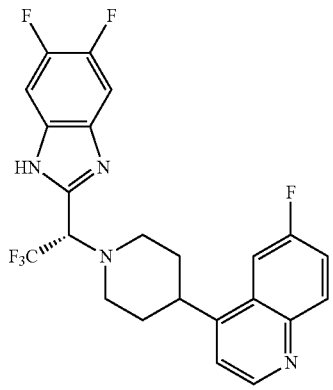 [SMILES: Fc1ccc2nccc(C3CCN([C@@H](c4nc5cc(F)c(F)cc5[nH]4)C(F)(F)F)CC3)c2c1]

Example B84: (S)-6-fluoro-4-(1-(2,2,2-trifluoro-1-(6-fluoro-1H-benzo[d]imidazol-2-yl)ethyl)piperidin-4-yl)quinoline

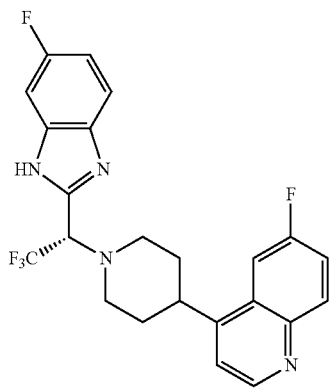 [SMILES: Fc1ccc2nc([C@H](N3CCC(c4ccnc5ccc(F)cc45)CC3)C(F)(F)F)[nH]c2c1]

Example B85: (S)-4-(1-(1-(6-chloro-1H-benzo[d]imidazol-2-yl)-2,2,2-trifluoroethyl)piperidin-4-yl)-6-fluoroquinoline

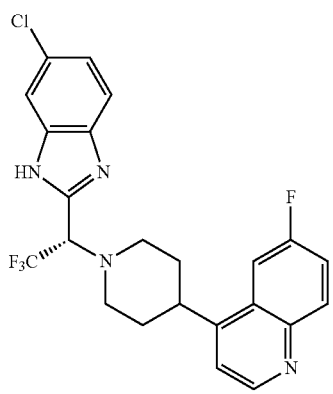 [SMILES: Fc1ccc2nccc(C3CCN([C@@H](c4nc5ccc(Cl)cc5[nH]4)C(F)(F)F)CC3)c2c1]

Example B86: (S)-4-(1-(1-(6-chloro-5-fluoro-1H-benzo[d]imidazol-2-yl)-2,2,2-trifluoroethyl)piperidin-4-yl)-6-fluoroquinoline

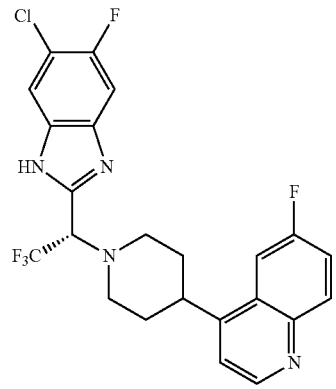

Example B87: (S)-6-fluoro-4-(1-(2,2,2-trifluoro-1-(4,5,6-trifluoro-1H-benzo[d]imidazol-2-yl)ethyl)piperidin-4-yl)quinoline

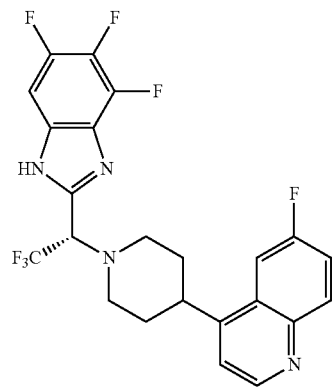 [SMILES: Fc1ccc2nccc(C3CCN([C@@H](c4nc5c(F)c(F)c(F)cc5[nH]4)C(F)(F)F)CC3)c2c1]

Example B88: (S)-6-fluoro-4-(1-(2,2,2-trifluoro-1-(4,6,7-trifluoro-1H-benzo[d]imidazol-2-yl)ethyl)piperidin-4-yl)quinoline

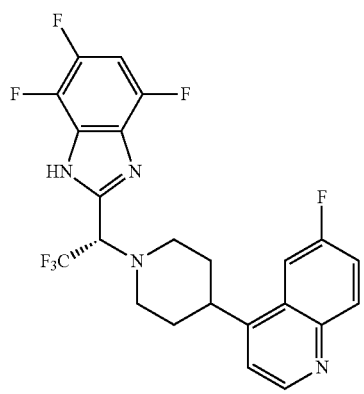 [SMILES: Fc1ccc2nccc(C3CCN([C@@H](c4nc5c(F)cc(F)c(F)c5[nH]4)C(F)(F)F)CC3)c2c1]

Example B89: (S)-4-(1-(1-(5,6-difluoro-7-methyl-1H-benzo[d]imidazol-2-yl)-2,2,2-trifluoroethyl)piperidin-4-yl)-6-fluoroquinoline

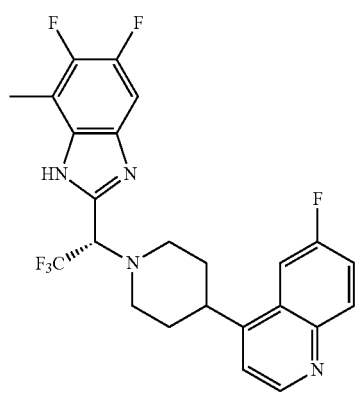 [SMILES: Cc1c(F)c(F)cc2nc([C@H](N3CCC(c4ccnc5ccc(F)cc45)CC3)C(F)(F)F)[nH]c12]

Example B90: (S)-4-(1-(1-(7-chloro-5,6-difluoro-1H-benzo[d]imidazol-2-yl)-2,2,2-trifluoroethyl)piperidin-4-yl)-6-fluoroquinoline

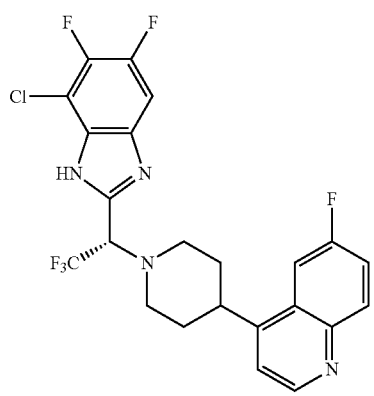 [SMILES: Fc1ccc2nccc(C3CCN([C@@H](c4nc5cc(F)c(F)c(Cl)c5[nH]4)C(F)(F)F)CC3)c2c1]

Example B91: (S)—N,N-dimethyl-2-(2,2,2-trifluoro-1-(4-(6-fluoroquinolin-4-yl)piperidin-1-yl)ethyl)-1H-benzo[d]imidazole-6-carboxamide

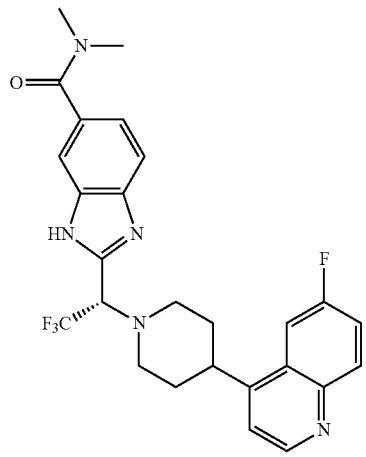 [SMILES: CN(C)C(=O)c1ccc2nc([C@H](N3CCC(c4ccnc5ccc(F)cc45)CC3)C(F)(F)F)[nH]c2c1]

Example B92: (S)—N-methyl-2-(2,2,2-trifluoro-1-(4-(6-fluoroquinolin-4-yl)piperidin-1-yl)ethyl)-1H-benzo[d]imidazole-6 carboxamide

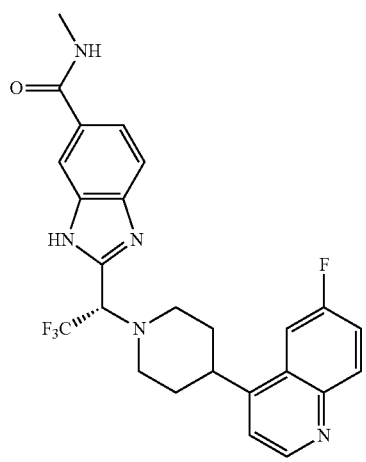 [SMILES: CNC(=O)c1ccc2nc([C@H](N3CCC(c4ccnc5ccc(F)cc45)CC3)C(F)(F)F)[nH]c2c1]

Example B93: (S)-(3-hydroxyazetidin-1-yl)(2-(2,2,2-trifluoro-1-(4-(6-fluoroquinolin-4-yl)piperidin-1-yl)ethyl)-1H-benzo[d]imidazol-6-yl)methanone

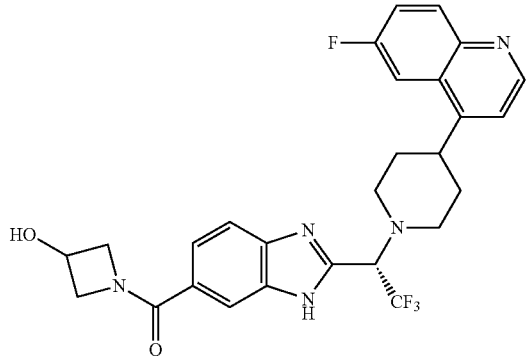 [SMILES: O=C(c1ccc2nc([C@H](N3CCC(c4ccnc5ccc(F)cc45)CC3)C(F)(F)F)[nH]c2c1)N1CC(O)C1]

Example B94: (S)—N-cyclopropyl-2-(2,2,2-trifluoro-1-(4-(6-fluoroquinolin-4-yl)piperidin-1-yl)ethyl)-1H-benzo[d]imidazole-6-carboxamide

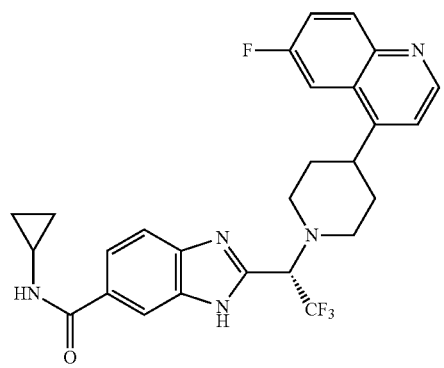 [SMILES: O=C(NC1CC1)c1ccc2nc([C@H](N3CCC(c4ccnc5ccc(F)cc45)CC3)C(F)(F)F)[nH]c2c1]

Example B95: 6-fluoro-4-((1S,4s)-4-((R)-methoxy(4,6,7-trifluoro-1H-benzo[d]imidazol-2-yl)methyl)cyclohexyl)quinoline

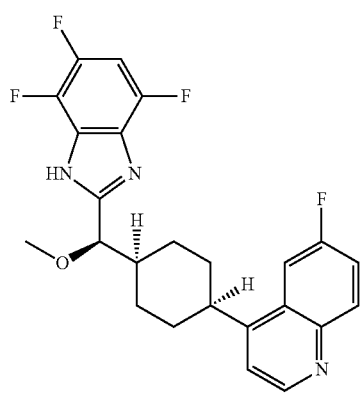 [SMILES: CO[C@@H](c1nc2c(F)cc(F)c(F)c2[nH]1)[C@H]1CC[C@@H](c2ccnc3ccc(F)cc32)CC1]

Example B96: 4-((1S,4s)-4-((R)-(5,6-difluoro-1H-benzo[d]imidazol-2-yl)(methoxy)methyl)cyclohexyl)-6-fluoroquinoline

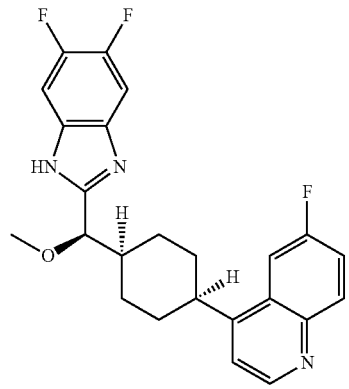 [SMILES: CO[C@@H](c1nc2cc(F)c(F)cc2[nH]1)[C@H]1CC[C@@H](c2ccnc3ccc(F)cc32)CC1]

Example B97: 6-fluoro-4-((1S,4s)-4-((R)-methoxy(5,6,7-trifluoro-1H-benzo[d]imidazol-2-yl)methyl)cyclohexyl)quinoline

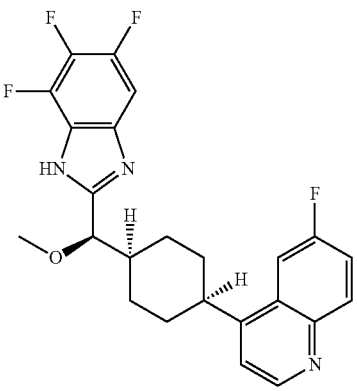

Example B98: 4-((1S,4s)-4-((R)-(5,6-difluoro-7-methyl-1H-benzo[d]imidazol-2-yl)(methoxy)methyl)cyclohexyl)-6-fluoroquinoline

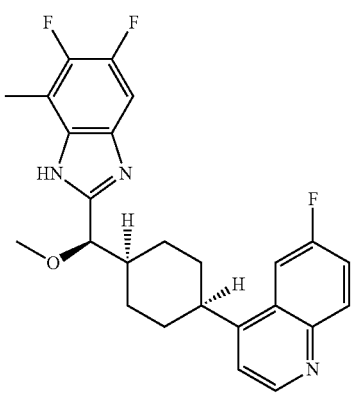 [SMILES: CO[C@@H](c1nc2cc(F)c(F)c(C)c2[nH]1)[C@H]1CC[C@@H](c2ccnc3ccc(F)cc32)CC1]

Example B99: methyl 2-((R)-((1s,4S)-4-(6-fluoro-quinolin-4-yl)cyclohexyl)(methoxy)methyl)-1H-benzo[d]imidazole-5-carboxylate

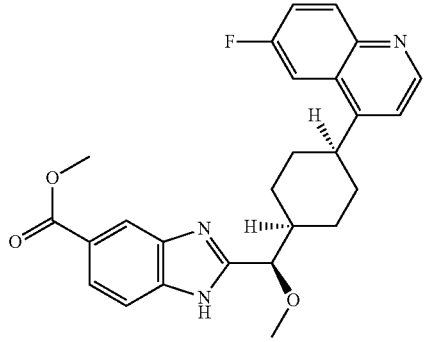 [SMILES: COC(=O)c1ccc2[nH]c([C@H](OC)[C@H]3CC[C@@H](c4ccnc5ccc(F)cc54)CC3)nc2c1]

Example B100: 4-((1S,4s)-4-((R)-(5-chloro-1H-benzo[d]imidazol-2-yl)(methoxy)methyl)cyclo-hexyl)-6-fluoroquinoline

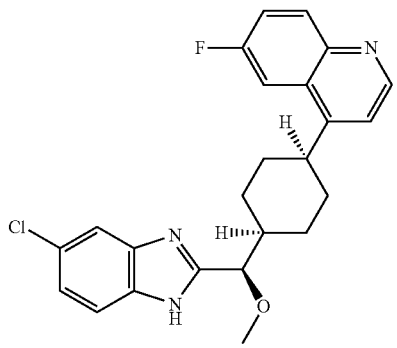 [SMILES: CO[C@@H](c1nc2cc(Cl)ccc2[nH]1)[C@H]1CC[C@@H](c2ccnc3ccc(F)cc32)CC1]

Example B101: 6-fluoro-4-((1S,4s)-4-((R)-(5-fluoro-1H-benzo[d]imidazol-2-yl)(methoxy)methyl)cyclohexyl)quinoline

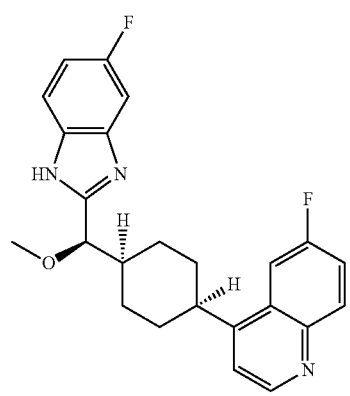 [SMILES: CO[C@@H](c1nc2cc(F)ccc2[nH]1)[C@H]1CC[C@@H](c2ccnc3ccc(F)cc32)CC1]

Example B102: 4-((1S,4s)-4-((R)-(6-chloro-5-fluoro-1H-benzo[d]imidazol-2-yl)(methoxy)methyl)cyclohexyl)-6-fluoroquinoline

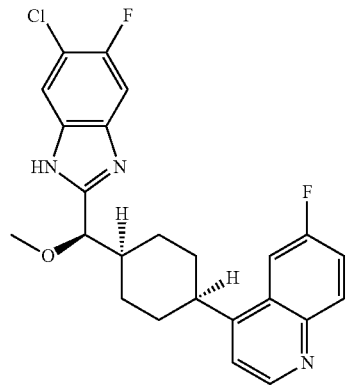 [SMILES: CO[C@@H](c1nc2cc(F)c(Cl)cc2[nH]1)[C@H]1CC[C@@H](c2ccnc3ccc(F)cc32)CC1]

Example B103: 2-((R)-((1s,4S)-4-(6-fluoroquinolin-4-yl)cyclohexyl)(methoxy)methyl)-N,N-dimethyl-1H-benzo[d]imidazole-5-carboxamide

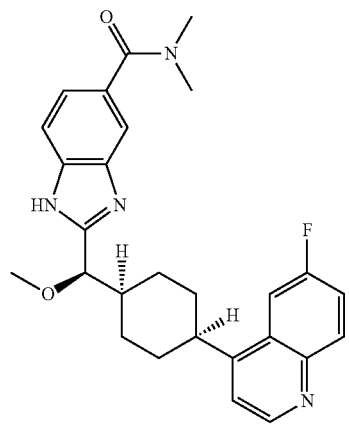 [SMILES: CO[C@@H](c1nc2cc(C(=O)N(C)C)ccc2[nH]1)[C@H]1CC[C@@H](c2ccnc3ccc(F)cc32)CC1]

Example B104: 2-((R)-((1s,4S)-4-(6-fluoroquinolin-4-yl)cyclohexyl)(methoxy)methyl)-1H-benzo[d]imidazole-5-carboxamide

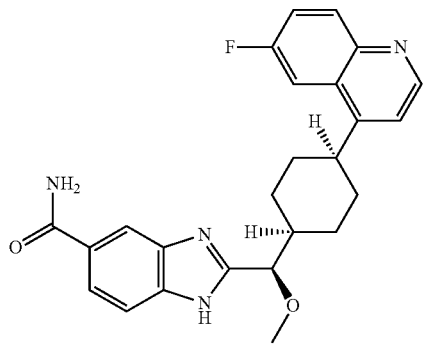 [SMILES: CO[C@@H](c1nc2cc(C(N)=O)ccc2[nH]1)[C@H]1CC[C@@H](c2ccnc3ccc(F)cc32)CC1]

227

Example B105: aziridin-1-yl(2-((R)-((1s,4S)-4-(6-fluoroquinolin-4-yl)cyclohexyl)(methoxy)methyl)-1H-benzo[d]imidazol-5-yl)methanone

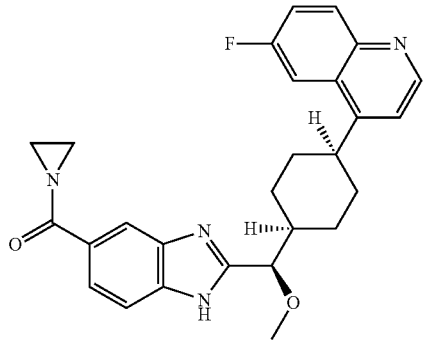 [SMILES: CO[C@@H](c1nc2cc(C(=O)N3CC3)ccc2[nH]1)[C@H]1CC[C@@H](c2ccnc3ccc(F)cc32)CC1]

Example B106: N-cyclopropyl-2-((R)-((1s,4S)-4-(6-fluoroquinolin-4-yl)cyclohexyl)(methoxy)methyl)-1H-benzo[d]imidazole-5-carboxamide

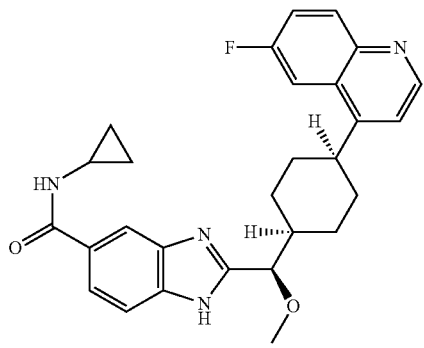 [SMILES: CO[C@@H](c1nc2cc(C(=O)NC3CC3)ccc2[nH]1)[C@H]1CC[C@@H](c2ccnc3ccc(F)cc32)CC1]

Example B107: 2-((R)-((1s,4S)-4-(6-fluoroquinolin-4-yl)cyclohexyl)(methoxy)methyl)-N-methyl-1H-benzo[d]imidazole-5-carboxamide

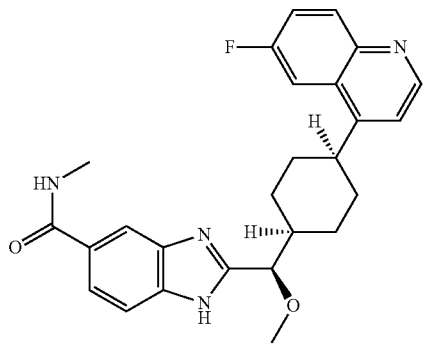 [SMILES: CNC(=O)c1ccc2[nH]c([C@H](OC)[C@H]3CC[C@@H](c4ccnc5ccc(F)cc54)CC3)nc2c1]

228

Example B108: N-cyclobutyl-2-((R)-((1s,4S)-4-(6-fluoroquinolin-4-yl)cyclohexyl)(methoxy)methyl-1H-benzo[d]imidazole-5-carboxamide

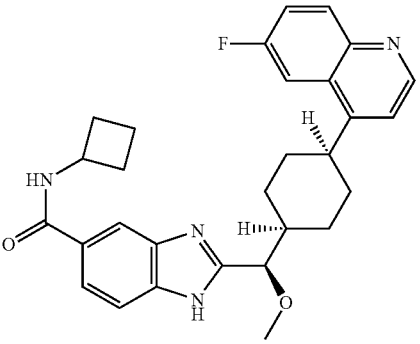 [SMILES: CO[C@@H](c1nc2cc(C(=O)NC3CCC3)ccc2[nH]1)[C@H]1CC[C@@H](c2ccnc3ccc(F)cc32)CC1]

Example B109: 2-((R)-((1s,4S)-4-(6-fluoroquinolin-4-yl)cyclohexyl)(methoxy)methyl)-N-(3-hydroxycyclobutyl)-1H-benzo[d]imidazole-5-carboxamide

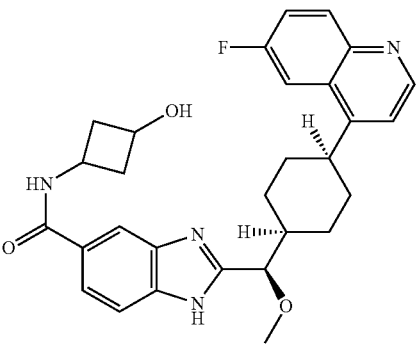 [SMILES: CO[C@@H](c1nc2cc(C(=O)NC3CC(O)C3)ccc2[nH]1)[C@H]1CC[C@@H](c2ccnc3ccc(F)cc32)CC1]

Example B110: azetidin-1-yl(2-((R)-((1s,4S)-4-(6-fluoroquinolin-4-yl)cyclohexyl)(methoxy)methyl)-1H-benzo[d]imidazol-5-yl)methanone

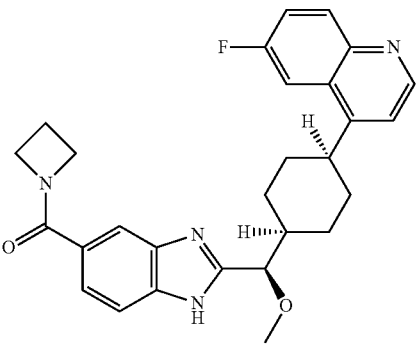 [SMILES: CO[C@@H](c1nc2cc(C(=O)N3CCC3)ccc2[nH]1)[C@H]1CC[C@@H](c2ccnc3ccc(F)cc32)CC1]

Example B111: (R)-4-(1-(1-(5,6-difluoro-1H-benzo[d]imidazol-2-yl)ethyl)piperidin-4-yl)-6-fluoroquinoline

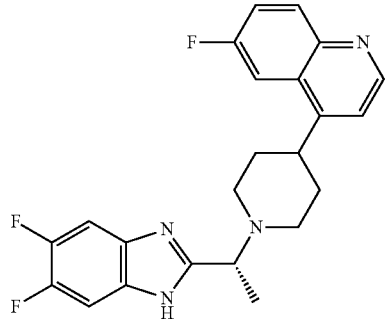 [SMILES: C[C@H](c1nc2cc(F)c(F)cc2[nH]1)N1CCC(c2ccnc3ccc(F)cc23)CC1]

Example B112: (R)-6-fluoro-4-(1-(1-(6-fluoro-1H-benzo[d]imidazol-2-yl)ethyl)piperidin-4-yl)quinoline

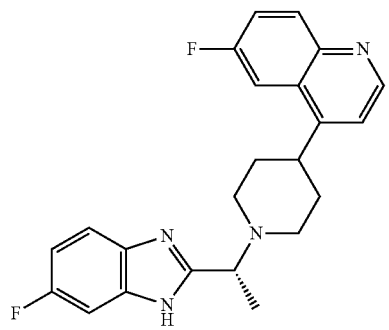 [SMILES: C[C@H](c1nc2ccc(F)cc2[nH]1)N1CCC(c2ccnc3ccc(F)cc23)CC1]

Example B113: (R)-4-(1-(1-(6-chloro-1H-benzo[d]imidazol-2-yl)ethyl)piperidin-4-yl)-6-fluoroquinoline

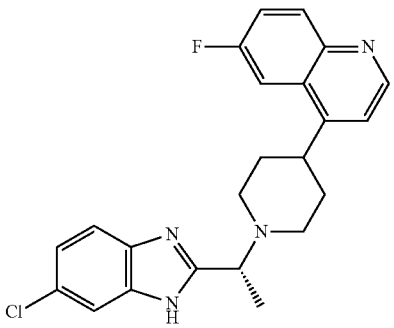 [SMILES: C[C@H](c1nc2ccc(Cl)cc2[nH]1)N1CCC(c2ccnc3ccc(F)cc23)CC1]

Example B114: (R)-4-(1-(1-(6-chloro-5-fluoro-1H-benzo[d]imidazol-2-yl)ethyl)piperidin-4-yl)-6-fluoroquinoline

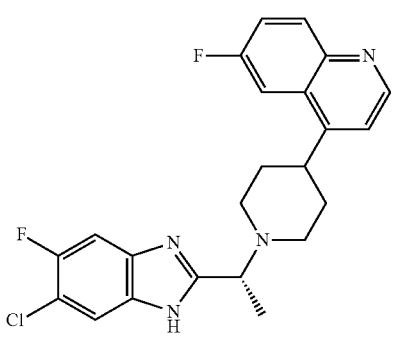 [SMILES: C[C@H](c1nc2cc(F)c(Cl)cc2[nH]1)N1CCC(c2ccnc3ccc(F)cc23)CC1]

Example B115: (R)-6-fluoro-4-(1-(1-(4,5,6-trifluoro-1H-benzo[d]imidazol-2-yl)ethyl)piperidin-4-yl)quinoline

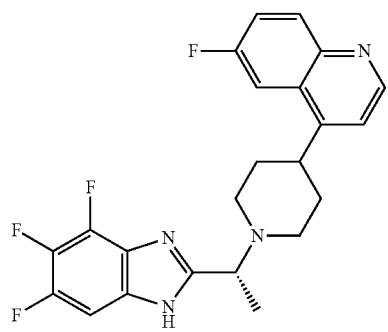 [SMILES: C[C@H](c1nc2c(F)c(F)c(F)cc2[nH]1)N1CCC(c2ccnc3ccc(F)cc23)CC1]

Example B116: (R)-6-fluoro-4-(1-(1-(4,6,7-trifluoro-1H-benzo[d]imidazol-2-yl)ethyl)piperidin-4-yl)quinoline

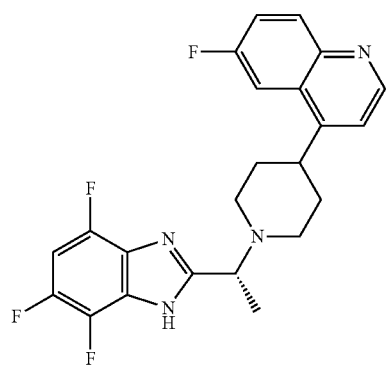 [SMILES: C[C@H](c1nc2c(F)cc(F)c(F)c2[nH]1)N1CCC(c2ccnc3ccc(F)cc23)CC1]

Example B117: (R)-4-(1-(1-(5,6-difluoro-7-methyl-1H-benzo[d]imidazol-2-yl)ethyl)piperidin-4-yl)-6-fluoroquinoline

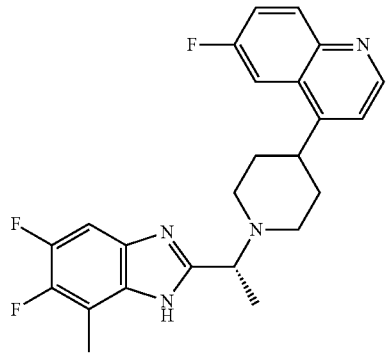 [SMILES: Cc1c(F)c(F)cc2nc([C@@H](C)N3CCC(c4ccnc5ccc(F)cc45)CC3)[nH]c12]

Example B118: (R)-4-(1-(1-(7-chloro-5,6-difluoro-1H-benzo[d]imidazol-2-yl)ethyl)piperidin-4-yl)-6-fluoroquinoline

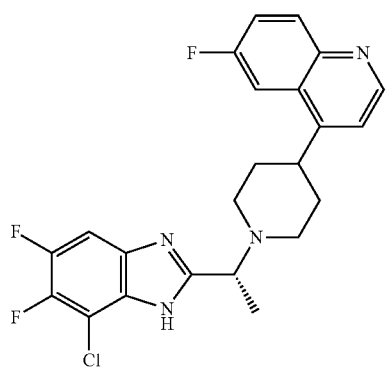 [SMILES: C[C@H](c1nc2cc(F)c(F)c(Cl)c2[nH]1)N1CCC(c2ccnc3ccc(F)cc23)CC1]

Example B119: (R)-2-(1-(4-(6-fluoroquinolin-4-yl)piperidin-1-yl)ethyl)-N,N-dimethyl-1H-benzo[d]imidazole-6-carboxamide

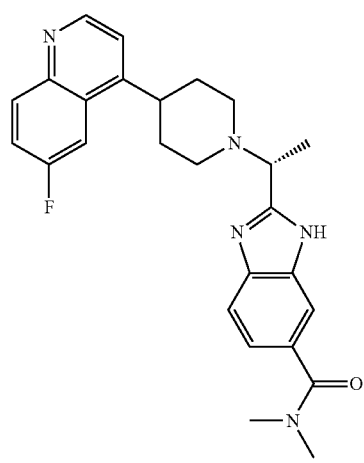 [SMILES: C[C@H](c1nc2ccc(C(=O)N(C)C)cc2[nH]1)N1CCC(c2ccnc3ccc(F)cc23)CC1]

Example B120: (R)-2-(1-(4-(6-fluoroquinolin-4-yl)piperidin-1-yl)ethyl)-N-methyl-1H-benzo[d]imidazole-6-carboxamide

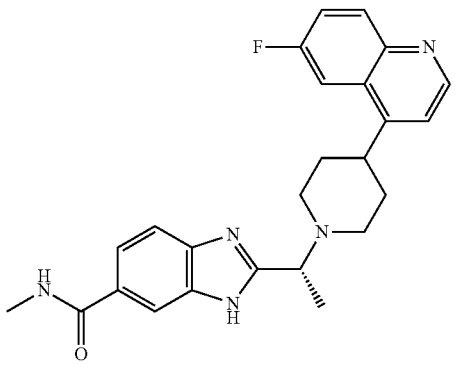 [SMILES: CNC(=O)c1ccc2nc([C@@H](C)N3CCC(c4ccnc5ccc(F)cc45)CC3)[nH]c2c1]

Example B121: (R)-(2-(1-(4-(6-fluoroquinolin-4-yl)piperidin-1-yl)ethyl)-1H-benzo[d]imidazol-6-yl)(3-hyroxyazetidin-1-yl)methanone

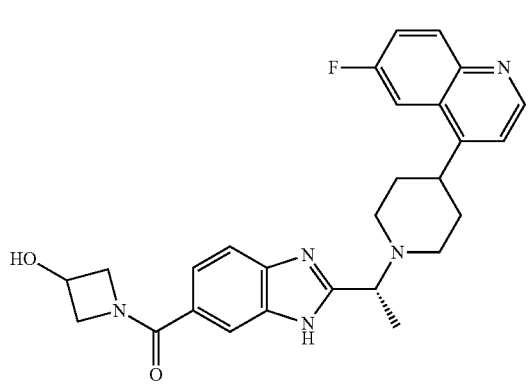 [SMILES: C[C@H](c1nc2ccc(C(=O)N3CC(O)C3)cc2[nH]1)N1CCC(c2ccnc3ccc(F)cc23)CC1]

Example B122: (R)—N-cyclopropyl-2-(1-(4-(6-fluoroquinolin-4-yl)piperidin-1-yl)ethyl)-1H-benzo[d]imidazole-6-carboxamide

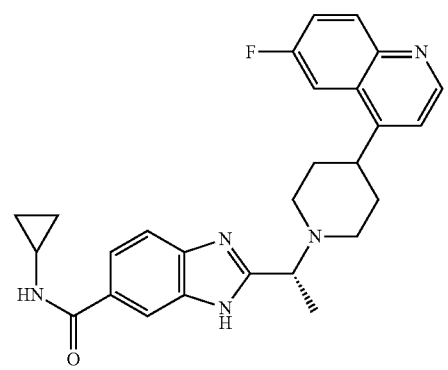

Example B123: 4-((1S,4s)-4-((R)-1-(4-chloro-5,7-difluoro-1H-benzo[d]imidazol-2-yl)ethyl)cyclohexyl)-6-fluoroquinoline

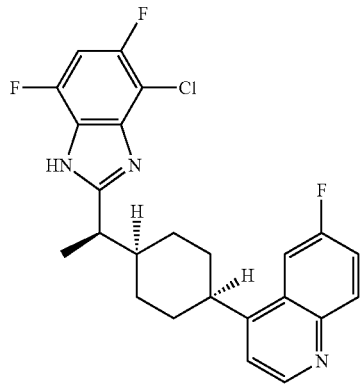 [SMILES: C[C@@H](c1nc2c(Cl)c(F)cc(F)c2[nH]1)[C@H]1CC[C@@H](c2ccnc3ccc(F)cc32)CC1]

Example B124: 4-((1S,4s)-4-((R)-1-(7-chloro-4,5-difluoro-1H-benzo[d]imidazol-2-yl)ethyl)cyclohexyl)-6-fluoroquinoline

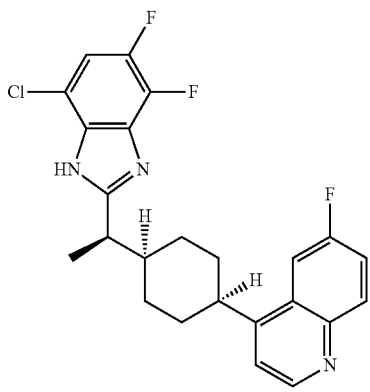 [SMILES: C[C@@H](c1nc2c(F)c(F)cc(Cl)c2[nH]1)[C@H]1CC[C@@H](c2ccnc3ccc(F)cc32)CC1]

Example B125: 4-((1S,4s)-4-((R)-1-(4-chloro-5,6-difluoro-1H-benzo[d]imidazol-2-yl)ethyl)cyclohexyl)-6-fluoroquinoline

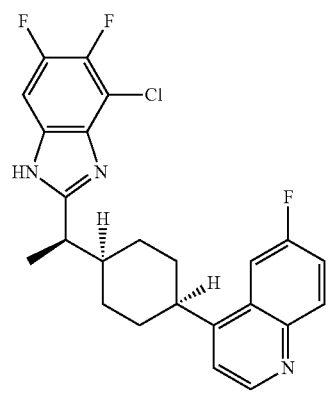 [SMILES: C[C@@H](c1nc2c(Cl)c(F)c(F)cc2[nH]1)[C@H]1CC[C@@H](c2ccnc3ccc(F)cc32)CC1]

Example B126: ethyl 4-chloro-2-((R)-1-((1s,4S)-4-(6-fluoroquinolin-4-yl)cyclohexyl)ethyl)-1H-benzo[d]imidazole-6-carboxylate

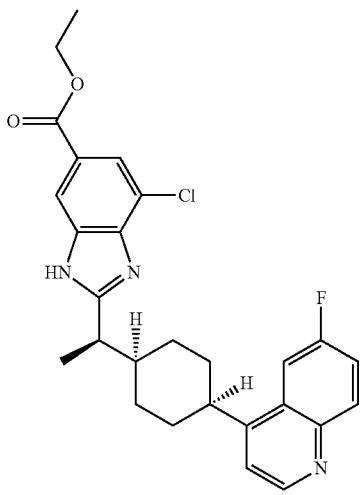 [SMILES: CCOC(=O)c1cc(Cl)c2nc([C@H](C)[C@H]3CC[C@@H](c4ccnc5ccc(F)cc54)CC3)[nH]c2c1]

Example B127: ethyl 2-((R)-1-((1s,4S)-4-(6-fluoroquinolin-4-yl)cyclohexyl)ethyl)-4-methyl-1H-benzo[d]imidazole-6-carboxylate

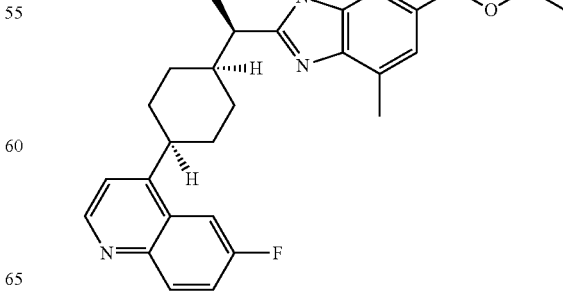

Example B128: ethyl 4-fluoro-2-((R)-1-((1s,4S)-4-(6-fluoroquinolin-4-yl)cyclohexyl)ethyl)-1H-benzo[d]imidazole-6-carboxylate

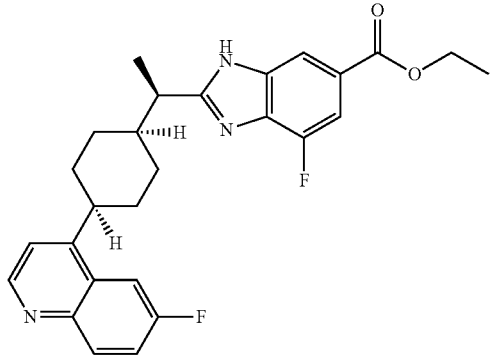 [SMILES: CCOC(=O)c1cc(C)c2nc([C@H](C)[C@H]3CC[C@@H](c4ccnc5ccc(F)cc54)CC3)[nH]c2c1]

Example B129: ethyl 7-fluoro-2-((R)-1-((1s,4S)-4-(6-fluoroquinolin-4-yl)cyclohexyl)ethyl)-1H-benzo[d]imidazole-6-carboxylate

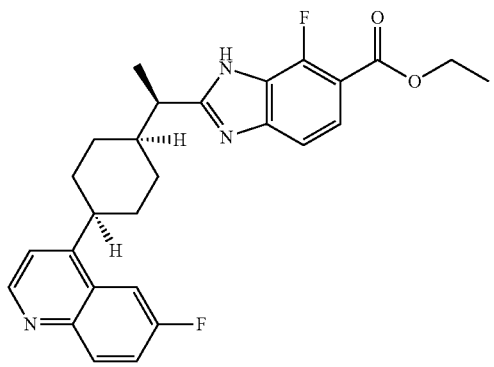 [SMILES: CCOC(=O)c1ccc2nc([C@H](C)[C@H]3CC[C@@H](c4ccnc5ccc(F)cc54)CC3)[nH]c2c1F]

Example B130: ethyl 2-((R)-1-((1s,4S)-4-(6-fluoroquinolin-4-yl)cyclohexyl)ethyl)-7-methyl-1H-benzo[d]imidazole-6-carboxylate

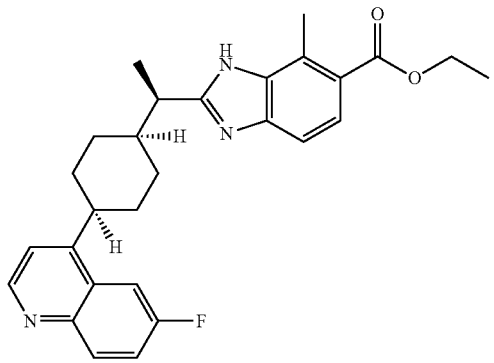 [SMILES: CCOC(=O)c1ccc2nc([C@H](C)[C@H]3CC[C@@H](c4ccnc5ccc(F)cc54)CC3)[nH]c2c1C]

Example B131: ethyl 5,7-difluoro-2-((R)-1-((1s,4S)-4-(6-fluoroquinolin-4-yl)cyclohexyl)ethyl)-1H-benzo[d]imidazole-6-carboxylate

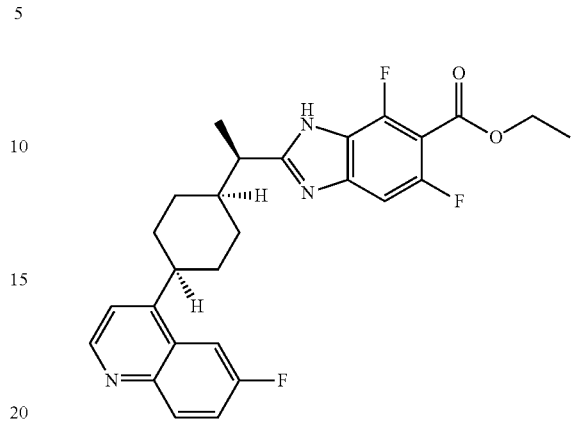

Example B132: ethyl 5-fluoro-2-((R)-1-((1s,4S)-4-(6-fluoroquinolin-4-yl)cyclohexyl)ethyl)-1H-benzo[d]imidazole-6-carboxylate

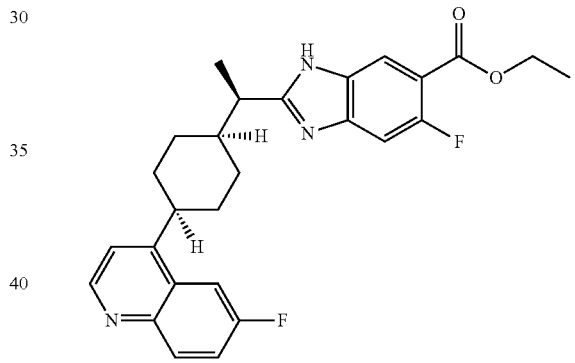

Example B133: tert-butyl 2-((R)-1-((1s,4S)-4-(6-fluoroquinolin-4-yl)cyclohexyl)ethyl)-1H-benzo[d]imidazole-6-carboxylate

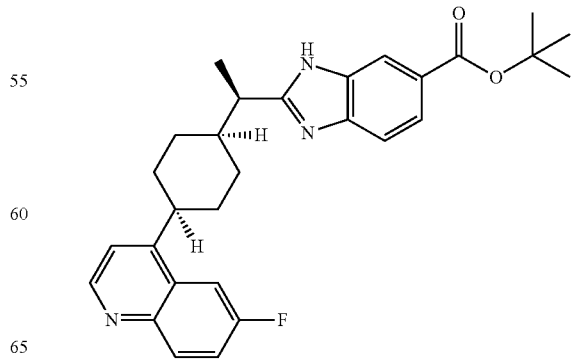

Example B134: cyclobutyl 2-((R)-1-((1s,4S)-4-(6-fluoroquinolin-4-yl)cyclohexyl)ethyl)-1H-benzo[d]imidazole-6-carboxylate

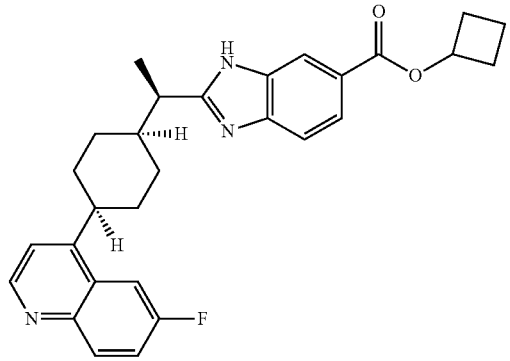 [SMILES: C[C@@H](c1nc2ccc(C(=O)OC3CCC3)cc2[nH]1)[C@H]1CC[C@@H](c2ccnc3ccc(F)cc32)CC1]

Example B135: 3-hydroxycyclobutyl 2-((R)-1-((1s,4S)-4-(6-fluoroquinolin-4-yl)cyclohexyl)ethyl)-1H-benzo[d]imidazole-6-carboxylate

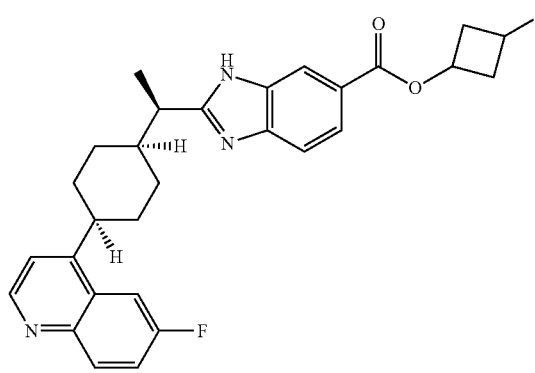

Example B136: N-(2-((R)-1-((1s,4S)-4-(6-fluoroquinolin-4-yl)cyclohexyl)ethyl)-1H-benzo[d]imidazol-6-yl)methanesulfonamide

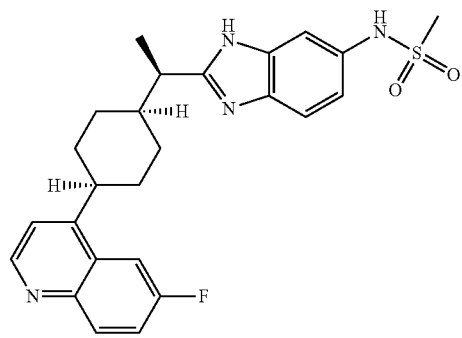 [SMILES: C[C@@H](c1nc2ccc(NS(C)(=O)=O)cc2[nH]1)[C@H]1CC[C@@H](c2ccnc3ccc(F)cc32)CC1]

Example B137: 2-((R)-1-((1s,4S)-4-(6-fluoroquinolin-4-yl)cyclohexyl)ethyl)-1H-benzo[d]imidazole-6-sulfonamide

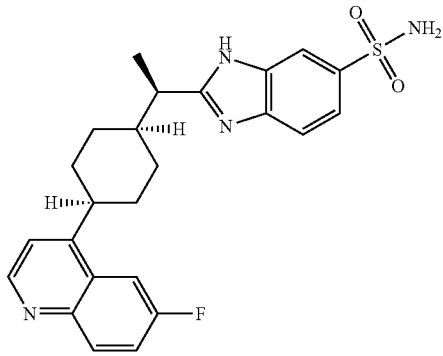 [SMILES: C[C@@H](c1nc2ccc(S(N)(=O)=O)cc2[nH]1)[C@H]1CC[C@@H](c2ccnc3ccc(F)cc32)CC1]

Example B138: 6-fluoro-4-((1S,4s)-4-((R)-1-(6-(methylsulfonyl)-1H-benzo[d]imidazol-2-yl)ethyl)cyclohexyl)quinoline

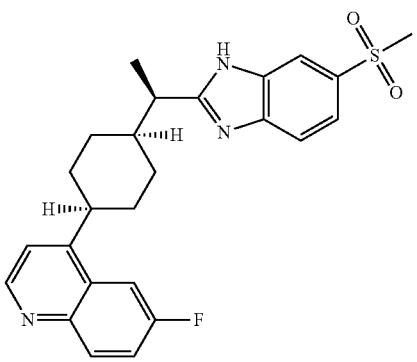 [SMILES: C[C@@H](c1nc2ccc(S(C)(=O)=O)cc2[nH]1)[C@H]1CC[C@@H](c2ccnc3ccc(F)cc32)CC1]

Example B139: 1-(2-((R)-1-((1s,4S)-4-(6-fluoroquinolin-4-yl)cyclohexyl)ethyl)-1H-benzo[d]imidazol-6-yl)ethanone

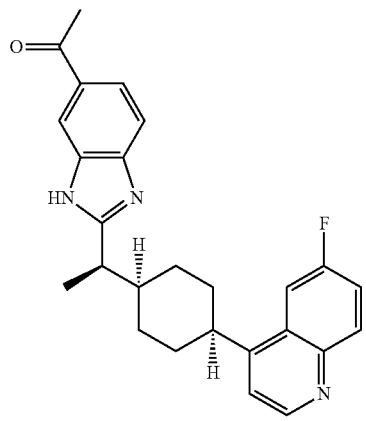 [SMILES: CC(=O)c1ccc2nc([C@H](C)[C@H]3CC[C@@H](c4ccnc5ccc(F)cc54)CC3)[nH]c2c1]

Example B140: methyl 2-((R)-1-((1s,4S)-4-(6-fluoroquinolin-4-yl)cyclohexyl)ethyl)-7-methyl-1H-benzo[d]imidazole-6-carboxylate

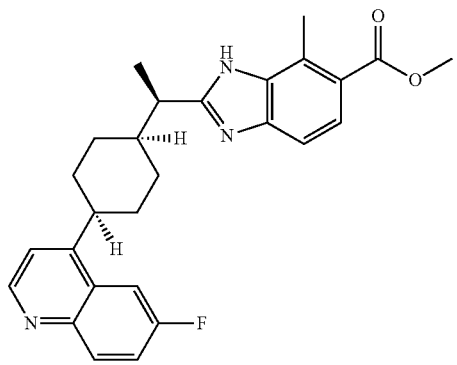 [SMILES: COC(=O)c1ccc2nc([C@H](C)[C@H]3CC[C@@H](c4ccnc5ccc(F)cc54)CC3)[nH]c2c1C]

Example B141: methyl 2-((R)-1-((1s,4S)-4-(6-fluoroquinolin-4-yl)cyclohexyl)ethyl)-4-methyl-1H-benzo[d]imidazole-6-carboxylate

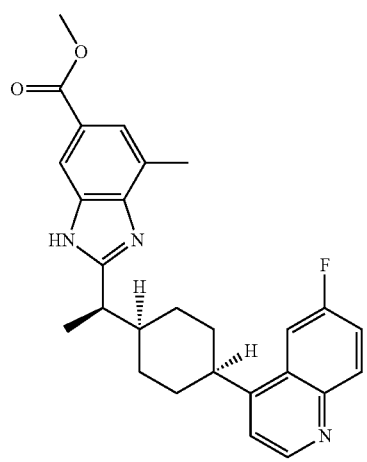 [SMILES: COC(=O)c1cc(C)c2nc([C@H](C)[C@H]3CC[C@@H](c4ccnc5ccc(F)cc54)CC3)[nH]c2c1]

Example B142: methyl 4-fluoro-2-((R)-1-((1s,4S)-4-(6-fluoroquinolin-4-yl)cyclohexyl)ethyl)-1H-benzo[d]imidazole-6-carboxylate

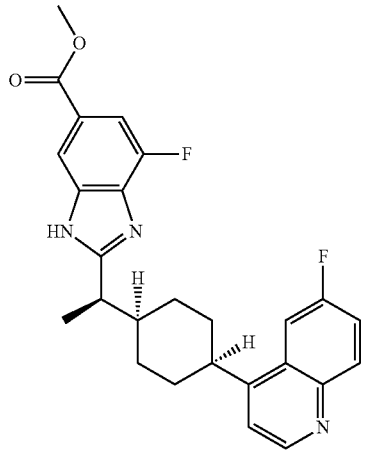 [SMILES: COC(=O)c1cc(F)c2nc([C@H](C)[C@H]3CC[C@@H](c4ccnc5ccc(F)cc54)CC3)[nH]c2c1]

Example B143: methyl 7-fluoro-2-((R)-1-((1s,4S)-4-(6-fluoroquinolin-4-yl)cyclohexyl)ethyl)-1H-benzo[d]imidazole-6-carboxylate

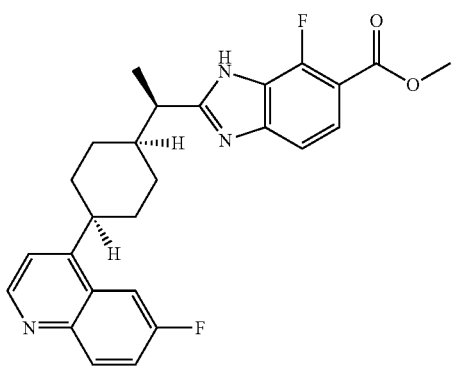 [SMILES: COC(=O)c1ccc2nc([C@H](C)[C@H]3CC[C@@H](c4ccnc5ccc(F)cc54)CC3)[nH]c2c1F]

Example B144: methyl 2-(1-cyano-1-((1s,4s)-4-(6-fluoroquinolin-4-yl)cyclohexyl)ethyl)-7-fluoro-1H-benzo[d]imidazole-6-carboxylate

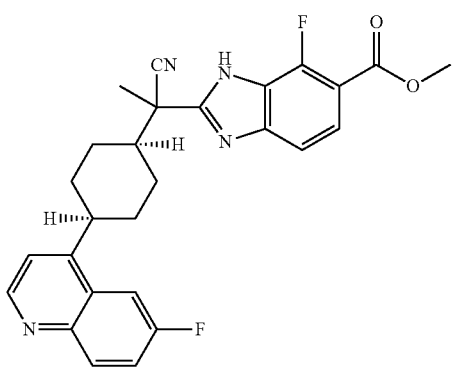 [SMILES: COC(=O)c1ccc2nc(C(C)(C#N)[C@H]3CC[C@@H](c4ccnc5ccc(F)cc54)CC3)[nH]c2c1F]

Example B145: methyl 2-(1-cyano-1-((1s,4s)-4-(6-fluoroquinolin-4-yl)cyclohexyl)ethyl)-7-methyl-1H-benzo[d]imidazole-6-carboxylate Example B147: 2-(5,6-difluoro-1H-benzo[d]imidazol-2-yl)-2-((1s,4s)-4-(6-fluoroquinolin-4-yl)cyclohexyl)propanenitrile

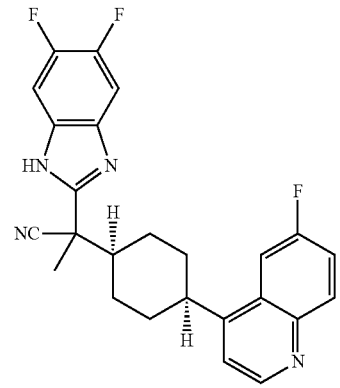

Example B148: N-(2-((R)-1-((1s,4S)-4-(6-fluoroquinolin-4-yl)cyclohexyl)ethyl)-1H-benzo[d]imidazol-6-yl)acetamide

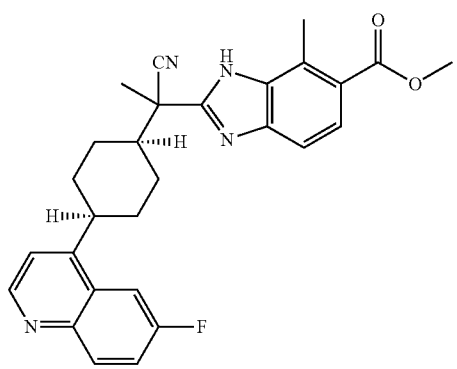 [SMILES: COC(=O)c1ccc2nc(C(C)(C#N)[C@H]3CC[C@@H](c4ccnc5ccc(F)cc54)CC3)[nH]c2c1C]

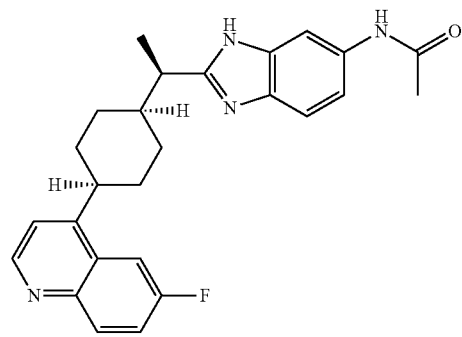

Example B146: methyl 2-(1-cyano-1-((1s,4s)-4-(6-fluoroquinolin-4-yl)cyclohexyl)ethyl)-1H-benzo[d]imidazole-6-carboxylate Example B151: 2-(1-((1s,4s)-4-(6-fluoroquinolin-4-yl)cyclohexyl)ethyl)-3,7-dihydro-8H-imidazo[4,5-g]quinazolin-8-one

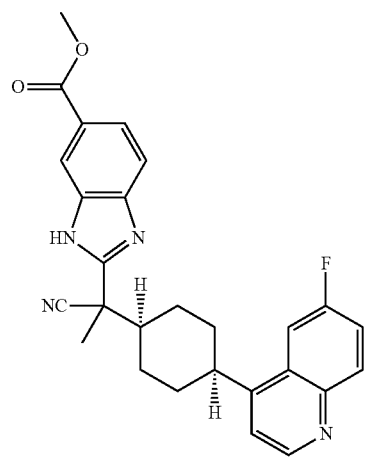 [SMILES: COC(=O)c1ccc2nc(C(C)(C#N)[C@H]3CC[C@@H](c4ccnc5ccc(F)cc54)CC3)[nH]c2c1]

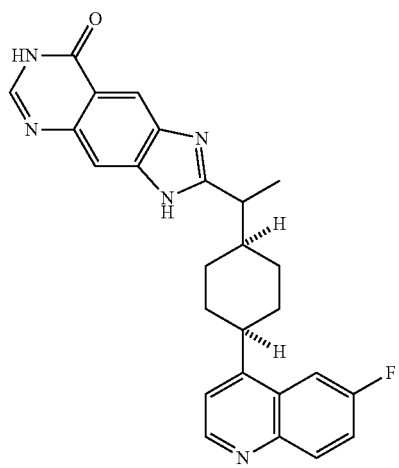 [SMILES: CC(c1nc2cc3c(=O)[nH]cnc3cc2[nH]1)[C@H]1CC[C@@H](c2ccnc3ccc(F)cc32)CC1]

¹H NMR (400 MHz, DMSO-d6) δ$_H$ 12.68 (m, 1H), 11.95 (s, 1H), 8.87 (d, J=4.4 Hz, 1H), 8.15-8.26 (m, 1H), 8.10 (dd, J=9.2, 6.0 Hz, 1H), 7.98 (m, 2H), 7.60-7.79 (m, 2H), 7.60 (d, J=4.4 Hz, 1H), 3.47 (m, 2H), 2.19 (m, 1H), 2.06 (m, 1H), 1.86 (m, 3H), 1.78 (m, 1H), 1.67 (m, 1H), 1.58 (m, 1H), 1.38 (m, 3H), 1.19 (m, 1H).

Example B157: 6-fluoro-4-((1S,4s)-4-((R)-1-(5-(pyrimidin-2-yl)-1H-benzo[d]imidazol-2-yl)ethyl)cyclohexyl)quinoline

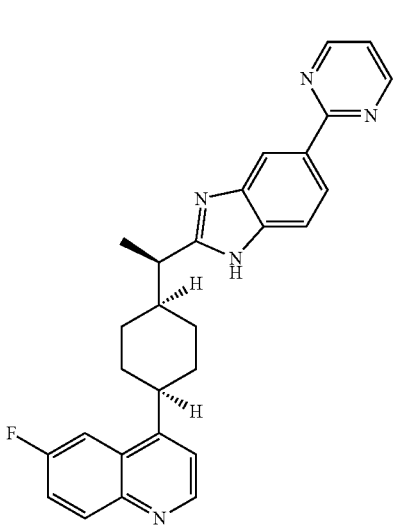 [SMILES: C[C@@H](c1nc2cc(-c3ncccn3)ccc2[nH]1)[C@H]1CC[C@@H](c2ccnc3ccc(F)cc32)CC1]

¹H NMR (400 MHz, DMSO-d) δ$_H$ 8.88 (t, J=4.9 Hz, 3H), 8.56 (s, 1H), 8.32 (d, J=8.6 Hz, 1H), 8.10 (dd, J=9.3, 5.8 Hz, 1H), 7.99 (dd, J=11.0, 2.6 Hz, 1H), 7.71-7.58 (m, 3H), 7.39 (t, J=4.8 Hz, 1H), 3.50-3.41 (m, 2H), 2.20-1.57 (m, 9H), 1.40 (d, J=6.9 Hz, 3H), 1.21 (m, 1H).

Example B159: 2-(1-((1s,4s)-4-(6-fluoroquinolin-4-yl)cyclohexyl)ethyl)-1,5,7,8-tetrahydro-6H-imidazo[4,5-g]quinolin-6-one

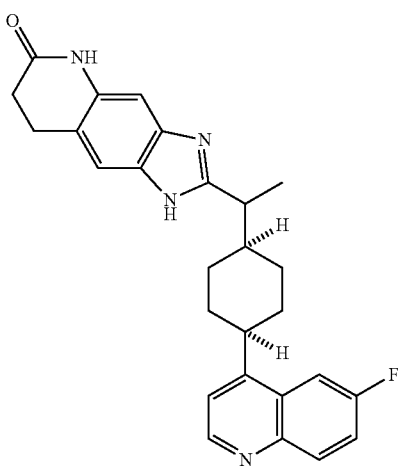 [SMILES: CC(c1nc2cc3c(cc2[nH]1)CCC(=O)N3)[C@H]1CC[C@@H](c2ccnc3ccc(F)cc32)CC1]

1H NMR (400 MHz, DMSO-d6) δ$_H$ 11.95-12.00 (m, 1H), 9.98 (m, 1H), 8.86 (d, J=4.4 Hz, 1H), 8.09 (dd, J=9.2, 6.0 Hz, 1H), 7.97 (d, J=8.8 Hz, 1H), 7.67 (t, J=8.4 Hz, 1H), 7.57 (d, J=4.4 Hz, 1H), 7.25 (m, 1H), 6.98 (m, 1H), 3.41 (m, 1H), 3.30 (m, 1H), 2.92 (s, 2H), 2.41 (m, 2H), 2.09 (m, 2H), 1.81 (m, 4H), 1.59 (m, 2H), 1.32 (d, J=6.8 Hz, 3H), 1.17 (m, 1H).

Example B160: 2-(1-((1s,4s)-4-(6-fluoroquinolin-4-yl)cyclohexyl)ethyl)-N,N-dimethyl-1H-benzo[d]imidazole-5-carboxamide

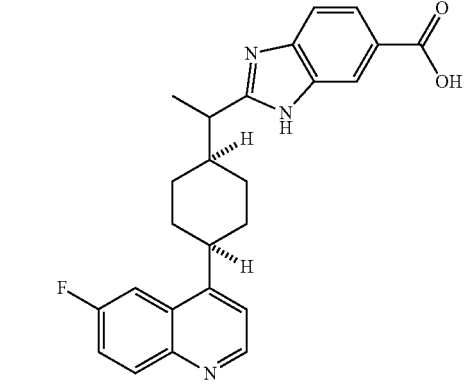 [SMILES: CC(c1nc2ccc(C(=O)O)cc2[nH]1)[C@H]1CC[C@@H](c2ccnc3ccc(F)cc32)CC1]

1H NMR (400 MHz, cd3od) δ$_H$ 8.69 (d, J=4.7 Hz, 1H), 7.98 (dd, J=9.2, 5.6 Hz, 1H), 7.79 (dd, J=10.6, 2.6 Hz, 1H), 7.62-7.44 (m, 3H), 7.21 (d, J=8.3 Hz, 1H), 3.48-3.28 (m, 2H), 3.03 (s, 3H), 2.96 (s, 3H), 2.16-2.09 (m, 2H), 2.00-1.73 (m, 4H), 1.66-1.60 (m, 2H), 1.37 (d, J=6.8 Hz, 3H), 1.22 (d, J=11.8 Hz, 1H).

Example B163: 2-(1-((1s,4s)-4-(6-fluoroquinolin-4-yl)cyclohexyl)ethyl)-1H-benzo[d]imidazole-6-carboxylic acid 1H NMR (400 MHz, dmso) δ 12.55 (s, 2H), 8.86 (d, J=4.3 Hz, 1H), 8.09 (dd, J=9.1, 6.0 Hz, 2H), 7.98 (d, J=10.3 Hz, 1H), 7.76 (s, 1H), 7.66 (t, J=7.6 Hz, 1H), 7.59 (d, J=4.2 Hz, 2H), 3.42 (s, 2H), 2.16-2.03 (m, 2H), 1.95-1.71 (m, 4H), 1.69-1.50 (m, 2H), 1.36 (d, J=6.6 Hz, 3H), 1.24-1.16 (m, 1H).

Example B164 N-cyclobutyl-2-(1-((1s,4s)-4-(6-fluoroquinolin-4-yl)cyclohexyl)ethyl)-1H-benzo[d]imidazole-6-carboxamide

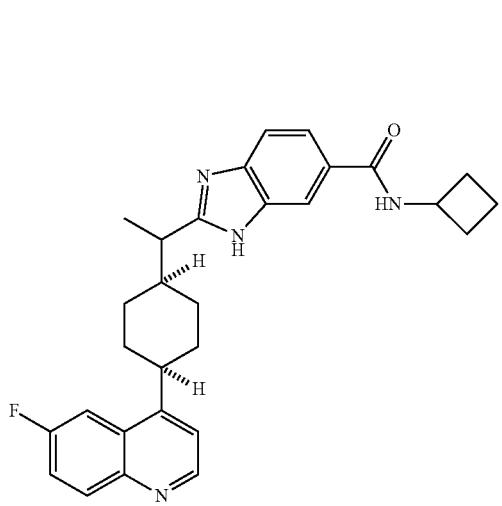 [SMILES: CC(c1nc2ccc(C(=O)NC3CCC3)cc2[nH]1)[C@H]1CC[C@@H](c2ccnc3ccc(F)cc32)CC1]

1H NMR (400 MHz, DMSO-d) δ$_H$ 12.43 (s, 1H), 8.87 (d, J=4.5 Hz, 1H), 8.52 (s, 1H), 8.12-8.08 (m, 1H), 7.98 (dd, J=11.0, 2.6 Hz, 1H), 7.69-7.64 (m, 2H), 7.59-7.47 (m, 2H), 4.44 (dd, J=16.3, 8.2 Hz, 1H), 3.45-3.41 (m, Hz, 2H), 2.28-1.98 (m, 6H), 1.95-1.73 (m, 4H), 1.72-1.52 (m, 4H), 1.36 (d, J=6.8 Hz, 3H), 1.17 (d, J=12.4 Hz, 1H).

Example B165: 2-(1-((1s,4s)-4-(6-fluoroquinolin-4-yl)cyclohexyl)ethyl)-N-methoxy-1H-benzo[d]imidazole-6-carboxamide

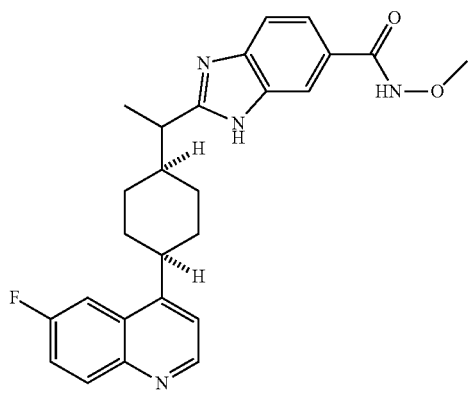 [SMILES: CONC(=O)c1ccc2nc(C(C)[C@H]3CC[C@@H](c4ccnc5ccc(F)cc54)CC3)[nH]c2c1]

$^1$H NMR (400 MHz, DMSO-d) δ$_H$ 12.52 (s, 1H), 11.64 (s, 1H), 8.87 (d, J=4.4 Hz, 1H), 8.10 (dd, J=9.2, 5.8 Hz, 1H), 7.98 (dd, J=11.0, 2.4 Hz, 1H), 7.91 (s, 1H), 7.67 (dd, J=11.6, 5.6 Hz, 1H), 7.62-7.46 (m, 3H), 3.72 (s, 3H), 3.46-3.41 (m, 6.6 Hz, 2H), 2.16-2.03 (m, 2H), 1.96-1.71 (m, 4H), 1.67-1.55 (m, 2H), 1.36 (d, J=6.7 Hz, 3H), 1.17-1.14 (m, 1H).

Example B166: 2-(1-((1s,4s)-4-(6-fluoroquinolin-4-yl)cyclohexyl)ethyl)-1H-naphtho[2,3-d]imidazole

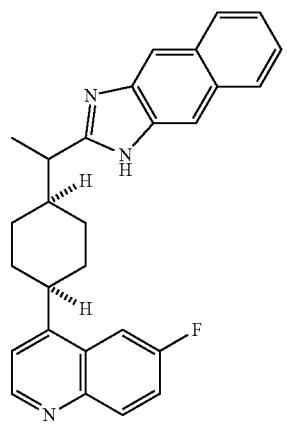 [SMILES: CC(c1nc2cc3ccccc3cc2[nH]1)[C@H]1CC[C@@H](c2ccnc3ccc(F)cc32)CC1]

$^1$H NMR (400 MHz, DMSO-d6) δ$_H$ 12.32 (s, 1H), 8.85-8.93 (m, 1H), 8.07-8.14 (m, 1H), 7.94-8.02 (m, 4H), 7.67 (t, J=8.8 Hz, 1H), 7.58-7.63 (m, 1H), 7.31-7.43 (m, 2H), 3.39-3.55 (m, 2H), 2.16-2.29 (m, 1H), 2.04-2.14 (m, 1H), 1.53-1.96 (m, 6H), 1.41 (d, J=6.4 Hz, 3H), 1.22-1.29 (m, 1H).

Example B167: 6-fluoro-4-((1s,4s)-4-(1-(6-(methylsulfonyl)-1H-benzo[d]imidazol-2-yl)ethyl)cyclohexyl)quinoline

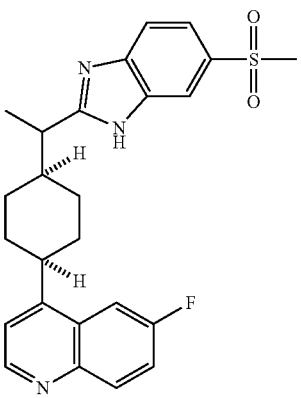 [SMILES: CC(c1nc2ccc(S(C)(=O)=O)cc2[nH]1)[C@H]1CC[C@@H](c2ccnc3ccc(F)cc32)CC1]

$^1$H NMR (400 MHz, CDCl$_3$) δ$_H$ 8.82 (s, 1H), 8.30-8.41 (m, 1H), 8.24 (s, 1H), 7.71-7.94 (m, 4H), 7.61 (t, J=8.0 Hz, 1H), 3.62-3.71 (m, 1H), 3.36-3.43 (m, 1H), 3.08 (s, 3H), 2.40-2.43 (m, 1H), 2.06-2.21 (m, 2H), 1.87-2.01 (m, 3H), 1.69-1.82 (m, 2H), 1.56 (d, J=6.0 Hz, 3H).

Example B169: 2-(1-((1s,4s)-4-(6-fluoroquinolin-4-yl)cyclohexyl)ethyl)-1H-benzo[d]imidazol-6-amine

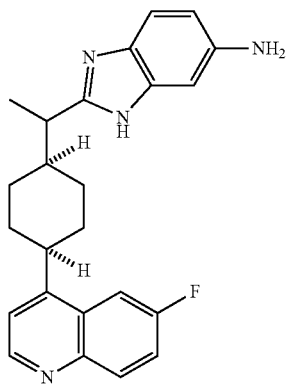 [SMILES: CC(c1nc2ccc(N)cc2[nH]1)[C@H]1CC[C@@H](c2ccnc3ccc(F)cc32)CC1]

1H NMR (400 MHz, DMSO-d6) δ$_H$ 8.85 (d, J=4.4 Hz, 1H), 8.09 (dd, J=9.2, 6.0 Hz, 1H), 7.97 (d, J=11.2 Hz, 1H), 7.66 (t, J=8.8 Hz, 1H), 7.56 (d, J=4.0 Hz, 1H), 7.13 (d, J=8.4 Hz, 1H), 6.61 (s, 1H), 6.44 (d, J=8.4 Hz, 1H), 5.76 (s, 1H), 4.84 (s, 1H), 3.37-3.45 (m, 1H), 3.20-3.29 (m, 1H), 1.96-2.14 (m, 2H), 1.81-1.92 (m, 2H), 1.71-1.80 (m, 2H), 1.52-1.67 (m, 2H), 1.30 (d, J=6.8 Hz, 3H), 1.16-1.21 (m, 1H).

Example B170: N-cyclopentyl-2-((R)-1-((1s,4S)-4-(6-fluoroquinolin-4-yl)cyclohexyl)ethyl)-1H-benzo[d]imidazole-6-carboxamide

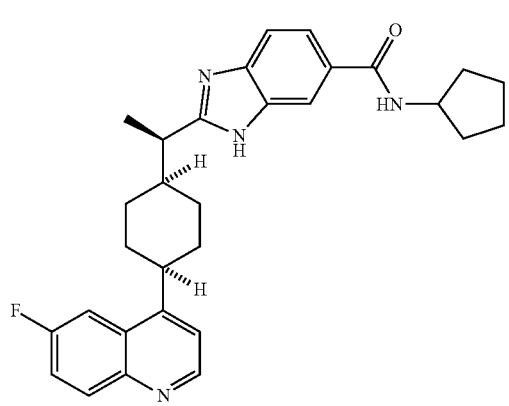 [SMILES: C[C@@H](c1nc2ccc(C(=O)NC3CCCC3)cc2[nH]1)[C@H]1CC[C@@H](c2ccnc3ccc(F)cc32)CC1]

1H NMR (400 MHz, DMSO-d) δ$_H$ 12.41 (s, 1H), 8.87 (d, J=4.5 Hz, 1H), 8.18 (s, 1H), 8.09 (dd, J=9.1, 5.9 Hz, 1H), 7.98 (dd, J=11.0, 2.4 Hz, 1H), 7.69-7.65 (m, 2H), 7.58 (d, J=4.4 Hz, 1H), 7.53-7.45 (m, 1H), 4.24 (dd, J=13.6, 6.8 Hz, 1H), 3.52-3.37 (m, 2H), 2.16-2.13 (m, 1H), 2.06-1.99 (m, 1H), 1.94-1.62 (m, 9H), 1.60-1.53 (m, 5H), 1.36 (d, J=6.8 Hz, 3H), 1.17-1.14 (m, 1H).

Example B171: N-cyclohexyl-2-((R)-1-((1s,4S)-4-(6-fluoroquinolin-4-yl)cyclohexyl)ethyl)-1H-benzo[d]imidazole-6-carboxamide

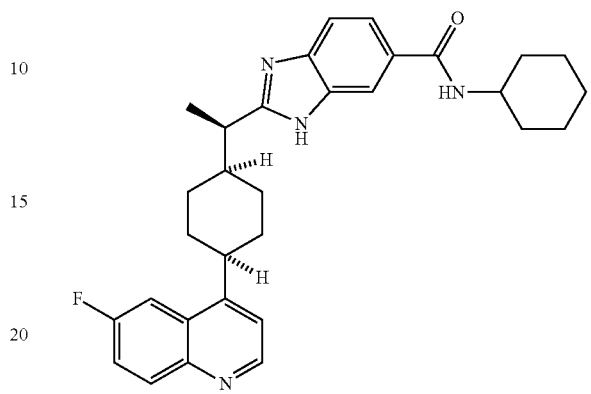

1H NMR (400 MHz, DMSO-d) δ$_H$ 8.90 (d, J=4.5 Hz, 1H), 8.33 (d, J=7.6 Hz, 1H), 8.19-8.06 (m, 2H), 8.01 (dd, J=10.9, 2.2 Hz, 1H), 7.90 (d, J=8.4 Hz, 1H), 7.79-7.65 (m, 2H), 7.62 (d, J=4.5 Hz, 1H), 3.78 (s, 1H), 3.68-3.64 (m, 1H), 3.45 (s, 1H), 2.21-2.18 (m, 1H), 2.08-2.05 (m, 1H), 1.95-1.71 (m, 9H), 1.63-1.57 (m, 2H), 1.46 (d, J=6.7 Hz, 3H), 1.32-1.23 (m, 4H), 1.17-1.04 (m, 2H).

Example B172: 4-((1s,4s)-4-(1-(7-chloro-4,5-difluoro-1H-benzo[d]imidazol-2-yl)ethyl)cyclohexyl)-6-fluoroquinoline

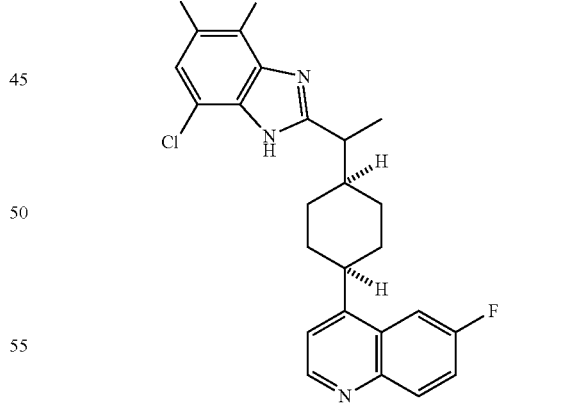

$^1$H NMR (400 MHz, DMSO-d6) δ$_H$ 12.96-13.40 (m, 1H), 8.87 (d, J=4.4 Hz, 1H), 8.10 (dd, J=9.2, 6.0 Hz, 1H), 7.98 (dd, J=11.2, 2.4 Hz, 1H), 7.67 (td, J=9.0, 2.8 Hz, 1H), 7.59 (d, J=4.4 Hz, 1H), 7.37-7.50 (m, 1H), 3.38-3.54 (m, 2H), 2.15-2.27 (m, 1H), 2.00-2.09 (m, 1H), 1.84-1.94 (m, 2H), 1.73-1.81 (m, 2H), 1.62-1.72 (m, 1H), 1.52-1.61 (m, 1H), 1.36 (d, J=6.8 Hz, 3H), 1.09-1.20 (m, 1H).

Example B173: 2-((R)-1-((1s,4S)-4-(6-fluoroquinolin-4-yl)cyclohexyl)ethyl)-1H-naphtho[2,3-d]imidazole

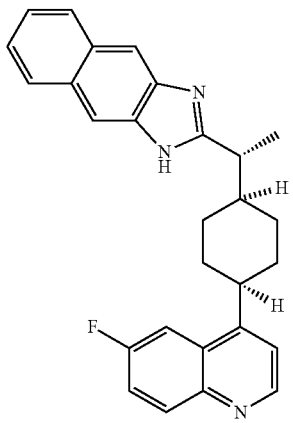 [SMILES: C[C@@H](c1nc2cc3ccccc3cc2[nH]1)[C@H]1CC[C@@H](c2ccnc3ccc(F)cc32)CC1]

¹H NMR (400 MHz, DMSO-d6) δ_H 12.79 (s, 1H), 8.81-8.94 (m, 1H), 8.25-8.44 (m, 1H), 8.06-8.17 (m, 1H), 7.94-8.04 (m, 2H), 7.53-7.76 (m, 5H), 7.36-7.48 (m, 1H), 3.40-3.45 (m, 1H), 3.13 (d, J=4.80 Hz, 2H), 1.85-2.01 (m, 4H), 1.65-1.79 (m, 4H).

Example B174: N-cyclobutyl-2-((R)-1-((1s,4S)-4-(6-fluoroquinolin-4-yl)cyclohexyl)ethyl)-1H-benzo[d]imidazole-5-carboxamide

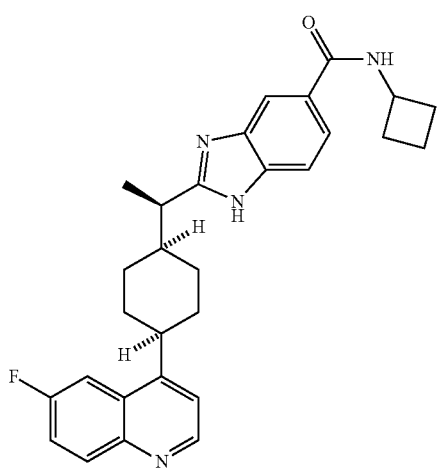 [SMILES: C[C@@H](c1nc2cc(C(=O)NC3CCC3)ccc2[nH]1)[C@H]1CC[C@@H](c2ccnc3ccc(F)cc32)CC1]

¹H NMR (400 MHz, DMSO-d) δ_H 12.46 (s, 1H), 8.87 (d, J=4.5 Hz, 1H), 8.53 (s, 1H), 8.10 (dd, J=9.2, 5.8 Hz, 1H), 8.02-7.93 (m, 2H), 7.69-7.64 (m, 2H), 7.59 (d, J=4.3 Hz, 1H), 7.50 (s, 1H), 4.44 (dd, J=16.0, 7.9 Hz, 1H), 3.45-3.39 (m, 2H), 2.28-2.00 (m, 7H), 1.96-1.74 (m, 4H), 1.71-1.50 (m, 4H), 1.36 (d, J=6.8 Hz, 3H), 1.16 (d, J=11.7 Hz, 1H).

Example B178: 6-fluoro-4-((1R,4r)-4-((R)-1-(6-(methylsulfonyl)-1H-benzo[d]imidazol-2-yl)ethyl)cyclohexyl)quinoline

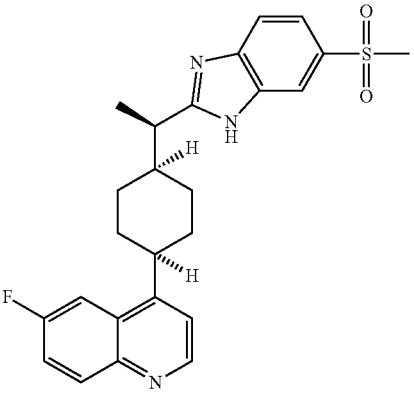 [SMILES: C[C@@H](c1nc2ccc(S(C)(=O)=O)cc2[nH]1)[C@H]1CC[C@@H](c2ccnc3ccc(F)cc32)CC1]

¹H NMR (400 MHz, DMSO-d6) δ_H 9.52 (s, 1H), 8.86 (d, J=4.4 Hz, 1H), 8.05-8.16 (m, 1H), 7.95-8.02 (m, 1H), 7.63-7.70 (m, 1H), 7.59 (d, J=4.4 Hz, 1H), 7.49 (d, J=8.4 Hz, 1H), 7.41 (s, 1H), 7.08 (d, J=8.4 Hz, 1H), 3.39-3.45 (m, 2H), 2.91 (s, 3H), 2.11-2.17 (m, 1H), 2.01-2.07 (m, 1H), 1.85-1.94 (m, 2H), 1.73-1.82 (m, 2H), 1.54-1.68 (m, 2H), 1.36 (d, J=6.8 Hz, 3H), 1.13-1.20 (m, 1H).

Example B179: N-(2-((R)-1-((1r,4R)-4-(6-fluoroquinolin-4-yl)cyclohexyl)ethyl)-1H-benzo[d]imidazol-6-yl)acetamide ¹H NMR (400 MHz, DMSO-d6) δ_H 12.08 (s, 1H), 9.87 (s, 1H), 8.85 (d, J=4.4 Hz, 1H), 8.09 (dd, J=9.2, 6.0 Hz, 1H), 7.83-8.02 (m, 2H), 7.61-7.71 (m, 1H), 7.57 (d, J=4.4 Hz, 1H), 7.38 (s, 1H), 7.05-7.22 (m, 1H), 3.37-3.48 (m, 2H), 2.07-2.14 (m, 1H), 1.98-2.06 (m, 4H), 1.83-1.94 (m, 2H), 1.70-1.81 (m, 2H), 1.52-1.64 (m, 2H), 1.33 (d, J=6.8 Hz, 3H), 1.18-1.24 (m, 1H).

Example B180: N-(2-((R)-1-((1r,4R)-4-(6-fluoroquinolin-4-yl)cyclohexyl)ethyl)-1H-benzo[d]imidazol-6-yl)methanesulfonamide

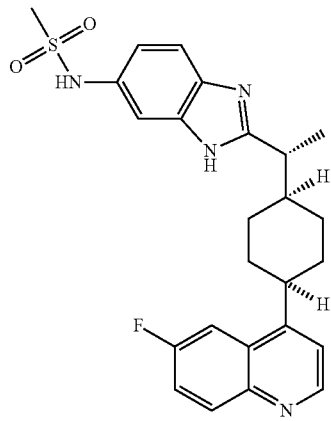 [SMILES: C[C@@H](c1nc2ccc(NS(C)(=O)=O)cc2[nH]1)[C@H]1CC[C@@H](c2ccnc3ccc(F)cc32)CC1]

¹H NMR (400 MHz, DMSO-d6) δ_H 12.72-12.87 (m, 1H), 8.78-8.90 (m, 1H), 7.92-8.14 (m, 3H), 7.64-7.78 (m, 3H), 7.59 (d, J=4.4 Hz, 1H), 3.41-3.52 (m, 2H), 3.17-3.22 (m, 3H), 2.14-2.20 (m, 1H), 2.03-2.09 (m, 1H), 1.85-1.93 (m, 2H), 1.71-1.83 (m, 2H), 1.62-1.69 (m, 1H), 1.54-1.60 (m, 1H), 1.37 (d, J=6.8 Hz, 3H), 1.13-1.18 (m, 1H).

Example B182: 2-(1-((1s,4s)-4-(6-fluoroquinolin-4-yl)cyclohexyl)ethyl)-N-phenyl-1H-benzo[d]imidazole-5-carboxamide

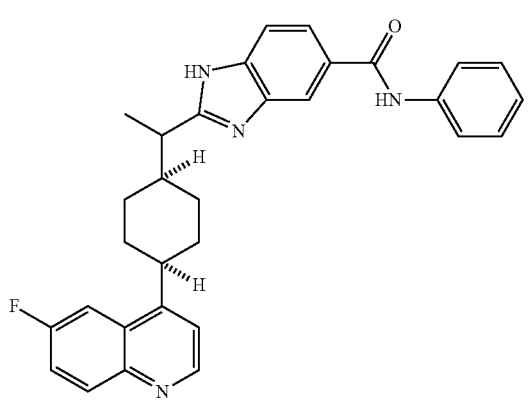 [SMILES: CC(c1nc2cc(C(=O)Nc3ccccc3)ccc2[nH]1)[C@H]1CC[C@@H](c2ccnc3ccc(F)cc32)CC1]

¹H NMR (400 MHz, DMSO-d) δ_H 12.53 (d, J=20.5 Hz, 1H), 10.18 (d, J=16.3 Hz, 1H), 8.87 (d, J=4.4 Hz, 1H), 8.28-7.93 (m, 3H), 7.84-7.73 (m, 2H), 7.71-7.50 (m, 3H), 7.34 (t, J=7.5 Hz, 2H), 7.08 (t, J=7.2 Hz, 1H), 3.44 (m, 2H), 2.22-1.52 (m, 8H), 1.38 (d, J=6.7 Hz, 3H), 1.23 (m, 1H).

Example B183: 2-(1-((1s,4s)-4-(6-fluoroquinolin-4-yl)cyclohexyl)ethyl)-N-((1-hydroxycyclobutyl)methyl)-1H-benzo[d]imidazole-5-carboxamide

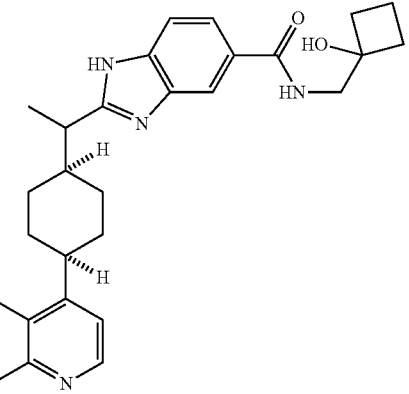

¹H NMR (400 MHz, DMSO-d) δ_H 12.32 (s, 1H), 8.79 (d, J=4.6 Hz, 1H), 8.07 (dd, J=9.0, 5.9 Hz, 1H), 7.98 (m, 2H), 7.66 (m, 2H), 7.43 (m, 2H), 4.90 (s, 1H), 4.17 (d, J=10.8 Hz, 1H), 3.98 (d, J=8.8 Hz, 1H), 3.55 (d, J=16.7 Hz, 1H), 2.98-2.87 (m, 2H), 1.95-1.50 (m, 6H), 1.38 (d, J=6.8 Hz, 3H)

Example B184: 2-(1-((1r,4r)-4-(6-fluoroquinolin-4-yl)cyclohexyl)ethyl)-N-((1-hydroxycyclobutyl)methyl)-1H-benzo[d]imidazole-5-carboxamide ¹H NMR (400 MHz, DMSO-d) δ_H 12.46 (s, 1H), 8.85 (d, J=4.3 Hz, 1H), 8.09 (dd, J=9.0, 5.9 Hz, 1H), 8.03-7.89 (m, 2H), 7.76-7.61 (m, 2H), 7.57 (d, J=4.0 Hz, 1H), 7.45 (dd, J=35.0, 8.4 Hz, 1H), 4.96-4.84 (m, 2H), 4.17 (d, J=10.6 Hz, 1H), 3.98 (d, J=10.7 Hz, 1H), 3.55 (d, J=16.8 Hz, 1H), 3.47-3.39 (m, 2H), 3.34 (d, J=5.4 Hz, 2H), 3.25 (d, J=16.9 Hz, 1H), 2.09 (m, 2H), 1.95-1.50 (m, 6H), 1.35 (d, J=6.6 Hz, 3H), 1.17 (m, 1H).

Example B185: 2-(1-((1s,4s)-4-(6-fluoroquinolin-4-yl)cyclohexyl)ethyl)-N-(4-methoxycyclohexyl)-1H-benzo[d]imidazole-5-carboxamide Example B189 and Example B190: 4-((1R,4s)-4-((S)-1-(7-chloro-5,6-difluoro-1H-benzo[d]imidazol-2-yl)ethyl)cyclohexyl)-6-fluoroquinoline and 4-((1R,4r)-4-((R)-1-(7-chloro-5,6-difluoro-1H-benzo[d]imidazol-2-yl)ethyl)cyclohexyl)-6-fluoroquinoline

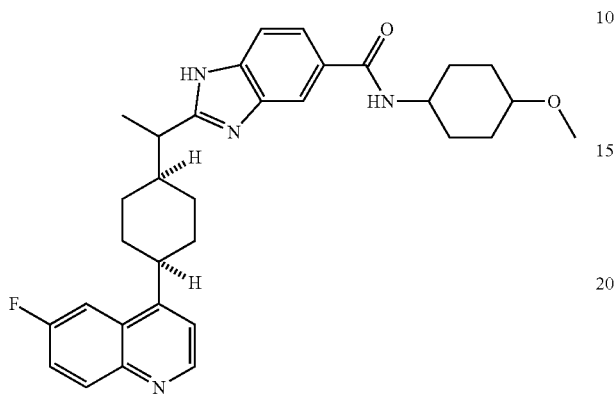

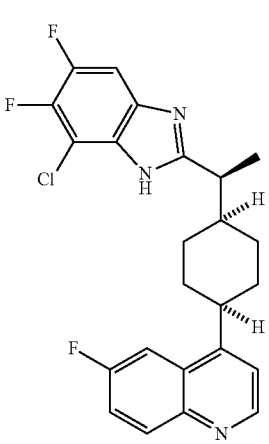

B189

¹H NMR (400 MHz, DMSO-d) δ$_H$ 12.41 (ds, 1H), 8.87 (d, J=4.5 Hz, 1H), 8.17-7.90 (m, 4H), 7.70-7.42 (m, 4H), 3.77 (m, 1H), 3.42 (m, 2H), 3.24 (s, 3H), 3.11 (m, 1H), 2.18-1.52 (m, 14H), 1.36 (d, J=6.6 Hz, 3H), 1.23 (m, 1H).

Example B186: 2-(1-((1r,4r)-4-(6-fluoroquinolin-4-yl)cyclohexyl)ethyl)-N-(4-methoxycyclohexyl)-1H-benzo[d]imidazole-5-carboxamide

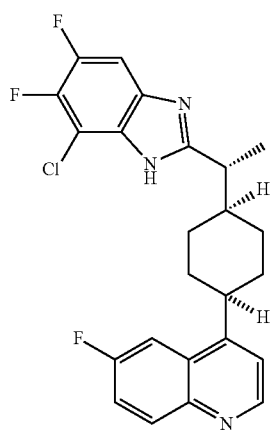

B190

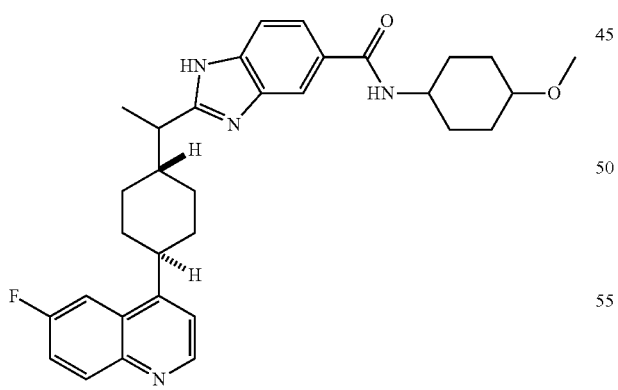

B189: ¹H NMR (400 MHz, DMSO-d6) δ$_H$ 12.77-12.92 (m, 1H), 8.86 (d, J=4.0 Hz, 1H), 8.10 (dd, J=8.8, 6.0 Hz, 1H), 7.98 (m, J=11.2 Hz, 1H), 7.63 (m, 3H), 3.45 (m, 2H), 2.17 (m, 1H), 2.03 (m, 1H), 1.82 (m, 4H), 1.62 (m, 2H), 1.34 (d, J=6.8 Hz, 3H), 1.14 (m, 1H).

B190: 1H NMR (400 MHz, DMSO-d6) δ$_H$ 12.77-12.92 (m, 1H), 8.87 (m, 1H), 8.09 (dd, J=9.2, 6.0 Hz, 1H), 7.98 (dd, J=11.2, 2.4 Hz, 1H), 7.62 (m, 3H), 3.45 (m, 2H), 2.16 (m, 1H), 2.03 (m, 1H), 1.84 (m, 4H), 1.64 (m, 2H), 1.34 (d, J=6.8 Hz, 3H), 1.14 (m, 1H).

¹H NMR (400 MHz, DMSO-d) δ$_H$ 12.41 (ds, 1H), 8.87 (d, J=4.5 Hz, 1H), 8.17-7.90 (m, 4H), 7.70-7.42 (m, 4H), 3.77 (m, 1H), 3.42 (m, 2H), 3.24 (s, 3H), 3.11 (m, 1H), 2.18-1.52 (m, 14H), 1.36 (d, J=6.6 Hz, 3H), 1.23 (m, 1H).

Example B193: N-cyclopropyl-2-((R)-1-((1s,4S)-4-(6-fluoroquinolin-4-yl)cyclohexyl)ethyl)-1H-benzo[d]imidazole-6-carboxamide

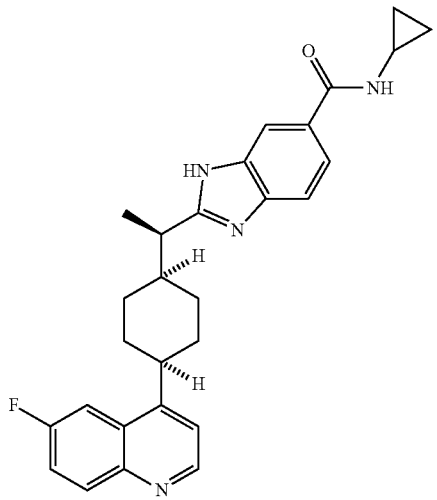 [SMILES: C[C@@H](c1nc2ccc(C(=O)NC3CC3)cc2[nH]1)[C@H]1CC[C@@H](c2ccnc3ccc(F)cc32)CC1]

$^1$H NMR (400 MHz, DMSO-d) $\delta_H$ 12.42 (d, J=114 Hz, 1H), 8.86 (d, J=4.5 Hz, 1H), 8.37-8.33 (m, 1H), 8.10 (dd, J=9.2, 5.8 Hz, 1H), 8.04 (s, 0.5H), 7.98 (dd, J=11.0, 2.7 Hz, 1H), 7.90 (s, 0.5H), 7.70-7.40 (m, 4H), 3.48-3.36 (m, 2H), 2.88-2.83 (m, 1H), 2.16-2.03 (m, 2H), 1.95-1.73 (m, 4H), 1.69-1.51 (m, 2H), 1.36 (d, J=6.8 Hz, 3H), 1.17-1.14 (m, 1H), 0.69-0.68 (m, 2H), 0.59-0.57 (m, 2H).

Example B194: 2-((R)-1-((1s,4S)-4-(6-fluoroquinolin-4-yl)cyclohexyl)ethyl)-N-isopropyl-1H-benzo[d]imidazole-6-carboxamide

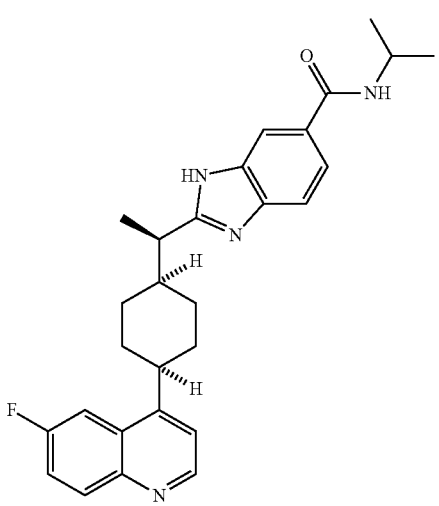 [SMILES: CC(C)NC(=O)c1ccc2nc([C@H](C)[C@H]3CC[C@@H](c4ccnc5ccc(F)cc54)CC3)[nH]c2c1]

1H NMR (400 MHz, DMSO-d) $\delta_H$ 12.40 (d, J=10.6 Hz, 1H), 8.87 (d, J=4.4 Hz, 1H), 8.15-8.08 (m, 3H), 7.98 (dd, J=11.0, 2.7 Hz, 1H), 7.92 (s, 0.5H), 7.71-7.62 (m, 2H), 7.58 (d, J=4.5 Hz, 1H), 7.55-7.43 (m, 1H), 4.14-4.09 (m, 1H), 3.42-3.42 (m, 2H), 2.20-2.00 (m, 2H), 1.95-1.70 (m, 4H), 1.69-1.50 (m, 2H), 1.36 (d, J=6.7 Hz, 3H), 1.17 (d, J=6.5 Hz, 6H).

Example B195: N-tert-butyl-2-((R)-1-((1s,4S)-4-(6-fluoroquinolin-4-yl)cyclohexyl)ethyl)-1H-benzo[d]imidazole-6-carboxamide

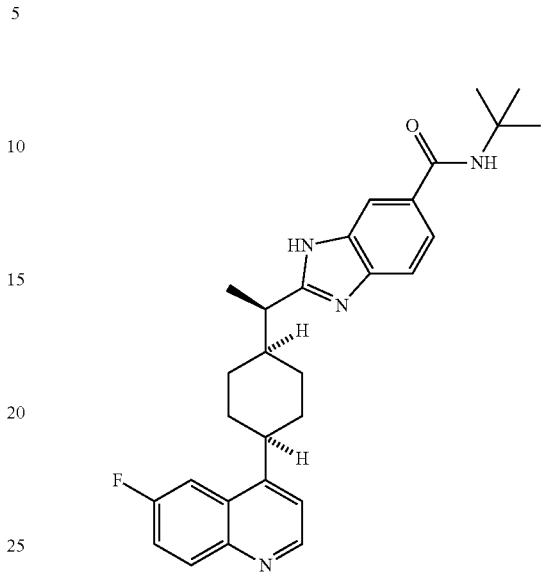

$^1$H NMR (400 MHz, DMSO-d) $\delta$ 12.39 (s, 1H), 8.87 (d, J=4.5 Hz, 1H), 8.14-7.82 (m, 3H), 7.72-7.37 (m, 5H), 3.45-3.40 (m, 2H), 2.19-1.96 (m, 2H), 1.95-1.72 (m, 4H), 1.67-1.54 (m, 2H), 1.43-1.34 (m, 12H), 1.16-1.13 (m, 1H).

Example B196: N-(tert-butyl)-2-((R)-1-((1s,4S)-4-(6-fluoroquinolin-4-yl)cyclohexyl)ethyl)-1H-benzo[d]imidazole-6-carboxamide

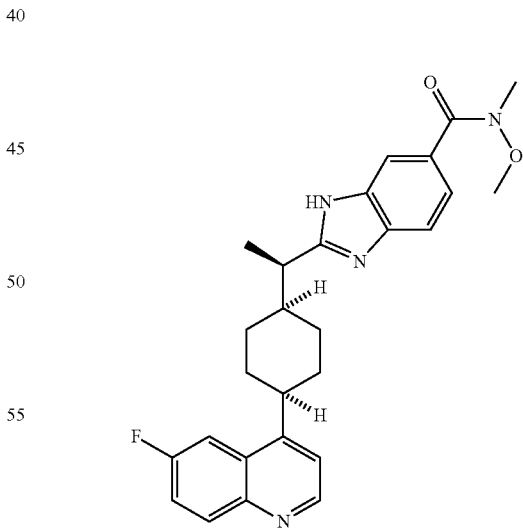

1H NMR (400 MHz, dmso) $\delta$ 12.44 (s, 1H), 8.86 (d, J=4.5 Hz, 1H), 8.09 (dd, J=9.1, 5.9 Hz, 1H), 7.98 (dd, J=11.0, 2.4 Hz, 1H), 7.85-7.35 (m, 5H), 3.56 (s, 3H), 3.43 (s, 2H), 3.27 (s, 3H), 2.20-1.96 (m, 3H), 1.94-1.71 (m, 4H), 1.68-1.56 (m, 2H), 1.36 (d, J=6.7 Hz, 3H).

Example B197: 2-(2-((R)-1-((1s,4S)-4-(6-fluoroquinolin-4-yl)cyclohexyl)ethyl)-1H-benzo[d]imidazol-6-yl)-4,5-dihydrooxazole

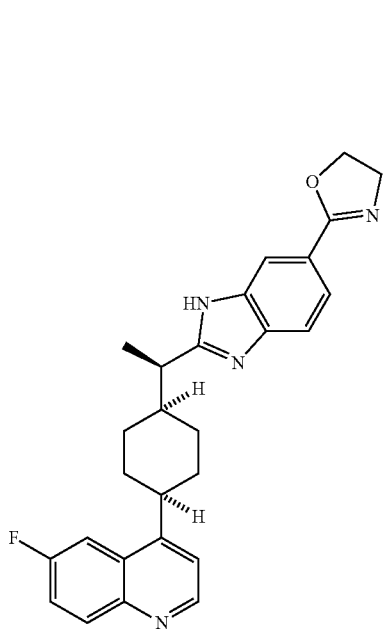 [SMILES: C[C@@H](c1nc2ccc(C3=NCCO3)cc2[nH]1)[C@H]1CC[C@@H](c2ccnc3ccc(F)cc32)CC1]

¹H NMR (400 MHz, dmso) δ 12.47 (d, J=8.5 Hz, 1H), 8.86 (d, J=4.5 Hz, 1H), 8.09 (dd, J=9.1, 5.9 Hz, 1H), 8.00-7.91 (m, 2H), 7.76-7.63 (m, 2H), 7.59-7.48 (m, 2H), 4.40 (t, J=9.2 Hz, 2H), 3.97-3.93 (m, 2H), 3.42 (s, 2H), 2.17-2.00 (m, 2H), 1.90-1.55 (m, 8H), 1.36 (d, J=6.7 Hz, 3H).

Example B198 and Example B199: methyl 5-fluoro-2-((S)-1-((1s,4R)-4-(6-fluoroquinolin-4-yl)cyclohexyl)ethyl)-1H-benzo[d]imidazole-4-carboxylate and methyl 5-fluoro-2-((R)-1-((1s,4S)-4-(6-fluoroquinolin-4-yl)cyclohexyl)ethyl)-1H-benzo[d]imidazole-4-carboxylate

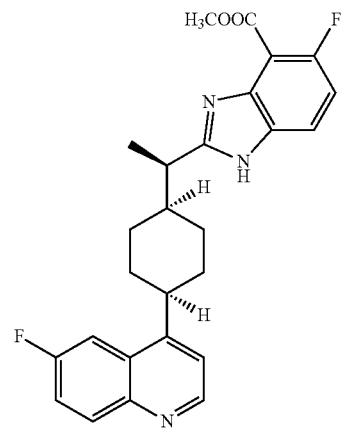

Example B198: 1H NMR (400 MHz, d-DMSO) δ 12.26 (s, 1H), 8.88 (t, J=4.4 Hz, 1H), 8.10 (dd, J=9.2, 6.0 Hz, 1H), 7.98 (dd, J=10.8, 2.4 Hz, 1H), 7.82 (dd, J=8.8, 4.4 Hz, 1H), 7.72-7.58 (m, 2H), 7.10 (dd, J=12.0, 8.4 Hz, 1H), 3.95 (s, 3H), 3.69-3.65 (m, 1H), 3.42 (br, 1H), 2.27-2.24 (m, 1H), 2.13-1.48 (m, 8H), 1.32 (d, J=6.8 Hz, 3H).

Example B199: 1H NMR (400 MHz, d-DMSO) δ 12.26 (s, 1H), 8.88 (t, J=4.4 Hz, 1H), 8.10 (dd, J=9.2, 6.0 Hz, 1H), 7.98 (dd, J=10.8, 2.4 Hz, 1H), 7.82 (dd, J=8.8, 4.4 Hz, 1H), 7.72-7.52 (m, 2H), 7.10 (dd, J=12.0, 8.4 Hz, 1H), 3.95 (s, 3H), 3.65 (m, 1H), 3.42 (br, 1H), 2.27-2.24 (m, 1H), 2.21-1.44 (m, 8H), 1.32 (d, J=6.8 Hz, 3H). [M+H]⁺=450.1

Example B200 and B201: ethyl 2-((S)-1-((1s,4S)-4-(6-fluoroquinolin-4-yl)cyclohexyl)ethyl)-6-methyl-1H-benzo[d]imidazole-5-carboxylate and ethyl 2-((R)-1-((1s,4S)-4-(6-fluoroquinolin-4-yl)cyclohexyl)ethyl)-6-methyl-1H-benzo[d]imidazole-5-carboxylate

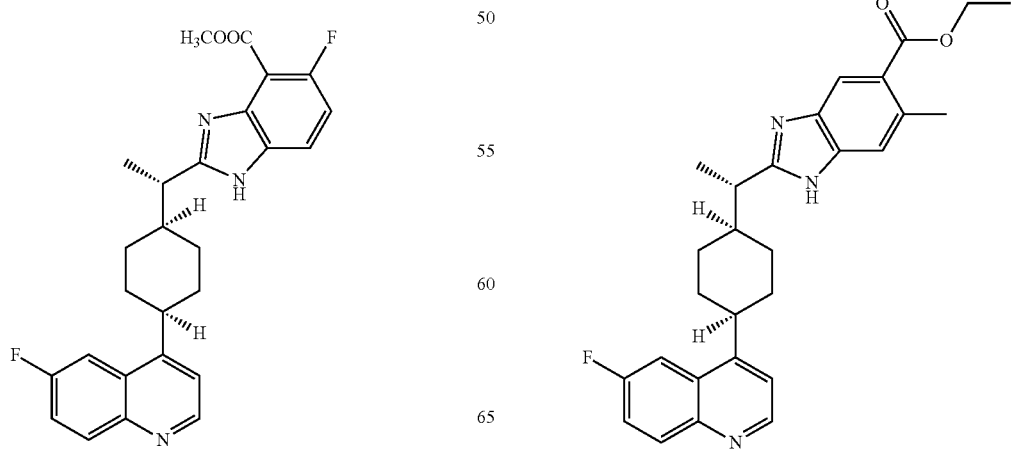

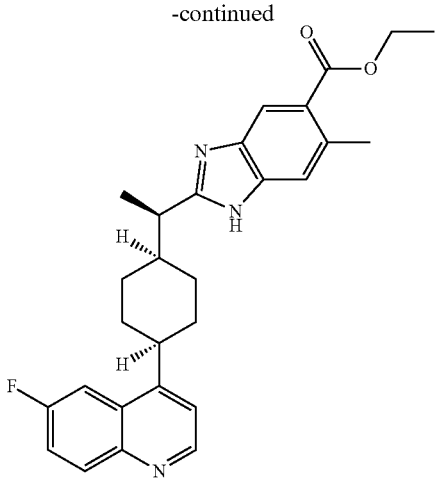

Example B200: 1H NMR (DMSO-d6) δ$_H$ 12.38 (s, 1H), 8.86 (d, J=4.4 Hz, 1H), 8.28-7.83 (m, 3H), 7.83-7.51 (m, 2H), 7.34 (br, 1H), 4.28 (q, J=7.2 Hz, 2H), 3.51-3.38 (m, 2H), 2.60 (s, 3H), 2.18-1.49 (m, 9H), 1.36-1.23 (m, 6H).

Example B201:1H NMR (DMSO-d6) δH 12.39 (s, 1H), 8.86 (d, J=4.4 Hz, 1H), 8.28-7.88 (m, 3H), 7.88-7.53 (m, 2H), 7.37 (s, 1H), 4.28 (q, J=7.2 Hz, 2H), 3.44-3.39 (m, 2H), 2.60 (s, 3H), 2.22-1.47 (m, 9H), 1.36-1.23 (m, 6H).

Example B202: 1-(2-((R)-1-((1s,4S)-4-(6-fluoroquinolin-4-yl)cyclohexyl)ethyl)-1H-benzo[d]imidazol-6-yl)ethan-1-one

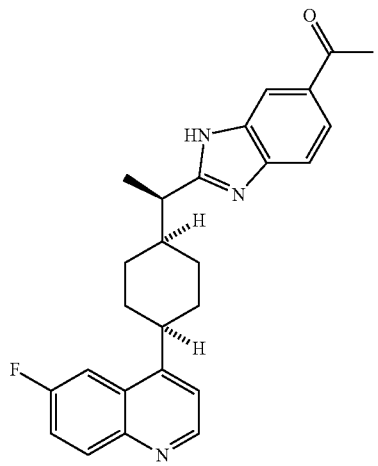 [SMILES: CC(=O)c1ccc2nc([C@H](C)[C@H]3CC[C@@H](c4ccnc5ccc(F)cc54)CC3)[nH]c2c1]

$^1$H NMR (400 MHz, dmso) δ 12.58 (d, J=11.3 Hz, 1H), 8.87 (d, J=4.5 Hz, 1H), 8.22 (s, 0.5 H), 8.10 (dd, J=9.2, 5.8 Hz, 1H), 8.04 (s, 0.5 H), 7.98 (dd, J=11.0, 2.7 Hz, 1H), 7.78 (d, J=8.4 Hz, 1H), 7.66 (td, J=9.1, 2.8 Hz, 1H), 7.63-7.47 (m, 2H), 3.45-3.43 (m, 2H), 2.61 (s, 3H), 2.21-2.01 (m, 2H), 1.94-1.73 (m, 4H), 1.69-1.52 (m, 2H), 1.37 (d, J=6.8 Hz, 3H), 1.16 (d, J=14.5 Hz, 1H).

Example B203: 4-((1s,4s)-4-(1-(7-chloro-5,6-difluoro-1H-benzo[d]imidazol-2-yl)ethyl)cyclohexyl)-6-fluoroquinoline

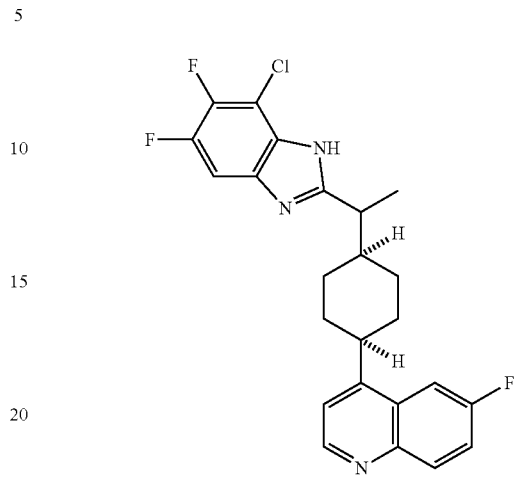

$^1$H NMR (400 MHz, DMSO-d6) δ$_H$ 12.69-13.25 (m, 1H), 8.76-9.04 (m, 1H), 8.09 (dd, J=8.8, 6.0 Hz, 1H), 7.98 (d, J=9.6 Hz, 1H), 7.53-7.73 (m, 3H), 3.41-3.50 (m, 2H), 2.12-2.23 (m, 1H), 1.99-2.07 (m, 1H), 1.73-1.95 (m, 4H), 1.48-1.69 (m, 2H), 1.34 (d, J=6.4 Hz, 3H), 1.11-1.19 (m, 1H).

Example B204 and Example B205: 4-((1R,4s)-4-((S)-1-(7-chloro-4,6-difluoro-1H-benzo[d]imidazol-2-yl)ethyl)cyclohexyl)-6-fluoroquinoline and 4-((1R,4r)-4-((R)-1-(7-chloro-4,6-difluoro-1H-benzo[d]imidazol-2-yl)ethyl)cyclohexyl)-6-fluoroquinoline

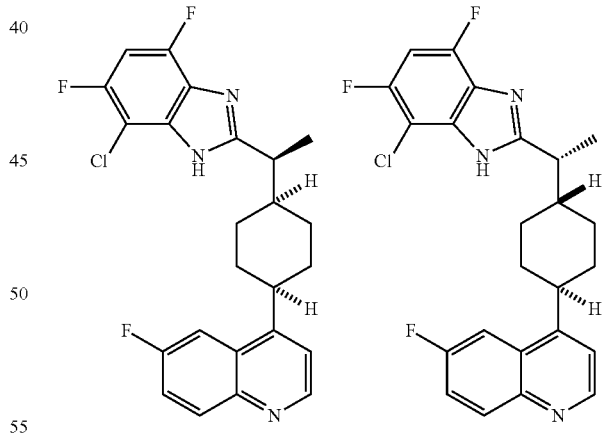

Example B204 $^1$H NMR (400 MHz, DMSO-d6) δ$_H$ 12.83-13.65 (m, 1H), 8.87 (d, J=4.4 Hz, 1H), 8.09 (dd, J=9.2, 6.0 Hz, 1H), 7.98 (dd, J=10.8, 2.4 Hz, 1H), 7.66 (td, J=8.8, 2.4 Hz, 1H), 7.59 (d, J=4.4 Hz, 1H), 7.37-7.50 (m, 1H), 3.37-3.50 (m, 2H), 2.15-2.26 (m, 1H), 2.00-2.06 (m, 1H), 1.84-1.94 (m, 2H), 1.72-1.82 (m, 2H), 1.62-1.70 (m, 1H), 1.53-1.60 (m, 1H), 1.36 (d, J=6.8 Hz, 3H), 1.10-1.19 (m, 1H).

Example B205 $^1$H NMR (400 MHz, DMSO-d6) δ$_H$ 12.87-13.42 (m, 1H), 8.81-8.88 (m, J=3.6 Hz, 1H), 8.07 (dd, J=9.2, 6.0 Hz, 1H), 7.96 (dd, J=11.2, 2.4 Hz, 1H), 7.61-7.68

(m, 1H), 7.56 (d, J=4.4 Hz, 1H), 7.36-7.48 (m, 6.2 Hz, 1H), 3.37-3.48 (m, 2H), 2.14-2.22 (m, 1H), 1.97-2.04 (m, 1H), 1.83-1.92 (m, 2H), 1.71-1.80 (m, 2H), 1.60-1.68 (m, 1H), 1.52-1.57 (m, 1H), 1.34 (d, J=6.8 Hz, 3H), 1.09-1.16 (m, 1H).

Example 206: N-cyclobutyl-2-(1-(4-(6-fluoroquinolin-4-yl)cyclohexyl)ethyl)-4-methyl-1H-benzo[d]imidazole-6-carboxamide

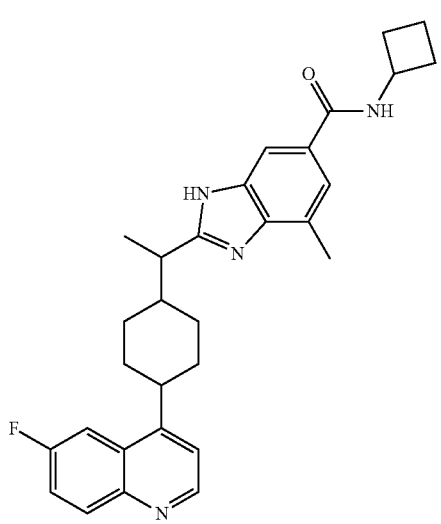 [SMILES: Cc1cc(C(=O)NC2CCC2)cc2[nH]c(C(C)C3CCC(c4ccnc5ccc(F)cc45)CC3)nc12]

Example B207: 2-(1-((1s,4s)-4-(6-fluoroquinolin-4-yl)cyclohexyl)ethyl)-N-methyl-1H-imidazo[4,5-c]pyridine-6-carboxamide

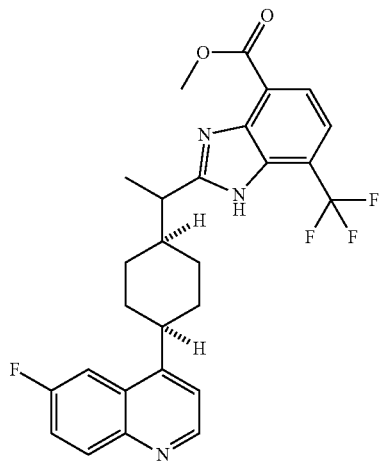

¹H NMR (400 MHz, dmso) δ 12.67 (s, 1H), 8.89 (d, J=4.4 Hz, 1H), 8.10 (dd, J=9.2, 6.0 Hz, 1H), 7.98 (dd, J=11.2, 2.8 Hz, 1H), 7.88 (d, J=8.0 Hz, 1H), 7.70-7.50 (m, 3H), 3.99 (s, 3H), 3.76 (dd, J=11.2, 6.8 Hz, 1H), 3.42 (s, 1H), 2.33 (s, 1H), 2.06 (d, J=12.0 Hz, 1H), 2.02-1.83 (m, 2H), 1.78 (s, 2H), 1.67 (d, J=13.2 Hz, 1H), 1.54 (d, J=9.4 Hz, 1H), 1.36 (d, J=6.8 Hz, 3H), 1.27-1.13 (m, 1H). [M+1]500.

Example B209 and B210: methyl 2-((S)-1-((1s,4R)-4-(6-fluoroquinolin-4-yl)cyclohexyl)ethyl)-1H-benzo[d]imidazole-4-carboxylate and methyl 2-((R)-1-((1s,4S)-4-(6-fluoroquinolin-4-yl)cyclohexyl)ethyl)-1H-benzo[d]imidazole-4-carboxylate

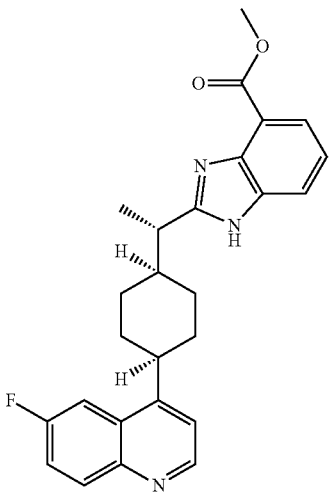

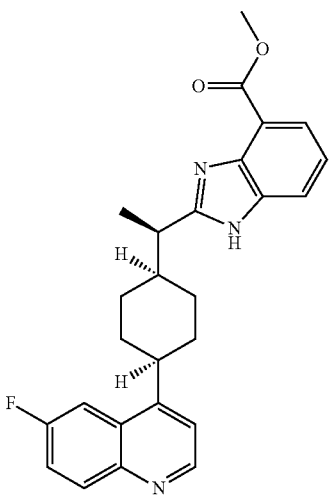

Example B209: ¹H NMR (DMSO-d6) δ$_H$ 12.22 (s, 1H), 8.89 (d, J=4.4 Hz, 1H), 8.10 (dd, J=9.2, 6.0 Hz, 1H), 7.98 (dd, J=10.8, 2.8 Hz, 1H), 7.85 (d, J=7.6 Hz, 1H), 7.76 (d, J=7.6 Hz, 1H), 7.72-7.59 (m, 2H), 7.25 (t, J=8.0 Hz, 1H), 3.95 (s, 3H), 3.71-3.67 (m, 1H), 3.40 (br, 1H), 2.31 (br, 1H), 2.13-1.47 (m, 8H), 1.34 (d, J=6.8 Hz, 3H).

Example B210: ¹H NMR (DMSO-d6) δ$_H$ 12.22 (s, 1H), 8.89 (d, J=4.4 Hz, 1H), 8.10 (dd, J=9.2, 6.0 Hz, 1H), 7.98 (dd, J=10.8, 2.8 Hz, 1H), 7.85 (d, J=7.6 Hz, 1H), 7.76 (d, J=7.6 Hz, 1H), 7.73-7.58 (m, 2H), 7.25 (t, J=8.0 Hz, 1H), 3.95 (s, 3H), 3.71-3.67 (m, 1H), 3.40 (br, 1H), 2.31 (br, 1H), 2.13-1.47 (m, 8H), 1.34 (d, J=6.8 Hz, 3H).

Example B211 and Example B212: 2-((S)-1-((1s, 4R)-4-(6-fluoroquinolin-4-yl)cyclohexyl)ethyl)-3H-naphtho[1,2-d]imidazole and 2-((R)-1-((1r,4R)-4-(6-fluoroquinolin-4-yl)cyclohexyl)ethyl)-3H-naphtho[1,2-d]imidazole

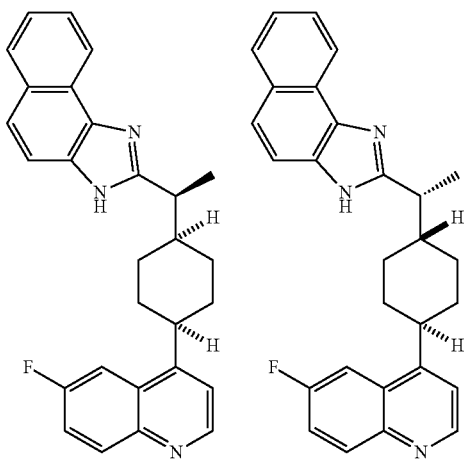 [SMILES: C[C@H](c1nc2c(ccc3ccccc32)[nH]1)[C@H]1CC[C@@H](c2ccnc3ccc(F)cc32)CC1 ; C[C@@H](c1nc2c(ccc3ccccc32)[nH]1)[C@H]1CC[C@H](c2ccnc3ccc(F)cc32)CC1]

Example B211: $^1$H NMR (400 MHz, DMSO-d6) $\delta_H$ 12.52-12.88 (m, 1H), 8.87 (d, J=4.4 Hz, 1H), 8.35 (s, 1H), 8.10 (dd, J=9.0, 6.0 Hz, 1H), 7.98 (m, 2H), 7.64 (m, 4H), 7.56 (t, J=7.2 Hz, 1H), 7.43 (m, J=7.2 Hz, 1H), 3.48 (m, 2H), 2.23 (m, 1H), 2.09 (m, 1H), 1.89 (m, 3H), 1.79 (m, 1H), 1.63 (m, 2H), 1.42 (d, J=6.8 Hz, 3H), 1.20 (m, 1H).

Example B212: $^1$H NMR (400 MHz, DMSO-d6) $\delta_H$ 12.54-12.90 (m, 1H), 8.87 (d, J=4.0 Hz, 1H), 8.35 (s, 1H), 8.10 (dd, J=8.8, 6.0 Hz, 1H), 7.97 (m, 2H), 7.62 (m, 5H), 7.43 (t, J=7.6 Hz, 1H), 3.49 (m, 2H), 2.23 (m, 1H), 2.09 (m, 1H), 1.89 (m, 3H), 1.78 (m, 1H), 1.61 (m, 2H), 1.42 (d, J=6.4 Hz, 3H), 1.21 (m, 1H).

Example B215: 2-(1-((1s,4s)-4-(6-fluoroquinolin-4-yl)cyclohexyl)ethyl)-N-(oxetan-3-yl)-1H-benzo[d]imidazole-6-carboxamide

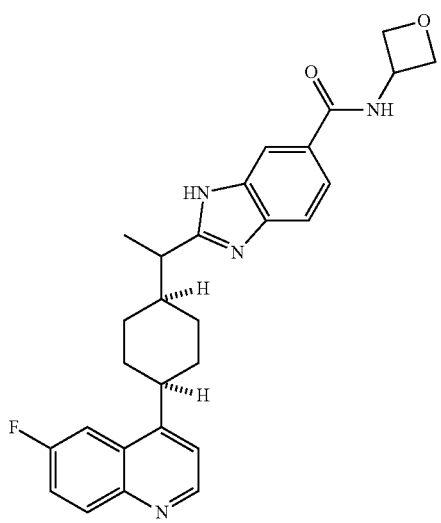 [SMILES: CC(c1nc2ccc(C(=O)NC3COC3)cc2[nH]1)[C@H]1CC[C@@H](c2ccnc3ccc(F)cc32)CC1]

$^1$H NMR (400 MHz, DMSO-d) $\delta_H$ 12.47 (d, J=13.0 Hz, 1H), 9.01 (dd, J=19.5, 6.3 Hz, 1H), 8.87 (d, J=4.5 Hz, 1H), 8.16-7.95 (m, 3H), 7.68 (m, 2H), 7.53 (m, 2H), 5.03 (m, 1H), 4.77 (t, J=6.7 Hz, 2H), 4.62 (td, J=6.4, 2.5 Hz, 2H), 3.43 (m, 2H), 2.19-1.53 (m, 8H), 1.37 (d, J=6.8 Hz, 3H), 1.17 (m, 1H).

Example B215: 2-(1-((1r,4r)-4-(6-fluoroquinolin-4-yl)cyclohexyl)ethyl)-N-(2-methoxyethyl)-1H-benzo[d]imidazole-5-carboxamide

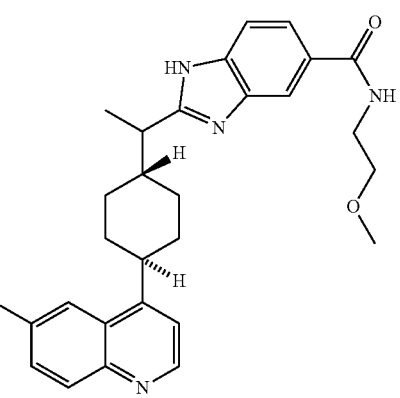

$^1$H NMR (400 MHz, DMSO-d) $\delta_H$ 12.39 (d, J=13.0 Hz, 1H), 8.79 (d, J=4.6 Hz, 1H), 8.43 (m, 1H), 8.02 (m, 3H), 7.72-7.38 (m, 4H), 3.52-3.40 (m, 4H), 3.28 (s, 3H), 2.94 (m, 1l), 1.98-1.41 (m, 8H), 1.40 (d, J=7.2 Hz, 3H).

Example B216: 2-(1-((1s,4s)-4-(6-fluoroquinolin-4-yl)cyclohexyl)ethyl)-N-(2-methoxyethyl)-1H-benzo[d]imidazole-5-carboxamide

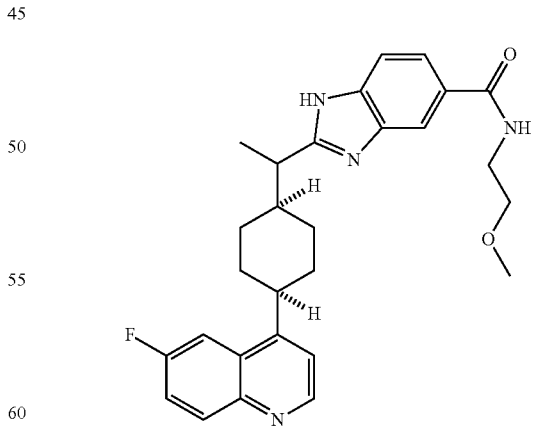

$^1$H NMR (400 MHz, DMSO-d) $\delta_H$ 12.43 (d, J=13.3 Hz, 1H), 8.86 (d, J=4.5 Hz, 1H), 8.42 (m, 1H), 8.14-7.91 (m, 3H), 7.71-7.42 (m, 4H), 3.49-3.37 (m, 6H), 3.27 (s, 3H), 2.10 (m, 2H), 1.95-1.53 (m, 6H), 1.36 (d, J=6.8 Hz, 3H), 1.16 (m, 1H).

Example B217: 5-(2-(1-((1s,4s)-4-(6-fluoroquinolin-4-ylcyclohexyl)ethyl)-1H-benzo[d]imidazol-5-yl)-3-methyl-1,2,4-oxadiazole

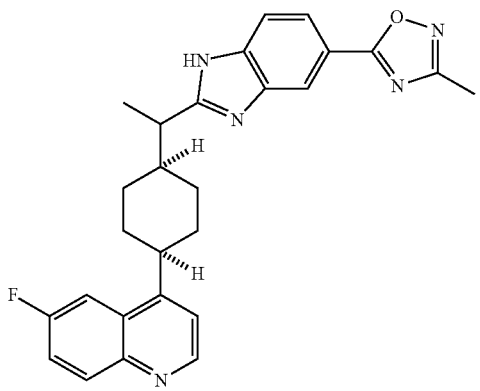 [SMILES: Cc1noc(-c2ccc3[nH]c(C(C)[C@H]4CC[C@@H](c5ccnc6ccc(F)cc65)CC4)nc3c2)n1]

$^1$H NMR (400 MHz, DMSO-d) $\delta_H$ 12.72 (s, 1H), 8.87 (d, J=4.5 Hz, 1H), 8.20 (m, 1H), 8.10 (dd, J=9.2, 5.9 Hz, 1H), 7.98 (dd, J=11.0, 2.7 Hz, 1H), 7.88 (d, J=8.0 Hz, 1H), 7.67 (m, 2H), 7.60 (d, J=4.6 Hz, 1H), 3.52-3.38 (m, 2H), 2.12 (m, 2H), 1.95-1.55 (m, 6H), 1.38 (d, J=6.8 Hz, 3H), 1.19 (m, 1H).

Example B220: 5-(2-((R)-1-((1s,4S)-4-(6-fluoroquinolin-4-yl)cyclohexyl)ethyl)-1H-benzo[d]imidazol-6-yl)-3-methyl-1,2,4-oxadiazole

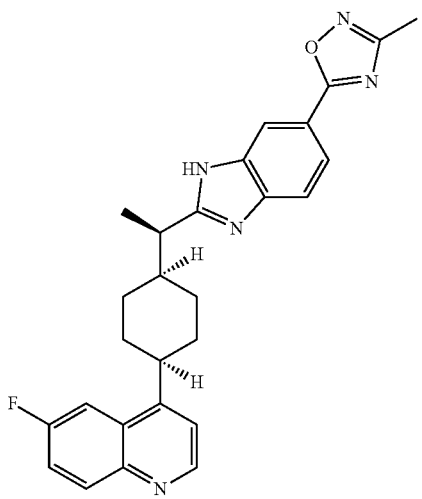 [SMILES: Cc1noc(-c2ccc3nc([C@H](C)[C@H]4CC[C@@H](c5ccnc6ccc(F)cc65)CC4)[nH]c3c2)n1]

$^1$H NMR (400 MHz, DMSO-d) $\delta_H$ 12.74 (s, 1H), 8.87 (d, J=4.5 Hz, 1H), 8.20 (s, 1H), 8.10 (dd, J=9.2, 5.9 Hz, 1H), 7.98 (dd, J=11.0, 2.6 Hz, 1H), 7.88 (d, J=8.1 Hz, 1H), 7.74-7.63 (m, 2H), 7.60 (d, J=4.6 Hz, 1H), 3.53-3.39 (m, 2H), 2.41 (s, 3H), 2.18 (d, J=10.9 Hz, 1H), 2.06 (d, J=12.6 Hz, 1H), 1.95-1.54 (m, 6H), 1.38 (d, J=6.8 Hz, 3H), 1.27-1.17 (m, 1H).

Example C1a and C1b: 4-(4-(5-chloro-6-fluoro-1H-benzo[d]imidazol-2-yl)cyclohexyl)-6-fluoroquinoline

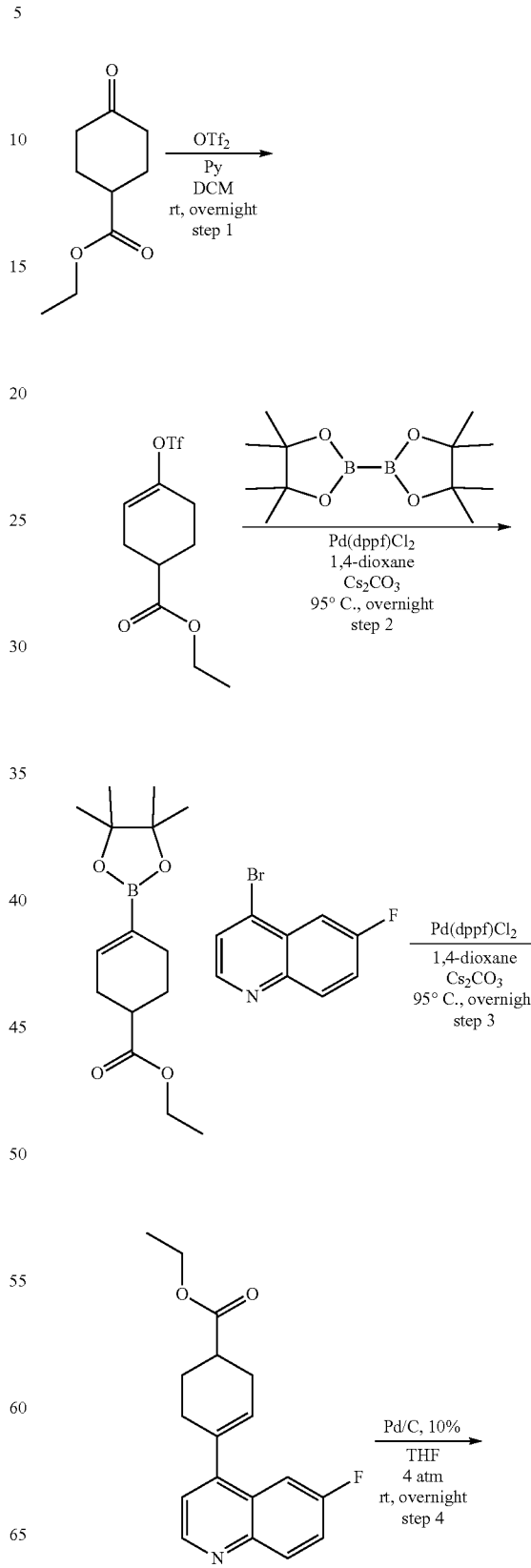

-continued

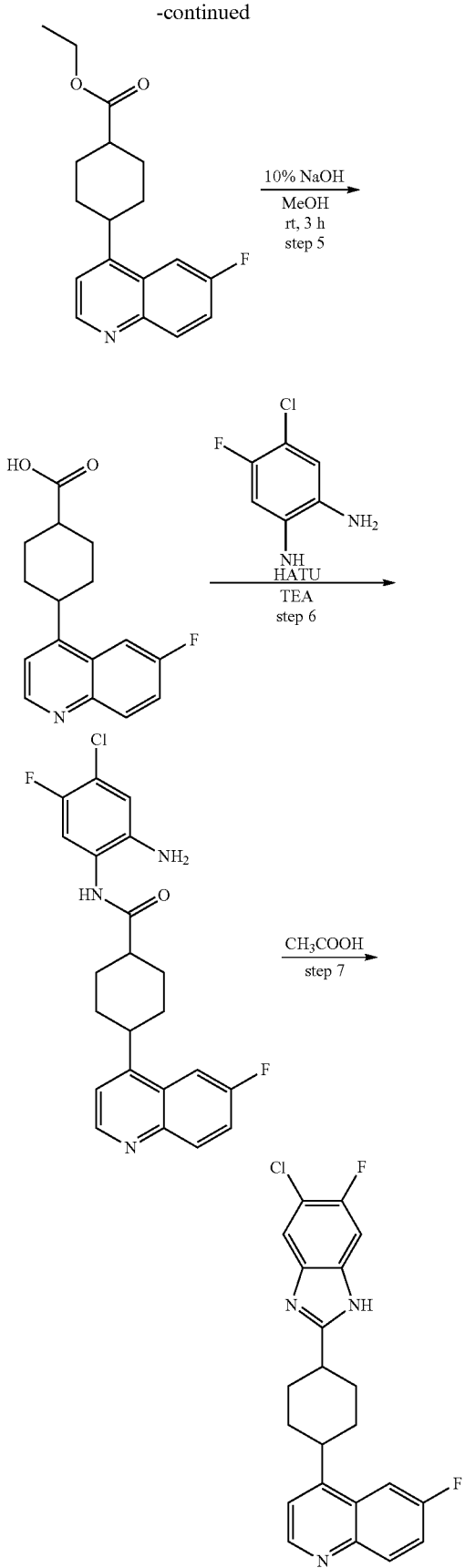

Step 1: ethyl 4-(((trifluoromethyl)sulfonyl)oxy)cyclohex-3-ene-1-carboxylate

To a solution of trifluoromethanesulfonic anhydride (67.8 g, 0.2365 mol) in DCM (400 mL) was added pyridine (14.9 g, 0.1892 mol in 100 ml DCM) dropwise with stirring in 10 mins. The mixture was stirred for 10 mins at r.t. Ethyl 4-oxocyclohexane-1-carboxylate (26.8 g, 0.1576 mol in 100 ml DCM) was added dropwise in 15 mins. Then the mixture was stirred overnight at r.t. The reaction mixture was washed with $H_2O$ (500 mL×2), and saturated $Na_2CO_3$ solution (400 ml×2), brine (500 mL×1), the organic layer was combined and dried over $Na_2SO_4$, filtered and concentrated to give the crude product (42.7 g) as a black oil, which was used for the next step without further purification. $[M+1]^+$ 303

Step 2: ethyl 4-(4,4,5,5-tetramethyl-1,3,2-dioxaborolan-2-yl)cyclohex-3-ene-1-carboxylate A mixture of ethyl 4-(((trifluoromethyl)sulfonyl)oxy)cyclohex-3-ene-1-carboxylate (42.7 g (crude), 0.148 mol), 4,4,4',4',5,5,5',5'-octamethyl-2,2'-bi(1,3,2-dioxaborolane) (41.4 g, 0.163 mol), $CH_3COOK$ (58.6 g, 0.296 mol), Pd(dppf)$Cl_2$(10.8 g, 0.0148 mol) in 1,4-dioxane (400 ml) was stirred overnight at 95° C. under $N_2$. After determined the reaction to be complete by LCMS, the reaction was cooled to r.t. The solvent was removed under vacuo. The mixture was diluted with 500 ml solution (PE:EA=5:1), the solid was filtered and the filtrate was concentrated in vacuo. The residue was purified by a short silica gel column from PE:EA=10:1 to PE:EA=8:1 to afford desired product 56.8 g (crude) as dark oil. $[M+1]^+$ 281

Step 3: ethyl 4-(6-fluoroquinolin-4-yl)cyclohex-3-ene-1-carboxylate

A mixture of ethyl 4-(4,4,5,5-tetramethyl-1,3,2-dioxaborolan-2-yl)cyclohex-3-ene-1-carboxylate (11.96 g, 0.0427 mol), 4-bromo-6-fluoroquinoline (11.48 g, 0.0512 mol), $Cs_2CO_3$(27.82 g, 0.0854 mol), and Pd(dppf)$Cl_2$(3.14 g, 0.0043 mol) in 1,4-dioxane was stirred overnight at 95° C. under $N_2$. After determined the reaction to be complete by LCMS, the reaction was cooled to r.t. The solvent was removed under vacuo. The mixture was diluted with EA (200 ml), the solid was filtered and the filtrate was concentrated in vacuo. The residue was purified by silica gel column from PE:EA=10:1 to PE:EA=5:1 to afford desired product 4.8 g as yellow oil. $[M+1]^+$ 300

Step 4: ethyl 4-(6-fluoroquinolin-4-yl)cyclohexane-1-carboxylate

To a solution of ethyl 4-(6-fluoroquinolin-4-yl)cyclohex-3-ene-1-carboxylate (4.8 g, 0.016 mol) in THF (80 mL) was added Pd/C (480 mg, 10%). The mixture was stirred overnight under 4 atm of $H_2$ at r.t. After determined the reaction to be complete by LCMS, the solid was filtered and the filtrate was concentrated to give the crude product (3.0 g) as a yellow oil, which was used for the next step without further purification. $[M+1]^+$ 302

Step 5: 4-(6-fluoroquinolin-4-yl)cyclohexane-1-carboxylic acid

To a solution of ethyl 4-(6-fluoroquinolin-4-yl)cyclohexane-1-carboxylate (3 g, 0.0099 mol) in MeOH (30 mL)

was added NaOH solution (10%, 6 ml). The mixture was stirred overnight at r.t. After determined the reaction to be complete by LCMS, MeOH was removed under vacuo. The residue was added to H₂O (10 ml), extracted with EA (10 mL×2), and aqueous layer was combined. Adjusted the pH value of aqueous layer to 5~6 with HCl (12M), extracted with EA (20 mL×2). The organic layer was combined and washed with brine (20 mL×1), dried over Na₂SO₄, filtered and concentrated to afford desired product 2.1 g as yellow solid. [M+1]⁺ 274

Step 6: N-(2-amino-4-chloro-5-fluorophenyl)-4-(6-fluoroquinolin-4-yl)cyclohexane-1-carboxamide A mixture of 4-(6-fluoroquinolin-4-yl)cyclohexane-1-carboxylic acid (540 mg, 1.978 mmol) and HATU (751 mg, 1.987 mmol) in DCM (10 mL) was stirred for 5 mins under N₂ at r.t. Then 4-chloro-5-fluorobenzene-1,2-diamine (316 mg, 1.978 mmol) and TEA (399 mg, 3.956 mmol) were added. The mixture was stirred overnight at r.t. After determined the reaction to be complete by LCMS, the reaction mixture was concentrated in vacuo to remove the solvent, and the residue was purified by silica gel column PE:EA=1:1 to afford desired product 400 mg as yellow oil. [M+1]416

Step 7: 4-(4-(5-chloro-6-fluoro-1H-benzo[d]imidazol-2-yl)cyclohexyl)-6-fluoroquinoline

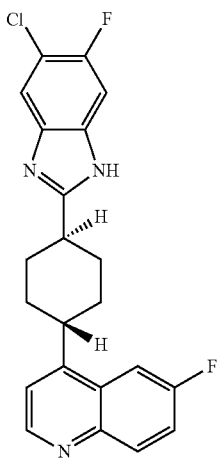

C1a

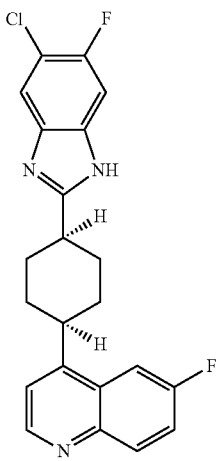

C1b

A solution of N-(2-amino-4-chloro-5-fluorophenyl)-4-(6-fluoroquinolin-4-yl)cyclohexane-1-carboxamide (355 mg, 0.855 mmol) in CH₃COOH (10 mL) was stirred for 3 h at 80° C. After determined the reaction to be complete by LCMS, the reaction mixture was concentrated in vacuo to remove the solvent, and the residue was purified by prep-TLC, PE:EA=1:2 to afford desired product C1a: (slow isomer in pre-TLC, 34.51 mg) ¹H NMR (DMSO-d₆) δ 12.54 (s, 1H), 8.85 (d, J=4.0 Hz, 1H), 8.15-8.00 (m, 2H), 7.69 (t, J=8.0 Hz, 2H), 7.53 (d, J=4.0 Hz, 2H), 3.45 (t, J=12.0 Hz, 1H), 3.01 (t, J=12.0 Hz, 1H), 2.24 (d, J=12.0 Hz, 2H), 2.09-1.91 (m, 4H), 1.77 (dd, J=24.0, 12.0 Hz, 2H), [M+1]⁺ 398; and C1b: (faster isomer in pre-TLC, 76.28 mg): ¹H NMR (DMSO-d₆) δ 12.51 (d, J=16.0 Hz, 1H), 8.73 (d, J=4.0 Hz, 1H), 8.15-7.96 (m, 2H), 7.89-7.41 (m, 3H), 7.26 (d, J=4.0 Hz, 1H), 3.54-3.28 (m, 2H), 3.32-3.24 (m, 1H), 2.46 (s, 1H), 2.12 (d, J=8.0 Hz, 2H), 1.81 (s, 4H), [M+1]398.

Compounds C2a to C20 were prepared in a procedure similar to Example C1a.

Example C2a: 4-((1r,4r)-4-(5-chloro-1H-benzo[d]imidazol-2-yl)cyclohexyl)-6-fluoroquinoline

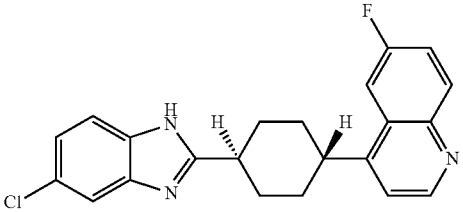 [SMILES: Fc1ccc2nccc([C@H]3CC[C@H](c4nc5cc(Cl)ccc5[nH]4)CC3)c2c1]

¹H NMR (DMSO-d₆) δ 12.40 (d, J=12.0 Hz, 1H), 8.85 (d, J=4.0 Hz, 1H), 8.19-7.95 (m, 2H), 7.78-7.37 (m, 4H), 7.16 (s, 1H), 3.45 (t, J=12.0 Hz, 1H), 3.00 (t, J=6.0 Hz, 1H), 2.25 (d, J=12.0 Hz, 2H), 2.10-1.90 (m, 4H), 1.77 (m, 2H), [M+1]⁺ 380

Example C2b: 4-((1s,4s)-4-(5-chloro-1H-benzo[d]imidazol-2-yl)cyclohexyl)-6-fluoroquinoline

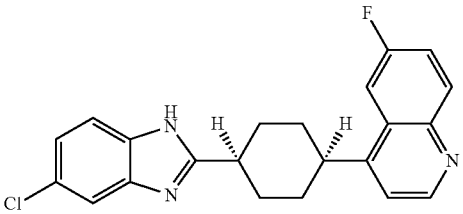 [SMILES: Fc1ccc2nccc([C@H]3CC[C@@H](c4nc5cc(Cl)ccc5[nH]4)CC3)c2c1]

¹H NMR (DMSO-d₆) δ 12.39 (d, J=12.0 Hz, 1H), 8.72 (d, J=4.0 Hz, 1H), 8.07 (dd, J=12.0, 8.0 Hz, 2H), 7.69-7.42 (m, 3H), 7.29-7.12 (m, 2H), 3.53-3.30 (m, 4H), 2.12 (d, J=8.0 Hz, 2H), 1.81 (s, 4H), [M+1]⁺ 380

Example C3: 6-fluoro-4-(4-(5-methyl-1H-benzo[d]imidazol-2-yl)cyclohexyl)quinoline

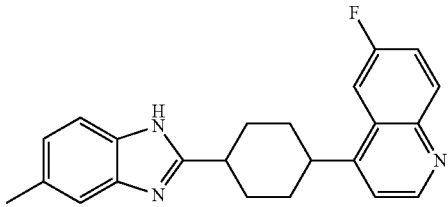 [SMILES: Cc1ccc2[nH]c(C3CCC(c4ccnc5ccc(F)cc45)CC3)nc2c1]

$^1$H NMR (DMSO-d$_6$) δ 12.06 (s, 1H), 8.72 (d, J=4.0 Hz, 1H), 8.17-7.96 (m, 2H), 7.74-7.57 (m, 1H), 7.29 (m, 3H), 6.95 (d, J=8.0 Hz, 1H), 3.46 (s, 1H), 3.35 (s, 1H), 2.48-2.44 (m, 1H), 2.40 (s, 3H), 2.20-1.70 (m, 7H), [M+1]$^+$ 360

Example C4: 4-(4-(5-bromo-1H-benzo[d]imidazol-2-yl)cyclohexyl)-6-fluoroquinoline

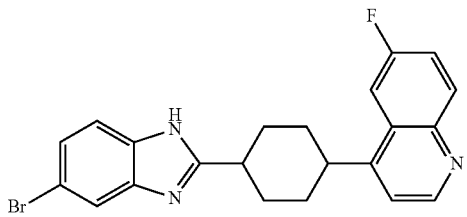 [SMILES: Fc1ccc2nccc(C3CCC(c4nc5cc(Br)ccc5[nH]4)CC3)c2c1]

$^1$H NMR (DMSO-d$_6$) δ 12.40 (d, J=16.0 Hz, 1H), 8.72 (d, J=4.0 Hz, 1H), 8.12-8.02 (m, 2H), 7.89-7.68 (m, 3H), 7.51-7.69 (m, 1H), 7.18-7.33 (m, 2H), 3.53-3.35 (m, 3H), 2.48-2.43 (m, 1H), 2.12 (d, J=8.0 Hz, 2H), 1.81 (s, 4H), [M+1]$^+$ 424.

Example C5a: 6-fluoro-4-((1r,4r)-4-(5-fluoro-1H-benzo[d]imidazol-2-yl)cyclohexyl)quinoline

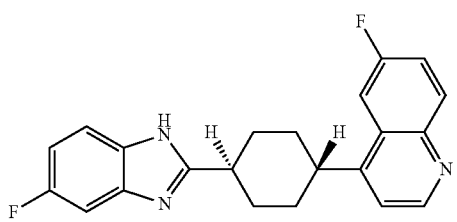 [SMILES: Fc1ccc2[nH]c([C@H]3CC[C@H](c4ccnc5ccc(F)cc54)CC3)nc2c1]

Example C5b: 6-fluoro-4-((1s,4s)-4-(5-fluoro-1H-benzo[d]imidazol-2-yl)cyclohexyl)quinoline

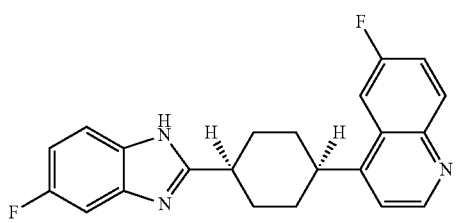 [SMILES: Fc1ccc2[nH]c([C@H]3CC[C@@H](c4ccnc5ccc(F)cc54)CC3)nc2c1]

Example C6a: 4-((1r,4r)-4-(5-cyclopropyl-1H-benzo[d]imidazol-2-yl)cyclohexyl)-6-fluoroquinoline

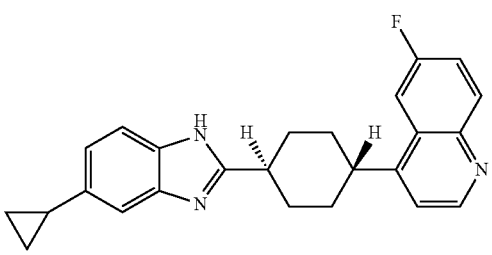 [SMILES: Fc1ccc2nccc([C@H]3CC[C@H](c4nc5cc(C6CC6)ccc5[nH]4)CC3)c2c1]

Example C6b: 4-((1s,4s)-4-(5-cyclopropyl-1H-benzo[d]imidazol-2-yl)cyclohexyl)-6-fluoroquinoline

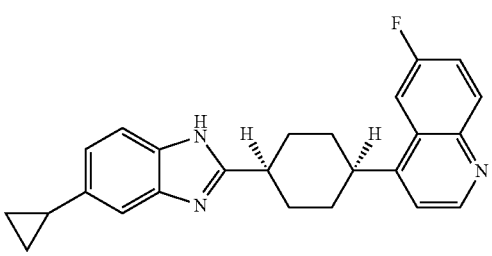 [SMILES: Fc1ccc2nccc([C@H]3CC[C@@H](c4nc5cc(C6CC6)ccc5[nH]4)CC3)c2c1]

$^1$H NMR (DMSO-d$_6$) δ 12.05 (s, 1H), 8.72 (d, J=4.0 Hz, 1H), 8.10-8.00 (m, 2H), 7.71-7.58 (m, 1H), 7.38 (s, 1H), 7.29-7.05 (m, 2H), 6.89 (d, J=8.0 Hz, 1H), 3.44 (d, J=12.0 Hz, 1H), 2.47 (s, 1H), 2.19-1.94 (m, 4H), 1.72-1.93 (m, 5H), 0.93 (d, J=8.0 Hz, 2H), 0.66 (d, J=4.0 Hz, 2H), [M+1]$^+$ 386.

Example C7a: 4-((1r,4r)-4-(5,6-difluoro-1H-benzo[d]imidazol-2-yl)cyclohexyl)-6-fluoroquinoline

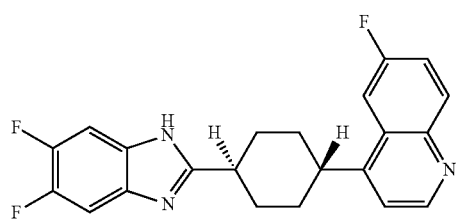 [SMILES: Fc1ccc2nccc([C@H]3CC[C@H](c4nc5cc(F)c(F)cc5[nH]4)CC3)c2c1]

$^1$H NMR (DMSO-d$_6$) δ 12.45 (s, 1H), 8.85 (d, J=4.0 Hz, 1H), 8.19-7.99 (m, 2H), 7.75-7.41 (m, 4H), 3.44 (t, J=12.0 Hz, 2H), 3.00 (t, J=12.0 Hz, 2H), 2.24 (d, J=12.0 Hz, 3H), 2.07-1.86 (m, 4H), 1.76 (dd, J=24.0, 12.0 Hz, 2H), [M+1]$^+$ 382.

Example C7b: 4-((1s,4s)-4-(5,6-difluoro-H-benzo[d]imidazol-2-yl)cyclohexyl)-6-fluoroquinoline

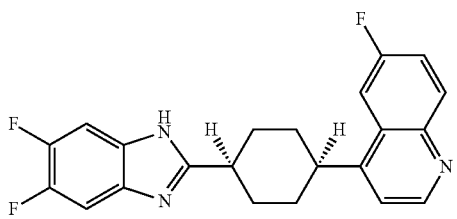 [SMILES: Fc1ccc2nccc([C@H]3CC[C@@H](c4nc5cc(F)c(F)cc5[nH]4)CC3)c2c1]

¹H NMR (DMSO-d₆) δ 12.46 (s, 1H), 8.73 (d, J=4.0 Hz, 1H), 8.17-7.96 (m, 3H), 7.75-7.43 (m, 3H), 7.26 (d, J=4.0 Hz, 1H), 3.56-3.41 (m, 2H), 3.37 (s, 1H), 2.46 (s, 2H), 2.12 (d, J=8.0 Hz, 2H), 1.81 (s, 4H), [M+1]⁺ 382.

Example C8a: methyl 2-((1r,4r)-4-(6-fluoroquinolin-4-yl)cyclohexyl)-1H-benzo[d]imidazole-5-carboxylate

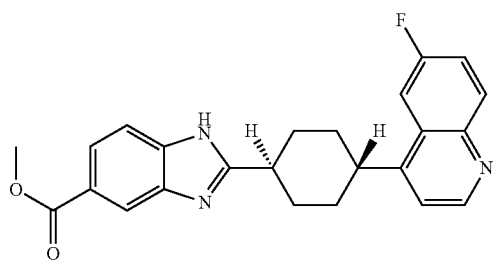 [SMILES: COC(=O)c1ccc2[nH]c([C@H]3CC[C@H](c4ccnc5ccc(F)cc54)CC3)nc2c1]

1H NMR (DMSO-d₆) δ 12.63 (s, 1H), 8.85 (d, J=4.0 Hz, 1H), 8.20-8.00 (m, 3H), 7.85-7.62 (m, 3H), 7.56-7.52 (m, 1H), 3.87 (s, 3H), 3.47 (t, J=12.0 Hz, 1H), 3.05 (s, 1H), 2.27 (d, J=12.0 Hz, 2H), 2.10-1.94 (m, 4H), 1.79 (t, J=12.0 Hz, 2H), [M+1]⁺ 404.

Example C8b: methyl 2-((1s,4s)-4-(6-fluoroquinolin-4-yl)cyclohexyl)-1H-benzo[d]imidazole-5-carboxylate

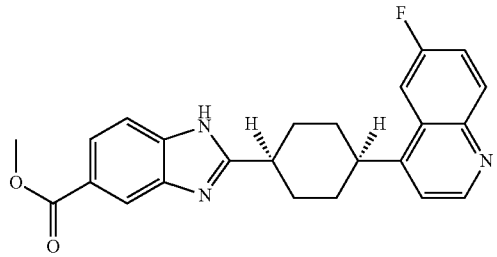 [SMILES: COC(=O)c1ccc2[nH]c([C@H]3CC[C@@H](c4ccnc5ccc(F)cc54)CC3)nc2c1]

¹H NMR (DMSO-d₆) δ 12.57 (s, 1H), 8.72 (d, J=8.0 Hz, 1H), 8.28-7.98 (m, 3H), 7.81 (dd, J=16.0, 8.0 Hz, 1H), 7.71-7.49 (m, 2H), 7.27 (s, 1H), 3.87 (s, 3H), 3.44 (s, 2H), 3.30 (s, 2H), 2.14 (s, 2H), 1.83 (s, 4H), [M+1]⁺ 404.

Example C9a: 2-((1r,4r)-4-(6-fluoroquinolin-4-yl)cyclohexyl)-1H-benzo[d]imidazole-5-carboxamide

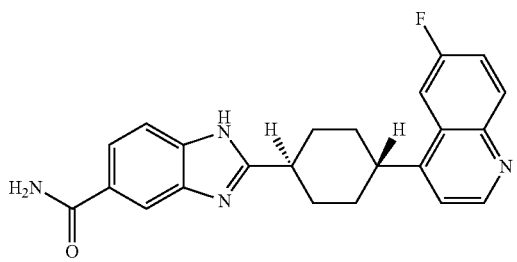 [SMILES: NC(=O)c1ccc2[nH]c([C@H]3CC[C@H](c4ccnc5ccc(F)cc54)CC3)nc2c1]

1H NMR (DMSO-d₆) δ 12.44 (d, J=16.0 Hz, 1H), 8.84 (s, 1H), 8.03 (dd, J=30.2, 18.9 Hz, 4H), 7.67 (s, 2H), 7.61-7.14 (m, 3H), 3.45 (s, 1H), 3.01 (s, 1H), 2.25 (d, J=12.0 Hz, 2H), 2.10-1.93 (m, 4H), 1.76 (d, J=12.0 Hz, 2H), [M+1]⁺ 389.

Example C9b: 2-((1s,4s)-4-(6-fluoroquinolin-4-yl)cyclohexyl)-1H-benzo[d]imidazole-5-carboxamide

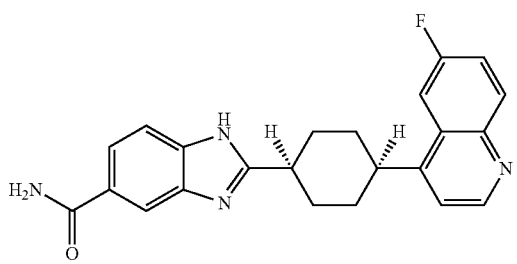 [SMILES: NC(=O)c1ccc2[nH]c([C@H]3CC[C@@H](c4ccnc5ccc(F)cc54)CC3)nc2c1]

¹H NMR (DMSO-d₆) δ 12.41 (d, J=16.0 Hz, 1H), 8.71 (s, 1H), 8.23-7.70 (m, 4H), 7.81-7.36 (m, 3H), 7.24 (s, 2H), 3.50-3.36 (m, 3H), 3.28 (s, 1H), 2.12 (s, 2H), 1.90-1.75 (m, 4H), [M+1]⁺ 389.

Example C10: 4-(4-(2-(5-cyclopropyl-1H-benzo[d]imidazol-2-yl)ethyl)cyclohexyl)-6-fluoroquinoline

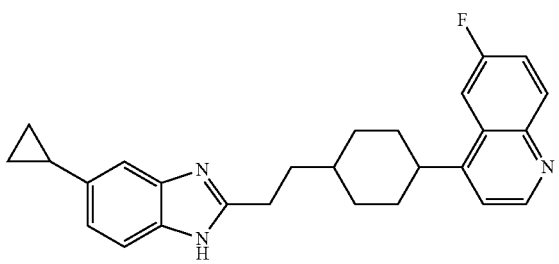 [SMILES: Fc1ccc2nccc(C3CCC(CCc4nc5cc(C6CC6)ccc5[nH]4)CC3)c2c1]

Example C1: 4-((1r,4r)-4-(2-(5-chloro-1H-benzo[d]imidazol-2-yl)ethyl)cyclohexyl)-6-fluoroquinoline

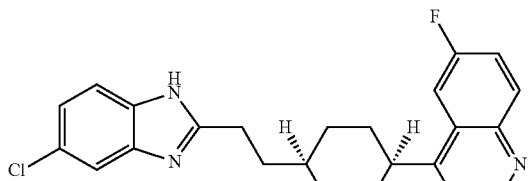

Example C14: 4-((1S,4s)-4-((R)-2-(5-chloro-6-fluoro-1H-benzo[d]imidazol-2-yl)propyl)cyclohexyl)-6-fluoroquinoline

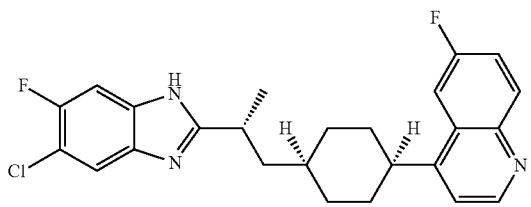

Example C12a: 4-((1R,4s)-4-((S)-2-(5-chloro-1H-benzo[d]imidazol-2-yl)propyl)cyclohexyl)-6-fluoroquinoline

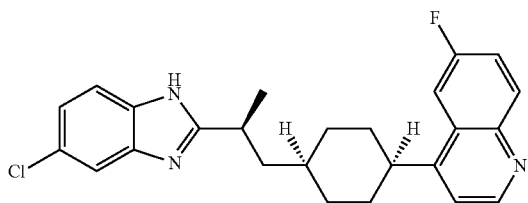 [SMILES: C[C@@H](C[C@H]1CC[C@@H](c2ccnc3ccc(F)cc32)CC1)c1nc2cc(Cl)ccc2[nH]1]

Example C15: 6-fluoro-4-((1S,4s)-4-((R)-2-(5,6,7-trifluoro-1H-benzo[d]imidazol-2-yl)propyl)cyclohexyl)quinoline

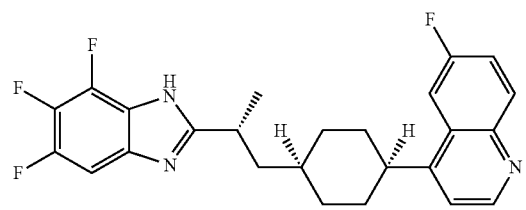

Example C12b: 4-((1S,4s)-4-((R)-2-(5-chloro-1H-benzo[d]imidazol-2-yl)propyl)cyclohexyl)-6-fluoroquinoline

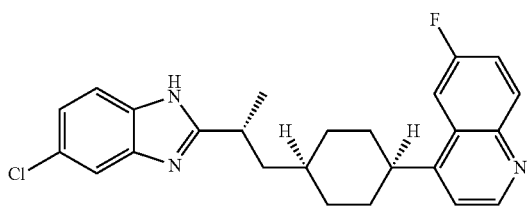 [SMILES: C[C@H](C[C@H]1CC[C@@H](c2ccnc3ccc(F)cc32)CC1)c1nc2cc(Cl)ccc2[nH]1]

Example C16: 4-((1S,4s)-4-((R)-2-(5,6-difluoro-7-methyl-1H-benzo[d]imidazol-2-yl)propyl)cyclohexyl)-6-fluoroquinoline

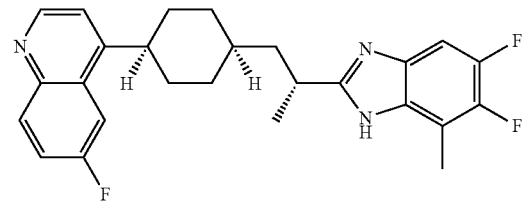

Example C13: 4-((1S,4s)-4-((R)-2-(5,6-difluoro-1H-benzo[d]imidazol-2-yl)propyl)cyclohexyl)-6-fluoroquinoline

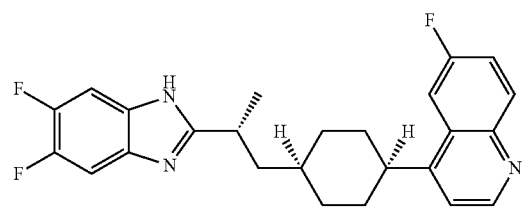 [SMILES: C[C@H](C[C@H]1CC[C@@H](c2ccnc3ccc(F)cc32)CC1)c1nc2cc(F)c(F)cc2[nH]1]

Example C17: 6-fluoro-4-((1S,4s)-4-((R)-2-(4,6,7-trifluoro-1H-benzo[d]imidazol-2-yl)propyl)cyclohexyl)quinoline

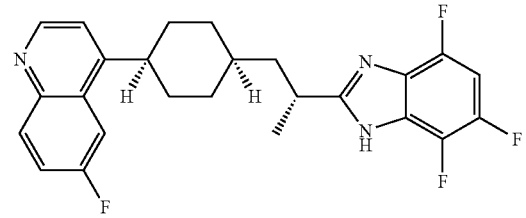 [SMILES: C[C@H](C[C@H]1CC[C@@H](c2ccnc3ccc(F)cc32)CC1)c1nc2c(F)cc(F)c(F)c2[nH]1]

Example C18: (R)-6-fluoro-4-(4-(2-(5,6,7-trifluoro-1H-benzo[d]imidazol-2-yl)propyl)piperazin-1-yl)quinoline

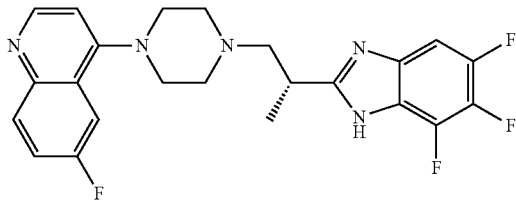

Example C19: (R)-4-(4-(2-(5,6-difluoro-7-methyl-1H-benzo[d]imidazol-2-yl)propyl)piperazin-1-yl)-6-fluoroquinoline

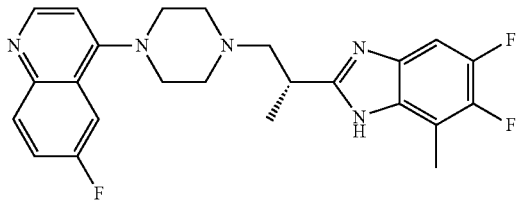 [SMILES: Cc1c(F)c(F)cc2nc([C@H](C)CN3CCN(c4ccnc5ccc(F)cc45)CC3)[nH]c12]

Example C20: (R)-6-fluoro-4-(4-(2-(4,6,7-trifluoro-1H-benzo[d]imidazol-2-yl)propyl)piperazin-1-yl)quinoline

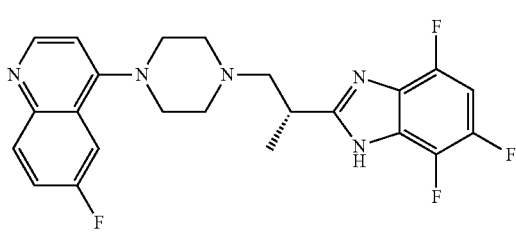 [SMILES: C[C@H](CN1CCN(c2ccnc3ccc(F)cc23)CC1)c1nc2c(F)cc(F)c(F)c2[nH]1]

Example D1: 6-chloro-2-(5-phenylbicyclo[2.2.1]heptan-2-yl)-1H-benzo[d]imidazole

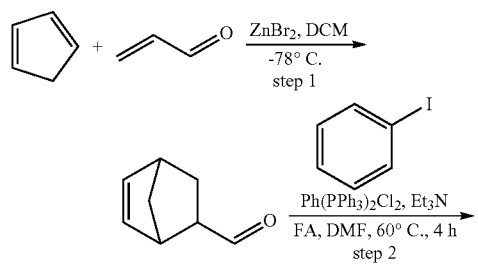

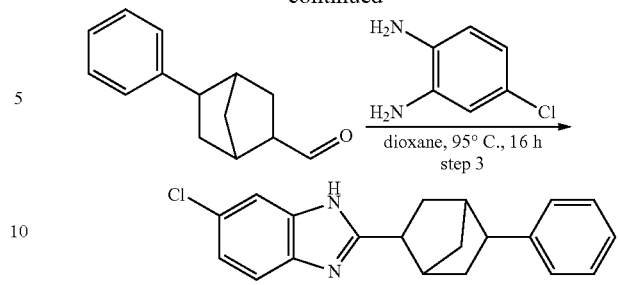

Step 1: bicyclo[2.2.1]hept-5-ene-2-carbaldehyde

At −78° C., to a mixture of ZnBr$_2$ (25 g, 111 mmol) in DCM (450 mL) was added cyclopenta-1,3-diene (30 mL, 363 mmol) dropwise, the reaction mixture was stirred for 30 min at −78° C., then acrylaldehyde (15 mL, 225 mmol) was added, the reaction mixture was stirred for 1 hour at −78° C., then the reaction mixture was poured into DCM (500 mL), washed with brine (200 ml×3), the DCM layer was concentrated and purified by sili-gel to give 20 g of the title compound as a yellow oil.

Step 2: 5-phenylbicyclo[2.2.1]heptane-2-carbaldehyde

Under N$_2$, a mixture of bicyclo[2.2.1]hept-5-ene-2-carbaldehyde (1.2 g, 10 mmol), iodobenzene (2.1 g, 10 mmol), Et$_3$N (4.0 mL, 29 mmol), formic acid (0.8 ml, 21 mmol) and Pd(PPh$_3$)$_2$Cl$_2$ (0.4 g, 0.57 mmol) in DMF (4.0 mL) was heated to 60° C. for 4 hours. After cooled down, EA was added, washed with water and brine, dried over Na$_2$SO$_4$, concentrated, purified by sili-gel to give 1.0 g of the title compound as a yellow oil. MS (ESI) m/e [M+1]$^+$=201.1

Step 3: 6-chloro-2-(5-phenylbicyclo[2.2.1]heptan-2-yl)-1H-benzo[d]imidazole A solution of 5-phenylbicyclo[2.2.1]heptane-2-carbaldehyde (760 mg, 3.8 mmol), 4-chlorobenzene-1,2-diamine (450 mg, 3.16 mmol) and benzoquinone (450 mg, 4.16 mmol) in 1,4-dioxane (30 mL) was stirred overnight at 95° C. under N$_2$. The reaction mixture was concentrated and purified by column chromatography to give 900 mg of the crude product, which was recrystallized from DCM and PE to give 100 mg of the title compound. $^1$H NMR (DMSO-d$_6$) δ$_H$12.40 (s, 1H), 7.38-7.61 (m, 2H), 7.25-7.32 (m, 4H), 7.12-7.18 (m, 2H), 3.02-3.08 (m, 1H), 2.86-2.90 (m, 1H), 2.60-2.63 (m, 1H), 2.41-2.42 (m, 1H), 2.23-2.29 (m, 1H), 1.93-1.99 (m, 1H), 1.83-1.89 (m, 1H), 1.71-1.77 (m, 1H), 1.43-1.56 (m, 2H), MS (ESI) m/e [M+1]$^+$=323.7.

Example D2: 5-chloro-2-(2-(5-phenylbicyclo[2.2.1]heptan-2-yl)ethyl)-1H-benzo[d]imidazole

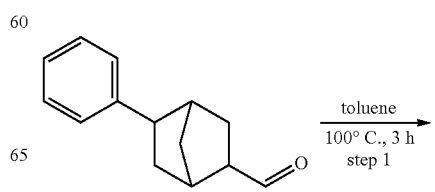

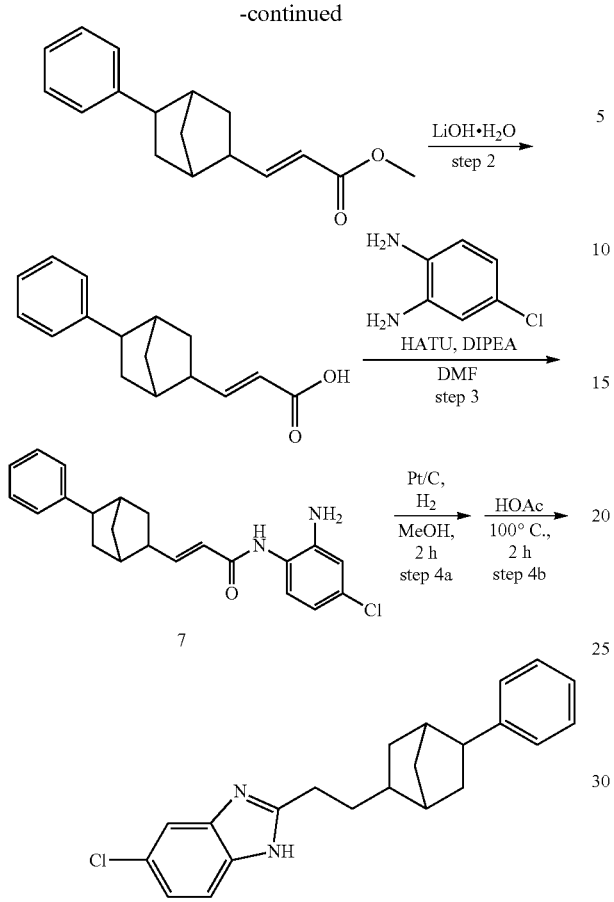

Step 1: methyl 3-(5-phenylbicyclo[2.2.1]heptan-2-yl)acrylate

A mixture of 5-phenylbicyclo[2.2.1]heptane-2-carbaldehyde (2.0 g, 10 mmol) and methyl (triphenylphosphoranylidene)acetate (3.3 g, 10 mmol) in toluene (50 mL) was heated to 110° C. for 3 hours, after cooled down, the reaction mixture was concentrated, purified by column chromatography to give 1.8 g of the title compound. MS (ESI) m/e [M+1]$^+$=257.1.

Step 2: 3-(5-phenylbicyclo[2.2.1]heptan-2-yl)acrylic acid

A mixture of methyl 3-(5-phenylbicyclo[2.2.1]heptan-2-yl)acrylate (1.8 g, 7.0 mmol) and LiOH.H$_2$O (600 mg, 14 mmol) in THF/MeOH/H2O (10 mL/10 mL/10 mL) was stirred for overnight at room temperature, the reaction mixture was concentrated, water was added, the pH value was adjusted to 5 with 1N HCl aq, extracted with EA, the EA layer was washed with brine, dried over Na$_2$SO$_4$, concentrated to give 1.6 g of the crude title compound. MS (ESI) m/e [M+1]$^+$=243.1.

Step 3: N-(2-amino-4-chlorophenyl)-3-(5-phenylbicyclo[2.2.1]heptan-2-yl)acrylamide To a solution of 3-(5-phenylbicyclo[2.2.1]heptan-2-yl)acrylic acid (400 mg, 1.65 mmol) in DMF (10 mL) were added DIPEA (0.7 mL, 4.0 mmol), HATU (950 mg, 2.5 mmol) and 4-chlorobenzene-1,2-diamine (300 mg, 2.1 mmol), the reaction mixture was stirred for overnight at room temperature, EA was added, washed with brine, dried over Na$_2$SO$_4$, concentrated and purified by sili-gel to give 240 mg of the title compound. MS (ESI) m/e [M+1]$^+$=367.1.

Step 4: 5-chloro-2-(2-(5-phenylbicyclo[2.2.1]heptan-2-yl)ethyl)-1H-benzo[d]imidazole

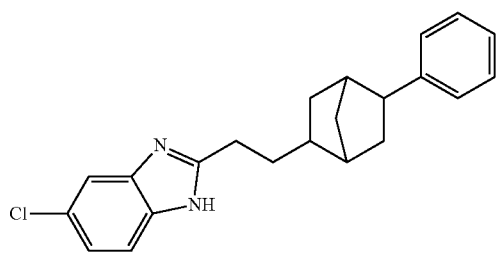 [SMILES: Clc1ccc2[nH]c(CCC3CC4CC3CC4c3ccccc3)nc2c1]

Under H$_2$(1 atm), a mixture of N-(2-amino-4-chlorophenyl)-3-(5-phenylbicyclo[2.2.1]heptan-2-yl)acrylamide (240 mg, 0.65 mmol) and Pt/C (50 mg) in MeOH (25 mL) was stirred for 1.5 hours, the mixture was filtered, concentrated. HOAc (7 mL) was added, the reaction mixture was heated to 100° C. for 2 hours, after cooled down, the reaction mixture was poured into water, the pH value was adjusted to 8 with sat.NaHCO$_3$aq, extracted with EA, the EA layer was washed with brine, dried over Na$_2$SO$_4$, concentrated and purified by sili-gel to give 100 mg of the title compound. $^1$H NMR (400 MHz, DMSO-d$_6$) δ$_H$ 12.37 (s, 1H), 7.39-7.59 (m, 2H), 7.08-7.33 (m, 6H), 2.76-2.88 (m, 2H), 2.62-2.72 (m, 1H), 2.25-2.32 (m, 1H), 2.05-2.13 (m, 1H), 1.47-1.84 (m, 7H), 1.20-1.34 (m, 2H), 1.07-1.16 (m, 1H), 0.80-0.88 (m, 1H), MS (ESI) m/e [M+1]$^+$=351.7

Compounds D3 to D34 were prepared in a procedure similar to Example D2.

Example D3: 4-(5-(2-(5-chloro-H-benzo[d]imidazol-2-yl)ethyl)bicyclo[2.2.1]heptan-2-yl)quinoline

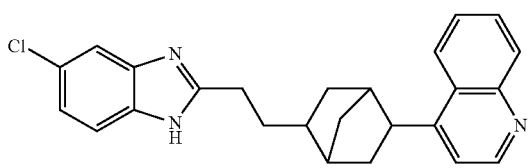 [SMILES: Clc1ccc2[nH]c(CCC3CC4CC3CC4c3ccnc4ccccc34)nc2c1]

Example D4: 4-(5-(2-(5-chloro-H-benzo[d]imidazol-2-ylethyl)bicyclo[2.2.1]heptan-2-yl)-6-fluoroquinoline

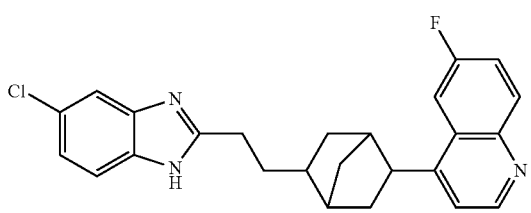

Example D5: 4-(5-((R)-2-(5-chloro-1H-benzo[d]imidazol-2-yl)propyl)bicyclo[2.2.1]heptan-2-yl)-6-fluoroquinoline

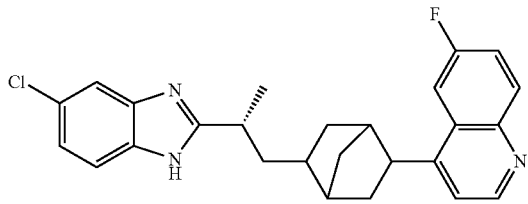

Example D6: 6-fluoro-4-(5-((R)-2-(5-fluoro-1H-benzo[d]imidazol-2-yl)propyl)bicyclo[2.2.1]heptan-2-yl)quinoline

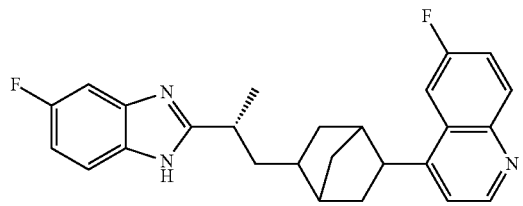 [SMILES: C[C@H](CC1CC2CC1CC2c1ccnc2ccc(F)cc12)c1nc2cc(F)ccc2[nH]1]

Example D7: methyl 2-((2R)-1-(5-(6-fluoroquinolin-4-yl)bicyclo[2.2.1]heptan-2-yl)propan-2-yl)-1H-benzo[d]imidazole-5-carboxylate

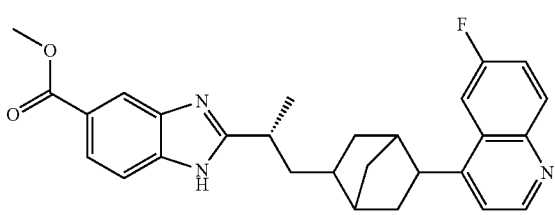 [SMILES: COC(=O)c1ccc2[nH]c([C@H](C)CC3CC4CC3CC4c3ccnc4ccc(F)cc34)nc2c1]

Example D8: 4-(5-((R)-2-(6-chloro-5-fluoro-1H-benzo[d]imidazol-2-yl)propyl)bicyclo[2.2.1]heptan-2-yl)-6-fluoroquinoline

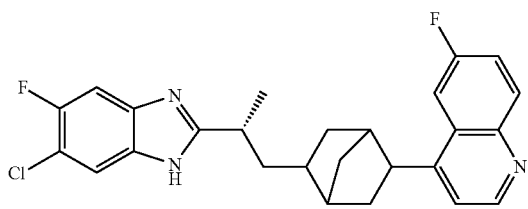 [SMILES: C[C@H](CC1CC2CC1CC2c1ccnc2ccc(F)cc12)c1nc2cc(F)c(Cl)cc2[nH]1]

Example D9: 4-(5-((R)-2-(5,6-difluoro-1H-benzo[d]imidazol-2-yl)propyl)bicyclo[2.2.1]heptan-2-yl)-6-fluoroquinoline

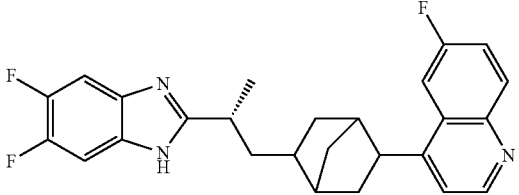 [SMILES: C[C@H](CC1CC2CC1CC2c1ccnc2ccc(F)cc12)c1nc2cc(F)c(F)cc2[nH]1]

Example D10: 6-fluoro-4-(5-((R)-2-(5,6,7-trifluoro-1H-benzo[d]imidazol-2-yl)propyl)bicyclo[2.2.1]heptan-2-yl)quinoline

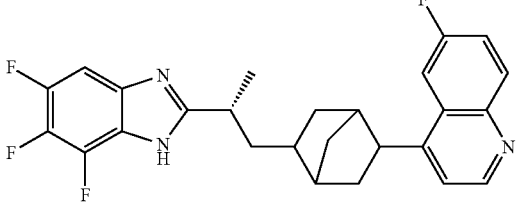

Example D11: 6-fluoro-4-(5-((R)-2-(4,5,7-trifluoro-H-benzo[d]imidazol-2-yl)propyl)bicyclo[2.2.1]heptan-2-yl)quinoline

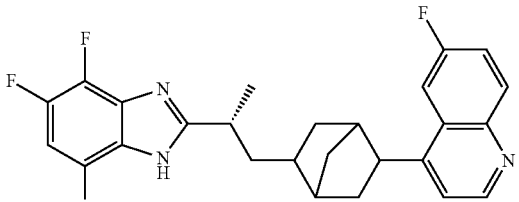

Example D12: 4-(5-((R)-2-(5,6-difluoro-7-methyl-1H-benzo[d]imidazol-2-yl)propyl)bicyclo[2.2.1]heptan-2-yl)-6-fluoroquinoline

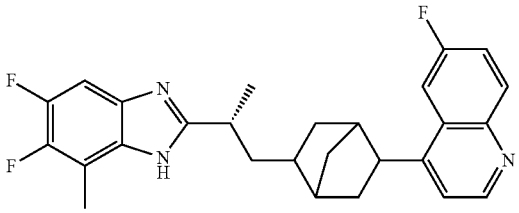 [SMILES: Cc1c(F)c(F)cc2nc([C@H](C)CC3CC4CC3CC4c3ccnc4ccc(F)cc34)[nH]c12]

Example D13: 2-((2R)-1-(5-(6-fluoroquinolin-4-yl)bicyclo[2.2.1]heptan-2-yl)propan-2-yl)-1H-benzo[d]imidazole-5-carboxamide

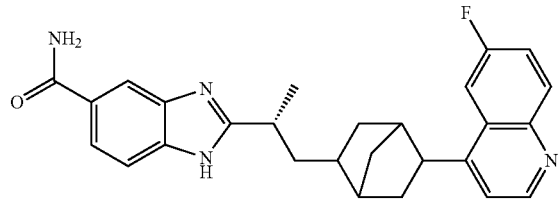 [SMILES: C[C@H](CC1CC2CC1CC2c1ccnc2ccc(F)cc12)c1nc2cc(C(N)=O)ccc2[nH]1]

Example D14: 2-((2R)-1-(5-(6-fluoroquinolin-4-yl)bicyclo[2.2.1]heptan-2-yl)propan-2-yl)-N-methyl-1H-benzo[d]imidazole-5-carboxamide

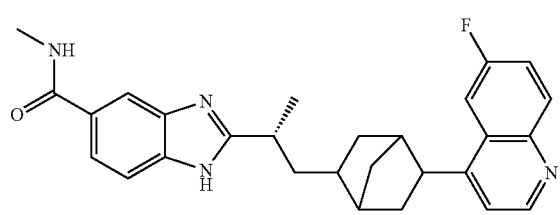 [SMILES: CNC(=O)c1ccc2[nH]c([C@H](C)CC3CC4CC3CC4c3ccnc4ccc(F)cc34)nc2c1]

Example D15: 2-((2R)-1-(5-(6-fluoroquinolin-4-yl)bicyclo[2.2.1]heptan-2-yl)propan-2-yl)-N,N-dimethyl-1H-benzo[d]imidazole-5-carboxamide

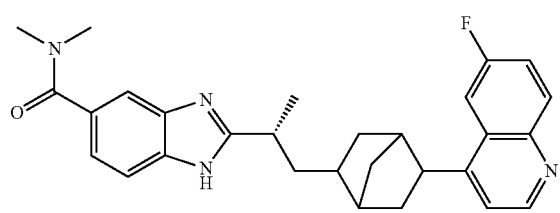 [SMILES: C[C@H](CC1CC2CC1CC2c1ccnc2ccc(F)cc12)c1nc2cc(C(=O)N(C)C)ccc2[nH]1]

Example D16: aziridin-1-yl(2-((2R)-1-(5-(6-fluoroquinolin-4-yl)bicyclo[2.2.1]heptan-2-yl)propan-2-yl)-1H-benzo[d]imidazol-5-yl)methanone

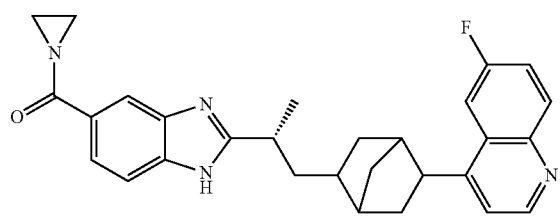 [SMILES: C[C@H](CC1CC2CC1CC2c1ccnc2ccc(F)cc12)c1nc2cc(C(=O)N3CC3)ccc2[nH]1]

Example D17: azetidin-1-yl(2-((2R)-1-(5-(6-fluoroquinolin-4-yl)bicyclo[2.2.1]heptan-2-yl)propan-2-yl)-1H-benzo[d]imidazol-5-yl)methanone

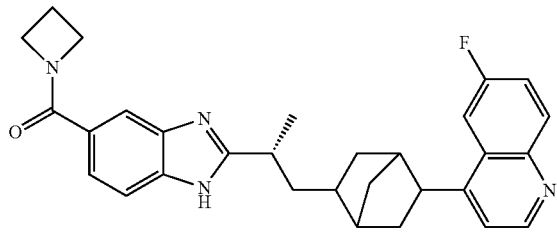 [SMILES: C[C@H](CC1CC2CC1CC2c1ccnc2ccc(F)cc12)c1nc2cc(C(=O)N3CCC3)ccc2[nH]1]

Example D18: N-cyclobutyl-2-((2R)-1-(5-(6-fluoroquinolin-4-yl)bicyclo[2.2.1]heptan-2-yl)propan-2-yl)-1H-benzo[d]imidazole-5-carboxamide

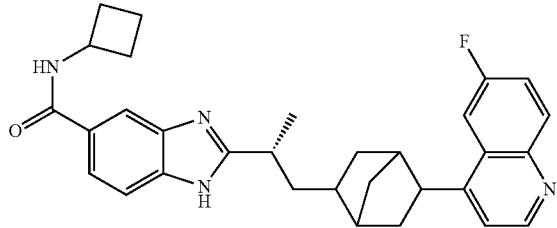 [SMILES: C[C@H](CC1CC2CC1CC2c1ccnc2ccc(F)cc12)c1nc2cc(C(=O)NC3CCC3)ccc2[nH]1]

Example D19: 2-((2R)-1-(5-(6-fluoroquinolin-4-yl)bicyclo[2.2.1]heptan-2-yl)propan-2-yl)-N-(3-hydroxycyclobutyl)-1H-benzo[d]imidazole-5-carboxamide

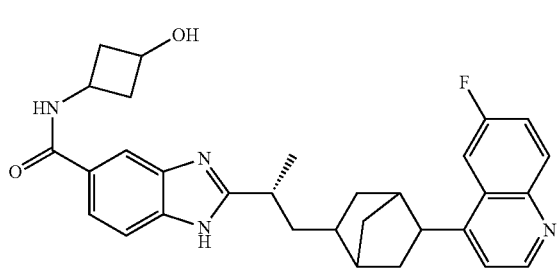 [SMILES: C[C@H](CC1CC2CC1CC2c1ccnc2ccc(F)cc12)c1nc2cc(C(=O)NC3CC(O)C3)ccc2[nH]1]

Example D20: 4-(5-((R)-1-(5-chloro-1H-benzo[d]imidazol-2-yl)propan-2-yl)bicyclo[2.2.1]heptan-2-yl)-6-fluoroquinoline

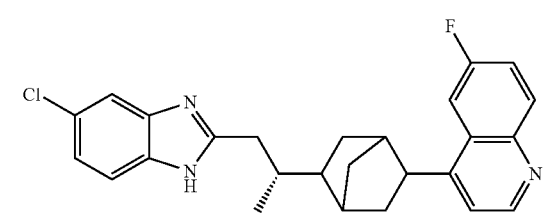

Example D21: 6-fluoro-4-(5-((R)-1-(5-fluoro-1H-benzo[d]imidazol-2-yl)propan-2-yl)bicyclo[2.2.1]heptan-2-yl)quinoline

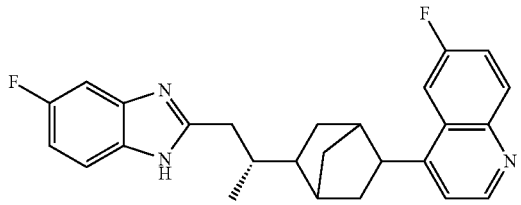

Example D22: methyl 2-((2R)-2-(5-(6-fluoroquinolin-4-yl)bicyclo[2.2.1]heptan-2-yl)propyl)-1H-benzo[d]imidazole-5-carboxylate

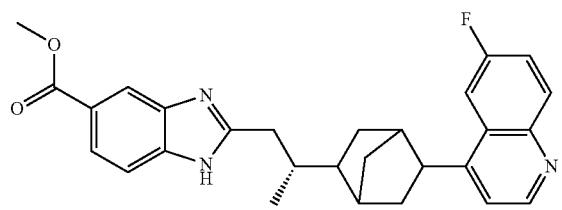 [SMILES: COC(=O)c1ccc2[nH]c(C[C@@H](C)C3CC4CC3CC4c3ccnc4ccc(F)cc34)nc2c1]

Example D23: 4-(5-((R)-1-(6-chloro-5-fluoro-1H-benzo[d]imidazol-2-yl)propan-2-yl)bicyclo[2.2.1]heptan-2-yl)-6-fluoroquinoline

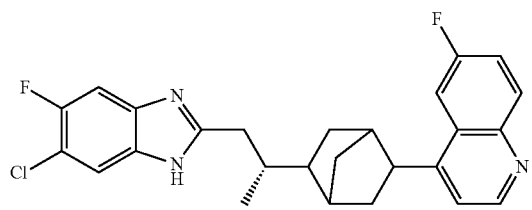 [SMILES: C[C@H](Cc1nc2cc(F)c(Cl)cc2[nH]1)C1CC2CC1CC2c1ccnc2ccc(F)cc12]

Example D24: 4-(5-((R)-1-(5,6-difluoro-1H-benzo[d]imidazol-2-yl)propan-2-yl)bicyclo[2.2.1]heptan-2-yl)-6-fluoroquinoline

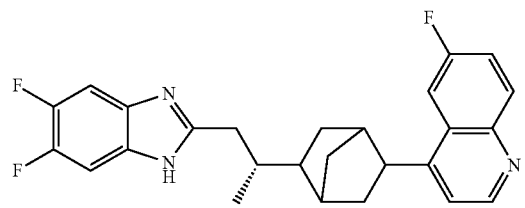 [SMILES: C[C@H](Cc1nc2cc(F)c(F)cc2[nH]1)C1CC2CC1CC2c1ccnc2ccc(F)cc12]

Example D25: 6-fluoro-4-(5-((R)-1-(5,6,7-trifluoro-1H-benzo[d]imidazol-2-yl)propan-2-yl)bicyclo[2.2.1]heptan-2-yl)quinoline

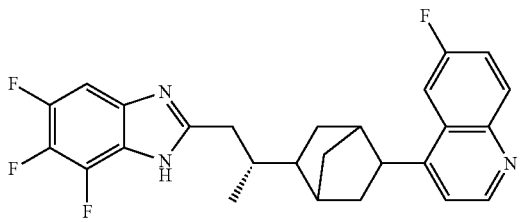 [SMILES: C[C@H](Cc1nc2cc(F)c(F)c(F)c2[nH]1)C1CC2CC1CC2c1ccnc2ccc(F)cc12]

Example D26: 6-fluoro-4-(5-((R)-1-(4,5,7-trifluoro-1H-benzo[d]imidazol-2-yl)propan-2-yl)bicyclo[2.2.1]heptan-2-yl)quinoline

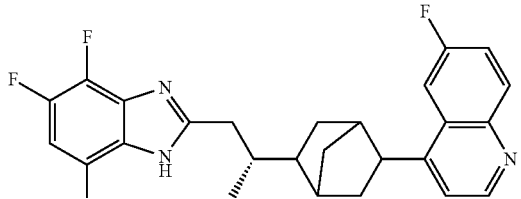

Example D27: 4-(5-((R)-1-(5,6-difluoro-7-methyl-1H-benzo[d]imidazol-2-yl)propan-2-yl)bicyclo[2.2.1]heptan-2-yl)-6-fluoroquinoline

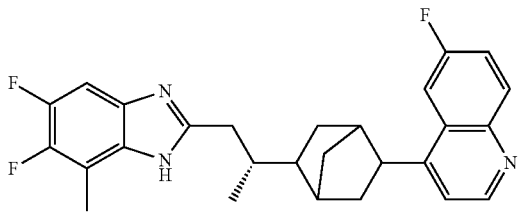

Example D28: 2-((2R)-2-(5-(6-fluoroquinolin-4-yl)bicyclo[2.2.1]heptan-2-yl)propyl)-1H-benzo[d]imidazole-5-carboxamide

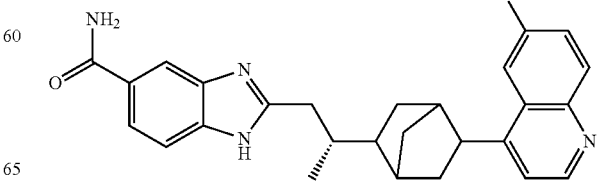

Example D29: 2-((2R)-2-(5-(6-fluoroquinolin-4-yl)
bicyclo[2.2.1]heptan-2-yl)propyl)-N-methyl-1H-
benzo[d]imidazole-5-carboxamide

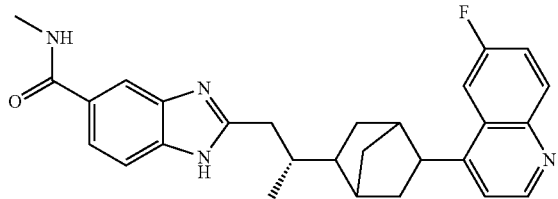 [SMILES: CNC(=O)c1ccc2[nH]c(C[C@@H](C)C3CC4CC3CC4c3ccnc4ccc(F)cc34)nc2c1]

Example D30: 2-((2R)-2-(5-(6-fluoroquinolin-4-yl)
bicyclo[2.2.1]heptan-2-yl)propyl)-N,N-dimethyl-1H-
benzo[d]imidazole-5-carboxamide

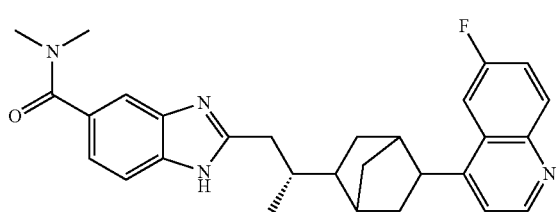 [SMILES: C[C@H](Cc1nc2cc(C(=O)N(C)C)ccc2[nH]1)C1CC2CC1CC2c1ccnc2ccc(F)cc12]

Example D31: aziridin-1-yl(2-((2R)-2-(5-(6-fluoro-
quinolin-4-yl)bicyclo[2.2.1]heptan-2-yl)propyl)-1H-
benzo[d]imidazol-5-yl)methanone

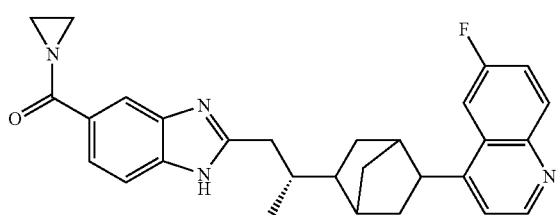 [SMILES: C[C@H](Cc1nc2cc(C(=O)N3CC3)ccc2[nH]1)C1CC2CC1CC2c1ccnc2ccc(F)cc12]

Example D32: azetidin-1-yl(2-((2R)-2-(5-(6-fluoro-
quinolin-4-yl)bicyclo[2.2.1]heptan-2-yl)propyl)-1H-
benzo[d]imidazol-5-yl)methanone

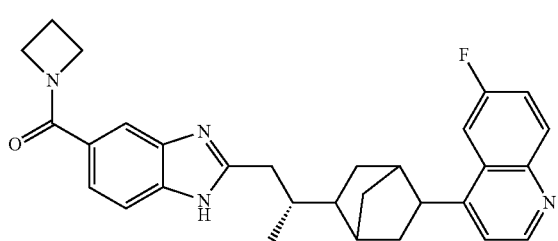 [SMILES: C[C@H](Cc1nc2cc(C(=O)N3CCC3)ccc2[nH]1)C1CC2CC1CC2c1ccnc2ccc(F)cc12]

Example D33: N-cyclobutyl-2-((2R)-2-(5-(6-fluoro-
quinolin-4-yl)bicyclo[2.2.1]heptan-yl)propyl)-1H-
benzo[d]imidazole-5-carboxamide

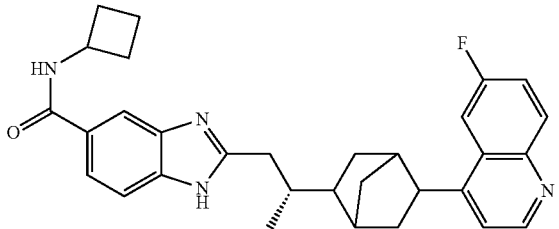 [SMILES: C[C@H](Cc1nc2cc(C(=O)NC3CCC3)ccc2[nH]1)C1CC2CC1CC2c1ccnc2ccc(F)cc12]

Example D34: 2-((2R)-2-(5-(6-fluoroquinolin-4-yl)
bicyclo[2.2.1]heptan-2-yl)propyl)-N-(3-hydroxycy-
clobutyl)-1H-benzo[d]imidazole-5-carboxamide

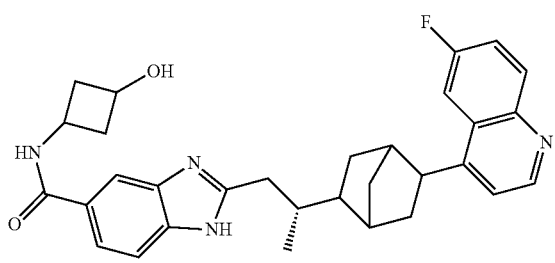 [SMILES: C[C@H](Cc1nc2cc(C(=O)NC3CC(O)C3)ccc2[nH]1)C1CC2CC1CC2c1ccnc2ccc(F)cc12]

Examples E1 to E8 were prepared in a similar procedure.

Example E1: 4-(3-(5-chloro-6-fluoro-1H-benzo[d]
imidazol-2-yl)cyclohexyl)-6-fluoroquinoline

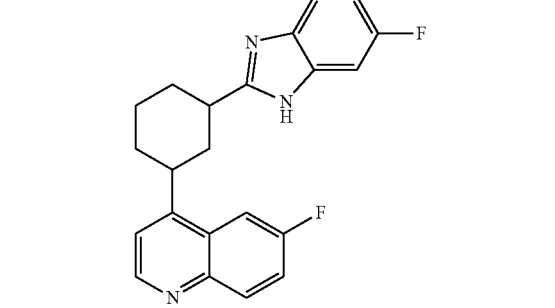

Example E2: 4-(3-(5,6-difluoro-H-benzo[d]imidazol-2-yl)cyclohexyl)-6-fluoroquinoline

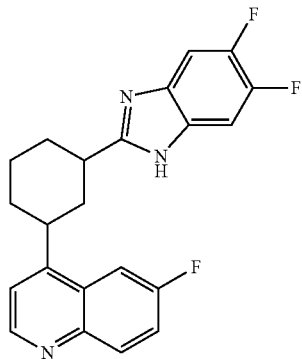 [SMILES: Fc1ccc2nccc(C3CCCC(c4nc5cc(F)c(F)cc5[nH]4)C3)c2c1]

Example E3: methyl 2-(3-(6-fluoroquinolin-4-yl)cyclohexyl)-1H-benzo[d]imidazole-6-carboxylate

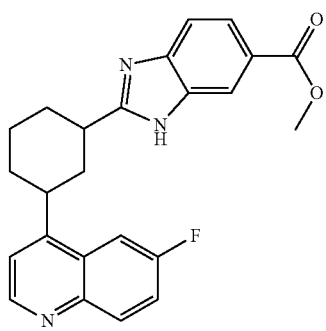 [SMILES: COC(=O)c1ccc2nc(C3CCCC(c4ccnc5ccc(F)cc45)C3)[nH]c2c1]

Example E4: 2-(3-(6-fluoroquinolin-4-yl)cyclohexyl)-N-methyl-1H-benzo[d]imidazole-6-carboxamide

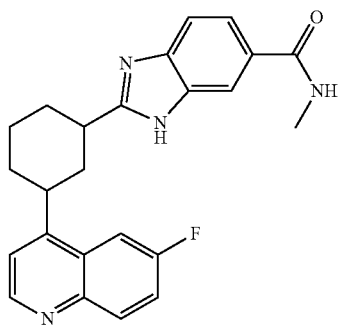 [SMILES: CNC(=O)c1ccc2nc(C3CCCC(c4ccnc5ccc(F)cc45)C3)[nH]c2c1]

Example E5: 2-(3-(6-fluoroquinolin-4-yl)cyclohexyl)-N,N-dimethyl-1H-benzo[d]imidazole-6-carboxamide

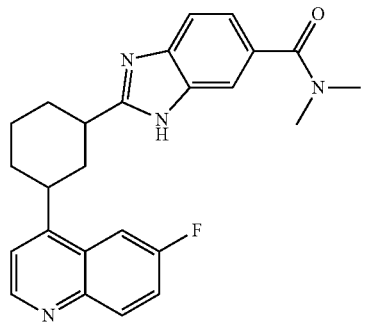 [SMILES: CN(C)C(=O)c1ccc2nc(C3CCCC(c4ccnc5ccc(F)cc45)C3)[nH]c2c1]

Example E6: N-cyclopropyl-2-(3-(6-fluoroquinolin-4-yl)cyclohexyl)-1H-benzo[d]imidazole-6-carboxamide

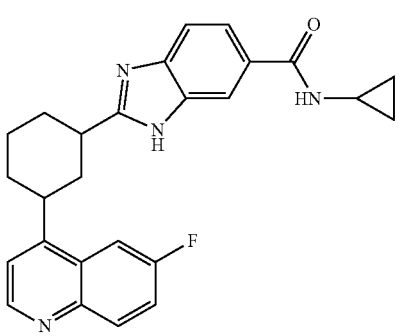 [SMILES: O=C(NC1CC1)c1ccc2nc(C3CCCC(c4ccnc5ccc(F)cc45)C3)[nH]c2c1]

Example E7: N-cyclobutyl-2-(3-(6-fluoroquinolin-4-yl)cyclohexyl)-1H-benzo[d]imidazole-6-carboxamide

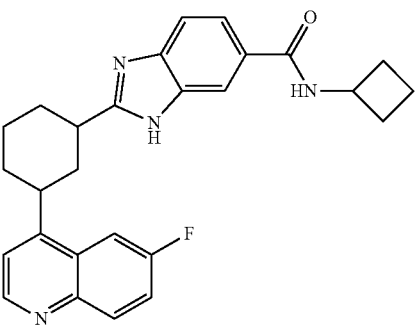 [SMILES: O=C(NC1CCC1)c1ccc2nc(C3CCCC(c4ccnc5ccc(F)cc45)C3)[nH]c2c1]

Example E8: 2-(3-(6-fluoroquinolin-4-yl)cyclo-hexyl)-N-(3-hydroxycyclobutyl)-1H-benzo[d]imidazole-6-carboxamide

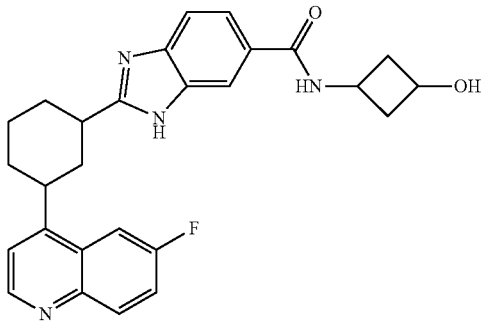 [SMILES: O=C(NC1CC(O)C1)c1ccc2nc(C3CCCC(c4ccnc5ccc(F)cc45)C3)[nH]c2c1]

Example F: Biological Assays

IDO1 Enzymatic Assay

Recombinant IDO1 was overexpressed and purified from E. coli cells with an N-terminal His tag. IDO1 enzymatic assay was carried out using a methodology similar to described in the literature (J. Biol. Chem. (1980), 255, 1339-1345). The reaction mixture contains 50 nM IDO1, 1.3 mM D-tryptophan, 5 mM L-ascorbic acid, 6.25 M methylene Blue, 0.4 mg/mL catalase and compound (or DMSO) in a buffer containing 50 mM potassium phosphate pH 7.5 and 0.1% BSA. After incubation at 24° C. for 1.5 hours, absorbance of the reaction mixture was continuously read at 321 nm to monitor the formation of N'-formylkynurenine by a FULOstar OMEGA plate reader (BMG LABTECH) for 1 hour. The enzymatic activity was determined by measuring the slope of the linear absorbance increase as a function of time. The $IC_{50}$s are calculated based on remaining enzyme activity in the presence of increasing concentrations of compounds.

As shown in Table 1 below, the representative compounds disclosed herein substantially show no enzymatic activity as their IC50s are larger than 10000.

293-TDO2 Cell-Based TDO2 Kyn (Kynurenine) Production Assay:

The inhibitory activity of TDO2 inhibitors is determined by using a colorimetric reaction to measure Kyn generated from L-Trp (L-Tryptophon) oxidation by cellular TDO2 in HEK293-TDO2 cells stably transfected with a plasmid expression of Tryptophan 2,3-dioxygenase (for short, 293-TDO2).

HEK293 cells were obtained from the American Type Culture Collection and 293-TDO2 were recovered in 10% FBS-containing phenol red-free DMEM medium. Cells were plated onto a 96-well plate (100p/well) at 10000 cells per well and kept at 37° C. in a humidified incubator supplied with 5% $CO_2$. 4 hours later, Compounds at different concentrations diluted in dimethylsulfoxide (DMSO) were added to plate. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 30 minutes and then centrifugation at 2500 rpm for 10 minutes to remove sediments. 80 μl supernatants were carefully removed to a new clean plate and added with an equal volume of 2% 4-(Dimethylamino)benzaldehyde (D2004, sigma) dissolved in glacial acetic acid. The absorbance at 480 nm wavelength derived from Kyn was measured using a PHERAstar FS plate reader (BMG LABTECH). The $IC_{50}$ for each compound was derived from fitting the dose-response data to the four-parameter logistic model by using XLfit software (IDBS).

HeLa Cell-Based IDO1 Kyn (Kynurenine) Production Assay:

The inhibitory activity of IDO1 inhibitors is determined by using a colorimetric reaction to measure Kyn generated from L-Trp (L-Tryptophon) oxidation by cellular IDO1 in HeLa cells after induction of IDO1 expression by IFN-γ.

Hela cells were obtained from the American Type Culture Collection and recovered in 10% FBS-containing phenol red-free DMEM medium. Cells were plated onto a 96-well plate (100 μl/well) at 8000 cells per well and kept at 37° C. in a humidified incubator supplied with 5% $CO_2$. 4 hours later, Human recombinant IFN-γ (8901SC, CST) was added to cells (final concentration 100 ng/mL) to stimulate endogenous IDOL. Compounds at different concentrations diluted in dimethylsulfoxide (DMSO) were added simultaneously with IFN-γ and 0.4 mM L-Trp. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 30 minutes and then centrifugation at 2500 rpm for 10 minutes to remove sediments. 80 μl supernatants were carefully removed to a new clean plate and added with an equal volume of 2% 4-(Dimethylamino)benzaldehyde (D2004, sigma) dissolved in glacial acetic acid. The absorbance at 480 nm wavelength derived from Kyn was measured using a PHERAstar FS plate reader (BMG LABTECH). The $IC_{5C}$ for each compound was derived from fitting the dose-response data to the four-parameter logistic model by using XLfit software (IDBS).

TABLE 1

Cellular activity data $EC_{50}$s (IDO1 enzymatic assay and Hela Cell-Based IDO1) of 1H-benzo[d] imidazol

| Ex. No. | Enzyme assay IC50(nM) | Cell-Based $EC_{50}$ (nM) Hela IDO1 |
|---|---|---|
| A1a | >10000 | 51 |
| A1b | >10000 | 8 |
| A2a | >10000 | 241 |
| A2b | >10000 | 53 |
| A3a | ND | 72 |
| A3b | ND | 6.8 |
| A4a | >10000 | 131 |
| A4b | >10000 | 13 |
| A5a | ND | 184 |
| A5b | ND | 23 |
| A6a | >10000 | 141 |
| A6b | >10000 | 14 |
| A7a | ND | 87 |
| A7b | ND | 3.6 |
| A8a | ND | 528 |
| A8b | ND | 50 |
| A9a | >10000 | 186 |
| A9b | >10000 | 24 |
| A10a | >10000 | 91 |
| A10b | >10000 | 10 |
| A11a | ND | 135 |
| A11b | ND | 14 |
| A12 | >10000 | 11 |
| A13 | >10000 | 8.4 |
| A14 | >10000 | >10000 |

TABLE 1-continued

Cellular activity data EC$_{50}$s (IDO1 enzymatic assay and Hela Cell-Based IDO1) of 1H-benzo[d] imidazol

| Ex. No. | Enzyme assay IC50(nM) | Cell-Based EC$_{50}$ (nM) Hela IDO1 |
|---|---|---|
| A15 | ND | 1953 |
| A16 | ND | 251 |
| A17 | ND | 5 |
| A18 | 5300 | 50 |
| A19 | >10000 | 8.2 |
| A20 | >10000 | 89 |
| A21 | >10000 | 131 |
| A22 | >10 | 148 |
| A23a | >10000 | 56 |
| A23b | 3250 | 24 |
| A24 | ND | 158 |
| A25 | ND | 268 |
| A26a | ND | 466 |
| A26b | ND | 205 |
| A27 | ND | 158 |
| A28 | ND | 1806 |
| A29 | ND | 179 |
| A30a | >10000 | 44 |
| A30b | >10000 | 39 |
| A31 | ND | 115 |
| A32 | 8100 | 143 |
| A33a | >10000 | >10000 |
| A33b | 8200 | 8.2 |
| A34a | 8000 | 168 |
| A34b | 4800 | 87 |
| A35 | >10000 | 107 |
| A36 | ND | 1670 |
| A37a | >10000 | 223 |
| A37b | 6900 | 99 |
| A38 | >10000 | 143 |
| A39 | ND | 150 |
| A40 | >10000 | 852 |
| A41 | >10000 | 481 |
| B1a | ND | 0.42 |
| B1b | ND | 59 |
| B1c | ND | ND |
| B1d | ND | ND |
| B2 | ND | 0.95 |
| B2a | ND | 0.38 |
| B2b | ND | 50 |
| B3 | ND | 1.3 |
| B3a | ND | 0.55 |
| B3b | ND | 81 |
| B4 | ND | 1.4 |
| B5 | ND | 1.4 |
| B6 | ND | 0.85 |
| B7 | ND | ND |
| B8 | ND | 6.9 |
| B9 | ND | ND |
| B10 | ND | ND |
| B11 | ND | 64.1 |
| B12 | ND | 46.0 |
| B13 | ND | ND |
| B14 | ND | 12.6 |
| B15 | ND | ND |
| B16 | ND | ND |
| B17 | ND | 0.58 |
| B18 | ND | ND |
| B19 | ND | ND |
| B20 | ND | ND |
| B21 | ND | ND |
| B22 | ND | ND |
| B23 | ND | ND |
| B24 | ND | ND |
| B25a | ND | 5.1 |
| B25b | ND | 3.1 |
| B26 | ND | ND |
| B27 | ND | ND |
| B28 | ND | ND |
| B29 | ND | ND |
| B30 | ND | ND |
| B31 | ND | ND |
| B32 | ND | ND |
| B33 | ND | ND |
| B34 | ND | ND |
| B35 | ND | ND |
| B36 | ND | ND |
| B37 | ND | ND |
| B38 | ND | ND |
| B39 | ND | ND |
| B40 | ND | ND |
| B41 | ND | ND |
| B42 | ND | ND |
| B43 | ND | ND |
| B44 | ND | ND |
| B45 | ND | ND |
| B46 | ND | ND |
| B47 | ND | ND |
| B48 | ND | ND |
| B49 | ND | ND |
| B50 | ND | ND |
| B51 | ND | ND |
| B52 | ND | ND |
| B53 | ND | ND |
| B54 | ND | ND |
| B55 | ND | ND |
| B56 | ND | ND |
| B57 | ND | ND |
| B58 | ND | ND |
| B59 | ND | ND |
| B60 | ND | ND |
| B61 | ND | ND |
| B62 | ND | ND |
| B63 | ND | ND |
| B64 | ND | ND |
| B65 | ND | ND |
| B66 | ND | ND |
| B67 | ND | ND |
| B68 | ND | ND |
| B69 | ND | ND |
| B70 | ND | ND |
| B71 | ND | ND |
| B72 | ND | ND |
| B73 | ND | ND |
| B74 | ND | ND |
| B75 | ND | ND |
| B76 | ND | ND |
| B77 | ND | ND |
| B78 | ND | ND |
| B79 | ND | ND |
| B80 | ND | ND |
| B81 | ND | ND |
| B82 | ND | ND |
| B83 | ND | ND |
| B84 | ND | ND |
| B85 | ND | ND |
| B86 | ND | ND |
| B87 | ND | ND |
| B88 | ND | ND |
| B89 | ND | ND |
| B90 | ND | ND |
| B91 | ND | ND |
| B92 | ND | ND |
| B93 | ND | ND |
| B94 | ND | ND |
| B95 | ND | ND |
| B96 | ND | ND |
| B97 | ND | ND |
| B98 | ND | ND |
| B99 | ND | ND |
| B100 | ND | ND |
| B101 | ND | ND |
| B102 | ND | ND |
| B103 | ND | ND |
| B104 | ND | ND |
| B105 | ND | ND |
| B106 | ND | ND |
| B107 | ND | ND |

TABLE 1-continued

Cellular activity data EC$_{50}$s (IDO1 enzymatic assay and Hela Cell-Based IDO1) of 1H-benzo[d] imidazol

| Ex. No. | Enzyme assay IC50(nM) | Cell-Based EC$_{50}$ (nM) Hela IDO1 |
|---|---|---|
| B108 | ND | ND |
| B109 | ND | ND |
| B110 | ND | ND |
| B111 | ND | ND |
| B112 | ND | ND |
| B113 | ND | ND |
| B114 | ND | ND |
| B115 | ND | ND |
| B116 | ND | ND |
| B117 | ND | ND |
| B118 | ND | ND |
| B119 | ND | ND |
| B120 | ND | ND |
| B121 | ND | ND |
| B122 | ND | ND |
| B123 | ND | 6.79 |
| B124 | ND | 16.42 |
| B125 | ND | 8.79 |
| B126 | ND | ND |
| B127 | ND | ND |
| B128 | ND | ND |
| B129 | ND | ND |
| B130 | ND | ND |
| B131 | ND | ND |
| B132 | ND | ND |
| B133 | ND | ND |
| B134 | ND | ND |
| B134 | ND | ND |
| B135 | ND | ND |
| B136 | ND | 296.2 |
| B137 | ND | ND |
| B138 | ND | 18.8 |
| B139 | ND | ND |
| B140 | ND | ND |
| B141 | ND | 6.89 |
| B142 | ND | ND |
| B143 | ND | ND |
| B144 | ND | ND |
| B145 | ND | ND |
| B146 | ND | ND |
| B147 | ND | ND |
| B148 | ND | ND |
| B149 | ND | 0.96 |
| B150 | ND | 10.94 |
| B151 | ND | 82.3 |
| B152 | ND | 62.9 |
| B153 | ND | 4.7 |
| B154 | ND | 50.0 |
| B155 | ND | 24.3 |
| B156 | ND | 3.1 |
| B157 | ND | 3.8 |
| B158 | ND | 6.9 |
| B159 | ND | 67.7 |
| B160 | ND | 46.0 |
| B161 | ND | 1.6 |
| B163 | ND | 567.4 |
| B164 | ND | 5.8 |
| B165 | ND | 470.3 |
| B166 | ND | 250.7 |
| B167 | ND | 18.8 |
| B168 | ND | 4.86 |
| B169 | ND | 19.6 |
| B170 | ND | 38.8 |
| B171 | ND | 40.2 |
| B172 | ND | 16.4 |
| B173 | ND | 12.7 |
| B174 | ND | 26.9 |
| B175 | ND | 1.7 |
| B176 | ND | 2.9 |
| B177 | ND | 6.9 |
| B178 | ND | 283.4 |
| B179 | ND | 36.2 |
| B180 | ND | 384.1 |
| B181 | ND | 2.7 |
| B182 | ND | 86.7 |
| B183 | ND | >1000 |
| B184 | ND | >1000 |
| B185 | ND | 122.3 |
| B186 | ND | 193.1 |
| B187 | ND | 17.1 |
| B188 | ND | 787.9 |
| B189 | ND | 45.9 |
| B190 | ND | 5.74 |
| B191 | ND | 1.14 |
| B192 | ND | 8.97 |
| B193 | ND | 12.6 |
| B194 | ND | 50.6 |
| B195 | ND | 74.5 |
| B196 | ND | 26.5 |
| B197 | ND | 8.1 |
| B198 | ND | 983.9 |
| B199 | ND | 21.9 |
| B200 | ND | 73.3 |
| B201 | ND | 1.6 |
| B202 | ND | 2.9 |
| B203 | ND | 8.8 |
| B204 | ND | 6.79 |
| B205 | ND | 28.9 |
| B206 | ND | 27.1 |
| B207 | ND | 18.4 |
| B208 | ND | >1000 |
| B210 | ND | 26.6 |
| B211 | ND | 1.3 |
| B212 | ND | 27.9 |
| B213 | ND | 1.8 |
| B214 | ND | 84.0 |
| B215 | ND | 958.8 |
| B216 | ND | 62.9 |
| B217 | ND | 1.2 |
| B218 | ND | 1.8 |
| B219 | ND | 13.7 |
| B220 | ND | 0.96 |
| C1a | ND | >10000 |
| C1b | ND | 24 |
| C2a | ND | 74 |
| C2b | ND | 11 |
| C3 | ND | 16 |
| C4 | ND | 9.1 |
| C5a | ND | 1434 |
| C5b | ND | 73 |
| C6a | ND | ND |
| C6b | ND | 14 |
| C7a | ND | 1360 |
| C7b | ND | 70 |
| C8a | ND | 1205 |
| C8b | ND | 37 |
| C9a | ND | >10000 |
| C9b | ND | 1243 |
| C10 | ND | 7 |
| C11 | ND | 12 |
| C12a | ND | ND |
| C12b | ND | ND |
| C13 | ND | ND |
| C14 | ND | ND |
| C15 | ND | ND |
| C16 | ND | ND |
| C17 | ND | ND |
| C18 | ND | ND |
| C19 | ND | ND |
| C20 | ND | ND |
| D1 | ND | 1086 |
| D2 | ND | 69 |
| D3 | ND | ND |
| D4 | ND | ND |
| D5 | ND | ND |

TABLE 1-continued

Cellular activity data EC$_{50}$s (IDO1 enzymatic assay and Hela Cell-Based IDO1) of 1H-benzo[d] imidazol

| Ex. No. | Enzyme assay IC50(nM) | Cell-Based EC$_{50}$ (nM) Hela IDO1 |
|---|---|---|
| D6 | ND | ND |
| D7 | ND | ND |
| D8 | ND | ND |
| D9 | ND | ND |
| D10 | ND | ND |
| D11 | ND | ND |
| D12 | ND | ND |
| D13 | ND | ND |
| D14 | ND | ND |
| D15 | ND | ND |
| D16 | ND | ND |
| D17 | ND | ND |
| D18 | ND | ND |
| D19 | ND | ND |
| D20 | ND | ND |
| D21 | ND | ND |
| D22 | ND | ND |
| D23 | ND | ND |
| D24 | ND | ND |
| D25 | ND | ND |
| D26 | ND | ND |
| D27 | ND | ND |
| D28 | ND | ND |
| D29 | ND | ND |
| D30 | ND | ND |
| D31 | ND | ND |
| D32 | ND | ND |
| D33 | ND | ND |
| D34 | ND | ND |
| E1 | ND | ND |
| E2 | ND | ND |
| E3 | ND | ND |
| E4 | ND | ND |
| E5 | ND | ND |
| E6 | ND | ND |
| E7 | ND | ND |
| E8 | ND | ND |

The representative compounds disclosed herein exhibited of inhibiting Hela Cell-Based IDO1 with EC$_{50}$ values ranging less than 10000 nM.

It is to be understood that, if any prior art publication is referred to herein, such reference does not constitute an admission that the publication forms apart of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

The invention claimed is:

1. A compound selected from:

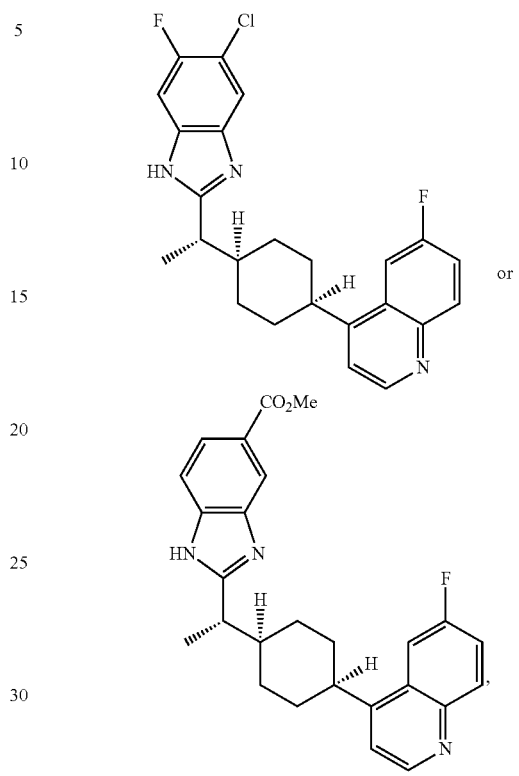

or a stereoisomer thereof, or a pharmaceutically acceptable salt thereof.

2. A pharmaceutical composition comprising at least one pharmaceutically acceptable excipient and a therapeutically effective amount of a compound of claim 1, or a pharmaceutically acceptable salt thereof.

3. A method for treating hyperproliferative disorders responsive to inhibition of IDO and/or TDO comprising administering to a subject in recognized need thereof a compound of claim 1, or a pharmaceutically acceptable salt thereof, in an amount effective to inhibit said IDO and/or TDO.

4. The method according to claim 3, wherein the hyperproliferative disorder is cancer.

5. The method according to claim 3, wherein the hyperproliferative disorder is selected from melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of biliary tract, non-small cell lung cancer, endometrium cancer, blood cancer, large intestinal colon carcinoma, histiocytic lymphoma, or lung adenocarcinoma.

6. A method for treating or preventing HIV infection/AIDS comprising administering to a subject in recognized need thereof therapeutically effective amount of a compound of claim 1, or a pharmaceutically acceptable salt thereof.

7. A method for enhancing the effectiveness of an antiretroviral therapy comprising administering to a subject in recognized need thereof therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 11,472,788 B2
APPLICATION NO. : 16/758203
DATED : October 18, 2022
INVENTOR(S) : Hexiang Wang et al.

It is certified that error appears in the above-identified patent and that said Letters Patent is hereby corrected as shown below:

In the Claims

Claim 1, Column 298, Line numbers 35-36: "or a stereoisomer thereof, or a pharmaceutically acceptable salt thereof." should read as —"or a pharmaceutically acceptable salt thereof."—

Signed and Sealed this
Twentieth Day of December, 2022

Katherine Kelly Vidal
*Director of the United States Patent and Trademark Office*